(12) United States Patent
Neville, Jr. et al.

(10) Patent No.: US 7,696,338 B2
(45) Date of Patent: Apr. 13, 2010

(54) IMMUNOTOXIN FUSION PROTEINS AND MEANS FOR EXPRESSION THEREOF

(75) Inventors: David M. Neville, Jr., Bethesda, MD (US); Jerry T. Thompson, Frenchville, PA (US); Huaizhong Hu, Madison, WI (US); Jung-Hee Woo, Rockville, MD (US); Shenglin Ma, Indianapolis, IN (US); Jonathan Mark Hexham, S. Orange, NJ (US); Mary Ellen Digan, Winchester, MA (US)

(73) Assignees: The United States of America as represented by the Department of Health and Human Services, Washington, DC (US); Novartis AG, Basel (CH)

( * ) Notice: Subject to any disclaimer, the term of this patent is extended or adjusted under 35 U.S.C. 154(b) by 1638 days.

(21) Appl. No.: 10/296,085

(22) PCT Filed: May 18, 2001

(86) PCT No.: PCT/US01/16125

§ 371 (c)(1),
(2), (4) Date: Jan. 13, 2004

(87) PCT Pub. No.: WO01/87982

PCT Pub. Date: Nov. 22, 2001

(65) Prior Publication Data

US 2004/0127682 A1 Jul. 1, 2004

Related U.S. Application Data

(63) Continuation-in-part of application No. 09/389,565, filed on Sep. 3, 1999, now Pat. No. 7,517,527, which is a continuation of application No. 08/739,703, filed on Oct. 29, 1996, now abandoned.

(60) Provisional application No. 60/008,104, filed on Oct. 30, 1995.

(51) Int. Cl.
C07H 21/04 (2006.01)
(52) U.S. Cl. .................. 536/23.4; 536/23.53; 536/23.7
(58) Field of Classification Search .................. None
See application file for complete search history.

(56) References Cited

U.S. PATENT DOCUMENTS

| | | | |
|---|---|---|---|
| 5,167,956 | A | 12/1992 | Neville |
| 5,725,857 | A | 3/1998 | Neville |
| 5,736,536 | A | 4/1998 | Siegall et al. |
| 5,747,474 | A | 5/1998 | Ojo-Amaize et al. |
| 5,801,193 | A | 9/1998 | Ojo-Amaize et al. |
| 5,977,316 | A * | 11/1999 | Chatterjee et al. ........ 530/387.2 |
| 6,103,235 | A | 8/2000 | Neville et al. |

FOREIGN PATENT DOCUMENTS

| | | |
|---|---|---|
| DE | 40/24/187 A1 | 7/1990 |
| EP | 217/327 | 4/1987 |
| EP | 0306 943 | 8/1988 |
| EP | 0 332 174 A | 3/1989 |
| EP | 0 616 034 A | 9/1994 |
| WO | WO 87/02987 | 5/1987 |
| WO | WO 89/06968 | 8/1989 |
| WO | WO 92/13562 | 8/1992 |
| WO | WO 91/13157 | 9/1992 |
| WO | WO 93/15113 | 8/1993 |
| WO | WO 84/00382 A | 2/1994 |
| WO | WO 9413804 A1 * | 6/1994 |
| WO | WO 95/33481 | 12/1995 |
| WO | WO 96/32137 | 10/1996 |
| WO | WO 98/39363 | 9/1998 |
| WO | WO 98/39425 | 9/1998 |
| WO | WO 99/53954 | 10/1999 |
| WO | WO 00/40270 | 7/2000 |
| WO | WO 00/41474 | 7/2000 |
| WO | WO 00/61132 | 10/2000 |

OTHER PUBLICATIONS

Murakami et al. Mol Cell Biol. May 1982;2(5):588-92.*
VanderSpek et al., J Biol Chem. Aug. 26, 1994;269(34):21455-9.*
Vajdos et al., J Mol Biol. Jul. 5, 2002;320(2):415-28.*
Romanos et al., Yeast. Jun. 1992;8(6):423-88.*
Janeway et al., Immunobiology, 5th Ed., Garland Science, pp. 94-105 (2001).*
Withers-Martinez et al., Protein Eng. Dec. 1999;12(12):1113-20.*
Rudikoff et al., Proc. Natl. Acad. Sci. USA, 79: 1979-1 983, Mar. 1982.*
Colman P. M., Research in Immunology, 145:33-36, 1994.*
Chien et al., Proc Natl Acad Sci U S A. Jul. 1989;86(14):5532-6.*
Peter Sudbery, Curr Opin Biotechnol. Oct. 1996;7(5):517-24.*
Shalaby et al., J Exp Med. Jan. 1, 1992;175(1):217-25.*
Pham et al., Anal Biochem. May 1, 2006;352(1):77-86.*
Anand et al. Bacterial Expression and Secretion of Various Single-chain Fv Genes Encoding Proteins Specific for a *Samonella* Serotype B O-Antigen. *J. Bio. Chem.* 266 (32):21874-2879 (1991).
Bach, Jean-Francois. Immunosuoressive therapy of autoimmune diseases. *TIPS* 14:213-216 (1993).
Barber et al. Long-Term Result Of A Controlled Prospective Study with transfusion Of Donor-Specific Bone marrow in 57 Cadaveric Renal Allograft Recipients. *Transplantation* 51:70-75 (1991).
Barr et al. Systemic Delivery of Recombinant proteins by Genetically Modifed Myoblasts. *Science* 254:1507-1509 (1991).
Behara et al. Intrathymic implants of genetically modifed fibroblasts. *The FASEB Journal* 6:2853-2858 (1992).
Bierhuizen et al. Expression cloning of a cDNA encoding UDP-GlcNac:Gallỹ-3-GalN Ac-R (GlcNAc to GalNac) ỹ-6GlcNAc transferase by gene transfer into CHO cells expressing polyoma large tumor antigen. *Proc. Natl. Acad. Sci. USA* 89:9326-9330 (1992).
Billingham et al. Actively Acquired Tolerance of Foreign Cells. *Nature* (1953) 172:603-606.

(Continued)

Primary Examiner—Zachary Skelding
(74) Attorney, Agent, or Firm—Edwards Angell Palmer & Dodge LLP; Peter F. Corless; Christine C. O'Day

(57) ABSTRACT

The present invention described and shown in the specification and drawings provides novel recombinant DT-based immunotoxins, and, more specifically anti-T cell immunotoxin fusion proteins. Also provided are immunotoxins that can be expressed in bacterial, yeast, or mammalian cells. The invention also provides means for expression of the immunotoxin fusion protein.

2 Claims, 54 Drawing Sheets

OTHER PUBLICATIONS

Blazar, B.R. et al. In Vivo Administration Of Anti-CD3 Monocional Antibodies Or Immuotoxins in Murine Recipients Of Allogeneic T Cell-Depleted marrow For The Promotion Of Engraftment. *J. Immunol.* 147:1492-1503 (1991).

Boussiotis et al. Blockade of the CD28 co-stimulatory pathway: a means to induce tolerance. *Curr Opin Immunol* 6:797 (1994).

Brent et al. Induction Of Tolerance Of Skin Homografts In Immunologically Competent Mice. *Nature* 196:1298-1301 (1962).

Caves et al. Hyperacute Rejection Of Orthotopic Cardiace Allografts In Dogs Following Solubilized Antigen Pretreatment. *Transplantation* 16:252-256 (1973).

Chaudhary et al., "A recominant single-chain immunotoxin composed of anit-Tac variable regions and a truncated diphtheria toxiln," *Pro. Natl. Acad. Sci.* (USA) 87:9491-9494 (1990).

Coffin. Superantigens and Endogenous Retroviruses: A Confluence of Puzzles. *Science* 255:411-413 (1992).

Contreras et al. Tolerability and side effects of anti-CD3-immunotoxin in preclinical testing in kidney and pancreatic islet transplant recipients. *Transplantation* 68(2):215-219 (1999).

Contreas et al. Peritransplant Tolerance Induction with Anti-CD3-Immunotoxin. *Transplantation* 65(9):1159-1169 (1998).

Cregg et al. Development of the methylotrophic yeast, *Pichia pastoris*, as a host system for the production of foreign proteins, *J. Indust. Microbi.* 29:33-41 (1988).

DeWet et al. Firefly Luciferase Gene: Structure and Expression in Mammalian Cells. *Moll. Cell. Biol.* 7:725-737 (1987).

Eckhoff et al. ASTS 25$^{th}$ Annual Meeting 1999. Synergy of 15-Deoxyspergualin With Aniti-CD3 Immunotoxin in Tolerance Induction In Rhesus Monkeys. *Transplantation* 67(9):60 (1999).

Fabre et al. The Effect of Donor Strain Blood Pretreatment On Renal Allograft Rejection In Rats. *Transplantation* 14:608-617 (1972).

Faustman, D. Strategies for circumventing transplant rejection: modification of cells, tissues and organs. *Trends in Biotechnology* 13(3):100-105 (1995).

Frankel, A.E. Antibody-toxin hybrids: a clinical review of their use. *J. of Biological Response* 4(5):437-446 (1985).

French et al. Immunological Enhancement Of Rat Kidney Grafts. *The Lancet* 1103-1106 (1969).

Gould et al. Phase I Study of an Anti-Breast Cancer Immuotoxin by Continuous Infusion: report of a Targeted Toxic Effect not Predicted by Animal Studies. *J. Natl. Cancer Inst.*. 81:775-781(May 1989).

Gowland. Induction Of Transplantation Tolerance In Adult Animals. *Brit Med. Bull.* 21:123-128 (1965).

Greenfield et al. Mutations in Diphtheris Toxin Separate Binding from Entry and Amplify Immunotoxin Selectivity. *Science* 238:536-539 (1987).

Haggerty et al. Effect of Deoxyspergualin or CTLA4Ig on the Immunogenicity and Pharmacokinetics of the Immunotoxin BR96sFv-PE40 in Dogs. *Journal of Allergy and Clinical Immunology* 99(1):708 (1997).

Hayden et al. Single-chain mono- and bispecific antibody derivatives with novel biological properties and antitumor activity from a COS cell transient expression system. *Therapeutic Immunology* 1:3-15 (1994).

Henretta et al. Six- to Eight-Month Survival of Discordant pig Islet Xenografts Documented by Differntial Species, Insulin, and C-Peptide in Animals Given Short-Term Immunosuppression. *Transplantation Proceedings* 26: 1138-1139 (1994).

Herold et al. Prevention od Autoimmune Diabetes with Nonactivating Anti-CD3 monoclonal Antibody. *Diabetes* 41:385-391 (1992).

Hertler et al. A Phase I Study of T101-Ricin A Chain Immunotoxin in Refractory Chronic Lymphocytic Leukemia. *J. Biol. Response Mod.* 7:97-113 (1988).

Hirsch et al. Anti-CD3 F(ab')$_2$ Fragments Are Immunosppressive In Vivo Without Evoking Either The Styrong Humoral Response Or Morbidity Associated With Whole mAb. *Transplantation* 49(6):1117-1123 (1990).

Hoffman, M. Putting New Muscle Into Gene Therapy. *Science* 254:1455-1456 (1991).

Hosaka et al. Arg-X-Lys/Arg-Arg Motif as a Signal for Precursor Cleavage Catalyzed by Furin within the Constitutive Secretory Pathway. *J. Bio. Chem.* 266(19):12127-12130 (1991).

Hu et al. Depletion of T Lymphocytes with Immunotoxin Retards the Progress of Experimental Allergic Encephalomyelitis in Rhesus Monkeys. *Cellular Immunology* 177:26-34 (1997).

Hullett et al.DAB486-II-2 (II-2-Toxin) in Combination With Low-Dose RS-61443 (Mycophenolate Mofetil) Prolongs Murine Thyroid Allograft Survival. *Transplantation Proceedings* 25(1):756-757 (1993).

Izquierdo et al. High Toxic Efficiency of Racin Immunotoxins Specific For The T-Cell Antigen Receptor Of A Human Leukemia T-Cell Line. *Int. J. Cancer* 43:697-702 (1989).

Janeway. Mls: makes a little sense. *Nature* 349:459-461 (1991).

Johnson et al. Improved tumor-specific immunotoxins in the treatment of CNS and leptomeningeal neoplasia. *J. Neurosurg.* 70:240 (1989).

Johnson et al. The Role of the Diphtheria Toxin Receptor in Cytosol Translocation. *J. Biol. Chem.* 263(3):1295-1300 (1988).

Jost et al. Mammalian expression and Secretion of Functional Single-chain Fv Molecules. *J. Biol. Chem.* 269(42):26267-26273 (1994).

Kaczoreck et al. Nucleotide Sequence and Expression of the Diphtheria tox228 Gene in *Escherichia coli*. *Science* 221:855-858 (1983).

Kamada et al. Fully Allogenic Liver Grafting and the Induction of Donor-Specific Unreactivity. *Transplantation* 13:837-841 (1981).

Kamada et al. Tranasplantation tolerance and immunosuppression following liver grafting in rats. *Immunology Today* 6:336-342 (1985).

Kappler et al. Vβ-Specific Stimulation of Human T Cells by Staphylococcal Toxins. *Science* 244:811-813 (1989).

Kieke et al. Isolation of anti-T cell receptor scFv mutants by yeast surface display. *Protein Engineering* 10(11):1303-1310 (1997).

Kimata et al. "Expression of non-ADP-ribosylatable, diphtheria toxin-resistant elongation factor 2 in *Saccharomyces cerevisiae*," *Biochem. and Biophys. Res. Comm.*, 191 (3): 1145-1151, 1993.

Knechtle et al. Induction of Specific Tolerance by Intrathymic Injection of Recipient Muscle Cells Transfected with Donnor Class I Major Histocompatibility Complex. *Transplantation* 57:990-996 (1994).

Knechtle et al. FN18-CRM9 Immunotoxin promotes Tolerance in Primate Renal Allografts. *Transplantation* 63:1-6 (1997).

Koehler et al. XomaZyme-CD5 Immunotoxin in conjuction with partial T cell depletion for prevention of graft rejection and graft-versus-host disease after bone marrow transplantation from matched unrelated donors. *Bone Marrow Transplantation* 13:571-575 (1994).

Laurence et al. Superantigent implicated in dependence of HIV-1 replication in T cells on TCR Vβ expression. *Nature* 358:255-259 (1992).

Lenschow et al. Long-Term Survival of Xenogeneic Pancreatic Islet Grafts Induced by CTLA4lg. *Science* 257:789-792 (1992).

Little et al. Detergent Solubilisation of Baboon Histocompatibility Antigents and Their Use in Prolong Allograft Survival, *Transplantation* 19:53-59 (1975).

Liu et al. Expression of an Anti-CD3 Single-Chain Immunotoxin with a Truncated Diphtheria Toxin in a Mutant CHO Cell Line *Protein Expression and Purification* 19:304-311 (2000).

Lu et al. Prevention and Treatment of Renal Allograft Rejection: new Therapeutic and New Insights into Established Therapies. *J. Am. Soc. Nephrol.* 4:1239-1256 (1993).

Ma et al. Epression and Characterization of a Divalent Chimeric Anti-Human CD3 Single Chain Antibody. *Scand. J. Immunol.* 43:134-139 (1996).

Ma et al. Genetic Construction and Characterization of an Anti-Monkey CD3 Single-Chain Immunotoxin with a Truncated Diphtheria Toxin. *Bioconj. Chem.* 8:695-701 (1997).

Madsen et al. Immunological unresponsiveness Induced by recipient cells transfected with donor MHC genes. *Nature* 332:161-164 (1988).

Marsh et al. Kinetic Comparison of Ricin Immunotoxins: Biricin Conjugate Has Potentiated Cytotoxicty. *Biochem.* 25(15):4461-4467 (1986).

Martins et al. The cDNA encoding canine dihydrolipoamide dehydrogenase contains multiple termination signals. *Gene* 161:253-257 (1995).

Mellor et al. A Nonpolymorphic Class I Gene in the Murine Major Histocompatibility Complex. *Cell* 36:139-144 (1984).

Mikayama et al. Molecular cloning and functional expression of a cDNA encoding glycosylation-inhibiting factor. *Proc. Natl. Acad. Sci. USA* 90:10056-10060 (1993).

Moller et al. Bias toward Use of a Specific T Cell Receptor β-chain Variable Region in a Subgroup of Individuals with Sarcoidosis. *J. Clin. Invest.* 82:1183-1191 (1988).

Murphy et al. Induction by Antigen of Intrathymic Apoptosis of $CD4^+CD8^+TCR^{10}$ Thymocytes in Vivo. *Science* 250:1720-1723 (1990).

Myers et al. The Effects of aromatic and aliphatic maleimide crosslinkers on anti-CD5 ricin immunotoxins. *J. Immunol. Meth.* 121:129-142 (1989).

Nemoto et al. Therapeutic activity of deoxyspegualin in comparison with cyclosporin A, and its combined use with cyclosporin A and prodin in highly allogeneic skin transplantation in the rat. *Agents Action* 36:306-311 (1992).

Neville et al. In vivo T-Cell ablation by a holo-immunotoxin direction at human Cd3. *Proc. Natl. Acad. Sci. USA* 89:2585-2589 (1992).

Neville & Marsh, Frankel ed. *Immunotoxins* Kluwer Academic Publishers, Chapter 21, methods for quantifying Immunotoxin Efficacy, 393-404 (1988).

Neville et al. Anti-T cell immunotoxins: a look at post-endocytptic receptor-mediated routing. *J. Controlled Release* 24(1-3):133-144 (1993).

Neville. Immunotoxins: Current Use and Future Prospects in Bone Marrow Transplantation and Cancer Treatment. in CRC Crit. Rev. in Therap. Drug Carrier Syst., CRC Press Inc., 2(4):329-352 (1986).

Neville et al. Enhancement of Immunotoxin efficacy by Acid-cleavage Cross-linking Agents Utilizing Diphtheria Toxin Mutants. *J. Biol. Chem.* 264(25):14653-14661 (1989).

Neville et al. Transmembrane transport of Diphtheria Toxin, Related Toxins, and Colicins. *Ann. Rev. Biochem.* 55:195-224 (1986).

Neville et al. A new Reagent for the induction of T-Cell Depletion, Anti-CD3-CRM9. *J. Immunotherapy* 19(2):85-92 (1996).

Ngo et al. Computational Complexity, Protein Structure Prediction, and the Levinthal Paradox. *The Protein Folding Problem and Tertiary Structure Prediction*, Merz and LeGrand (eds.), Birkhauser, Boston, MA, pp. 443 and 492-495 (1994).

Nooij et al. Differentiation antigens on rhesus monkey lymphocytes I. Identification of T cells bearing CD3 and CD8, and of a subset of CD8-bearing cells. *Eur. J. Immunol.* 16:975-979 (1986).

Nooij et al. The effect on skin allograft survival of a monoclonal antibody specific for a polymorphic CD3-like cell surface molecule in rhesus monkeys. *Eur. J. Immunol.* 17:1089-1093 (1987).

Ohzato et al. Tolerance Induction to Skin Allografts Following Intrathymic Injection with Donor-Specific Splenocytes in Major Histocompatibility Complex Class I, Class I + MLS, and Class I + II Disparities. *Transplantation Proceedings* 25(1):297-298 (1993).

Oksenbberg et al. Selection for T-cell receptor Vβ-Dβ-Jβ gene rearrangements with specificity for a myelin basic protein peptide in brain lesions of multiple sclerosis. *Nature* 362:68-70 (1993).

Oluwole et al. Induction of Tolerance to Rat Cardiac Allografts by Intrathymic Donor MHC-Class I Antigen. Transplantation Immunity and GVH Disease II Abstract 2723 FASEB (1992).

Oluwole et al. Induction of Specific Unresponiveness to Rat cardiac Allografts by Pretreatment With Intrathymic Donor Major Histocompatibility Complex Class I Antigens. *Transplantation Proceedings* (1993) 25(1):299-300.

Osband et al. Problems in the Investigational study and clinical use of cancer immunotherapy. *Immunology Today* 11(6):193-195 (1990).

Pankewycz et al. Interleukin-2-Diphtheria Toxin Fusion Protein Prolongs Murine Islet Cell Engraftment. *Transplantation* 47(2):318-322 (1989).

Parlevliet et al. Anti-CD3 Murine Monoclonal Isotype Switch Variants Tested For Toxicity and Immunologic monitoring in Four *Transplantation* 50:889-892 (1990).

Parren et al. Induction of T-cell proliferation by recombinant mouse and chimeric mouse/human anti-CD3 monoclonal antibodies *Res. Immunol.* 142:749763 (1992).

Pastan et al. Recombinant Toxins for Cancer Treatment. *Science* 254:1173-1177 (1991).

Pearson et al. Indudction of Transplantation Tolerance In Adults Using Donor Antigen ands Anti-CD4 Monoclonal Antibody. *Transplantation* 54:475-483 (1992).

Perentesis et al. Protein toxin inhibitors of protein synthesis, *Biofactors*, 3; (3):173-184 (1992).

Perentesis et al. "Expression of diphtheria toxin fragment A and hormone-toxin fusion proteins in toxin-resistant yeast mutants," P.N. A.S., 85:8386-8390, Nov. 1988.

Plückthun et al. New protein engineering approaches to multivalent and bispecific anitbody fragments. *Immunotechnology* 3:83-105 (1997).

Posselt et al. Induction of Donor-Specific Unresponsiveness byt Intrathymic Islet Transplantation. *Science* 249:1293-1295 (1990).

Posselt et al. Promotion of Pancreatic Islet Allograft Survival by Intrathymic Transplantation of Bone Marrow. *Diabetes* 41:771-775 (1992).

Priestley et al. A Detailed Analysis of the Potential of Water-Soluble Classical Class I MHC Molecules Fro The Suppression of Kidney Allograft Rejection and In Vitro Cytoxic T Cell Responses. *Transplantation* 48:1031-1038 (1989).

Rada et al. Concerted evolution of class I genes in the major histocompatibility complex of murine rodents. *Proc. Natl. Acac. Sci. USA* 87:2167-2171 (1990).

Ralston et al. Intracellular and Surface Distribution of a Membrane Protein (CD8) Derived from a Single Nucleus in Multinucleated Myotubes. *J. Cell Biol.* 109:2345-2352 (1989).

Remuzzi et al. Kidney graft survival in rats without immunosuppressants after intrathymic glomerular transplantation. *Lancent* 337:750-752 (1991).

Recordi et al. Liver-Islet Transplantation in Type 2 Diabetes. *Transplantation Proceedings* 29:2240 (1997).

Rilo et al. Human Islet Transplantation: Results in the First 37 Patients. *Transplantation Proceedings* 27:3162-3163 (1995).

Rostaing-Capaillon et al. Parameters Affecting Tumor-specific Delivery of Anti-Ricin A chain Immunotoxins in Vivo. *Cancer Res.* 50:2909-2916 (1990).

Salmeron et al. A Conformational Epitopoe Expressed Upon Association of CD3-δ or CD3-γ is the Main Target for Recognition by Anti-CD3 Monoclonal Antibodies. *J. of Immunol.* 147(9):3045-3052 (1991).

Schaffar et al. Monoclonal Antibody Internalization and Degradation during Modulation of the CD3/T-Cell Receptor Complex. *Cellular Immun.* 116:52-59 (1988).

Schwartz. Models of T Cell Anergy: Is There A Common Molecular Mechanism? *J Exp Med* 184:1 (1996).

Scorer et al. The intracellular production and secretion of HIV-1 envelope protein in the methylotrophic yeast *Pichia pastoris*. *Gene* 136:111-119 (1993).

Shalaby et al. Development of Humanized Bispecific Antibodies Reactive with Cytotoxic Lymphocytes and Tumor Cells Overexpressing the HER2 Protooncogene. *J. Exp. Med.* 175:217-225 (1992).

Shapiro et al. Tolerance of Skin Homografts Induced in Adult Mice by Multiple Injections of Spleen Cells. *Proc. Soc. Exp. Biol.* 106:472-475 (1961).

Shu et al. Secretion of a single-gene-encoded immunoglobulin from myeloma cells. *PNAS* 9:7995-7999 (1993).

Siegall et al. Prevention of Immunotoxin -Mediated Vascular Leak Syndrome in Rats with Retention of Antitumor Activity. *Proc. Natl Acad. Sci. USA* 91(20):9514-9518 (1994).

Skolnick et al. From genes to protein structure and function: novel applications of comutational approaches in the genomic era. *Trends in Biotechnology* 18(1):34-39 (2000).

Sreekrishna, K. Strategies for Optimizing Protin Expression and Secretion in the Methylotrophic Yeast *Pichia pastoris*. *Industrial Microorganisms: Basic and Applied Molecular Genetics* 16:119-126 (1993).

Stuart et al. Rejection of Renal Allografts: Specific Immunologic Suppression. *Science* 160:1463-1465 (1968).

Sumimoto et al. Specific Supression of Aligraft Rejection by Soluble Class I Antigen and Complexes with Monoclonal Antibody. *Transplantation* 50:678-682 (1990).

Thomas et al. Further Studies of Veto Activity In Rhesus Monkey Bone Marrow in Relation to Allograft Tolerance and Chimerism. *Transplantation* 57:101-115 (1994).

Thomas et al. Preclinical studies of Allograft Tolerance in Rhesus Monkeys. *Transplantation* 64: 124-135 (1997).

Thomas et al. Peritransplant Tolerance Induction in Macaques: Early Events Reflecting the Unique Synergy Between Immunotoxin and Deoxyspergualin. *Transplantation* 68(11):1660-1673 (1999).

Thomas et al. Reversal of naturally occurring diabetes in primates by unmodified islet xenografts without chronic immunosuppression. *Transplantation* 67(6):846-854 (1999).

Thomas et al. Reversal of Type II (NIDDM) Diabetes by Pancreas Islet Transplantation: An Emerging New Concept in Pathophysiology of an Enigmatic Disease. *Transplantation Proceedings* 27: 3167-3169 (1995).

Thompson et al. An Anti-CD3 Single-chain Immunotoxin with a Truncated Diphtheria Toxin Avoids Inhibition by Pre-existing Antibodies In Human Blood. *J. Biol. Chem.* 270(47):28037-28041 (1995).

Thorpe et al. An Immunotoxin Composed of Monoclonal Anti-Thy 1.1 Antibody and a Ribosome-Inactivating Protein From Saponaria officnalis: Potent Antitumor Effects in Vitro and In Vivo. *J. Nat'l Cancer Inst.* 75(1):151-159 (1985).

Traunecker et al. Bispecific single chain molecul;es (Janusins) target cytotoxic lymphocytes on HIV infected cells. *The EMBO Journal* 1(12):3655-3659 (1985).

Urban et al. Restricted Use of T Cell Receptor V Genes in Murine Autoimmune Encephalomyelitis Raise Possibilities for Antibody Therapy. *Cell* 54:577-592 (1988).

Vallera et al. Anti-CD3 Immunotoxin Prevents Low-Dose STZ/Interferon-Induced Autoimmune Diabetes In Mouse. *Diabetes* 41:457-464 (1992).

Vallera et al. Anti-Graft-Versus-Host Disease Effect of $DT_{390}$Anti-CD3sFv, a Single-Chain Fv Fusion Immunotoxin Specifically Targeting the CD3δ Moiety of the T-Cell Receptor. *Blood* 88(6):2642-2353 (1996).

Vitetta et al. Phase I Immunotoxin Trial in Patients with B-cell Lymphoma. *Cancer Res.* 51:4052-4053 (1991).

Waldmann. Monoclonal Antibodies in Diagnosis and Therapy. *Science* 252:1657-1662 (1991).

Waldmann et al. The use of monoclonal antibodies to achieve immunological tolerance. *TiPS* 14:143-148 (May 1991).

Whitlow et al. Single-Chain Fv Proteins and Their Fusion Proteins. *Methods* 2 (2):97-105 (1991).

Wilson et al. Prolonged Canine Renal Allograft Survival After Pretreatment With Solubililzed Antigen. *Transplantation* 7:360-371 (1969).

Woo et al. Gene optimization is necessary to express a bivalent anti-human anti-T cell immunotoxin in *Pichia pastoris*. *Protein Expression & Purification* 25:270-282 (2002).

Wood et al. Suppression Of Renal Allograft Rejection in The Rat By Class I Antigens on Purified Erythrocytes. *Transplantation* 39:56-62 (1985).

Wray et al. IgM and IgG Alloantibody response to MHC Class I and II Following Rat Renal Allograft Rejection. *Transplantation* 52:167-174 (1992).

Yamaguchi et al. The Effect of Pretreatment with Class I Major Histocompatibility Complex (MHC) Antigens on Hepatic or Cardiac Allograft Survival in the Rat. *Transplant. Proc.* 21:3555 (1989).

Yasumura et al. Prolongation of Rat Kidney Allografts by Pretransplant Adminstration of Donor Antigen Extract of Whole Blood Transfusiion Combined with a Short Course of Cyclosporine. *Transplantation* 36:603-609 (1983).

Youle et al. Hybridoma Cells containing Intracellular Anti-ricnin Antibodies Show Ricin meets Secretory Antibody before Entering the Cytosol. *J. Biol. Chem.* 262:4676-4682 (1987).

Youte et al. Kinetics of Protein Synthesis Inactivation by Ricin-Anti-Thy 1.1 Monoclonal Antibody Hybrids. *J. Biol. Chem.* 257:1598-1601 (1982).

Youle et al. Studies on the Galactose-Binding Site of Ricin and The Hybrid Toxin Man6P-Ricin. *Cell* 23:551-558 (1981).

Youle et al. Immunotoxins Show Rapid Entry of Diphtheria Toxin But Not Ricin via the T3 Antigen[1]. *J. Immunol.*, (1986) 136(1):93-98.

Zur Hausen. Viruses in Human Cancers. *Science* 254:1167-1172 (1992).

Sreekrishna, Koti "Strategies for Optimizing Protein Expression and Secretion in the Methylotrophic Yeast *Pichia pastoris*," *Industrial Microorganisms: Basic and Applied Molecular Genetics* 16:119-126 (1993).

Woo et al. "Gene optimization is necessary to express a bivalent anti-human anti-T cell immunotoxin in *Pichia pastoris*," *Protein Expression and Purification* 25:270-282 (2002).

\* cited by examiner

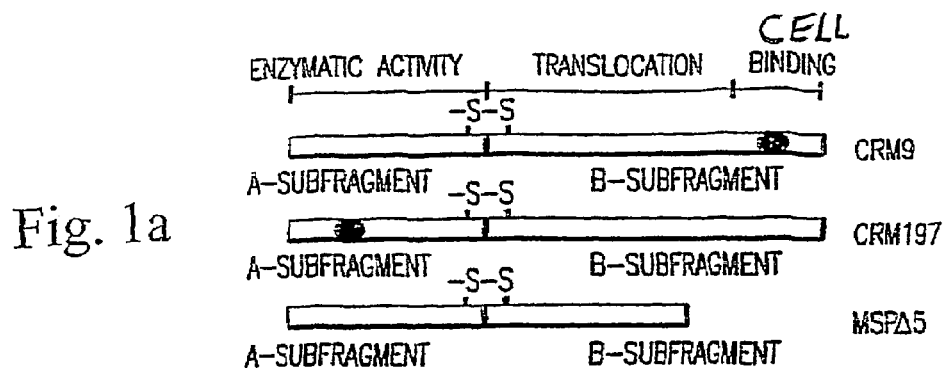
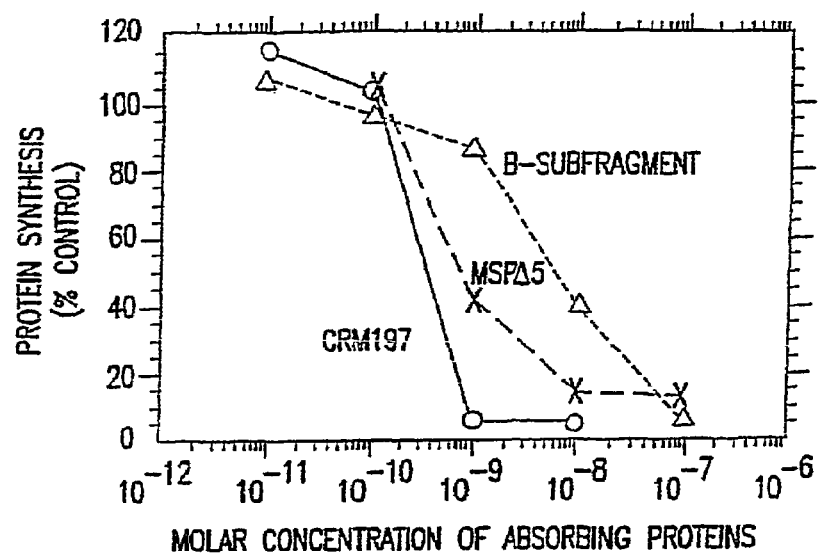
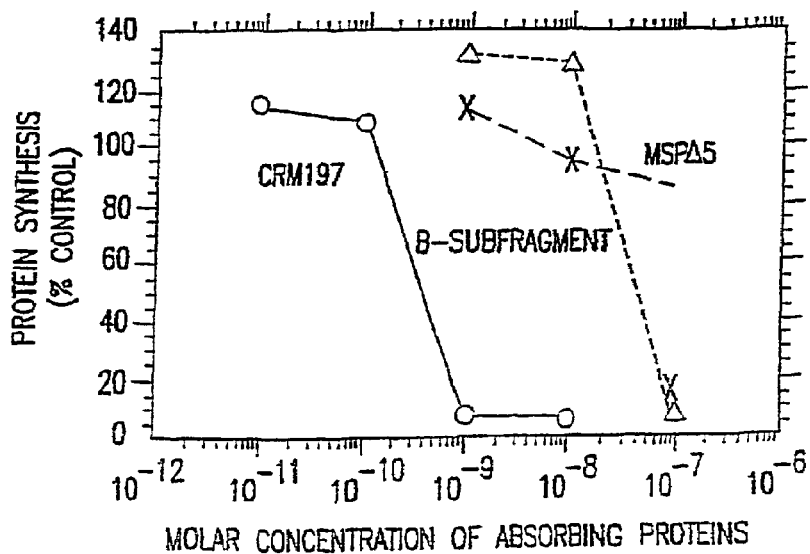
Fig. 1a
Fig. 1b
Fig. 1c

Western Blotting of anti-CD3 Diavalent DT390-scAb 1, 2. non-reduced condition.
2, 4. reduced condition
1, 3 and 2, 4 are two samples

DIVALENT SINGLE CHAIN COUPLED IMMUNOTOXINS

Fig. 12
DIVALENT DICYSTRONIC COUPLED IMMUNOTOXINS
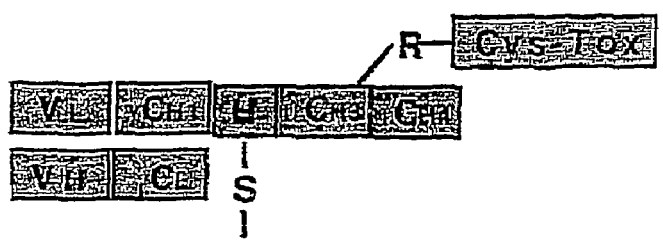
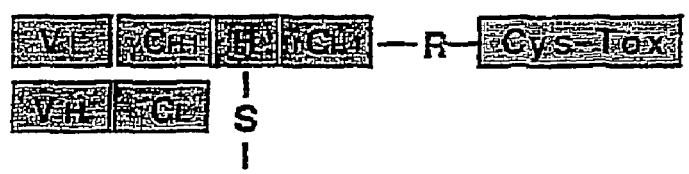
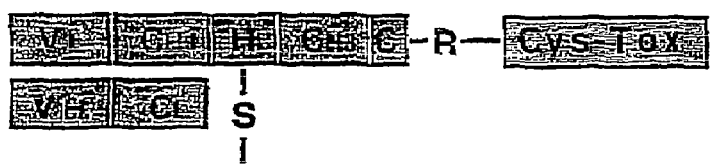
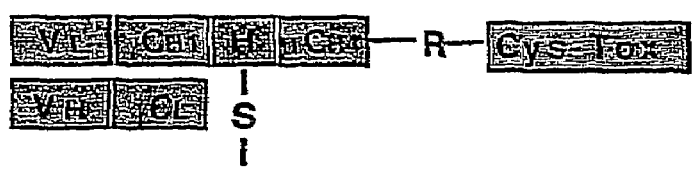

Fig. 13

DIVALENT ETA BASED FUSION IMMUNOTOXINS

| VL | L | VH | H | CH3 | Tox |

|
    S
    |

| VL | L | VH | H | CH4 | Tox |

|
    S
    |

| VL | L | VH | CH2 | CH4 | Tox |

|
    S
    |

| VL | L | VH | CH2 | CH3 | CH4 | Tox |

|
    S
    |

| VL | L | VH | H | Tox |

|
    S
    |

Fig. 14
DT BASED DIVALENT FUSION IMMUNOTOXINS
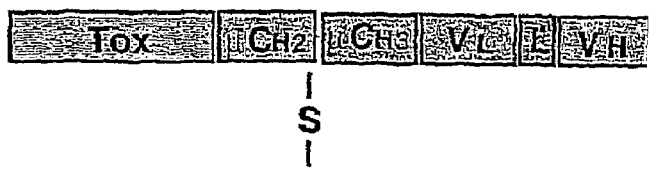
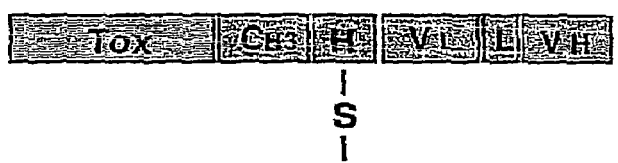
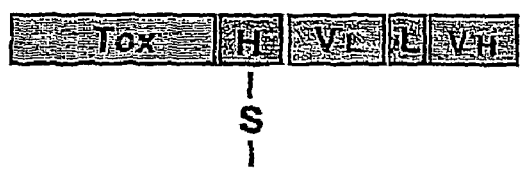
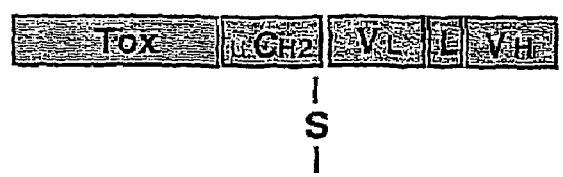

Figure 19H

Ala | G | dmDT390 | C | $V_L$ | L | $V_H$ | L | $V_L$ | L | $V_H$

Single chain Fv | Single chain Fv 390    2   107    122    107    122
               15       15       15

Figure 19I

TyrValGluPhe | G | dmDT390 | C | $V_L$ | L | $V_H$ | L | $V_L$ | L | $V_H$

Single chain Fv | Single chain Fv 390          2   107    122    107    122
                      15       15       15

Fig. 20
A Comparison of the Amino Acid Sequences of Various Constructs of DT390-bisFv (UCHT1) from Bacterial, CHO cell and Pichia Expression Vectors by Construct Number (see Table 9)

```
7.      MGADDVVDSSK SFVMENFSSY HGTKPGYVDS IQKGIQKPKS GTQGNYDDDW  -051
9.      MGADDVVDSSK SFVMENFSSY HGTKPGYVDS IQKGIQKPKS GTQGNYDDDW  -051
12/13.  AGADDVVDSSK SFVMENFASY HGTKPGYVDS IQKGIQKPKS GTQGNYDDDW  -051
14.      GADDVVDSSK SFVMENFASY HGTKPGYVDS IQKGIQKPKS GTQGNYDDDW  -050
15.YVEFGADDVVDSSK SFVMENFASY HGTKPGYVDS IQKGIQKPKS GTQGNYDDDW  -054

7.      KGFYSTDNKY DAAGYSVDNE NPLSGKAGGV VKVTYPGLTK VLALKVDNAE  -101
9.      KGFYSTDNKY DAAGYSVDNE NPLSGKAGGV VKVTYPGLTK VLALKVDNAE  -101
12/13.  KGFYSTDNKY DAAGYSVDNE NPLSGKAGGV VKVTYPGLTK VLALKVDNAE  -101
14.     KGFYSTDNKY DAAGYSVDNE NPLSGKAGGV VKVTYPGLTK VLALKVDNAE  -100
15.     KGFYSTDNKY DAAGYSVDNE NPLSGKAGGV VKVTYPGLTK VLALKVDNAE  -104

7.      TIKKELGLSL TEPLMEQVGT EEFIKRFGDG ASRVVLSLPF AEGSSSVEYI  -151
9.      TIKKELGLSL TEPLMEQVGT EEFIKRFGDG ASRVVLSLPF AEGSSSVEYI  -151
12/13.  TIKKELGLSL TEPLMEQVGT EEFIKRFGDG ASRVVLSLPF AEGSSSVEYI  -151
14.     TIKKELGLSL TEPLMEQVGT EEFIKRFGDG ASRVVLSLPF AEGSSSVEYI  -150
15.     TIKKELGLSL TEPLMEQVGT EEFIKRFGDG ASRVVLSLPF AEGSSSVEYI  -154

7.      NNWEQAKALS VELEINFETR GKRGQDAMYE YMAQACAGNR VRRSVGSSLS  -201
9.      NNWEQAKALS VELEINFETR GKRGQDAMYE YMAQACAGNR VRRSVGSSLS  -201
12/13.  NNWEQAKALS VELEINFETR GKRGQDAMYE YMAQACAGNR VRRSVGSSLS  -201
14.     NNWEQAKALS VELEINFETR GKRGQDAMYE YMAQACAGNR VRRSVGSSLS  -200
15.     NNWEQAKALS VELEINFETR GKRGQDAMYE YMAQACAGNR VRRSVGSSLS  -204

7.      CINLDWDVIR DKTKTKIESL KEHGPIKNKM SESPNKTVSE EKAKQYLEEF  -251
9.      CINLDWDVIR DKTKTKIESL KEHGPIKNKM SESPNKTVSE EKAKQYLEEF  -251
12/13.  CINLDWDVIR DKTKTKIESL KEHGPIKNKM SESPAKTVSE EKAKQYLEEF  -251
14.     CINLDWDVIR DKTKTKIESL KEHGPIKNKM SESPAKTVSE EKAKQYLEEF  -250
15.     CINLDWDVIR DKTKTKIESL KEHGPIKNKM SESPAKTVSE EKAKQYLEEF  -254

7.      HQTALEHPEL SELKTVTGTN PVFAGANYAA WAVNVAQVID SETADNLEKT  -301
9.      HQTALEHPEL SELKTVTGTN PVFAGANYAA WAVNVAQVID SETADNLEKT  -301
12/13.  HQTALEHPEL SELKTVTGTN PVFAGANYAA WAVNVAQVID SETADNLEKT  -301
14.     HQTALEHPEL SELKTVTGTN PVFAGANYAA WAVNVAQVID SETADNLEKT  -300
15.     HQTALEHPEL SELKTVTGTN PVFAGANYAA WAVNVAQVID SETADNLEKT  -304

7.      TAALSILPGI GSVMGIADGA VHHNTEEIVA QSIALSSLMV AQAIPLVGEL  -351
9.      TAALSILPGI GSVMGIADGA VHHNTEEIVA QSIALSSLMV AQAIPLVGEL  -351
12/13.  TAALSILPGI GSVMGIADGA VHHNTEEIVA QSIALSSLMV AQAIPLVGEL  -351
14.     TAALSILPGI GSVMGIADGA VHHNTEEIVA QSIALSSLMV AQAIPLVGEL  -350
15.     TAALSILPGI GSVMGIADGA VHHNTEEIVA QSIALSSLMV AQAIPLVGEL  -354

7.      VDIGFAAYNF VESIINLFQV VHNSYNRPAY SPGHKTQPFL PWDIQMTQTT  -401
9.      VDIGFAAYNF VESIINLFQV VHNSYNRPAY SPGHKTQPFL PWDIQMTQTT  -401
12/13.  VDIGFAAYNF VESIINLFQV VHNSYNRPAY SPGHKTQPFL PWDIQMTQTT  -401
14.     VDIGFAAYNF VESIINLFQV VHNSYNRPAY SPGHKTQPFL PWDIQMTQTT  -400
15.     VDIGFAAYNF VESIINLFQV VHNSYNRPAY SPGHKTQPFL PWDIQMTQTT  -404

7.      SSLSASLGDR VTISCRASQD IRNYLNWYQQ KPDGTVKLLI YYTSRLHSGV  -451
9.      SSLSASLGDR VTISCRASQD IRNYLNWYQQ KPDGTVKLLI YYTSRLHSGV  -451
12/13.  SSLSASLGDR VTISCRASQD IRNYLNWYQQ KPDGTVKLLI YYTSRLHSGV  -451
14.     SSLSASLGDR VTISCRASQD IRNYLNWYQQ KPDGTVKLLI YYTSRLHSGV  -450
15.     SSLSASLGDR VTISCRASQD IRNYLNWYQQ KPDGTVKLLI YYTSRLHSGV  -454
```

Fig. 20

```
7.      PSKFSGSGSG  TDYSLTISNL  EQEDIATYFC  QQGNTLPWTF  AGGTKLEIKG  -501
9.      PSKFSGSGSG  TDYSLTISNL  EQEDIATYFC  QQGNTLPWTF  AGGTKLEIKG  -501
12/13.  PSKFSGSGSG  TDYSLTISNL  EQEDIATYFC  QQGNTLPWTF  AGGTKLEIKG  -501
14.     PSKFSGSGSG  TDYSLTISNL  EQEDIATYFC  QQGNTLPWTF  AGGTKLEIKG  -500
15.     PSKFSGSGSG  TDYSLTISNL  EQEDIATYFC  QQGNTLPWTF  AGGTKLEIKG  -504

7.      GGGSGGGGSG  GGGSEVQLQQ  SGPELVKPGA  SMKISCKASG  YSFTGYTMNW  -551
9.      GGGSGGGGSG  GGGSEVQLQQ  SGPELVKPGA  SMKISCKASG  YSFTGYTMNW  -551
12/13   GGGSGGGGSG  GGGSEVQLQQ  SGPELVKPGA  SMKISCKASG  YSFTGYTMNW  -551
14.     GGGSGGGGSG  GGGSEVQLQQ  SGPELVKPGA  SMKISCKASG  YSFTGYTMNW  -550
15.     GGGSGGGGSG  GGGSEVQLQQ  SGPELVKPGA  SMKISCKASG  YSFTGYTMNW  -554

7.      VKQSHGKNLE  WMGLINPYKG  VSTYNQKFKD  KATLTVDKSS  STAYMELLSL  -601
9.      VKQSHGKNLE  WMGLINPYKG  VSTYNQKFKD  KATLTVDKSS  STAYMELLSL  -601
12/13.  VKQSHGKNLE  WMGLINPYKG  VSTYNQKFKD  KATLTVDKSS  STAYMELLSL  -601
14.     VKQSHGKNLE  WMGLINPYKG  VSTYNQKFKD  KATLTVDKSS  STAYMELLSL  -600
15.     VKQSHGKNLE  WMGLINPYKG  VSTYNQKFKD  KATLTVDKSS  STAYMELLSL  -604

7.      TSEDSAVYYC  ARSGYYGDSD  WYFDVWGAGT  TVTVSS GGGG  SGGGGSGGGG  -651
9.      TSEDSAVYYC  ARSGYYGDSD  WYFDVWGAGT  TVTVSS GGGG  SGGGGSGGGG  -651
12/13.  TSEDSAVYYC  ARSGYYGDSD  WYFDVWGAGT  TVTVSS GGGG  SGGGGSGGGG  -651
14.     TSEDSAVYYC  ARSGYYGDSD  WYFDVWGAGT  TVTVSS GGGG  SGGGGSGGGG  -650
15.     TSEDSAVYYC  ARSGYYGDSD  WYFDVWGAGT  TVTVSS GGGG  SGGGGSGGGG  -654

7.      SDIQMTQTTS  SLSASLGDRV  TISCRASQDI  RNYLNWYQQK  PDGTVKLLIY  -701
9.      SDIQMTQTTS  SLSASLGDRV  TISCRASQDI  RNYLNWYQQK  PDGTVKLLIY  -701
12/13.  SDIQMTQTTS  SLSASLGDRV  TISCRASQDI  RNYLNWYQQK  PDGTVKLLIY  -701
14.     SDIQMTQTTS  SLSASLGDRV  TISCRASQDI  RNYLNWYQQK  PDGTVKLLIY  -700
15.     SDIQMTQTTS  SLSASLGDRV  TISCRASQDI  RNYLNWYQQK  PDGTVKLLIY  -704

7.      YTSRLHSGVP  SKFSGSGSGT  DYSLTISNLE  QEDIATYFCQ  QGNTLPWTFA  -751
9.      YTSRLHSGVP  SKFSGSGSGT  DYSLTISNLE  QEDIATYFCQ  QGNTLPWTFA  -751
12/13.  YTSRLHSGVP  SKFSGSGSCT  DYSLTISNLE  QEDIATYFCQ  QGNTLPWTFA  -751
14.     YTSRLHSGVP  SKFSGSGSGT  DYSLTISNLE  QEDIATYFCQ  QGNTLPWTFA  -750
15.     YTSRLHSGVP  SKFSGSGSGT  DYSLTISNLE  QEDIATYFCQ  QGNTLPWTFA  -754

7.      GGTKLEIK GG  GGSGGGGSGG  GGS EVQLQQS  GPELVKPGAS  MKISCKASGY  -801
9.      GGTKLEIK GG  GGSGGGGSGG  GGS EVQLQQS  GPELVKPGAS  MKISCKASGY  -801
12/13.  GGTKLEIK GG  GGSGGGGSGG  GGS EVQLQQS  GPELVKPGAS  MKISCKASGY  -801
14.     GGTKLEIK GG  GGSGGGGSGG  GGS EVQLQQS  GPELVKPGAS  MKISCKASGY  -800
15.     GGTKLEIK GG  GGSGGGGSGG  GGS EVQLQQS  GPELVKPGAS  MKISCKASGY  -804

7.      SFTGYTMNWV  KQSHGKNLEW  MGLINPYKGV  STYNQKFKDK  ATLTVDKSSS  -851
9.      SFTGYTMNWV  KQSHGKNLEW  MGLINPYKGV  STYNQKFKDK  ATLTVDKSSS  -851
12/13.  SFTGYTMNWV  KQSHGKNLEW  MGLINPYKGV  STYNQKFKDK  ATLTVDKSSS  -851
14.     SFTGYTMNWV  KQSHGKNLEW  MGLINPYKGV  STYNQKFKDK  ATLTVDKSSS  -850
15.     SFTGYTMNWV  KQSHGKNLEW  MGLINPYKGV  STYNQKFKDK  ATLTVDKSSS  -854

7.      TAYMELLSLT  SEDSAVYYCA  RSGYYGDSDW  YFDVWGAGTT  VTVSS  -896 (SEQ ID NO:18)
9.      TAYMELLSLT  SEDSAVYYCA  RSGYYGDSDW  YFDVWGQGTT  LTVFS  -896 (SEQ ID NO:17)
12/13.  TAYMELLSLT  SEDSAVYYCA  RSGYYGDSDW  YFDVWGQGTT  LTVFS  -896 (SEQ ID NO:26)
14.     TAYMELLSLT  SEDSAVYYCA  RSGYYGDSDW  YFDVWGQGTT  LTVFS  -895 (SEQ ID NO:27)
15.     TAYMELLSLT  SEDSAVYYCA  RSGYYGDSDW  YFDVWGQGTT  LTVFS  -899 (SEQ ID NO:28)

7.      (Met)DT390-bisFv(UCHT1) corrected sequence (exists only in pET15b)
9.      (Met)DT390-bisFv(UCHT1*) uncorrected sequence (exists in pET15b)
12/13.  (Ala)dmDT390-bisFv(UCHT1*) double glycos. neg. mutant (exists in
        pSRαneo expressed in CHO and in pPICZα expressed in Pichia).
```

Fig. 20

14. dmDT390-bisFv(UCHT1*) double glycos. neg. mutant (exists in pPICZα expressed in Pichia)
15. (TyrValGluPhe)dmDT390-bisFv(UCHT1*) double glycos. neg. mutant (exists in pPIC9K expressed in Pichia)

Amino acid symbols underlined are those not present in wild type DT390 and not present in the VL and VH domains of UCHT1 including G4S linkers.

Figure 21

Comparison of Monovalent and Divalent Single Chain Immunotoxin Toxicity and Binding Data to Jurkat Cells With Reference to the Parental UCHT1 Antibody, Derived Recombinant Fragments and the Chemical Conjugate, UCHT1-CRM9
All CD3 Binding is relative to intact anti-CD3 antibody.
All toxicity is relative to UCHT1-CRM9.

| Ab/IT | Produced In | Binding | Toxicity |
|---|---|---|---|
| UCHT1 | mouse ascites | 1.0 | |
| SFv(UCHT1') | E. coli refolded | 3.0 | |
| BisFv(UCHT1*) | E. coli refolded | 20. | |
| UCHT1-CRM9 | chemical conjugate | 0.3 | 1.0* |
| (Met)DT389-sFv(UCHT1) | E. coli refolded | 0.016 | 1.0 |
| (Ala)dmDT390-sFv(UCHT1')His | CHO Cells | | 0.5 |
| (Ala)dmDT390-bisFv(UCHT1*) | CHO Cells | | 25 |
| (Ala)dmDT390-bisFv(UCHT1*) | Pichia | 0.10 | 25 |

* $IC_{60}$ for 20 hour assay on Jurkat cells =2 X $10^{-12}$ M. This is similar to that for FN18-CRM9, the anti-rhesus Immunotoxin used to generate pre-clinical data on the effectiveness of this immunotoxin in inducing systemic T cell depletion and organ transplantation tolerance.

FIG. 25

1. 235Gln mutation

```
Met Ser Glu Ser Pro Asn Lys Thr Val Ser Glu Glu        (SEQ ID NO:70)
ATG AGC GAA AGT CCC AAT AAA ACA GTA TCT GAG GAA        (SEQ ID NO:71) pET17b
  G AGC GAA AGT CCC cAg AAg ACA GTA TCT GAG G          (SEQ ID NO:72) oligo
                   Gln Lys
```

For selection the new restriction site for BbsI was introduced:
5'-GAAGAC(N)₂-3'     (SEQ ID NO:73)
3'-CTTCTG(N)₆-5'     (SEQ ID NO:74)

2. 235Ala mutation

```
Met Ser Glu Ser Pro Asn Lys Thr Val Ser Glu Glu        (SEQ ID NO:75)
ATG AGC GAA AGT CCC AAT AAA ACA GTA TCT GAG GAA        (SEQ ID NO:76) pET17b
  G AGC GAA AGT CCg gcc AAA ACA GTA TCT GAG G          (SEQ ID NO:77) oligo
                   Ala Lys
```

For selection the new restriction site for EaeI was introduced:
5'-CGGCCA-3'     (SEQ ID NO:78)
3'-GCCGGT-5'     (SEQ ID NO:79)

3. 237Ala mutation

```
Met Ser Glu Ser Pro Asn Lys Thr Val Ser Glu Glu Lys Ala    (SEQ ID NO:80)
ATG AGC GAA AGT CCC AAT AAA ACA GTA TCT GAG GAA AAA CCT    (SEQ ID NO:81) pET17b
  G AGC GAA AGT CCC AAT AAA gCg GTc TCT GAG GAA AAA CC     (SEQ ID NO:82) oligo
                            Ala Val
```

For selection the new restriction site for BsaI was introduced:
5'-GGTCTC(N)₁-3'     (SEQ ID NO:83)
3'-CCAGAG(N)₅-5'     (SEQ ID NO:84)

4. 16Ala mutation

```
Ser Phe Val Met Glu Asn Phe Ser Ser Tyr His Gly       (SEQ ID NO:85)
TCT TTT GTG ATG GAA AAC TTT TCT TCG TAC CAC GGG       (SEQ ID NO:86) pET17b
 CT TTT GTG ATG GAA gct TTT TCT TCG TAC CAC G         (SEQ ID NO:87) oligo
                    Ala
```

For selection the new restriction site for HindIII was introduced:
5'-AAGCTT-3'     (SEQ ID NO:88)
3'-TTCGAA-5'     (SEQ ID NO:89)

5. 18Ala mutation

```
Phe Val Met Glu Asn Phe Ser Ser Tyr His Gly Thr Lys Pro   (SEQ ID NO:90)
TTT GTG ATG GAA AAC TTT TCT TCG TAC CAC GGG ACT AAA CCT   (SEQ ID NO:91) pET17b
    GTG ATG GAA AAC TTT gCT agc TAC CAC GGG ACT AAA CC    (SEQ ID NO:92) oligo
                        Ala Ser
```

For selection the new restriction site for NheI was introduced:
5'-GCTAGC-3'     (SEQ ID NO:93)
3'-CGATCG-5'     (SEQ ID NO:94)

Protein Synthesis Assay on Jurkat Cells, 20 hr by (Ala)dmDT390-sFv(UCHT1*) from Pichia 6 L fermentation.

Figure 28

```
              10          20         30          40         50         60
Ori  ggcgctgatg atgttgttga ttcttctaaa tcttttgtga tggaaaactt ttcttcgtac
Reb  ggcgctgatg atgtCgtCga CtcCtcCaaG tcCttCgtCa tggaGaactt CGcttcCtac 70          80         90         100        110        120
Ori  cacgggacta aacctggtta tgtagattcc attcaaaaag gtatacaaaa gccaaaatct
Reb  cacgggacCa aGccAggtta CgtCgaCtcc atCcaGaaGg gtatCcaGaa gccaaaGtcC 130         140        150         160        170        180
Ori  ggtacacaag gaaattatga cgatgattgg aaagggttt  atagtaccga caataaatac  (SEQ ID NO:95)
Reb  ggCacCcaag gTaaCtaCga cgaCgaCtgg aaGgggtcCt aCTCCaccga caaCaaGtac  (SEQ ID NO:96)

----------  ----------  ----------  ----------  ----------  ----------

670         680        690         700        710        720
Ori  aaagagcatg gccctatcaa aaataaaatg agcgaaagtc ccaataaaac agtatctgag
Reb  aaagagcatg gcccAatcaa GaaCaaGatg TCcgaaTCCc ccGCtaaGac CgtCtcCgag 730         740        750         760        770        780
Ori  gaaaagcta  aacaatacct agaagaattt catcaaacgg cattagagca tcctgaattg  (SEQ ID NO:97)
Reb  gaaaaGgcCa aGcaatacct agaagaGttC caCcaaaCCg cCttGgagca tcctgaattg  (SEQ ID NO:98)

----------  ----------  ----------  ----------  ----------  ----------

970         980        990        1000       1010       1020
Ori  gttcaccaca atacagaaga gatagtggca caataaatag ctttatcgtc ttaatggtt
Reb  gttcaccaca atacagaaga gatagtggca caatcCatCg ctttGtcCtc tttGatggtt 1030        1040       1050        1060       1070       1080
Ori  gctcaagcta ttccattggt aggagagcta gttgatattg gtttcgctgc atataatttt
Reb  gctcaagcta tCccattggt CggTgagTTG gttgaCatCg gtttcgctgc CtaCaaCttC 1090        1100       1110        1120       1130       1140
Ori  gtagagagta ttatcaattt atttcaagta gttcataatt cgtataatcg tccgcgtat
Reb  gtCgaGTCCa tCatcaaCtt GttCcaagtC gtCcaCaaCt cCtaCaaCcg tccGgcTtaC 1150        1160       1170
Ori  tctccggggc ataaaacgca accatttctt  (SEQ ID NO: 99)
Reb  tcCccAggTc aCaaGacCca accattCTTG  (SEQ ID NO: 35)
``` mEF2 gene : gly to arg at the position 700

--- 696 697 698 699 700 701 702 ---
--- ala ile his arg arg gly gly ---   SEQ ID NO:23
--- gct atc cac aga aga ggt ggt ---   SEQ ID NO:22

Diphtheria Toxin-UCHT1 constructs:
Sequence 1 is DT389-scFv(UCHT1); Sequence 2 is HisDT390-sFv.
Regions/residues differing between the two clones are underlined.

1.  M------------------
2.  M<u>GSSHHHHHHSSGLVPRGSH</u>

1.  GADDVVDSSKSFVMENFSSYHGTKPGYVDSIQKGIQKPKSGTQGNYDDDWKGFYSTDN
2.  GADDVVDSSKSFVMENFSSYHGTKPGYVDSIQKGIQKPKSGTQGNYDDDWKGFYSTDN

1.  KYDAAGYSVDNENPLSGKAGGVVKVTYPGLTKVLALKVDNAETIKKELGLSLTEPLMEQ
2.  KYDAAGYSVDNENPLSGKAGGVVKVTYPGLTKVLALKVDNAETIKKELGLSLTEPLMEQ

1.  VGTEEFIKRFGDGASRVVLSLPFAEGSSSVEYINNWEQAKALSVELEINFETRGKRGQD
2.  VGTEEFIKRFGDGASRVVLSLPFAEGSSSVEYINNWEQAKALSVELEINFETRGKRGQD

1.  AMYEYMAQACAGNRVRRSVGSSLSCINLDWDVIRDKTKTKIESLKEHGPIKNKMSESPN
2.  AMYEYMAQACAGNRVRRSVGSSLSCINLDWDVIRDKTKTKIESLKEHGPIKNKMSESPN

1.  KTVSEEKAKQYLEEFHQTALEHPELSELKTVTGTNPVFAGANYAAWAVNVAQVIDSETA
2.  KTVSEEKAKQYLEEFHQTALEHPELSELKTVTGTNPVFAGANYAAWAVNVAQVIDSETA

1.  DNLEKTTAALSILPGIGSVMGIADGAVHHNTEEIVAQSIALSSLMVAQAIPLVGELVDI
2.  DNLEKTTAALSILPGIGSVMGIADGAVHHNTEEIVAQSIALSSLMVAQAIPLVGELVDI

1.  GFAAYNFVESIINLFQVVHNSYNRPAYSPGHKTQPF<u>ASAGGS</u>DIQMTQTTSSLSASLGD
2.  GFAAYNFVESIINLFQVVHNSYNRPAYSPGHKTQPF<u>LPW---</u>DIQMTQTTSSLSASLGD

1.  RVTISCRASQDIRNYLNWYQQKPDGTVKLLIYYTSRLHSGVPSKFSGSGSGTDYSLTIS
2.  RVTISCRASQDIRNYLNWYQQKPDGTVKLLIYYTSRLHSGVPSKFSGSGSGTDYSLTIS

1.  NLEQEDIATYFCQQGNTLPWTFAGGTKLEIKR<u>AGGGSGGGSGGGSGGGS</u>EVQLQQSGPE
2.  NLEQEDIATYFCQQGNTLPWTFAGGTKLEIKR-<u>GGGGSGGGGSGGGGS</u>-EVQLQQSGPE

1.  LVKPGASMKISCKASGYSFTGYTMNWVKQSHGKNLEWMGLINPYKGVSTYNQKFKDKAT
2.  LVKPGASMKISCKASGYSFTGYTMNWVKQSHGKNLEWMGLINPYKGVSTYNQKFKDKAT

1.  LTVDKSSSTAYMELLSLTSEDSAVYYCARSGYYGDSDWYFDVWGAGTTVTVSS SEQ ID NO:69
2.  <u>F</u>TVDKSSSTAYMELLSLTSEDSAVYYCARSGYYGDSDWYFDVWG<u>Q</u>GTT<u>L</u>TV<u>F</u>S SEQ ID NO:68

Nucleotide and deduced amino acid sequence of DT389-scFv(UCHT1)

Cloning sites introduced to facilitate the generation of this construct are underlined.

```
       M  G  A  D  D  V  V  D  S  S  K  S  F  V  M  E  N  F  S  S
   1   ccatgggcgctgatgatgttgttgattcttctaaatcttttgtgatggaaaacttttcttcg        60
       NcoI Y  H  G  T  K  P  G  Y  V  D  S  I  Q  K  G  I  Q  K  P  K
  61   taccacgggactaaacctggttatgtagattccattcaaaaaggtatacaaaagccaaaa       120

S  G  T  Q  G  N  Y  D  D  D  W  K  G  F  Y  S  T  D  N  K
 121   tctggtacacaaggaaattatgacgatgattggaaagggttttatagtaccgacaataaa       180

Y  D  A  A  G  Y  S  V  D  N  E  N  P  L  S  G  K  A  G  G
 181   tacgacgctgcgggatactctgtagataatgaaaacccgctctctggaaaagctggaggc       240

V  V  K  V  T  Y  P  G  L  T  K  V  L  A  L  K  V  D  N  A
 241   gtggtcaaagtgacgtatccaggacttacgaaagcttctcgcactaaaagtggataatgcc       300

E  T  I  K  K  E  L  G  L  S  L  T  E  P  L  M  E  Q  V  G
 301   gaaactattaagaaagagttaggtttaagtctcactgaaccgttgatggagcaagtcgga       360

T  E  E  F  I  K  R  F  G  D  G  A  S  R  V  V  L  S  L  P
 361   acggaagagtttatcaaaaggttcggtgatggtgcttcgcgtgtagtgctcagccttccc       420

F  A  E  G  S  S  S  V  E  Y  I  N  N  W  E  Q  A  K  A  L
 421   ttcgctgaggggagttctagcgttgaatatattaataactgggaacaggcgaaagcgtta       480

S  V  E  L  E  I  N  F  E  T  R  G  K  R  G  Q  D  A  M  Y
 481   agcgtagaacttgagattaattttgaaaccgtggaaaacgtggccaagatgcgatgtat       540

E  Y  M  A  Q  A  C  A  G  N  R  V  R  R  S  V  G  S  S  L
 541   gagtatatggctcaagcctgtgcaggaaatcgtgtcaggcgatcagtaggtagctcattg       600

S  C  I  N  L  D  W  D  V  I  R  D  K  T  K  T  K  I  E  S
 601   tcatgcataaatcttgattgggatgtcataagggataaaactaagacaaagatagagtct       660

L  K  E  H  G  P  I  K  N  K  M  S  E  S  P  N  K  T  V  S
 661   ttgaaagagcatggccctatcaaaaataaaatgagcgaaagtcccaataaaacagtatct       720

E  E  K  A  K  Q  Y  L  E  E  F  H  Q  T  A  L  E  H  P  E
 721   gaggaaaaagctaaacaatacctagaagaatttcatcaaacggcattagagcatcctgaa       780

L  S  E  L  K  T  V  T  G  T  N  P  V  F  A  G  A  N  Y  A
 781   ttgtcagaacttaaaaccgttactgggaccaatcctgtattcgctggggctaactatgcg       840

A  W  A  V  N  V  A  Q  V  I  D  S  E  T  A  D  N  L  E  K
 841   gcgtgggcagtaaacgttgcgcaagttatcgatagcgaaacagctgataatttggaaaag       900

T  T  A  A  L  S  I  L  P  G  I  G  S  V  M  G  I  A  D  G
 901   acaactgctgctctttcgatacttcctggtatccgtagcgtaatgggcattgcagacggt       960

A  V  H  H  N  T  E  E  I  V  A  Q  S  I  A  L  S  S  L  M
 961   gccgttcaccacaatacagaagagatagtggcacaatcaatagctttatcgtcttttaatg      1020

V  A  Q  A  I  P  L  V  G  E  L  V  D  I  G  F  A  A  Y  N
1021   gttgctcaagctattccattggtaggagagctagttgatattggtttcgctgcatataat      1080

F  V  E  S  I  I  N  L  F  Q  V  V  H  N  S  Y  N  R  P  A
1081   tttgtagagagtattatcaatttatttcaagtagttcataattcgtataatcgtcccgcg      1140

Y  S  P  G  H  K  T  Q  P  F  A  S  A  G  G  S  D  I  Q  M
1141   tattctccggggcataaaacgcaaccatttgcttccgcggtggatccgacatccagatg      1200
                                                       BamHI T  Q  T  T  S  S  L  S  A  S  L  G  D  R  V  T  I  S  C  R
1201   acccagaccacctcctccctgtctgcctctctgggagacagagtcaccatcagttgcagg      1260
```

```
          A  S  Q  D  I  R  N  Y  L  N  W  Y  Q  Q  K  P  D  G  T  V
1261 gcaagtcaggacattagaaattatttaaactggtatcaacagaaaccagatggaactgtt      1320

K  L  L  I  Y  Y  T  S  R  L  H  S  G  V  P  S  K  F  S  G
1321 aaactcctgatctactacacatcaagattacactcaggagtcccatcaaagttcagtggc      1380

S  G  S  G  T  D  Y  S  L  T  I  S  N  L  E  Q  E  D  I  A
1381 agtgggtctggaacagattattctctcaccattagcaacctggagcaagaggatattgcc      1440

T  Y  F  C  Q  Q  G  N  T  L  P  W  T  F  A  G  G  T  K  L
1441 acttactttgccaacagggtaatacgcttccgtggacgttcgctggaggcaccaagctg      1500

E  I  K  R  A  G  G  G  S  G  G  G  S  G  G  G  S  G  G  G
1501 gaaatcaaacgggctggaggcggtagtggcggtggatcaggtggaggcagcggtggcgga      1560

S  E  V  Q  L  Q  Q  S  G  P  E  L  V  K  P  G  A  S  M  K
1561 tctgaggtgcagctccagcagtctggacctgagctggtgaagcctggagcttcaatgaag      1620

I  S  C  K  A  S  G  Y  S  F  T  G  Y  T  M  N  W  V  K  Q
1621 atatcctgcaaggcttctggttactcattcactggctacaccatgaactgggtgaagcag      1680

S  H  G  K  N  L  E  W  M  G  L  I  N  P  Y  K  G  V  S  T
1681 agtcatggaaagaaccttgagtggatgggacttattaatccttacaaaggtgttagtacc      1740

Y  N  Q  K  F  K  D  K  A  T  L  T  V  D  K  S  S  S  T  A
1741 tacaaccagaagttcaaggacaaggccacattaactgtagacaagtcatccagcacagcc      1800

Y  M  E  L  L  S  L  T  S  E  D  S  A  V  Y  Y  C  A  R  S
1801 tacatggaactcctcagtctgacatctgaggactctgcagtctattactgtgcaagatcg      1860

G  Y  Y  G  D  S  D  W  Y  F  D  V  W  G  A  G  T  T  V  T
1861 gggtactacggtgatagtgactggtacttcgatgtctggggcgcagggaccacggtcacc      1920

V  S  S  *  *     (SEQ ID NO:69)
1921  gtctcctcatgatagagatct   (SEQ ID NO:40)     1929
                   BglII
```

FIG. 35

```
a.a  AGADDVVDSS  KSFVMENFAS  YHGTKPGYVD  SIQKGIQKPK  SGTQGNYDDD  WKGFYSTDNK   60
pre  A*ADDVVDSS  KSFVMENFAS  YH*TKPGYVD  SIQKGIQKPK  S*TQGNYDDD  WK*FYSTDNK
reb  AGADDVVDSS  KSFVMENFAS  YH*TKPGYVD  SIQKGIQKPK  S*TQGNYDDD  WK*FYSTDNK
                                           AT content: 60.19%→51.41%
a.a  YDAAGYSVDN  ENPLSGKAGG  VVKVTYPGLT  KVLALKVDNA  ETIKKELGLS  LTEPLMEQVG  120
pre  YDA**YS*D*  ENSA**  *V**P*  KV***D  ETIK*E*G**  *TE*LMEQV*
reb  YDA**YS*D*  ENSA**  *VKVTYPG*T  KVLALKVDNA  ETIKKELGLS  LTEPLMEQVG a.a  TEEFIKRFGD  GASRVVLSLP  FAEGSSSVEY  INNWEQAKAL  SVELEINFET  RGKRGQDAMY  180
pre  *EE*IFGD  GA****  FAES*VE*  I*NWEQ**  E*EIET  ***QD*M*
reb  TEEFIKRFGD  GASRVVLSLP  FAEGSS*VE*  I*NWEQ****  **E*EI**ET  *****QD*M*
                 AT content: 66.66%→53.69%
a.a  EYMAQACAGN  RVRRSVGSSL  SCINLDWDVI  RDKTKTKIES  LKEHGPIKNK  MSESPAKTVS  240
pre  E*MAQ*C***  *V****G**L  *****DWDV*  *D*TK*K*ES  L*E**PIKNK  MSES*AKTVS
reb  E*MAQ*CAGN  RVR*SVGSSL  SCIN*DWDVI  RDKTKTKIES  L*E**PIKNK  MSES*AKTVS a.a  EEKAKQYLEE  FHQTALEHPE  LSELKTVTGT  NPVFAGANYA  AWAVNVAQVI  DSETADNLEK  300
pre  EEK*KQY*EE  FHQT*LE*PE  L*E**TVT*T  *P*FA*AN**  *W**NV*QVI  D*E*AD*LEK
reb  EEK*KQY*EE  FHQT*LE*PE  L*E**TVT*T  *P*FA*AN**  *W**NV*QVI  D*E*AD*LEK a.a  TTAALSILPG  IGSVMGIADG  AVHHNTEEIV  AQSIALSSLM  VAQAIPLVGE  LVDIGFAAYN  360
pre  *TAA**PG  IGM*I*DG  *VHHEE  *QSIALSSLM  VAQAIPLVGE  LVDIGFA*YN
reb  *TAA**PG  IGM*I*DG  *VHHEE  *QSIALSSLM  VAQAIPLVGE  LVDIGFA*YN a.a  FVESIINLFQ  VVHNSYNRPA  YSPGHKTQPF  LPWDIQMTQT  TSSLSASLGD  RVTISCRASQ  420
pre  FVESIINLFQ  VVHNSYN**A  YSPGHKTQPF  LPWDIQMTQT  TSS*S*SD  RVTI***Q
reb  FVESIINLFQ  VVHNSYN**A  YSPGHKTQPF  LPWDIQMTQT  TSS*S*SD  RVTI***Q
     AT content: 67.90%→56.78%
a.a  DIRNYLNWYQ  QKPDGTVKLL  IYYTSRLHSG  VPSKFSGSGS  GTDYSLTISN  LEQEDIATYF  480
pre  DIR***NW*Q  Q*PD*TV***  IYY**R*H**  VP*KF****S  **D*S*TI*N  *EQEDI*TY*
reb  DIRNYLNW*Q  QKPDGTVKLL  IYYTSRLHSG  VPSKFS*SGS  GTDYSLTISN  LEQEDI*TY* a.a  CQQGNTLPWT  FAGGTKLEIK  GGGGSGGGGS  GGGGSEVQLQ  QSGPELVKPG  ASMRISCKAS  540
pre  *QQG***W*  FA**TK*E  ***G  *****E*Q*Q  QS*PE**KP*  A*MK*S*KAS
reb  *QQG***W*  FATKLEIK  GGS*GG*S  *G*GSEVQLQ  QS*PE**KP*  A*MK*S*KAS
                 AT content: 64.56%→56.25%
a.a  GYSFTGYTMN  WVKQSHGKNL  EWMGLINPYK  GVSTYNQKFK  DKATFTVDKS  SSTAYMELLS  600
pre  GY*FT*YTMN  W*KQ***KN*  EWM**I*PY*  GV*TYNQKFK  DK**FT*DK*  S***YME***
reb  GY*FT*YTMN  W*KQ***KN*  EWMGLINPYK  GV*TYNQKFK  DKATFT*DK*  S*YME* a.a  LTSEDSAVYY  CARSGYYGDS  DWYFDVWGAG  TTVTVSSGGG  GSGGGGSGGG  GS          652
pre  **SEDS*V*Y  C*R**YYGD*  DWYFDVW***  TTV*VS**G*  *S*G**  G*
reb  **SEDS*V*Y  C*R**YYGD*  DWYFDVWGAG  TTVTVSS*G*  *S**GGSGG*  GS 653 ooooooooo   Second sFv (UCHT1)   ooooooooo  896
```

Figure 38. Prediction of regions required for codon optimization.
* for pre and reb : non-preferred codon. Occurrence of non-preferred codon is less than 30% in highly expressed gene products in Pichia pastoris.
a.a, partial amino acid sequence of Ala-DT390-bisFv (SEQ ID NO:119); pre, before second rebuilding work; reb, after rebuilding. Double underlining in the line of a.a indicates an AT rich region and underlining in the line of reb represents a region to be rebuilt with preferred codons. The amino acid sequences shown in the lines of pre and reb are the same as for line a.a.

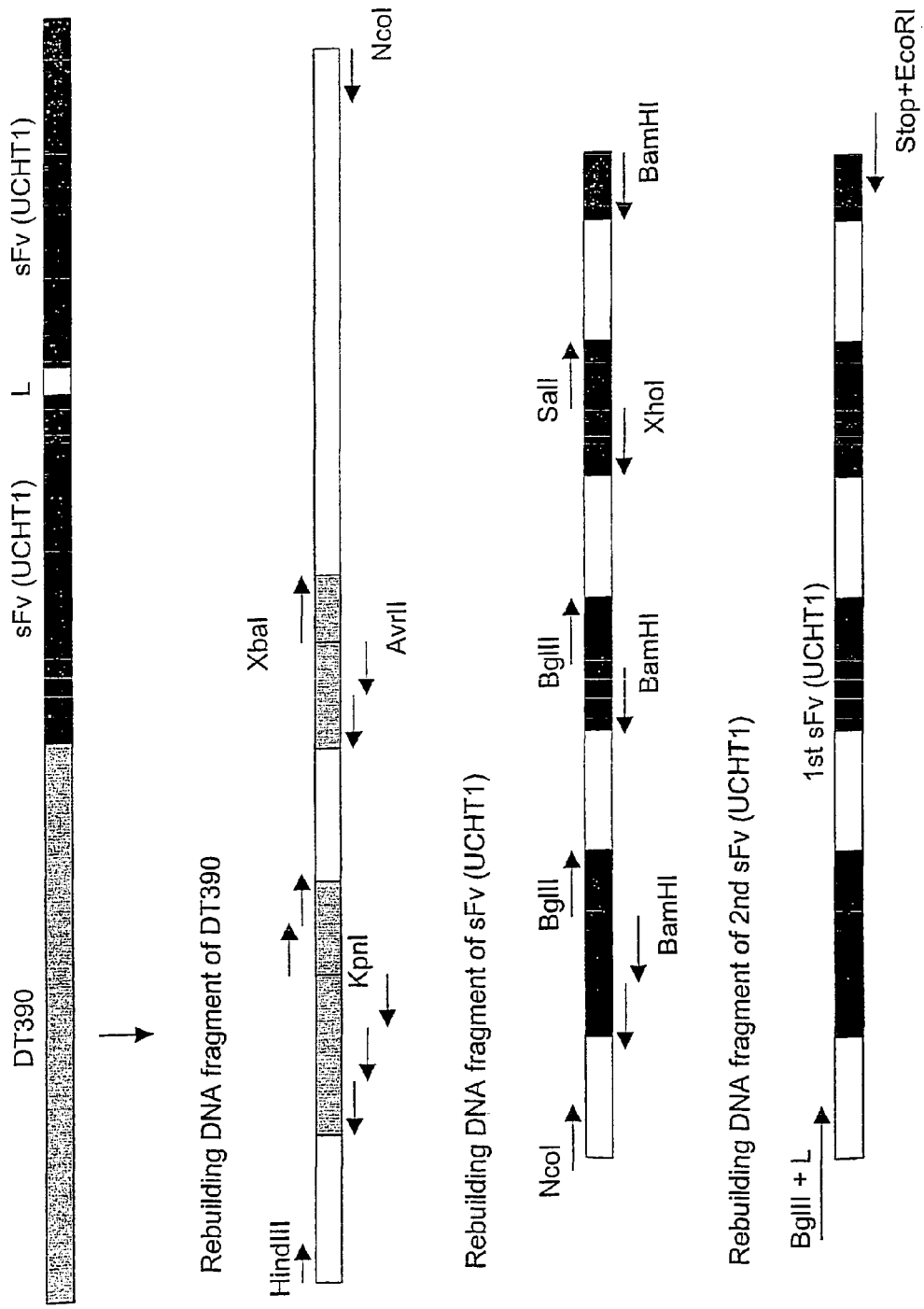
Figure 39. The scheme of rebuilding work.

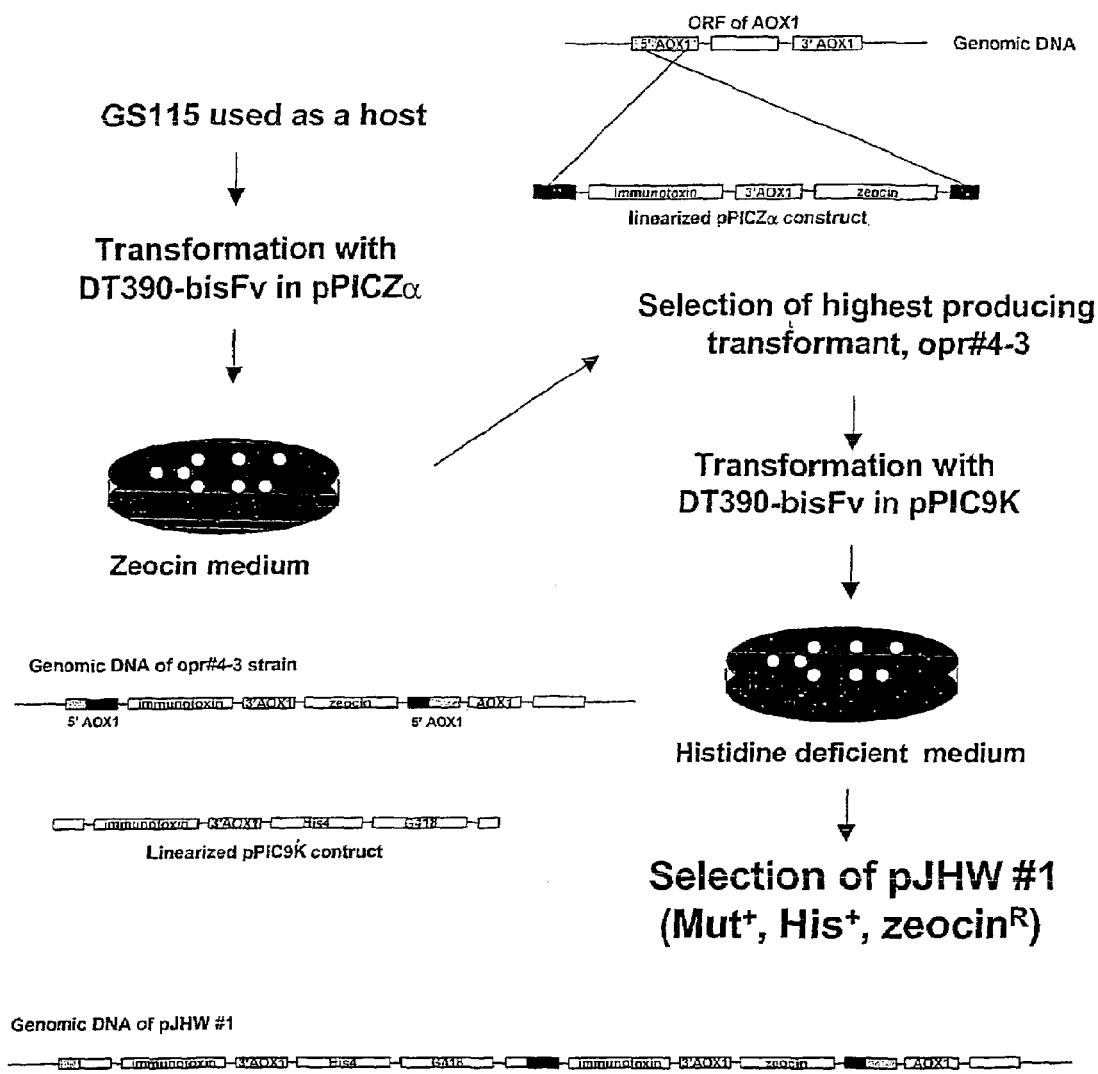
Figure 40. Selection of expression strain, pJHW#1 by double transformation

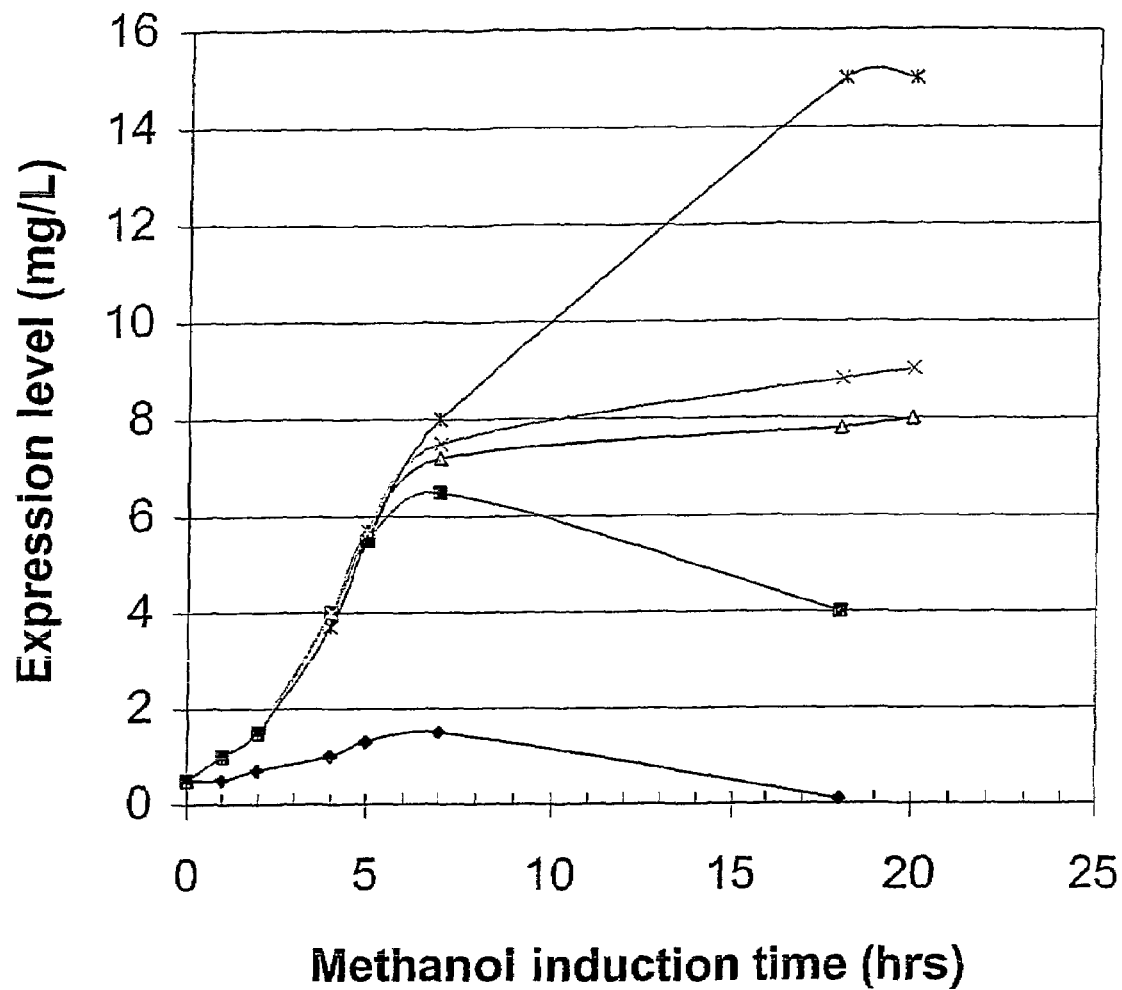
Figure 42. Change of expression level by modifying fermentation condition
→ 5mM EDTA  → w/o PMSF  → 1mM PMSF
→ pH shift+PMSF  → pH + 3mM PMSF 1717 ATGACTGCCCTGTCCAAGTCTCAGAACAAGCATAACAGAATTTACCTGAAGGCTCAACCA 1776
 573 MetThrAlaLeuSerLysSerGlnAsnLysHisAsnArgIleTyrLeuLysAlaGlnPro  592

1777 ATTGACGAGGAATTGTCTTTGGCTATCGAAGAAGGTAAGGTTCACCCAAGAGACGACTTT 1836
 593 IleAspGluGluLeuSerLeuAlaIleGluGluGlyLysValHisProArgAspAspPhe  612

1837 AAAGCCAGAGCCAGAATCATGGCTGATGAATACGGTTGGGACGTCACTGATGCCAGAAAG 1896
 613 LysAlaArgAlaArgIleMetAlaAspGluTyrGlyTrpAspValThrAspAlaArgLys  632

1897 ATCTGGTGTTTCGGTCCAGACGGTACTGGTGCCAACTTAGTTGTTGACCAGTCTAAGGCT 1956
 633 IleTrpCysPheGlyProAspGlyThrGlyAlaAsnLeuValValAspGlnSerLysAla  652

1957 GTCCAATACTTGCACGAGATCAAGGACTCTGTTGTTGCCGGTTTCCAATTGGCTACCAAG 2016
 653 ValGlnTyrLeuHisGluIleLysAspSerValValAlaGlyPheGlnLeuAlaThrLys  672

2017 GAAGGTCCAATTTTGGGAGAAAACATGAGATCCGTCAGAGTCAACATCTTGGATGTTACC 2076
 673 GluGlyProIleLeuGlyGluAsnMetArgSerValArgValAsnIleLeuAspValThr  692

2077 CTGCACGCCGATGCTATCCACCGCCGCGGAGGACAAGTCATTCCAACCATGAAGAGAGTT 2136
 693 LeuHisAlaAspAlaIleHisArgArgGlyGlyGlnValIleProThrMetLysArgVal  712
                            G-R

2137 ACCTACGCCGCCTTCCTGTTGGCTGAGCCAGCTATCCAGGAGCCTATCTTCTTGGTGGAG 2196
 713 ThrTyrAlaAlaPheLeuLeuAlaGluProAlaIleGlnGluProIlePheLeuValGlu  732

2197 ATCCAATGTCCAGAGAATGCCATTGGTGGTATCTACTCTGTTTTGAACAAGAAGAGAGGT 2256
 733 IleGlnCysProGluAsnAlaIleGlyGlyIleTyrSerValLeuAsnLysLysArgGly  752

2257 CAAGTTATCTCTGAGGAACAAAGACCAGGTACC 2289
 753 GlnValIleSerGluGluGlnArgProGlyThr  763

Figure 43. DNA sequence of a large fragment of Pichia EF-2 DNA used for site-specific mutagenesis (bold).

IMMUNOTOXIN FUSION PROTEINS AND MEANS FOR EXPRESSION THEREOF

The present application is a 35 U.S.C. 0371 national phase application from, and claims priority to, international application PCT/US01/16125, filed May 18, 2001 (published under PCT Article 21(2) in English), which claims priority to U.S. patent application Ser. No. 09/573,797, now abandoned, filed May 18, 2000, which application is incorporated herein in its entirety by this reference and which is a continuation-in-part of U.S. patent application Ser. No. 09/380,484 now U.S. Pat. No. 6,632,928, filed on Dec. 6, 1999, which is a 35 U.S.C. 0371 national phase application from, and claims priority to, international application PCT/US98/04303, filed on Mar. 5, 1998, which claims the benefit of U.S. Provisional Application No. 60/039,987, filed on Mar. 5, 1997. The present application is also a continuation-in-part of U.S. application Ser. No. 09/389,565, filed Sep. 3, 1999, now U.S. Pat. No. 7,517,527 which is a continuation of and claims priority to U.S. application Ser. No. 08/739,703, now abandoned, filed on Oct. 29, 1996, which claims the benefit of U.S. Provisional Application No. 60/008,104, filed on Oct. 30, 1995.

BACKGROUND OF THE INVENTION

1. Field of the Invention

This invention generally relates to immunotoxins, and specifically to anti-T cell immunotoxin fusion proteins comprising a diphtheria toxin moiety and a targeting moiety, and methods of inducing immune tolerance in primates. The immunotoxins are well suited to provide a method for inhibiting rejection of transplanted organs. The invention further relates to a method of treating T cell leukemias or lymphomas, graft-versus-host diseases, and autoimmune diseases by administering the immunotoxins.

2. Background Art

The number of organ transplants performed in the United States is approximately 19,000 annually and consists predominantly of kidney transplants (11,000), liver transplants (3,600), heart transplants (2,300), and smaller numbers of pancreas, lung, heart-lung, and intestinal transplants. Since 1989 when the United Network for Organ Sharing began keeping national statistics, approximately 190,000 organ transplants have been performed in the United States. A large but difficult to ascertain number of transplants were performed in the United States prior to 1989 and a similarly large number of transplants are performed in Europe and Australia and a smaller number in Asia.

Transplant tolerance remains an elusive goal for patients and physicians whose ideal would be to see a successful, allogeneic organ transplant performed without the need for indefinite, non-specific maintenance immunosuppressive drugs and their attendant side effects. Over the past 10 years the majority of these patients have been treated with cyclosporin, azathioprine, and prednisone with a variety of other immunosuppressive agents being used as well for either induction or maintenance immunosuppression. The average annual cost of maintenance immunosuppressive therapy in the United States is approximately $10,000. While the efficacy of these agents in preventing rejection is good, the side effects of immunosuppressive therapy are considerable because the unresponsiveness which they induce is nonspecific. For example, recipients can become very susceptible to infection. A major goal in transplant immunobiology is the development of specific immunologic tolerance to organ transplants with the potential of freeing patients from the side effects of continuous pharmacologic immunosuppression and its attendant complications and costs.

Anti-T cell therapy (anti-lymphocyte globulin) has been used in rodents in conjunction with thymic injection of donor cells (Posselt et al. *Science* 1990; 249: 1293-1295 and Remuzzi et al. *Lancet* 1991; 337: 750-752). Thymic tolerance has proved successful in rodent models and involves the exposure of the recipient thymus gland to donor alloantigen prior to an organ allograft from the same donor. However, thymic tolerance has never been reported in large animals, and its relevance to tolerance in humans in unknown.

One approach to try to achieve such immunosuppression has been to expose the recipient to cells from the donor prior to the transplant, with the hope of inducing tolerance to a later transplant. This approach has involved placement of donor cells (e.g. bone marrow) presenting MHC Class I antigens in the recipient's thymus shortly after application of anti-lymphocyte serum (ALS) or radiation. However, this approach has proved difficult to adapt to live primates (e.g., monkeys and humans). ALS and/or radiation render the host susceptible to disease or side-effects and/or are insufficiently effective.

If a reliable, safe approach to specific immunologic tolerance could be developed, this would be of tremendous value and appeal to patients and transplant physicians throughout the world with immediate application to new organ transplants and with potential application to existing transplants in recipients with stable transplant function. Thus, a highly specific immunosuppression is desired. Furthermore, there is a need for a means for imparting tolerance in primates, without the adverse effects of using ALS or radiation. Moreover, the goal is to achieve more than simply delaying the rejection response. Rather, an important goal is to inhibit the rejection response to the point that rejection is not a factor in reducing average life span among transplant recipients.

The present invention meets these needs by providing immunotoxins that can be used in a method of inducing immune tolerance.

*Pseudomonas* exotoxin A (ETA) has been widely employed for immunotoxin construction (62-63). However, the only form of available ETA having reduced receptor binding activity that can be coupled or fused with a divalent antibody under the restrictions enumerated above, ETA-60EF61Cys161, is non-toxic to human T cells at 10 nM over 20 hours when using anti-CD3 antibody UCHT1 or anti-CD5 antibody T101 (Hybritech Corp., San Diego, Calif.). ETA-60EF61 achieves loss of binding site activity by insertion of two amino acids at position between residues 60 and 61. In addition, coupling is achieved by converting Met 161 to cysteine permitting thioether linkage. This toxin construct exhibits very high toxicity when targeted at the human transferrin receptor (IC50=1 pM) or the murine B cell IgM receptor (64). ETA is known to be much more difficult to proteolytically process than DT and many cells cannot perform this function (53-55). It also appears that the ability to process the toxin by a cell is dependent on the targeted epitope or the routing pathway (55). The toxin cannot be processed in vitro like DT because the processing site is "hidden" at neutral pH and only becomes available at acidic pH which inactivates toxin in vitro (53).

Derivatives of ETA which do not require processing have been made by truncating binding domain I back to the processing site at residue 280. However, covalent non-reducible couplings cannot be made to the distal 37 kD structure without greatly decreasing translocation efficiency. Therefore, these derivatives cannot be used with divalent antibodies as thioether coupled structures or fusion structures.

Disulfide conjugates with divalent antibodies have been described but they suffer from low in vivo life times due to reduction of the disulfide bond within the vascular compartment (62). A sc truncated ETA fusion protein has been described containing two Fv domains. However, dose response toxicity curves show only a three fold increase in affinity at best compared to single Fv constructs, suggesting that the double Fv construct is not behaving as a typical divalent antibody (65). Consequently, it would be of considerable utility to have either a form of ETA-60EF61Cys161 that had less stringent processing characteristics or did not require processing.

The present invention provides these derivatives. They can be used to target T cells with anti-CD3 or other anti-T cell antibodies either by coupling to available cysteines or as fusion proteins with the single chain divalent antibodies added at the amino terminus.

SUMMARY OF THE INVENTION

It is an object of this invention to provide an immunotoxin for treating immune system disorders.

It is a further object of the invention to provide a method of treating an immune system disorder not involving T cell proliferation, comprising administering to the afflicted animal an immunotoxin comprising a mutant diphtheria toxin (DT) or pseudomonas exotoxin A (ETA) toxin moiety linked to an antibody moiety. The antibody or targeting moiety preferably routes by a T cell epitope pathway, for example, the CD3 pathway. Thus, the present method can treat graft-versus-host disease.

It is a further object of the invention to provide a method of inducing immune tolerance. Thus, the invention provides a method of inhibiting a rejection response by inducing immune tolerance in a recipient to a foreign mammalian donor tissue or cells, comprising the steps of: a) exposing the recipient to an immunotoxin so as to reduce the recipients's peripheral blood and lymph node T-cell lymphocyte population by at least 75%, preferably 80%, wherein the immunotoxin is anti-CD3 antibody linked to a diphtheria protein toxin, wherein the protein has a binding site mutation; or the antibody is linked to a pseudomonas protein exotoxin A wherein the protein has a binding site mutation and a second mutation achieving or facilitating proteolytic processing of the toxin, and b) transplanting the donor cells into the recipient, whereby a rejection response by the recipient to the donor organ cell is inhibited, and the host is made tolerant to the donor cell.

The objects of the invention therefore include providing immunotoxins for use in methods of the above kind for inducing tolerance to transplanted organs or cells from those organs. Specifically, it is an object of the invention to provide anti-T cell immunotoxin fusion proteins and means for expression thereof. This and still other objects and advantages of the present invention will be apparent from the description which follows.

BRIEF DESCRIPTION OF THE DRAWINGS

FIGS. 1a, 1b and 1c show that the epitopes involved in human serum's inhibition of toxicity lie in the last 150 amino acids of DT. A schematic diagram of the DT mutants CRM9, CRM197 and MSPΔ5 is presented (FIG. 1a). The A- and B-subfragments and their relative size and position are shown. The filled circle represents a point mutation as described in the text. Goat (FIG. 1b) or human (FIG. 1c) serum (human serum was a pool from all samples with positive ELISA for anti-DT antibodies) was incubated with increasing molar concentrations of CRM197 (-○-), MSPΔ5 (-X-) or the B-subfragment (-Δ-) of DT for 30 minutes at room temperature. To this reaction, UCHT1-CRM9 was added to a final concentration of $1\times10^{-10}$ M. This mixture was then diluted 10-fold onto Jurkat cells in a protein synthesis inhibition assay as described in the Materials and Methods. Immunotoxin incubated with medium only inhibited protein synthesis to 4% of controls. The results are representative of two independent assays.

FIG. 2a shows increasing concentrations of sFv-DT390 (-Δ-) or UCHT1-CRM9 (-○-) tested in protein synthesis inhibition assays as described in the Materials and Methods. The results are an average of four separate experiments. FIG. 2b shows increasing concentrations of UCHT1 antibody mixed with a $1\times10^{-10}$ M UCHT1-CRM9 (-○-) or $3.3\times10^{-10}$ M sFv-DT390 (-Δ-) and then added to cells for a protein synthesis inhibition assay.

FIG. 12 shows a schematic of several divalent coupled immunotoxins similar to FIG. 11 except that the VL and VH domains are generated on separate chains from a dicystronic expression vector. These constructs have the advantage of enhanced antibody moiety stability.

FIG. 13 shows a schematic of several divalent immunotoxin single chain fusion proteins based on ETA wherein the ETA catalytic domain occupies the carboxy terminus of the fusion protein. Interchain disulfides are generated as in FIG. 11. The ETA based mutant toxins have been additionally altered to render them independent of proteolytic processing at acidic pH, permitting translocation of the free 37 kD catalytic domain following neutral pH processing and reduction.

FIG. 14 shows a schematic of several divalent single chain immunotoxin fusion proteins similar to FIG. 13 except based on DT wherein the DT catalytic domain occupies the amino terminus of the fusion protein, permitting translocation of the free toxin A chain following neutral pH processing and reduction.

FIG. 19 shows a schematic diagram of nine species of the immunotoxin fusion protein showing domain organization and number of amino acid residues comprising each domain.

FIG. 19H shows the same domain organization and number of amino acids in each domain as FIG. 19G with the addition of an extra alanine residue at the N-terminus of the protein. This immunotoxin fusion protein has the same two glycosylation site mutations in the diphtheria toxin sequence and the same group of mutations in the C-terminal $V_H$ region as the protein depicted in FIG. 19G.

FIG. 19I shows the same domain organization and number of amino acids in each domain as FIG. 19G with the addition of four extra residues at the amino terminus (Tyr-Val-Glu-Phe) (SEQ ID NO: 49), which are left due to restriction sites used in the cloning. In addition, this immunotoxin fusion protein has the same two glycosylation site mutations in the diphtheria toxin sequence and the same group of mutations in the C-terminal $V_H$ region as the protein depicted in FIG. 19G.

FIG. 20 shows the amino acid sequences for various DT390-bisFv(UCHT1) constructs for expression in various systems. The second sequence (SEQ ID NO:17), designated "(Met)DT390-bisFv(UCHT1*)," is the amino acid sequence for DT390-bisFv(UCHT1) that has an uncorrected primer error in the first VH region, located toward the amino terminal, of the antibody moiety and an N-terminal methionine residue. In the first sequence (SEQ ID NO:18), designated "(Met)DT390-bisFv(UCHT1)," the amino acid sequence for the primer error in the first and second VH is corrected and the N-terminal amino acid is methionine. The third (SEQ ID NO:26), fourth (SEQ ID NO:27), and fifth (SEQ ID NO:28) sequences are double glycosylation mutants for expression in CHO cells and Pichia. The third sequence, designated "(Ala)dmDT390-bisFv(UCHT1*)," has an N-terminal alanine. The fourth sequence, "dmDT390-bisFv(UCHT1*)," has the N-terminal glycine present in native DT, and the fifth sequence, designated "(TyrValGluPhe)dmDT390-bisFv(UCHT1*)" has a YVEF (SEQ ID NO:49) sequence at its N-terminal. The underlined residues are those not present in wild type DT390 or not present in VL and VH domains of UCHT1 including the linkers.

FIG. 21 shows a summary of binding and toxicity data for various antibody and immunotoxin constructs.

FIG. 25 shows the sequences surrounding selected mutations in glycosylation sites in DT390 and the oligonucleotides used to generate the mutations. These mutations were introduced in vitro into a bacterial pET17b plasmid that carried the DT390-sFv(UCHT1')His insert. The selected changes were: Asn to Gln at position 235 (235Gln), Asn to Ala at position 235 (235Ala), Thr to Ala at position 237 (237Ala), Asn to Ala at position 16 (16Ala), and Ser to Ala at position 18 (18Ala).

FIG. 28 shows a comparison of DNA sequence between original DT390 and rebuilt DT390 domain. Upper case indicates changed DNA sequence to reduce AT content in the corresponding region.

FIG. 34 shows the amino acid sequences for (Met)DT389-sFv(UCHT1), shown as sequence 1 (SEQ ID NO:69), and (Met)(His-throm)DT390-sFv, shown as sequence 2 (SEQ ID NO:68). The regions/residues differing between the two clones are underlined.

FIG. 35 shows the complete nucleic acid sequence of DT389-sFv(UCHT1) including restriction sites and the deduced amino acid sequence. The nucleic acid sequence is provided as SEQ ID NO:40, and the deduced amino acid sequence is provided as SEQ ID NO:69. The cloning sites introduced to facilitate the generation of this construct are underlined.

FIG. 36 shows the results of a two-step anion exchange purification of DT389-sFv(UCHT1) refolded under 0.3M DTE/8 mmM GSSG redox conditions.

FIG. 38 shows a partial amino acid sequence for DT390-bisFv (a.a.) with regions indicated for the second rebuilding to optimize expression. The line designated "pre" indicates the same sequence with the amino acids encoded by non-preferred codons indicated by an asterisk. The line designated "reb" indicates the sequence after the second rebuilding work, in which the remaining amino acids encoded by non-preferred codons are indicated by an asterisk. The double underlining in the a.a. line indicates AT-rich regions, which are still left in the gene of interest after the rebuilding work described in Example 23. The underlining in the reb line indicate regions that were rebuilt.

FIG. 39 shows a schematic of the second rebuilding work. The gene of interest was divided into three parts—the DT region, and two sFv regions. Each fragment was rebuilt as shown and then ligated using compatible cohesive ends or unique enzyme sites.

FIG. 40 shows a schematic of the selection of expression strain, pJHW#1 by double transformation.

FIG. 42 shows the changes in expression levels with pJHW#1 clone having a double copy of the gene of interest using five different fermentation parameters in each fermentation run: 5 mM EDTA, pH shift, pH shift with 1 mM PMSF, pH shift with 3 mM PMSF, and 1 mM PMSF without pH shift.

FIG. 43 shows the DNA sequence (513 base pairs) and amino acid sequence for a partial fragment of the EF-2 strain used to develop a mutated EF-2 strain. The mutation on amino acid 701 is shown in bold.

FIG. 4A shows depletion of double positive splenic T cells (human CD3e+, murine CD3e+) assayed by FACS. Open symbols are the mean values for the the immunotoxin with a single sFv, and closed symbols are the mean values for immunotoxin with two sFvs. Dashed and solid lines are the probit model fits performed individually. FIG. 4B shows depletion of double positive lymph node T cells (human CD3e+, murine CD3e+) assayed by FACS. In this case all data points are fit together generating a single regression coefficient for both immunotoxins. The listed dose is the total dose given over 4 days.

DETAILED DESCRIPTION OF THE INVENTION

Figure 2A:
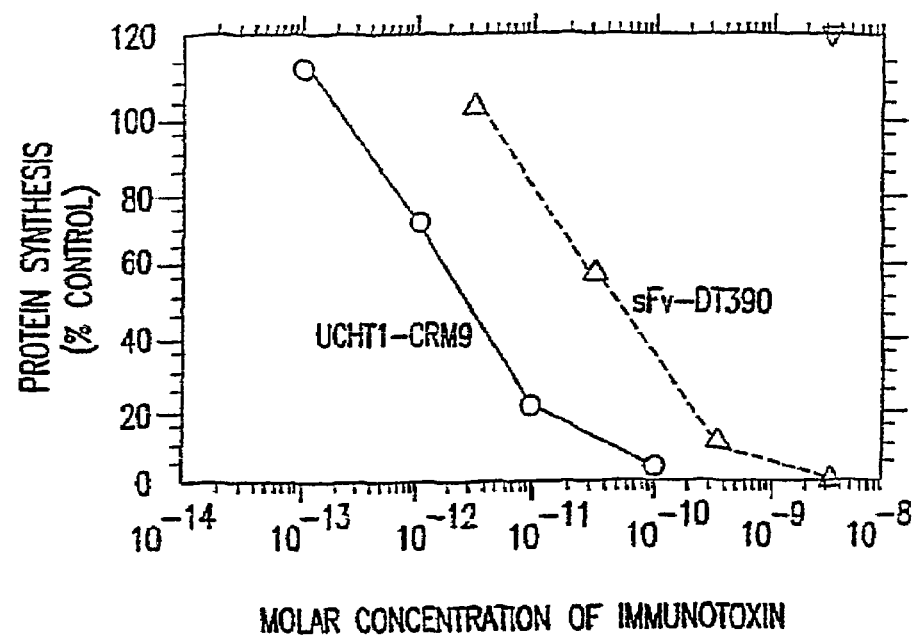
FIGS. 2a and 2b show that sFv-DT390 maintains specificity for the CD3 complex but is 16-fold less toxic than UCHT1-CRM9 to Jurkat cells.

The invention provides immunotoxins and methods of using them to induce immune tolerance and to treat disease.

Immunotoxin.

The present invention relates to an immunotoxin. More specifically, an immunotoxin comprising a mutant toxin moiety (e.g., DT toxin or ETA toxin) linked to a single chain (sc) variable region antibody moiety (targeting moiety) is provided. Thus, the invention provides an immunotoxin having recombinantly produced antibody moiety linked (coupled) to a recombinantly produced toxin moiety and a fusion immunotoxin (where both toxin and antibody domains are produced from a recombinant construct). As the application provides the necessary information regarding the arrangement of toxin and antibody domains, and the sub regions within them, it will be recognized that any number or chemical coupling or recombinant DNA methods can be used to generate an immunotoxin or the invention. Thus, reference to a fusion toxin or a coupled toxin is not necessarily limiting.

The antibody moiety preferably routes by the anti-CD3 pathway or other T cell epitope pathway. The immunotoxin can be monovalent, but divalent antibody moieties are presently preferred since they have been found to enhance cell killing by about 15 fold. The immunotoxin can be a fusion protein produced recombinantly. The immunotoxin can be made by chemical thioether linkage at unique sites of a recombinantly produced divalent antibody (targeting moiety) and a recombinantly produced mutant toxin moiety. The targeting moiety of the immunotoxin can comprise the human μCH2, μCH3 and μCH4 regions and VL and VH regions from murine Ig antibodies. These regions can be from the antibody UCHT1 so that the antibody moiety is scUCHT1, which is a single chain CD3 antibody having human μCH2, μCH3 and μCH4 regions and mouse variable regions as shown in the figures. These are believed to be the first instances of sc anti-CD3 antibodies. Numerous DT mutant toxin moieties are described herein, including for example, DT390 and DT389, with a variety of mutations or as the wild type toxin moiety. Thus, as just one specific example the immunotoxin, the invention provides scUCHT1-DT390. Derivatives of this immunotoxin are designed and constructed as described herein. Likewise, ETA immunotoxins are also described herein.

The toxin moiety retains its toxic function, and membrane translocation function to the cytosol in full amounts. The loss in binding function located in the receptor binding domain of the protein diminishes systemic toxicity by reducing binding to non-target cells. Thus, the immunotoxin can be safely administered. The routing function normally supplied by the toxin binding function is supplied by the targeting antibody anti-CD3. The essential routing pathway is (1) localization to coated pits for endocytosis, (2) escape from lysosomal routing, and (3) return to the plasma membrane. In addition, ETA may also route through late endosomes and into endoplasmic reticulum through the Golgi compartment. An advantage of using ETA rather than DT is that its different routing may better complement T cell epitopes other than CD3 which may exist on certain T cell subsets. A further advantage is that very few humans contain antibodies to ETA as is the case with DT. Specific examples are described below.

Any antibody that can route in this manner will be effective with the toxin moiety, irrespective of the epitope to which the antibody is directed, provided that the toxin achieves adequate proteolytic processing along this route. Adequate processing can be determined by the level of cell killing. This processing is particularly important for ETA and is absent in certain cells (53-55). Therefore, ETA mutants in which the processing has been performed during synthesis or mutants which facilitate in vitro or in vivo processing are described. Thus, a wide variety of cell types can be targeted.

When antibodies dissociate from their receptors due to changes in receptor configuration induced in certain receptors as a consequence of endosomal acidification, they enter the lysosomal pathway. This can be prevented or minimized by directing the antibody towards an ecto-domain epitope on the same receptor which is closer to the plasma membranes (Ruud, et al. (1989) *Scand. J. Immunol.* 29:299; Herz et al. (1990) *J. Biol. Chem.* 265:21355).

The mutant DT toxin moiety can be a truncated mutant, such as DT390, DT389, DT383, DT370 or other truncated mutants, with and without point mutations or substitutions, as well as a full length toxin with point mutations, such as DTM1, as described in Examples 9-11, or CRM9 (cloned in *C. ulcerans*), scUCHT1 fusion proteins with DTM1 and DT483, DT390, DT389, and DT370 have been cloned and expressed in *E. coli*. The antibody moiety can be scUCHT1 or other anti-CD3 or anti-T cell antibody having the routing and other characteristics described in detail herein. Thus, one example of an immunotoxin for use in the present methods is the fusion protein immunotoxin UCHT1-DT390. In principal, described immunotoxins can be used in the methods of the invention.

The recombinant immunotoxins can be produced from recombinant sc divalent antibody or recombinant dicystronic divalent antibody and recombinant mutant toxins each containing a single unpaired cysteine residue. An advantage of this method is that the toxins are easily produced and properly folded by their native bacteria while the antibodies are better produced and folded in eukaryote cells. In addition, this addresses differences in coding preferences between eukaryotes and prokaryotes which can be troublesome with some immunotoxin fusion proteins.

The general principles of producing the present divalent recombinant anti-T cell immunotoxins are:

1. The disulfide bond bridging the two monovalent chains is chosen from a natural Ig domain, for example from μCH2 (C337 of residues 228-340 or the γIgG hinge region, C227 of residues 216-238 [with C220P])(see FIGS. 11-14).

2. Sufficient non-covalent interaction between the monovalent chains is supplied by including domains having high affinity interactions and close crystallographic or solution contacts, such as μCH2, μCH4 (residues 447-576) or γCH3 (residues 376-346). These non-covalent interactions facilitate proper folding for formation of the interchain disulfide bond.

3. For fusion immunotoxins the orientation of the antibody to the toxin is chosen so that the catalytic domain of the toxin moiety becomes a free entity when it undergoes proteolysis at its natural processing site under reducing conditions. Thus, in the ETA based IT, the toxin moiety is at the carboxy terminus (FIG. 13) and in DT based fusion IT the DT based toxin moiety is at the amino terminus of the fusion protein (FIG. 14).

Figure 11:
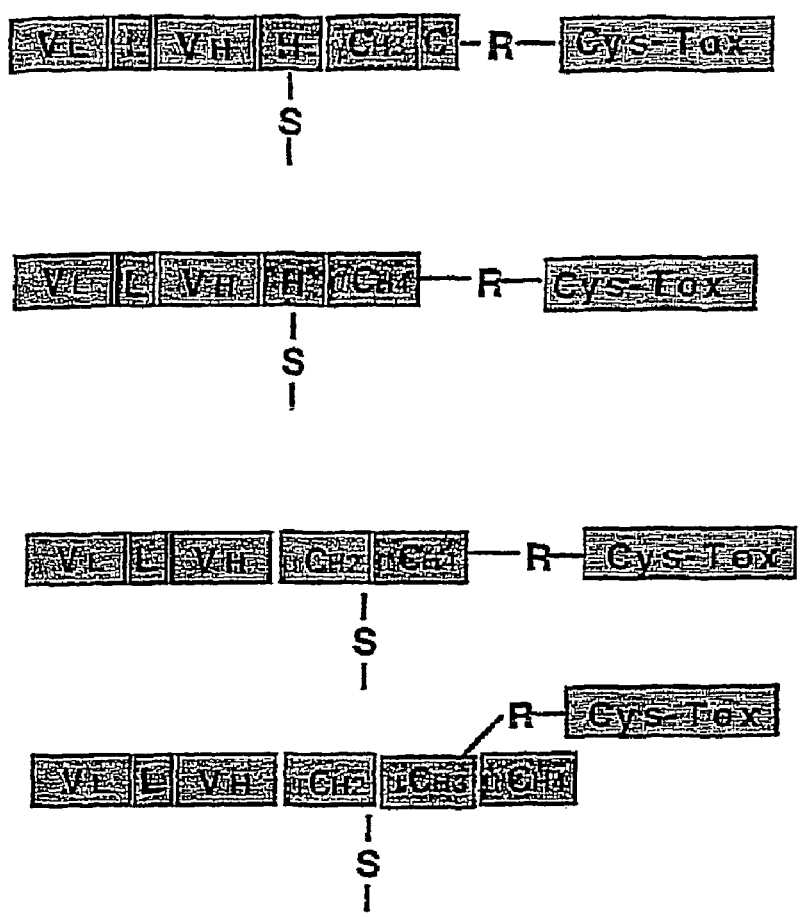
FIG. 11 shows a schematic of several divalent coupled immunotoxins wherein the single chain antibody variable light (VL) and variable heavy (V$_H$) cloned murine domains are connected by a linker (L) and fused with either the μCH2 of human IgM or hinge region of γIgG (H) to provide the interchain disulfide that forms the divalent structure. The toxins are coupled either to a added carboxy terminal cysteine (C) of γCH3 or to C414 of μCH3 or to C575 of μCH4 via a thioether linkage. The toxin moieties based on DT or ETA are binding site mutants containing a cysteine replacement within the binding chain. ETA based toxins have been additionally altered to render them independent of proteolytic processing at acidic pH. Schematics show proteins with amino terminus on the left.

4. For chemically coupled immunotoxins, a single cysteine is inserted within the toxin binding domain. The antibody is engineered to have only a single free cysteine per chain which projects into the solvent away from interchain contacts such as μCH3 414, μCH4 575 or the addition to μCH3 at C447. Crystal structure indicates this region is highly solvent accessible. Excess free cysteines are converted to alanine (FIGS. 11-12).

5. Toxins are mutated in their binding domain by point mutations, insertions or deletions, have at least a 1000 fold reduction in binding activity over wild type, and are free of translocation defects.

6. Toxin binding site mutants, if not capable of proteolytic processing at neutral pH, are modified in the processing region to achieve this result.

A binding site mutant (CRM9) of full length diphtheria toxin residues 1-535 using the numbering system described by Kaczovek et al. (56) S525F (57) can be further modified for chemical coupling by changing a residue in the binding domain (residues 379-535) to cysteine. Presently preferred residues are those with exposed solvent areas greater than 38%. These residues are K516, V518, D519, H520, T521, V523, K526, F530, E532, K534 and S535 (57). Of these K516 and F530 are presently preferred since they are likely to block any residual binding activity (57). However, maximal coupling of the new cysteine residue will be enhanced by the highest exposed solvent surface and proximity to a positively charged residue (which has the effect of lowering cysteine —SH pKa). These residues are at D519 and S535 so that these are presently preferred from the above list of possibilities.

These and other mutations are accomplished by gapped plasmid PCR mutagenesis (58) using the newly designed *E. coli/C. ulcerans* shuttle vector yCE96 containing either the double mutant DT S508F S525F or a CRM9 COOH terminus fusion protein construct having reduced toxicity due to the COOH terminal added protein domain (59). The sequence of vector yCE96 is shown in SEQ ID NO:1. Residues from positions 1 to 373 and 2153 to 3476 are from the vector LITMUS 29 and contain the polycloning linker sites and the ampicillin resistance marker respectively. Residues from positions 374 to 2152 were the origin sequences from the plasmid pNG2. Both of these constructs follow current NIH guidelines for cloning DT derivatives into *E. coli* (60) in that they contain two mutations which both individually diminish toxicity and therefore greatly reduce the chance of introducing a wild type toxin into *E. coli* by a single base pair reversion.

The mutagenesis is performed by deleting the COOH terminal 52 base pairs of the toxin construct using the restriction site Sph 1 at the toxin nucleotide position 1523 (56) and the restriction site used to clone the COOH terminal part of the toxin into the polylinker cloning sites of CE96 (Xba or BamHI for example). Since Sph I, Xba, and BamHI only occur singly within vector yCE96 containing the inserted toxin construct, a gapped linearized plasmid deleted in the COOH terminal coding region is the result. Using PCR the COOH terminal region of CRM9 is rebuilt introducing the desired mutation and including 30-40 base pairs homologous to the down stream and upstream regions adjacent to the gap. The amplified product is gel purified and electroporated into *C. ulcerans* along with the gapped plasmid (58). Recombination at the homologous regions occurs intracellularly accomplishing site specific mutagenesis of DT products within Corynebacteriae which are not specifically subject to NIH toxin cloning restrictions (60). An example of a novel vectors is the yCE96, the sequence of which is provided in SEQ ID NO: 1.

The mutated toxins are produced and purified analogously to the parent toxin except that low levels of reducing agent (equivalent to 2 mM betamercaptoethanol) are included in the purification to protect the unpaired introduced —SH group. Thioether chemical coupling is achieved to a single unpaired cysteine within the divalent antibody construct at either residue 414 in domain μCH3 (see FIGS. 11-12) or residue 575 in domain μCH4 when this domain is included. In this case domain μCH3 is mutated C414A to provide only a single coupling site. An advantage of including μCH4 is enhanced stability of the divalent antibody. A disadvantage is that the extra domain increases size and thereby reduces the secretion efficiency during antibody production. The advantage of terminating with the CH3 domain is that, in another variant, a His6 purification tag can be added at the μCH3 COOH terminus to facilitate antibody purification. Another variant is to use the γ hinge region to form the interchain disulfide and to couple through a μCH3 or μCH4. This variant has the advantage of being smaller in size and places the toxin moiety closer to the CD3 epitope binding domains, which could increase toxin membrane translocation efficiency (see FIGS. 11-12). A His tag can be included at the carboxy terminus as a purification aid. SH-CRM9 is concentrated to 10 mg/ml in PBS pH 8.5 and reacted with a 15 fold molar excess of bismaleimidohexane (BMW (Pierce, Rockford, Ill.). Excess BMH is removed by passing over a small G25F column (Pharmacia, Piscataway, N.J.). The maleimide derived toxin at about 5 mg/ml is now added to scUCHT1 divalent antibody at 10 mg/ml at room temperature. After 1 hr the conjugate is separated from non-reactive staring products by size exclusion HPLC on a 2 inch by 10 inch MODcol column packed with Zorbax (DuPont) GF250 6 micron resin (for large scale production). Derivatives of ETA60EF61cys161 are also coupled to scUCHT1 divalent antibody by the same method.

Another variant of the divalent antibody that can be used for coupling to CRM9 containing an added cysteine is an engineered chimeric antibody containing the VL and VH regions of UCHT1. However, in this case the VL domain is followed by the kappa CL domain followed by a stop codon. The amino terminus of this construct contains the VL signal sequence. This gene is inserted in an appropriate vector dependent on the expression system and preceded by an appropriate promoter. The vector also contains a second promoter followed by the VH signal sequence, VH from UCHT1 followed by μCH1, μCH2, μCH3 and μCH4. If μCH4 is included Cys 575 is changed to alanine and coupling is performed as previously described through Cys 414 of μCH3. μCH4 may however be deleted. A carboxy terminal His tag can be used to facilitate purification. This construct will be secreted as a properly folded divalent antibody containing μ heavy chains from eukaryote cells. It will be a monomeric antibody due to the deletion of Cys 575. The advantage of this construct is the enhanced stability of the VL VH association provided by the CH1 and CL domains, and the enhanced secretion due to the fact that the heavy chains are preceded by a heavy chain signal sequence, in contrast to the case in single chain antibody construction where the light chain signal sequence is used for secreting the entire single chain structure (Peisheng et al., 1995).

Divalent anti-T cell fusion immunotoxins based on DT are provided, wherein the toxin domain (also referred to herein as "toxin moiety" or "tox") is either full length mutant S525F (CRM9) or truncated at 390 or 486 (collectively Tox) and the sequence of domains from the amino terminus from left to right can be selected from among the following:

Tox, μCH2, μCH3, VL, L, VH where L is a (G4S)3 (SEQ ID NO:105) linker and VL and VH are the variable light and heavy domains of the anti-CD3 antibody UCHT1.

Tox, μCH2, μCH3, μCH4, VL, L, VH
Tox, γCH3, H, VL, L, VH where H is the γIgG hinge
Tox, H, VL, L, VH
Tox, μCH2, VL, L, VH
Tox, VL, L, VH, H, γCH3
Tox, VL, L, VH, μCH2
Tox, VL, L, VH, L, VL, L, VH (see FIG. 14).

Requirements of Non-diphtheria Toxin Based Anti-T Cell Divalent Immunotoxins

Figure 2B:
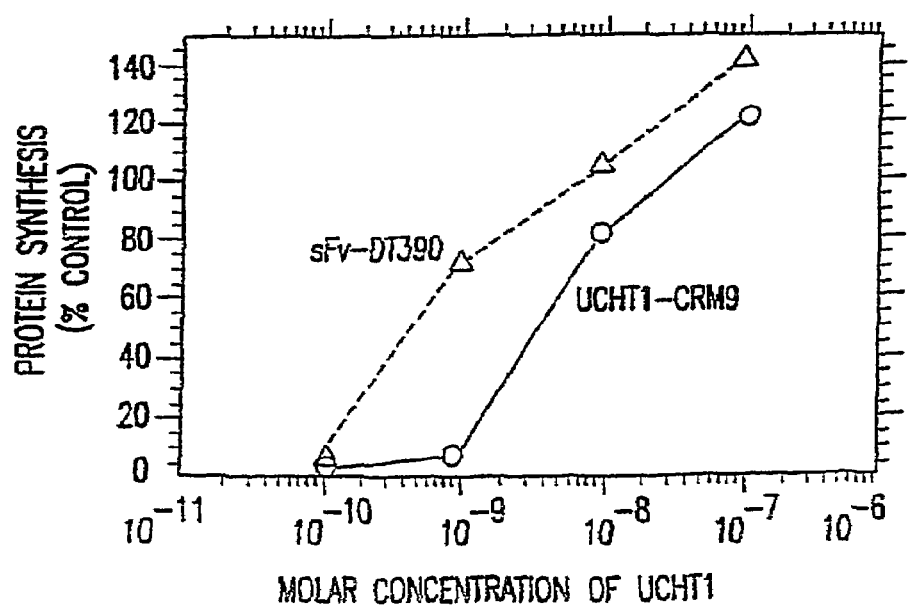

Other types of protein toxin moieties can be utilized in anti-T cell immunotoxins for the induction of tolerance and the treatment of autoimmune diseases and GVHD. All that is required is that a 1-2 log kill of T cells within the blood and lymph node compartments can be achieved without undue systemic toxicity. This in turn requires that the routing epitope routes in parallel with the toxin intoxication pathway and that binding site mutants are available or that toxins truncated in their binding domain are available that reduce toxin binding by 1000 fold compared to wild type toxins without compromising toxin translocation efficiency (see U.S. Pat. No. 5,167,956, issued Dec. 1, 1992). In addition, when using targeting via antibodies, divalent antibodies are generally required under in vivo conditions to achieve sufficient cell killing due to the 15 fold lower affinity of monovalent antibodies (FIGS. 2a, 2b). However, the method of linking the toxin to the divalent antibody either as a single chain fusion protein or through specific engineered coupling sites must not interfere with translocation efficiency. This could occur due to the larger size of many divalent antibodies compared to monovalent sFv antibodies unless care is taken so that the catalytic domain of the toxin can achieve unencumbered translocation. This is achieved for DT based immunotoxins using DT based binding site mutants where the fusion protein antibody moiety is contiguous with the COOH terminus of the toxin binding chain as described above (FIG. 14). This allows the catalytic A chain to translocate as soon as the disulfide loop spanning the Arg/Ser proteolytic processing site residues 193/194 is reduced. Most targeted cells are capable of performing this processing event, and when chemically coupled CRM9 is used the processing is performed by trypsin prior to coupling. The impact of this relationship for non-DT immunotoxins is further described below.

Pseudomonas Exotoxin A Derivatives Freed from Processing Restrictions

ETA-60EF61Cys161 can be made with a break in the peptide backbone between residues 279-280, when the proteolytic processing site is synthesized from a dicystronic message. Nucleotides coding residues 1-279 are placed behind the toxin promoter and followed by a stop codon. The promoter is repeated followed by a second stop codon. ITs made in this manner are referred to as a "dicystronic". A large fraction of the secreted protein will be in the form of the full length properly folded protein held together by the S-S loop 265-287 spanning the peptide backbone break at 279/280 much the same way that antibody Fd pieces are produced from dicystronic messages of heavy and light chains (66). Other expression vectors can be used. This construct is referred to as ETA-60EF61Cys161,279//280.

ETA-60EF61Cys161 and ETA-60EF61 can be modified by site specific mutagenesis in the region of the processing site and bridging S-S loop 265-287 to make this region more similar to that in DT which is easily processed in vitro at neutral pH or in vivo ecto cell membrane associated furin prior to endosomal acidification. Three additional mutants are described having increasing similarity to DT in this area. They are shown for the Cys 161 derivative, but can also be made without the Cys substitution for use in fusion proteins, the added residues for the antibody domains being supplied at the amino terminus (FIGS. 11, 12, 13).

Divalent anti-T cell fusion immunotoxins based on pseudomonas exotoxin A is provided, wherein the toxin moiety (collectively known as Tox2) is a full length mutant binding site insertional mutant ETA60EF61 that has been further modified in its proteolytic processing region to permit neutral pH proteolytic trypsin/furin like processing can be as follows:

ETA-60EF61, M161C, P278R

ETA-60EF61, M161C, P278R, Q277V, H275N, R274G

ETA-60EF61, M161C, P278R, Q277V, H275N, R274G, T273A, F272C, C265A.

The sequence of domains in these immunotoxins from the amino terminus from left to right can be selected from the following:

VL, L, VH, H, μCH3, Tox2
VL, L, VH, H, μCH4, Tox2
VL, L, VH, μCH2, μCH4, Tox2
VL, L, VH, μCH2, μCH3, μCH4, Tox2
VL, L, VH, H, Tox2.

Divalent anti-T cell thioether coupled immunotoxins the full length toxin binding site mutant moiety contains a binding domain conversion to cysteine (collectively known as Tox3) based on pseudomonas exotoxin A ETA60EF61Cys161, where Cys161 is an engineered replacement of Met161 for coupling purposes. The ETA toxin moiety can be further modified to permit proteolytic processing or synthesized in a processed form. Alternatively, if the toxin moiety is based on full length diphtheria toxin, it can include the following mutations:

S525F, K530C
S525F, K516C
S525F, D519C
S525F, S535C.

In these immunotoxins, the sequence of domains from the amino terminus from left to right can be selected from the following:

VL, L, VH, H, γCH3, C where C is a non-native C terminal cysteine coupling residue,
VL, L, VH, H, μCH4 where coupling is via μCH4 C575,
VL, L, VH, μCH2, μCH4 where coupling is via μCH4 C575, and
VL, L, VH, μCH2, μCH3, 1CH4 where C575A where coupling is via μCH3 C414.

Divalent dicystronic anti-T cell thioether coupled immunotoxins wherein the full length toxin binding site mutant moiety contains a binding domain conversion to cysteine (collectively known as Tox2) based on pseudomonas exotoxin A ETA60EF61Cys161 or further modified to permit proteolytic processing, or synthesized in a processed form are provided. Alternatively, if based on full length diphtheria toxin they can include the following mutations:

S525F, K530C
S525F, K516C
S525F, D519C
S525F, S535C.

In these immunotoxins, one cystron secretes from the amino terminus a fusion protein of the variable heavy domain of UCHT1 followed by the γ constant light domain and the other cystron secretes one of the following domains from the amino terminus from left to right:

VL, γCH1, H, μCH3, μCH4, where C575A and coupling is via μCH3 C414,
VL, γCH1, H, μCH4, and coupling is via μCH4 C575,
VL, γCH1, H, μCH3, C, where C is an engineered C terminal cysteine coupling residue, and
VL, γCH1, H, μCH4, where coupling is via μCH4 C575.

*Pseudomonas* exotoxin A ETA60EF61Cys161 can be further modified to achieve a peptide backbone break between residue 279/280 by expression in a dicystronic construct encoding separate Minas for *Pseudomonas* residues 1-279 and residues 280-612. This immunotoxin does not require proteolytic processing.

The antibody-toxin constructs of the invention can be expected to be effective as immunotoxins, because the relevant parameters are known. The following discussion of parameters is relevant to the use of the immunotoxin in tolerance induction. The relevant binding constants, number of receptors and translocation rates for humans have been determined and used. Binding values for anti-CD3-CRM9 for targeted and non-targeted cells in vitro and rates of translocation for the anti-CD3-CRM9 conjugate to targeted and non-targeted cells in vitro are described (Greenfield et al. (1987) *Science* 238:536; Johnson et al. (1988) *J. Biol. Chem.* 263:1295; Johnson et al. (1989) *J. Neurosurg.* 70:240; and Neville et al. (1989) *J. Biol. Chem.* 264:14653). The rate limiting translocation rate to targeted cells in vitro is recited in FIG. 2a, wherein it is shown that an anti-CD3-CRM9 conjugate at $10^{-11}$ M is translocated to about 75% of the target cells present as measured by inhibition of protein synthesis in about 75% of cells with 20 hours. Inhibition of protein synthesis is complete in cells into which the conjugate translocates.

Parameters determined in in vivo studies in nude mice include the following: Tumor burden is described in Example 1 as a constant mass equal to 0.1% of body weight; the receptor number and variation of receptor number are described in Example 3; "favorable therapeutic margin" is defined as an in vivo target cell 3 log kill at 0.5 MLD (minimum lethal dose) comparison of efficacy with an established treatment of 0.5 MLD immunotoxin equivalent (group 1) to a radiation dose of 500-600 cGy (groups 8 and 9).

The parameters determined in vitro allowed the prediction of success in the in vivo nude mouse study. The prediction of in vivo success was verified by the data in Examples 3-4. Using the target cell number from the mouse study as being equivalent to the local T cell burden in a monkey or man successful T cell ablation and immunosuppression in monkeys could be predicted. This prediction has been verified by the monkey data in Examples 5 and 7-8. Using the same parameters, a scientist skilled in this field can make a prediction of success in humans with confidence, because these parameters have been previously shown to have predictive success.

In another embodiment, the present invention relates to a pharmaceutical composition comprising anti-CD3-DT mutant in an amount effective to treat T cell leukemias or lymphomas which carry the CD3 epitope, graft-versus-host disease or autoimmune diseases, and a pharmaceutically acceptable diluent, carrier, or excipient. One skilled in the art will appreciate that the amounts to be administered for any particular treatment protocol can readily be determined. Suitable amounts might be expected to fall within the range of 0.1 to 0.2 mg (toxin content) per kg of body weight over one to three days.

Non-Toxic Mutant of Diphtheria Toxin.

Most human sera contain anti-DT neutralizing antibodies from childhood immunization. To compensate for this the therapeutic dose of anti-CD3-CRM9 can be appropriately raised without affecting the therapeutic margin. Alternatively, the present application provides a non-toxic DT mutants reactive with neutralizing antisera (e.g., CRM197) that can be administered in conjunction with the immunotoxin.

A non-toxic mutant of diphtheria toxin for use in the present methods can be DTM2 or CRM197. DTM2 and CRM197 are non-toxic mutants of DT, having a point mutation in the enzymatic chain. The non-toxic mutant can be DT E148S, S525F. However, they have the full antigenic properties of DT and CRM9, and CRM197 is used for immunization (Barbour et al. 1993. *Pediatr Infect. Dis. J* 12:478-84). Other non-toxic DT mutants that can be used in the present method will share the characteristic of either totally lacking A chain enzymatic activity or attenuating its activity by about a 1000 fold or more.

The purpose of administering the non-toxic toxin is to bind preexisting anti-CRM9 anti-DT antibodies in a subject and compete with their effect and/or induce their removal from the circulation. This substantially avoids any host immune response to the immunotoxin that might interfere with the activity of the immunotoxin.

The protein synthesis inhibition assay in the presence of human serum samples or pooled human sera described in the Examples becomes an important part of the evaluation of the optimal immunotoxin for the individual patient and is provide for this purpose. This assay makes routine the systematic evaluation of additional combinations of DT point mutations and carboxy terminal deletions for the purpose of minimizing blockade of immunotoxin in vivo by anti-human antitoxin.

The non-toxic mutant is preferably administered concurrently with or shortly before the immunotoxin. For example, the non-toxic DT mutant can be administered within an hour, and preferably about 5 minutes prior to the administration of immunotoxin. A range of doses of the non-toxic mutant can be administered. For example, an approximately 3 to 100 fold excess of non-toxic mutant over the CRM9 content of the immunotoxin to be administered can be administered by i.v. route.

Another use of the non-toxic DT mutant in the present methods is to run recipient patient's blood through a column containing the non-toxic DT mutant to remove some or all of the patients serum antibodies against DT.

Method of Inducing Immune Tolerance.

One embodiment to the invention provides a method of inhibiting a rejection response by inducing immune tolerance in a recipient to a foreign mammalian donor organ cell by exposing the recipient to an immunotoxin so as to reduce the recipients's peripheral blood T-cell lymphocyte population by at least 80%, and preferably 95% or higher, wherein the immunotoxin is an anti-CD3 antibody linked to a diphtheria protein toxin, and wherein the protein has a binding site mutation. The term "donor cell" refers to a donor organ or a cell or cells of the donor organ, as distinguished from donor lymphocytes or donor bone marrow. When the donor organ or cells of the donor is transplanted into the recipient, a rejection response by the recipient to the donor organ cell is inhibited and the recipient is tolerized to the donor organ cell. Alternatively, a non-toxic DT mutant such as DTM2 or CRM197 can first be administered followed by the immunotoxin. This method can use any of the immunotoxins (e.g., anti-CD3-CRM9, scUCHT1-DT390, etc.) or non-toxic DT mutants described herein with the dosages and modes of administration as described herein or otherwise determined by the practitioner.

As further described in the Examples, the above-described method for inducing tolerance can be augmented by additional treatment regimens. For example, the method can further include administering to the thymus gland a thymic apoptosis signal before, at the same time, or after, the immunotoxin exposure step. The thymic apoptosis signal can be high dose corticosteroids (also referred to as "immunosuppressants" in this context). The thymic apoptosis signal can be lymphoid irradiation.

In a further example of the method of inducing tolerance, thymic injection of donor leukocytes or lymphocytes having MHC antigen of the same haplotype as the MHC of the donor cell can be administered to the recipient. Thymic injection of a saline solution or a crystalloid or colloid solution to disrupt thymic integrity and increase access of immunotoxin to the thymus can also be beneficial.

The present tolerance induction method can also include administering an immunosuppressant compound before, at the same time, or after, the immunotoxin exposure step. The immunosuppressant compound can be cyclosporin or other cyclophylins, mycophenolate mofetil (Roche), deoxyspergualin (Bristol Myers) FK506 or other known immunosuppressants. It will be appreciated that certain of these immunosuppressants have major effects on cytokine release occurring in the peritransplant period that may aid in the induction of the tolerant state. The method of inducing immune tolerance can further comprise administering donor bone marrow at the same time, or after, the exposure step.

Any one, two, or more of these adjunct therapies can be used together in the present tolerance induction method. Thus, the invention includes at least six methods of inducing tolerance using immunotoxin (IT): (1) tolerance induction by administering IT alone; (2) tolerance induction by administering IT plus other drugs that alter thymic function such as high dose corticosteroids; (3) tolerance induction by administering IT plus immunosuppressant drugs such as mycophenolate mofetil and/or deoxyspergualin (4) tolerance induction by administering IT plus other drugs that alter thymic function, plus immunosuppressant drugs; (5) tolerance induction by administering IT and bone marrow; and (6) tolerance induction by administering IT plus bone marrow, plus other drugs that alter thymic function, plus immunosuppressant drugs. The adjunct therapy can be administered before, at the same time or after the administration of immunotoxin. Different adjunct therapies can be administered to the recipient at different times or at the same time in relation to the transplant event or the administration of immunotoxin, as further described below.

Because the immunosuppressant can be administered before the immunotoxin and/or other treatments, the present method can be used with a patient that has undergone an organ transplant and is on an immunosuppressant regimen. This presents a significant opportunity to reduce or eliminate traditional immunosuppressant therapy and its well documented negative side-effects. Also, as described below, treatment with immunosuppressants prior to transplantation could be particularly useful in cadaveric transplants. In such a setting of pre-transplant treatment with immunosuppressant, the administration of immunotoxin can be delayed for up to seven or more days post-transplantation.

An example of a schedule of immunotoxin and immunosuppressant administration for patients receiving organ transplants is as follows:

| | |
|---|---|
| day-6-0 hours | begin immunosuppressant treatment; |
| day 0 | perform transplant; |
| day 0 | immediately following transplant administer 1st immunotoxin dose |
| day 1 | 2nd immunotoxin dose |
| day 2 | 3rd and final immunotoxin dose; |

Immunosuppressant treatment may end at day 3 or extend to day 14. Immunosuppressant treatment is also effective if begun at the time of transplantation, and can continue for up to several weeks after transplantation.

The immunotoxin injection can, alternatively, be made within a week or two prior to the donor cell treatment. If the donor organ or cell from donor organ is from a live donor, the immunotoxin is administered from 15 hours to 7 days before the transplanting step or just after transplantation. If the donor organ is kidney or kidney cells and is from a cadaver, the immunotoxin is preferably administered from 6 to 15 hours before the transplanting step. If the donor organ or cell from the donor organ is cadaveric and is selected from the group consisting of heart, lung, liver, pancreas, pancreatic islets and intestine, the immunotoxin is preferably administered from 0 to 6 hours before the transplanting step. For practical reasons immunotoxin treatment and transplantation generally take place at about the same time (e.g., within 15 hours), because advanced planning for cadaveric transplants is difficult. Various schedules of apoptotic and immunosuppressant therapies can be used with the above methods. In any of the above scenarios, donor bone marrow, if desired, can be administered at approximately the time of the transplant or after.

The presently preferred doses of the immunotoxin are those sufficient to deplete peripheral blood T-cell levels to 80%, preferably 90% (or especially preferably 95% or higher) of preinjection levels. This should require mg/kg levels for humans similar to those for monkeys (e.g., 0.05 mg/kg to 0.2 mg/kg body weight), which toxicity studies indicate should be well tolerated by humans. Thus, the immunotoxin can be administered to safely reduce the recipients T cell population.

Method of Treating Graft-Versus-Host Disease.

In another embodiment, the invention relates to a method of treating an immune system disorder not involving T cell proliferation which is amenable to T cell suppression. More specifically, a method of treating graft-versus-host disease in an animal is also provided. It comprises administering to the animal an immunotoxin comprising a diphtheria toxin binding mutant moiety or an ETA binding mutant moiety and an antibody moiety which routes by the anti-CD3 pathway or other T cell epitope pathway, or derivatives thereof under conditions such that the graft-versus-host disease is treated, i.e., the symptoms of the graft-versus-host disease improve. Alternatively, as further described, a non-toxic DT mutant such as DTM2 or CRM197 (or mutants having combinations of the mutations in CRM9 and CRM197) can first be administered followed by the immunotoxin. This method can use any of the immunotoxins or non-toxic DT mutants described herein with the dosages and modes of administration as described herein or otherwise determined by the practitioner. As with the induction of tolerance, certain immunosuppressants that modify cytokine release patterns, such as corticosteroids, deoxyspergualin and mycophenolate mofetil may also be used short term to increase efficacy and reduce side effects.

GVHD is a morbid complication of bone marrow transplantation which is often performed as antileukemia/lymphoma therapy. GVHD is caused by circulating donor T cells within the host which are acquired in bone marrow grafts unless specifically depleted prior to grafting (Gale and Butturini (1988) *Bone Marrow Transplant* 3:185; Devergie et al. (1990) ibid 5:379; Filipovich et al. (1987) *Transplantation* 44). Successful donor T cell depletion techniques have been associated with a higher frequency of graft rejection and leukemia relapses (Gale and Butturini (1988) *Bone Marrow Transplant* 3:185; Devergie et al. (1990) ibid 5:379; Filipovich et al. (1987) *Transplantation* 44). Therefore, the donor T cells appear to aid engraftment and to provide a graft-versus-leukemia effect as well as causing GVHD. Because the T cell burden following bone marrow transplantation is low for the first 14 days (<10% of normal) the log kill of donor T cells would be proportionally enhanced (Marsh and Neville (1987) *Ann. N.Y. Acad. Sci.* 507:165; Yan et al., submitted; Gale and Butturini (1988) *Bone Marrow Transplant* 3:185; Devergie et al. (1990) ibid 5:379; Filipovich et al. (1987) *Transplantation* 44). It is expected that donor T cells can be eliminated at set times during the early post transplantation period using the present method. In this way the useful attributes of grafted T cells might be maximized and the harmful effects minimized.

Method of Treating an Autoimmune Disease.

Another embodiment of the invention provides a method of treating an autoimmune disease in an animal comprising administering to the animal an immunotoxin comprising a diphtheria toxin binding mutant moiety or an ETA binding mutant moiety and an antibody moiety which routes by the anti-CD3 pathway or other T cell epitope pathway, or derivatives thereof, under conditions such that the autoimmune disease is treated, e.g., the symptoms of the autoimmune disease improve. A further method of treating an autoimmune disease in an animal comprises administering to the animal a non-toxic mutant of diphtheria toxin followed by an antibody CRM9 conjugate which routes by the anti-CD3 pathway, or derivatives thereof, under conditions such that the autoimmune disease is treated. This method can use any of the immunotoxins or non-toxic DT mutants described herein with the dosages and modes of administration as described herein or otherwise determined by the practitioner. Again, certain immunosuppressants modifying cytokine release may be beneficial as short term adjuncts to IT.

Method of Treating T Cell Leukemias or Lymphomas.

A further embodiment of the invention provides a method of treating T cell leukemias or lymphomas which carry the CD3 epitope in an animal comprising administering to the animal an immunotoxin comprising a binding site mutant of diphtheria toxin moiety and an antibody moiety which routes by the anti-CD3 pathway, or derivatives thereof, under conditions such that the T cell leukemias or lymphomas are treated. Alternatively, a further embodiment is a method of treating T cell leukemias or lymphomas in an animal comprising administering to the animal a non-toxic mutant of diphtheria toxin followed by an antibody-CRM9 conjugate which routes by the anti-CD3 pathway, or derivatives thereof, under conditions such that the T cell leukemias or lymphomas are treated. This method can use any of the immunotoxins or non-toxic DT mutants described herein with the dosages and modes of administration as described herein or otherwise determined by the practitioner.

Anti-T Cell Immunotoxin Fusion Proteins

The invention provides an anti-T cell immunotoxin fusion protein. In one embodiment the anti-T cell immunotoxin fusion protein comprises from the amino terminus, a truncated diphtheria toxin moiety and one single chain Fv (sFv) from the variable regions of the UCHT1 antibody. More specifically, the sFv can comprise VL, L, VH, wherein L is a linker.

In another embodiment, the anti-T cell immunotoxin fusion protein comprises from the amino terminus, a truncated diphtheria toxin moiety and two sFv domains from the variable regions of the UCHT1 antibody. Thus, the two sFv regions can comprise VL, L, VH, L, VL, VH, wherein L is a linker. The VL, L, VH, L, VL, VH structure is also referred to herein as "bisFv."

As used herein, "sFv" refers to the single chain variable regions of the UCHT1 antibody or any modification thereof. The sFv of the immunotoxin fusion protein can modified to contain one or more mutations compared to the sequence for parental UCHT1. For example, the sFv can comprise mutations in the C-terminal $V_H$ region. Optionally, these mutations can be located in the FR4 region of the C-terminal $V_H$ region. For example, these mutations can include Ala to Gln at residue 886, Val to Leu at residue 891 and Ser to Phe at residue 894. As used throughout, "UCHT1" and "sFv" refer to either the modified or unmodified UCHT1 and sFV(UCHT1) unless the text clearly indicates otherwise. Modified UCHT1 can include UCHT1 with one or more primer errors in the VH region of the antibody moiety. Preferably, the modified UCHT1 or sFv has a binding activity that is at least 60% of the binding activity of the parental antibody UCHT1. More preferably, the binding activity of the modified UCHT1 moiety or sFv moiety is at least 65, 70, 75, 80, 85, 90, 95, 100%, or any percentage in between these values, of the binding activity of parental UCHT1.

Optionally, the immunotoxin fusion protein can further comprise a modified amino terminal. Thus, one embodiment of the immunotoxin fusion protein has a methionine residue at its N-terminal. Another embodiment has an alanine residue at its N-terminal, and yet another embodiment has a Tyr-Val-Glu-Phe (SEQ ID NO:49) sequence at its amino terminal.

Optionally, the immunotoxin fusion protein can further comprise a signal peptide (sp) at its amino terminal, following translation but prior to secretion. The signal peptide can be selected to optimize secretion of the immunotoxin fusion protein. For example, for mammalian cell expression, the signal peptide can comprise a mouse κ-immunoglobulin signal peptide. The sequence of the mouse κ-immunoglobulin signal peptide, more specifically, can have the amino acid sequence METDTLLLWVLLLWVPGADAA (SEQ ID NO:25). Alternatively, for yeast cell expression, the signal peptide can comprise an alpha mating factor signal peptide. The alpha mating factor signal peptide has the amino acid sequence MRFPSIFTAVLFAASSALAAPCNTTTE-DETAQIPAEAVIGYSDLEGDFDVAVL PFSNSTNNGLL-FINTTIASIAAKEEGVSLEKR! EAEA (SEQ ID NO:29). Preferably, the alpha mating factor signal peptide used for yeast expression comprises the peptide encoded by the portion of the alpha mating factor signal peptide nucleic acid that is 5' to the Kex2 cleavage site, which is indicated by the symbol "!" above. More specifically, the alpha mating factor signal peptide up to the Kex2 cleavage site comprises the amino acid sequence of SEQ ID NO:31. As an alternative embodiment, the signal peptide can be the *Corynebacterium diphtheriae* signal peptide.

Optionally, the immunotoxin fusion protein can further comprise a histidine tag. The histidine tag can be added to either the amino or carboxyl terminus of the immunotoxin fusion protein in order to facilitate purification. The histidine tag can comprise 4 or more histidine residues, preferably at least six histidine residues.

Optionally, the immunotoxin fusion protein can further comprise a connector (C) between the toxin moiety and the VL region. The connector between the toxin moiety and the VL region can be, for example, an amino acid connector of one to ten amino acid residues. Preferably, the connector is two to six amino acid residues. More specifically, the connector can be the six amino acid flexible connector segment ASAGGS (SEQ ID NO:37).

As used herein, a "truncated diphtheria toxin moiety" can be any truncated diphtheria toxin in the presence or absence of modifications as compared to the native diphtheria toxin. The truncated toxin moiety can comprise, for example, 389 residues from the N-terminal glycine of mature diphtheria toxin (referred to herein as "DT389") or 390 residues from the N-terminal glycine of mature diphtheria toxin (referred to herein as "DT390"). For example, the truncated toxin can include various point mutations and substitutions. In one embodiment, the truncated toxin moiety comprises mutations that eliminate glycosylation of the immunotoxin fusion protein, which occurs during secretion in the mammalian system and does not occur during secretion in *Corynebacterium diphtheriae*. More specifically, the immunotoxin fusion protein can comprise two mutations located at residues 18 and 235 of the protein, and even more specifically, can comprise Ser to Ala at residue 18 and Asn to Ala at residue 235. The double glycosylation mutation is referred to as "dm."

The linker (L) can be a Gly-Ser linker. The Gly-Ser linker can be $(Gly_4Ser)_n$ or $(Gly_3Ser)_n$. More specifically, the linker can be a $(Gly_4Ser)_3$ (SEQ ID NO:105) linker, also referred to herein as (G4S), or a $(Gly_3Ser)_4$ (SEQ ID NO: 104) linker, also referred to herein as (G3S).

Figure 19A:
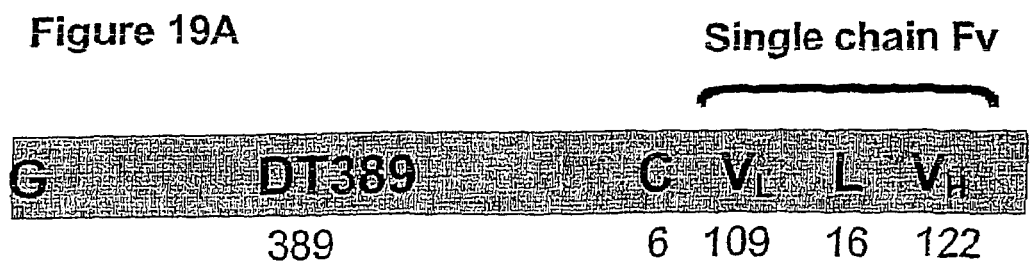
FIG. 19A shows a immunotoxin fusion protein comprising, from the amino terminus, 389 residues from the N-terminal glycine of mature diphtheria toxin, a six amino acid flexible connector segment (ASAGGS (SEQ ID NO:37)) and a single Fv (sFv) made from the variable regions of the UCHT1 antibody. The single chain Fv domain is comprised of 109 residues from the variable region of the light chain of UCHT1, a 16 amino acid linker comprised of glycine and serine residues [(Gly$_3$Ser)$_4$ (SEQ ID NO:104)], and the 122 residue variable region from the heavy chain of UCHT1.
Figure 19B:
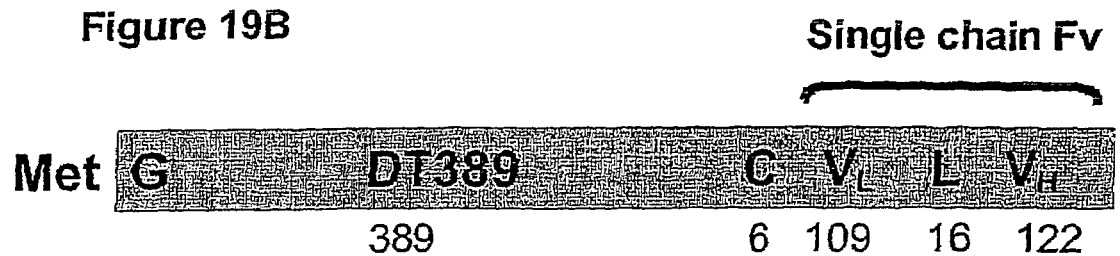
FIG. 19B shows the same domain organization and number of amino acids in each domain as FIG. 19A with the addition of an extra methionine residue at the N-terminus of the protein.

In one embodiment the immunotoxin fusion protein comprises DT389-sFv(UCHT1). More specifically, the immunotoxin can comprise DT389-C-VL-L-VH. The immunotoxin fusion protein, designated Met)DT389-sFv, can further comprise an amino terminal methionine residue. More specifically, the immunotoxin comprises, from the amino terminal, a methionine residue, 389 residues from the N-terminal glycine of mature diphtheria toxin, a six amino acid flexible connector segment (ASAGGS (SEQ ID NO:37)) and a single Fv (sFv) made from the variable regions of the UCHT1 antibody. The single chain Fv domain is comprised of 109 residues from the variable region of the light chain of UCHT1, a 16 amino acid linker comprised of glycine and serine residues [$(Gly_3Ser)_4$ (SEQ ID NO:104)], and the 122 residue variable region from the heavy chain of UCHT1. See FIG. 19A and FIG. 19B. Even more specifically, the immunotoxin fusion protein can comprise SEQ ID NO:38 or SEQ ID NO: 69.

Figure 19C:
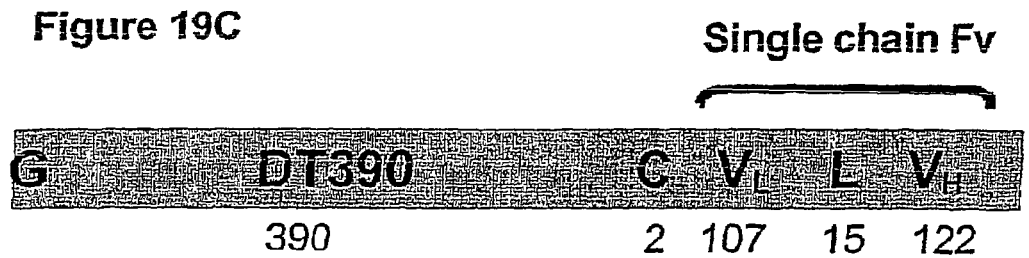
FIG. 19C shows the immunotoxin fusion protein comprising, from the amino terminus, 390 residues from the N-terminal glycine of mature diphtheria toxin, a two amino acid flexible connector segment and a single Fv (sFv) made from the variable regions of the UCHT1 antibody. The single chain Fv domain is comprised of 107 residues from the variable region of the light chain of UCHT1, a 15 amino acid linker comprised of glycine and serine residues [(Gly$_4$Ser)$_3$ (SEQ ID NO:105)], and the 122 residue variable region from the heavy chain of UCHT1.
Figure 19D:
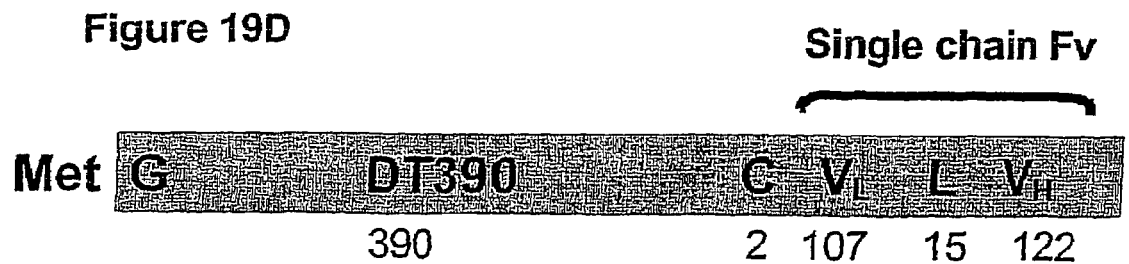
FIG. 19D shows the same domain organization and number of amino acids in each domain as FIG. 19C with the addition of an extra methionine residue at the N-terminus of the protein.

In another embodiment the immunotoxin fusion protein can comprise DT390-sFv(UCHT1), or, more specifically, DT390-C-VL-L-VH. See FIG. 19C. Even more specifically the immunotoxin fusion protein can comprise the amino acid sequence of SEQ ID NO:16. The immunotoxin fusion protein, designated (Met)DT390-sFv(UCHT1), can further comprise an amino terminal methionine residue, or, more specifically, can comprise (Met)DT390-C-VL-L-VH. See FIG. 19D. Even more specifically, the immunotoxin can comprise the amino acid sequence of SEQ ID NO:21 or 68.

Figure 19E:
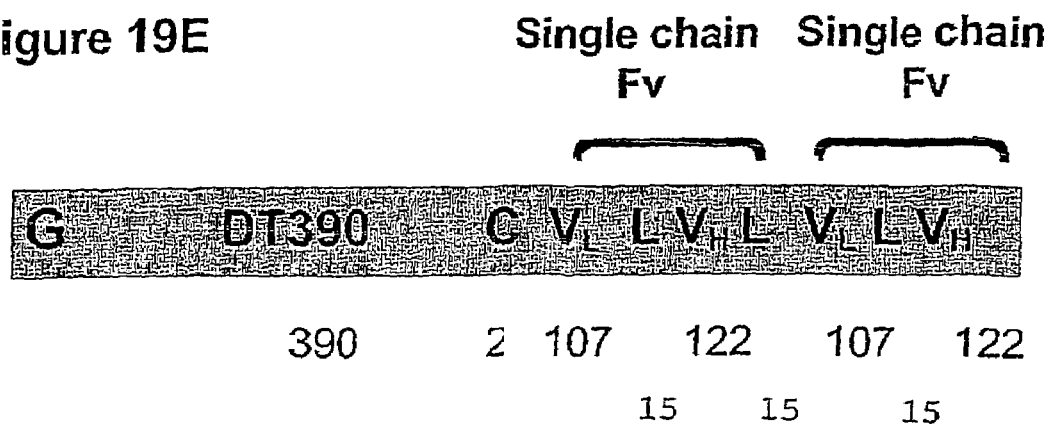
FIG. 19E shows the immunotoxin fusion protein comprising, from the amino terminus, 390 residues from the N-terminal glycine of mature diphtheria toxin, a two amino acid flexible connector segment, and two single chain Fv (sFv) domains (referred to collectively herein as the "bisFv" domain) made from the variable regions of the UCHT1 antibody. The bisFv domain is comprised of 107 residues from the variable region of the light chain of UCHT1, a 15 amino acid linker comprised of glycine and serine residues [(Gly$_4$Ser)$_3$ (SEQ ID NO: 105)], the 122 residue variable region from the heavy chain of UCHT1, a 15 amino acid linker comprised of glycine and serine residues [(Gly$_4$Ser)$_3$ (SEQ ID NO:105)], 107 residues from the variable region of the light chain of UCHT1, a 15 amino acid linker comprised of glycine and serine residues [(Gly$_4$Ser)$_3$ (SEQ ID NO: 105)], and the 122 residue variable region from the heavy chain of UCHT1.
Figure 19F:
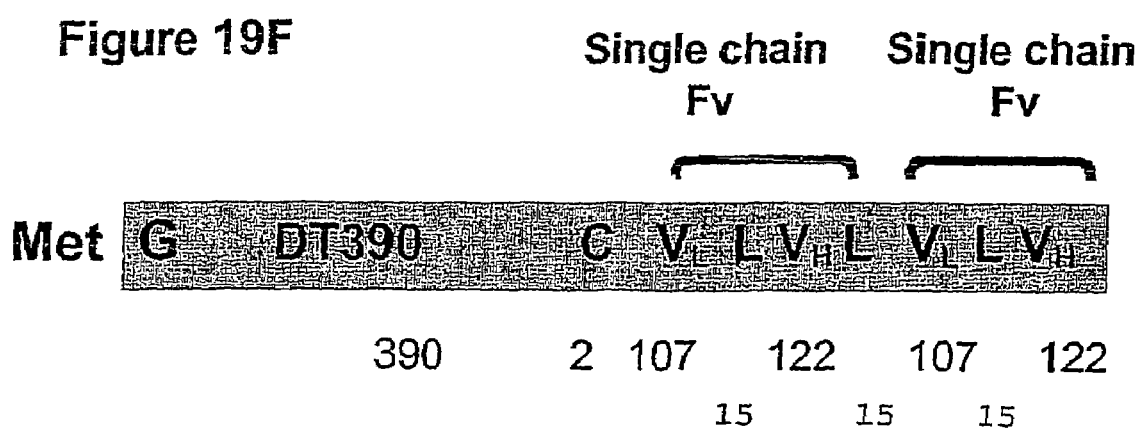
FIG. 19F shows the same domain organization and number of amino acids in each domain as FIG. 19E with the addition of an extra methionine residue at the N-terminus of the protein. Optionally, the C-terminal V$_H$ domain is that reported by Shalaby et al. (1992). Alternatively, the bisFv domain can contain several mutations in the C-terminal V$_H$ regions. The group of mutations in the C-terminal V$_H$ region result from consensus PCR primers used in the cloning of the variable regions from hybridoma cells (Thompson et al., 1995). These mutations, relative to the sequence published by Shalaby et al. (1992) are AlaGln at residue 886, ValLeu at residue 891 and SerPhe at residue 894. These mutations are located in the FR4 region of the C-terminal V$_H$ domain.

In another embodiment the immunotoxin fusion protein can comprise DT390-bisFv(UCHT1). More specifically, the immunotoxin fusion protein can comprise DT390-C-VL-L-VH-L-VL-L-VH. See FIG. 19E. More specifically, the immunotoxin designated DT390-bisFv(UCHT1) can comprise the amino acid sequence of SEQ ID NO: 19 or 20. The immunotoxin fusion protein, designated (Met)DT390-bisFv (UCHT1), can further comprise an amino terminal methionine residue. See FIG. 19F. Optionally, the immunotoxin fusion protein can comprise one or more mutations in the C-terminal $V_H$ region. More specifically, the immunotoxin designated (Met)DT390-bisFv(UCHT1) can comprise the amino acid sequence of SEQ ID NO:17 or 18.

Figure 19G:
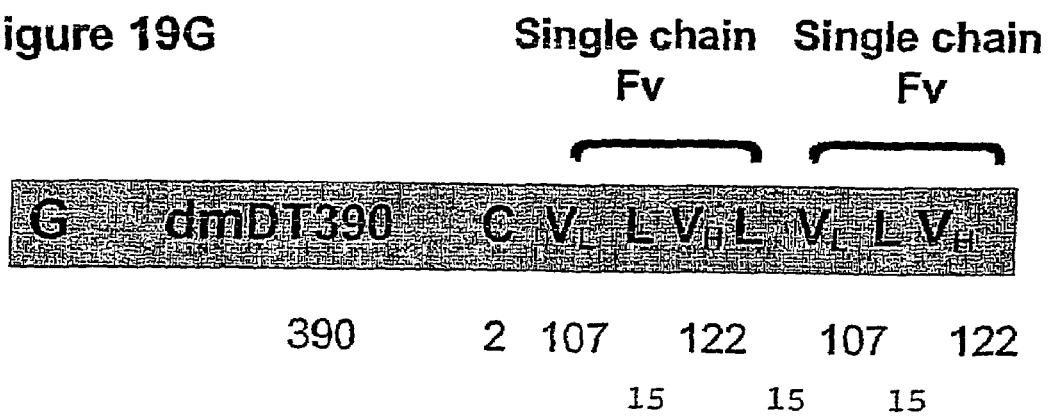
FIG. 19G shows an immunotoxin fusion protein containing two mutations in the diphtheria toxin portion of the protein. The two mutations in diphtheria toxin were introduced to eliminate glycosylation of the protein which occurs during secretion in the mammalian system and does not occur during secretion in *Corynebacterium diphtheriae*. These two mutations are located at residues 18 and 235 of the protein and are SerAla at residue 18 and AsnAla at residue 235. Thus, the protein comprises, from the amino terminus, 390 residues from the N-terminal glycine of mature diphtheria toxin with two mutations ("dm"), a two amino acid flexible connector segment, and a bisFv domain made from the variable regions of the UCHT1 antibody. The bisFv domain contains several mutations in the C-terminal V$_H$ regions. The group of mutations in the C-terminal V$_H$ region result from consensus PCR primers used in the cloning of the variable regions from hybridoma cells (Thompson et al., 1995). These mutations, relative to the sequence published by Shalaby et al. (1992) are AlaGln at residue 886, ValLeu at residue 891 and SerPhe at residue 894. These mutations are located in the FR4 region of the C-terminal $V_H$ domain.

In one embodiment, the immunotoxin fusion protein, designated dmDT390-bisFv(UCHT1), further comprises mutations to remove glycosylation sites. See FIG. 19G. More specifically, the mutations eliminate glycosylation that occurs during secretion in the mammalian system and does not occur during secretion in *Corynebacterium diphtheriae*. Even more specifically, the mutations are located at residues 18 and 235 of the protein and include, for example, Ser to Ala at residue 18 and Asn to Ala at residue 235. Optionally, the immunotoxin fusion protein can comprise one or more mutations in the C-terminal $V_H$ region. Even more specifically, the immunotoxin fusion protein comprises the amino acid sequence of SEQ ID NO:27.

In yet another embodiment, the immunotoxin fusion protein, designated (Ala)dmDT390-bisFv(UCHT1*), further comprises an N-terminal alanine residue. See FIG. 19H. The (Ala)dmDT390-bisFv(UCHT1*) can further comprise one or more mutations in the C-terminal V$_H$ regions of sFv. Even more specifically, the immunotoxin fusion protein can comprise the amino acid sequence of SEQ ID NO:26.

In another embodiment, the immunotoxin fusion protein, designated (TyrValGluPhe)dmDT390-bisFv(UCHT1*) or (YVEF)dmDT390-bisFv(UCHT1*), further comprises four extra residues at the amino terminus (Tyr-Val-Glu-Phe) (SEQ ID NO:49. The ((TyrValGluPhe)dmDT390-bisFv(UCHT1*) can further comprise one or more mutations in the C-terminal V$_H$ regions of sFv. See FIG. 19I. Even more specifically, the immunotoxin fusion protein can comprise the amino acid sequence of SEQ ID NO:28.

It is understood that the immunotoxin fusion protein includes functional variants of either the antibody moiety or the toxin moiety or both. These variants are produced by making amino acid substitutions, deletions, and insertions, as well as post-translational modifications. Such variations may arise naturally as allelic variations (e.g., due to genetic polymorphism) or may be produced by human intervention (e.g., by mutagenesis of cloned DNA sequences), such as induced point, deletion, insertion and substitution mutants. These modifications can result in changes in the amino acid sequence, provide silent mutations, modify a restriction site, or provide other specific mutations.

Amino acid sequence modifications fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence, including, for example, truncated mutants. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues but may include multiple substitutions at different positions; insertions usually will be on the order of about from 1 to 10 amino acid residues but can be more; and deletions will range about from 1 to 30 residues, but can be more. Deletions or insertions preferably are made in adjacent pairs, i.e., a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with Table 1 and are referred to as conservative substitutions.

TABLE 1

Amino Acid Substitutions

| Original Residue | Exemplary Substitutions |
| --- | --- |
| Ala | ser |
| Arg | lys |
| Asn | gln |
| Asp | glu |
| Cys | ser |
| Gln | asn |
| Glu | asp |
| Gly | pro |
| His | gln |
| Ile | leu; val |
| Leu | ile; val |
| Lys | arg; gln |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

In one embodiment of the invention the immunotoxin fusion protein is modified at the amino terminus of the toxin domain to promote amino terminal homogeneity upon expression by E. coli. Thus, the invention provides an immunotoxin fusion protein with amino terminal homogeneity. More specifically, the immunotoxin fusion protein has an amino terminal sequence comprising MLADD (SEQ ID NO:106), MLDD (SEQ ID NO:107), or SADD (SEQ ID NO:108). When the immunotoxin fusion protein is DT389-sFv (UCHT1), for example, and either MLADD (SEQ ID NO:106) or MLDD (SEQ ID NO:107) is the modified amino terminal, the immunotoxin fusion protein further comprises amino acid residues 6-643 of the amino acid sequence of SEQ ID NO:69. When the immunotoxin fusion protein is DT389-sFv (UCHT1), for example, and SADD (SEQ ID NO: 108) is the modified amino terminal, the immunotoxin fusion protein further comprises the amino acid residues 5-642 amino acid sequence of SEQ ID NO:38.

Similarly, when the immunotoxin fusion protein is DT390-sFv (UCHT1) and the amino terminal of the toxin domain is modified to promote amino terminal homogeneity upon expression by E. coli, the modified amino terminal can be MLADD (SEQ ID NO: 106), MLDD (SEQ ID NO: 107), or SADD (SEQ ID NO: 108). Embodiments of the amino terminal modified DT390 comprise MLADD (SEQ ID NO:106), MLDD (SEQ ID NO:107) and further comprise the remaining amino acid residues of DT390-sFv (e.g., amino acid residues 6-638 of SEQ ID NO:21). When the immunotoxin fusion protein is DT390-sFv (UCHT1) and SADD (SEQ ID NO: 108) is the modified amino terminal, the immunotoxin fusion protein further comprises amino acid residues 5-637 of the amino acid sequence of SEQ ID NO:16.

The amino terminus of the toxin domain can also be modified to promote amino terminal homogeneity upon expression by E. coli when the immunotoxin fusion protein, comprising, from the amino terminus, a truncated diphtheria toxin moiety, a connector, and two single chain Fvs of the variable region of a UCHT1 antibody, wherein the two single chain Fvs comprise VL, L, VH, L, VL, L, VH, wherein L is a Gly-Ser linker, and wherein VL and VH are the variable light and heavy domains of the anti-CD3 antibody UCHT1. MLADD (SEQ ID NO:106), MLDD (SEQ ID NO:107), or SADD (SEQ ID NO:108) can be the modified amino terminal. Thus, embodiments comprise, for example, MLADD (SEQ ID NO:106) or MLDD (SEQ ID NO:107) at the amino terminus of Met-DT389bisFv (UCHT1) or Met-DT390bisFv. More specifically, the modified immunotoxin fusion protein can comprise MLADD (SEQ ID NO:106) or MLDD (SEQ ID NO:107) and further comprise amino acid residues 6-896 of SEQ ID NO:17 or 18. Other embodiments comprise, for example, SADD (SEQ ID NO:108) at the amino terminus of DT389bisFv or DT390bisFv. More specifically, the modified fusion protein can comprise SADD (SEQ ID NO:108) and further comprise amino acid residues 5-895 of SEQ ID NO:19 or 20.

By "amino terminal homogeneity" is meant that 100% or about 100% of the immunotoxin fusion proteins in a sample are homogeneous at the amino terminal. Amino terminal homogeneity includes 4, 5, 6, 7, 8, 9, or 10 amino acid residues at the amino terminal with the same amino acid sequence or with 95%, 96%, 97%, 98%, 99% identity or any amount in between.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (Creighton, 1983), acetylation of the N-terminal amine and, in some instances, amidation of the C-terminal carboxyl.

In all mutational events, it is understood that the controlling aspect of the mutation is the function that the subsequent immunotoxin fusion protein possesses. The most preferred mutations are those that do not detectably change toxicity or increase toxicity for the target cells but which reduce binding and toxicity to non-target cells and/or to anti-diphtheria toxin antibodies, as compared to the native toxin moiety.

There are numerous assays provided herein for determining the relative function of the disclosed immunotoxin fusion protein. These assays allow the close analysis of the desired mutations.

It is also understood that there is degeneracy in the relationship between nucleic acids and proteins so that there can be multiple nucleic acid codons for a given immunotoxin sequence. There are numerous reasons one may wish to alter the sequence of the cDNA while maintaining the unique coding of the fusion protein. For example, one may wish to insert or remove specific nucleic acid restriction enzyme sites contained or desired in the cDNA.

The invention also provides a nucleic acid encoding the immunotoxin fusion protein. For example, the nucleic acid can comprise a nucleic acid sequence that encodes the anti-T cell immunotoxin fusion protein comprising from the amino terminus, a truncated diphtheria toxin moiety and one single chain Fv (sFv) from the variable regions of the UCHT1 antibody (for example, DT390-sFv(UCHT1) and DT389-sFv (UCHT1)).

In an alternative embodiment, the nucleic acid can comprise a nucleic acid sequence that encodes an anti-T cell immunotoxin fusion protein comprising from the amino terminus, a truncated diphtheria toxin moiety and two sFv domains from the variable regions of the UCHT1 antibody, including, for example, DT390-bisFv(UCHT1) and DT389-bisFv(UCHT1).

The nucleic acid can comprise a nucleic acid sequence that encodes the immunotoxin fusion protein having a modified amino terminal (e.g., a methionine residue, an alanine residue, or a Tyr-Val-Glu-Phe (SEQ ID NO:49) sequence at its N-terminal). Optionally, the nucleic acid can comprise a nucleic acid sequence that encodes the immunotoxin fusion protein with a signal peptide (e.g., mouse κ-immunoglobulin signal peptide, the alpha mating factor signal peptide, or the Corynebacterium diphtheriae signal peptide. Optionally, the nucleic acid can further comprise a nucleic acid that encodes a histidine tag. Optionally the nucleic acid can further comprise a nucleic acid sequence that encodes a connector between the toxin moiety and the VL region. The nucleic acid can comprise a nucleic acid sequence that encodes the anti-T cell immunotoxin fusion protein, comprising, from the amino terminus, a truncated diphtheria toxin moiety, VL, L, VH, L, VL, L, VH, wherein L is a linker and wherein VL and VH are the variable light and heavy domains of the anti-CD3 antibody UCHT1.

In one embodiment, the nucleic acid can comprise the nucleic acid sequence that encodes DT389-sFv(UCHT1) or Met)DT389-sFv(UCHT1). Even more specifically, the nucleic acid can comprise the nucleic acid sequence of SEQ ID NO:40 or 41. In another embodiment, the nucleic acid can comprise a nucleic acid sequence that encodes DT390-bisFv (UCHT1). Optionally, the nucleic acid can encode a signal peptide and/or one or more mutations in the in the C-terminal $V_H$ regions of sFv. Optionally, the nucleic acid can further comprise a nucleic acid sequence that encodes DT390-bisFv (UCHT1) with a modified amino terminal, including, for example, a nucleic acid that encodes (Met)DT390-bisFv (UCHT1).

The nucleic acid can comprise a nucleic acid that encodes dmDT390-bisFv(UCHT1), wherein the dmDT390-bisFv (UCHT1) has one or more mutations that eliminate glycosylation that occurs during secretion in the mammalian system and does not occur during secretion in Corynebacterium diphtheriae. More specifically, the nucleic acid encodes mutations located at residues 18 and 235 of the protein, including, for example, Ser to Ala at residue 18 and Asn to Ala at residue 235. Optionally, the nucleic acid encodes an immunotoxin fusion protein comprising one or more mutations in the C-terminal $V_H$ region. Optionally, the nucleic acid can further comprise a nucleic acid sequence that encodes a signal peptide. In another embodiment, the nucleic acid encodes (Met)dmDT390-bisFv(UCHT1) in the presence or absence of one or more mutations in the C-terminal $V_H$ regions of sFv.

In yet another embodiment, the nucleic acid encodes (Ala) dmDT390-bisFv(UCHT1*), wherein the (Ala)dmDT390-bisFv(UCHT1*) has one or more mutations in the C-terminal $V_H$ regions of sFv. Optionally, the nucleic acid sequence is deleted of its BamH1 restriction site to allow assembly of a multi-copy vector using, for example, pAO815 Invitrogen). See U.S. Pat. No. 5,324,639, which is incorporated herein by reference in its entirety for the methods related to a multi-copy vector. Briefly, the expression cassette are cut out with BamH1 and Bgl11 and one or more copies ligated together through their cohesive ends. The ligated copies are reinserted into the vector to introduce multiple gene copies and increase production. For example, the nucleic acid can comprise the nucleic acid sequence of SEQ ID NO:30.

In another embodiment, the nucleic acid encodes (TyrVal-GluPhe)dmDT390-bisFv(UCHT1*), wherein the (TyrValGluPhe)dmDT390-bisFv(UCHT1*) further comprises four extra residues at the amino terminus (Tyr-Val-Glu-Phe) (SEQ ID NO: 49). Optionally, the nucleic acid further encodes one or more mutations in the C-terminal $V_H$ regions of sFv.

As used herein, the term "nucleic acid" refers to single- or multiple stranded molecules which may be DNA or RNA, or any combination thereof, including modifications to those nucleic acids. The nucleic acid may represent a coding strand or its complement, or any combination thereof. Nucleic acids may be identical in sequence to the sequences which are naturally occurring for any of the moieties discussed herein or may include alternative codons which encode the same amino acid as that which is found in the naturally occurring sequence. These nucleic acids can also be modified from their typical structure. Such modifications include, but are not limited to, methylated nucleic acids, the substitution of a non-bridging oxygen on the phosphate residue with either a sulfur (yielding phosphorothioate deoxynucleotides), selenium (yielding phosphorselenoate deoxynucleotides), or methyl groups (yielding methylphosphonate deoxynucleotides), a reduction in the AT content of AT rich regions, or replacement of non-preferred codon usage of the expression system to preferred codon usage of the expression system.

The nucleic acid can be directly cloned into an appropriate vector, or if desired, can be modified to facilitate the subsequent cloning steps. Such modification steps are routine, an example of which is the addition of oligonucleotide linkers which contain restriction sites to the termini of the nucleic acid. General methods are set forth in Sambrook et al., "Molecular Cloning, a Laboratory Manual," Cold Spring Harbor Laboratory Press (1989).

Once the nucleic acid sequence is obtained, the sequence encoding the specific amino acids can be modified or changed at any particular amino acid position by techniques well known in the art. For example, PCR primers can be designed which span the amino acid position or positions and which can substitute any amino acid for another amino acid. Then a nucleic acid can be amplified and inserted into the immunotoxin fusion protein coding sequence in order to obtain any of a number of possible combinations of amino acids at any position. Alternatively, one skilled in the art can introduce specific mutations at any point in a particular nucleic acid sequence through techniques for point mutagenesis. General methods are set forth in Smith, M "In vitro mutagenesis" Ann. Rev. Gen., 19:423-462 (1985) and Zoller, M. J. "New molecular biology methods for protein engineering" Curr. Opin. Struct. Biol., 1:605-610 (1991), which are incorporated herein in their entirety for the methods. These techniques can be used to alter the coding sequence without altering the amino acid sequence that is encoded.

Also provided is a vector, comprising the nucleic acid of the present invention. The vector can direct the in vivo or in vitro synthesis of the immunotoxin fusion protein. The vector is contemplated to have the necessary functional elements that direct and regulate transcription of the inserted nucleic acid. These functional elements include, but are not limited to, a promoter, regions upstream or downstream of the promoter, such as enhancers that may regulate the transcriptional activity of the promoter, an origin of replication, appropriate restriction sites to facilitate cloning of inserts adjacent to the promoter, antibiotic resistance genes or other markers which can serve to select for cells containing the vector or the vector containing the insert, RNA splice junctions, a transcription termination region, or any other region which may serve to facilitate the expression of the inserted gene or hybrid gene. (See generally, Sambrook et al.). The vector, for example, can be a plasmid. The vectors can contain genes conferring hygromycin resistance, gentamicin resistance, or other genes or phenotypes suitable for use as selectable markers, or methotrexate resistance for gene amplification. The vector can comprise the nucleic acid in pET15b, pSRα-Neo, pPICZα, or pPIC9K1.

There are numerous other *E. coli* (*Escherichia coli*) expression vectors, known to one of ordinary skill in the art, which are useful for the expression of the nucleic acid insert. Other microbial hosts suitable for use include bacilli, such as *Bacillus subtilis*, and other enterobacteriaceae, such as *Salmonella*, *Serratia*, and various *Pseudomonas* species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary, an amino terminal methionine can be provided by insertion of a Met codon 5' and in-frame with the downstream nucleic acid insert. Also, the carboxy-terminal extension of the nucleic acid insert can be removed using standard oligonucleotide mutagenesis procedures.

Also, nucleic acid modifications can be made to promote amino terminal homogeneity. Such modifications are useful in other types of immunotoxin fusion proteins having a truncated diptheria toxin moiety. Thus, the invention provides an anti-T cell immunotoxin fusion protein, comprising, from the amino terminus, a truncated diphtheria toxin moiety, a connector, and a single chain Fv of the variable region of an antibody, wherein the amino terminus is modified to promote amino terminal homogeneity upon expression by *E. coli*. The immunotoxin fusion protein with the modified amino terminal includes the immunotoxin fusion protein having an amino terminal sequence comprising MLADD (SEQ ID NO: 106), MLDD (SEQ ID NO:107), or SADD (SEQ ID NO:108).

Additionally, yeast expression can be used. The invention provides a nucleic acid encoding a diphtheria toxin-containing fusion protein, wherein the nucleic acid can be expressed by a yeast cell. More specifically, the nucleic acid can be expressed by *Pichia pastoris* or *S. cerevisiae*. The nucleic capable of being expressed by yeast, comprises a modified native diphtheria-encoding sequence. More specifically, one or more AT rich regions of the native diphtheria-encoding sequence are modified to reduce the AT content. The AT rich regions include regions of at least 150 contiguous nucleotides having an AT content of at least 60% or regions of at least 90 contiguous nucleotides having an AT content of at least 65%, and the AT content of the AT rich regions is preferably reduced to 55% or lower. The AT rich regions also include regions of at least 150 contiguous nucleotides having an AT content of at least 63% or regions of at least 90 contiguous nucleotides having an AT content of at least 68%, and the AT content of the AT rich regions is reduced to 55% or lower. The native diphtheria-encoding sequence preferably is further modified to encode a diphtheria toxin truncated at its C-terminal. Furthermore, the native diphtheria-encoding sequence preferably is further modified to encode one or more amino acids prior to the amino terminal glycine residue of the native diphtheria toxin. Furthermore, the native diphtheria-encoding sequence preferably is further modified to encode the alpha mating factor signal peptide or a portion thereof.

AT rich regions in the non-toxin moiety (e.g., sFv or bisFv) can also be modified to further promote yeast expression. For example, in FIG. 38, the double underlining in the line of amino acids indicates AT-rich regions, which are still left in the gene of interest after the rebuilding work described in Example 23. The underlining in the reb (rebuilt) line indicates regions that were rebuilt, including regions in the Fv domains. In one embodiment, for example, the nucleic acid comprises the nucleic acid sequence of SEQ ID NO: 102.

In yet another embodiment, the nucleic acid is modified to promote yeast expression such that one or more regions of the nucleic acid that include non-preferred codon usages are modified to include preferred codon usages to promote expression of the encoded immunotoxin fusion protein by yeast. Each species has preferred codons for efficient protein translation, and codon optimization can increase expression levels. Table 15 shows the frequency of codon usage in highly expressed *P. pastoris* genes. By "preferred codon" is meant a codon that is used 30% or more in AOX1, AOX2, dihydroxy acetone synthetase 1 and 2, and glyceraldehydes phosphate dihydrogenase genes for a given amino acid. By "non-preferred codon" is meant a codon that is used less than 30% in AOX1, AOX2, dihydroxy acetone synthetase 1 and 2, and glyceraldehydes phosphate dihydrogenase genes for a given amino acid. FIG. 38 shows an example of regions encoded by non-preferred codons (see stars). One or more of these non-preferred codons are replaced with preferred codons. In one embodiment, for example, the nucleic acid comprises the nucleic acid sequence of SEQ ID NO: 102.

There are several advantages to yeast expression systems, which include, for example, *Saccharomyces cerevisiae* and *Pichia pastoris*. First, evidence exists that proteins produced in a yeast secretion systems exhibit correct disulfide pairing. Second, efficient large scale production can be carried out using yeast expression systems. The *Saccharomyces cerevisiae* pre-pro-alpha mating factor leader region (encoded by the MFα-1 gene) can be used to direct protein secretion from yeast (Brake, et al. (82)). The leader region of pre-pro-alpha mating factor contains a signal peptide and a pro-segment which includes a recognition sequence for a yeast protease encoded by the KEX2 gene: this enzyme cleaves the precursor protein on the carboxyl side of a Lys-Arg dipeptide cleavage signal sequence. The nucleic acid coding sequence can be fused in-frame to the pre-pro-alpha mating factor leader region. This construct can be put under the control of a strong transcription promoter, such as the alcohol dehydrogenase I promoter, alcohol oxidase I promoter, a glycolytic promoter, or a promoter for the galactose utilization pathway. The nucleic acid coding sequence is followed by a translation termination codon which is followed by transcription termination signals. Alternatively, the nucleic acid coding sequences can be fused to a second protein coding sequence, such as Sj26 or beta-galactosidase, used to facilitate purification of the fusion protein by affinity chromatography. The insertion of protease cleavage sites to separate the components of the fusion protein is applicable to constructs used for expression in yeast.

Diphtheria toxin is toxic to yeast when the toxin A chain is synthesized within the cytosol compartment without a secretory signal (Perentesis et al., 1988). This toxin-catalyzed activity is specific for EF-2 and occurs at a unique post-translational histidine residue at the position 699, found in a conserved amino acid sequence in the EF-2 of all eukaryotes. According to mutagenesis studies, change of glycine to arginine residue at the position 701 in yeast EF-2 results in resistance to DT. Therefore a mutated yeast EF-2 gene from *S. cerevisiae* was made by site-directed mutagenesis (FIG. 31) and constructed into pGAPZ vector used for expressing constitutively mEF-2 gene product under control of promoter of GAPD (glyceraldehyde-3-phosphate dehydrogenase) gene. Strain KM71 was transformed by this vector and the presence of mutated EF-2 was confirmed by the absence of the Bst XI site deleted by the mutagenesis. (Ala)dmDT390-bisFv (UCHT1) was then transformed into this mEF-2 containing strain and the double transformants were selected by His+ and the G418 selection.

The surprising result of these studies was the fact that (Ala)dmDT390-bisFv(UCHT1*) was produced in the *Pichia* medium at a level of 5 mg/μl whether or not the mutant EF-2 gene was present. This was contrary to the case in CHO cells where production of (Ala)dmDT390-bisFv(UCHT1*) was not achieved in wild type CHO cells that contained toxin sensitive EF-2. This was also contrary to a previous study in yeast mentioned above. However, the alpha-mating factor signal sequence was used in production in *Pichia*. This indicates an extremely tight coupling between the presence of the alpha-mating factor signal sequence and the compartmentalization of (Ala)dmDT390-bisFv(UCHT1*) into the secretory pathway and away from the EF-2 toxin substrate in the cytosol compartment, since one molecule of toxin in the cytosol can inactivate 99% of the EF-2 in 24 hours. The successful outcome of producing (Ala)dmDT390-bisFv(UCHT1*) in *Pichia* utilizing the alpha-mating factor signal sequence without mutating the *Pichia* to toxin resistance was novel and unobvious. Another combination of a yeast produced toxin (ricin A chain) and signal sequence, Kar2, resulted in death of the producing cells (Simpson et al., 1999 (80)). It is possible that, at higher gene dosages of immunotoxin fusion protein in *Pichia*, mEF-2 may confer a benefit in production. A further advantage of yeast over mammalian cells for immunotoxin fusion protein production is the fact that intact yeast are highly resistant to diphtheria toxin present in the external medium to levels as high as $3.3 \times 10^{-6}$ M. Evidently the yeast capsule prevents retrograde transport of toxin back into the cytosol compartment as occurs in mammalian cells and in yeast spheroplasts (Chen et al. 1985 (81)).

The invention also provides a cell comprising the nucleic acid that encodes the immunotoxin fusion protein. The cell can be a prokaryotic cell, including, for example, a bacterial cell. More particularly, the bacterial cell can be an *E. coli* cell. Alternatively, the cell can be a eukaryotic cell, including, for example, a Chinese hamster ovary (CHO) cell (including for example, the DT resistance CHO-K1 RE 1.22c cell line, as selected by Moehring & Moehring (73)), myeloma cell, a *Pichia* cell, or an insect cell. The immunotoxin fusion protein coding sequence can be introduced into a Chinese hamster ovary (CHO) cell line, for example, using a methotrexate resistance-encoding vector, or other cell lines using suitable selection markers. Presence of the vector DNA in transformed cells can be confirmed by Southern blot analysis. Production of RNA corresponding to the insert coding sequence can be confirmed by Northern blot analysis. A number of other suitable host cell lines have been developed and include myeloma cell lines, fibroblast cell lines, and a variety of tumor cell lines such as melanoma cell lines. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the nucleic acid segments of interest can be transferred into the host cell by well-known methods, which vary depending on the type of cellular host. For example, calcium chloride transformation is commonly utilized for prokaryotic cells, whereas calcium phosphate, DEAE dextran, or lipofectin mediated transfection or electroporation may be used for other cellular hosts.

The nucleic acids of the present invention can be operatively linked to one or more of the functional elements that direct and regulate transcription of the inserted nucleic acid and the nucleic acid can be expressed. For example, a nucleic acid can be operatively linked to a bacterial or phage promoter and used to direct the transcription of the nucleic acid in vitro.

To promote expression of the nucleic acids of the present invention by yeast cells, regions of the nucleic acid rich in A and T nucleotides are modified to permit expression of the encoded immunotoxin fusion protein by yeast. For example, such modification permit expression by *Pichia pastoris*. The modifications are designed to inhibit polyadenylation signals and/or to decrease early termination of RNA transcription. By the term "regions of the nucleic acid rich in A and T" or "AT rich regions" is meant regions of about 90 or more contiguous nucleotides having an AT content of at least about 60%. More preferably, "regions of the nucleic acid rich in A and T" or "AT rich regions regions" are regions of at least 150 contiguous nucleotides having an AT content of at least 60-65% or regions of at least 90 contiguous nucleotides having an AT content of at least 65-70%. The modifications of the AT rich region preferably reduce the AT content of those regions to 55% or lower, including for example, 50%, 45%, 40%, 35%, 30%, 25%, 20%, 10%, 5%, 0% or any amount in between. For example, the AT rich regions can be regions of at least 150 contiguous nucleotides having an AT content of at least 63% or regions of at least 90 contiguous nucleotides having an AT content of at least 68%, and the modification reduces the AT content of those regions to 55% or lower. Thus, the nucleic acids modified for expression by yeast cells can comprise the nucleic acid sequence that encodes sp-(Ala)dmDT390-bisFv (UCHT1*) (SEQ ID NO:30), the nucleic acid sequence that encodes sp-dmDT390-bisFv(UCHT1*) (SEQ ID NO:31), or the nucleic acid sequence that encodes sp-(TyrValGluPhe) dmDT390-bisFv(UCHT1*) (SEQ ID NO:32), wherein the signal peptide is alpha mating factor signal peptide sequence up to the Kex2 signal cleavage site. The modified nucleic acids are preferably expressed in *Pichia pastoris* cells or in CHO cells.

Therapeutic Uses of the Anti-T Cell Immunotoxin Fusion Proteins

The immunotoxin fusion proteins described herein are utilized to effect at least partial T-cell depletion in order to treat or prevent T-cell mediated diseases or conditions of the immune system. The immunotoxin fusion proteins may be utilized in methods carried out in vivo, in order to systemically reduce populations of T cells in a subject. The immunotoxin fusion proteins may also be utilized ex vivo in order to effect T-cell depletion from a treated cell population.

In Vivo Applications

It is within the scope of the present invention to provide a prophylaxis or treatment for T-cell mediated diseases or conditions by administering immunotoxin fusion protein to a subject in vivo for the purpose of systemically killing T cells in the subject, and as a component of a preparation or conditioning regimen or induction tolerance treatment in connection with bone marrow or stem cell transplantation, or solid organ transplantation from either a human (allo-) or non-human (xeno-) source.

For example, the immunotoxin fusion proteins can usefully be administered to a subject who is or will be a recipient of an allotransplant (or xenotransplant), in order to effect T-cell depletion in the subject and thereby prevent or reduce T-cell mediated acute or chronic transplant rejection of the transplanted allogeneic (or xenogeneic) cells, tissue or organ in the subject.

The immunotoxin fusion protein can be administered in vivo either alone or in combination with other pharmaceutical agents effective in treating acute or chronic transplant rejection including cyclosporin A, cyclosporin G, rapamycin, 40-O-2-hydroxyethyl-substituted rapamycin, FK-506, mycophenolic acid, mycophenolate mofetil (MMF), cyclophosphamide, azathioprene, brequinar, leflunamide, mizoribine, a deoxyspergualine compound or derivative or analog thereof (e.g., 15-DSG), 2-amino-2-[2-(4-octylphenyl)ethyl] propane-1,3-diol (FTY 720) (preferably as a hydrochloride salt), corticosteroids (e.g., methotrexate, prednisolone, methylprednisolone, dexamethasone), or other immunomodulatory compounds (e.g., CTLA4-Ig); anti-LFA-1 or anti-ICAM antibodies, or other antibodies that prevent co-stimulation of T cells, for example antibodies to leukocyte receptors or their ligands (e.g., antibodies to MHC, CD2, CD3, CD4, CD7, CD25, CD28, B7, CD40, CD45, CD58, CD152 (CTLA-4), or CD 154 (CD40 ligand).

In particular, prolonged graft acceptance and even apparent immunologic tolerance can be achieved by combined administration of an anti-CD3 immunotoxin of the invention and a spergualin derivative, such as a deoxyspergualine compound, or other spergualin analog, and this invention, in a preferred embodiment, comprises the combined administration of anti-CD3 immunotoxin and a deoxyspergualine compound in a tolerance induction regimen, see for example, Eckhoff et al., abstract presented to American Society of Transplant Surgeons, May 15, 1997, and Contreras, et al., Transplantation 65:1159 (1998), both incorporated by reference herein for the regimen. The term "deoxyspergualine compound" includes 15-deoxy-spergualin (referred to as "DSG", and also known as gusperimus), i.e., N-[4-(3-aminopropyl)aminobutyl]-2-(7-N-guanidinoheptanamido)-2-hydroxyethanamide, and its pharmaceutically acceptable salts, as disclosed in U.S. Pat. No. 4,518,532, incorporated by reference in its entirety for deoxyspergualine compounds; and in particular (−)-15-deoxyspergualin and its pharmaceutically acceptable salts as disclosed in U.S. Pat. No. 4,525,299, incorporated by reference in its entirety for (−)-15-deoxyspergualin and its pharmaceutically acceptable salts. The optically active (S)-(−) or (R)-(+)-15-deoxyspergualin isomers and salts thereof are disclosed in U.S. Pat. No. 5,869,734 and EP 765,866, both incorporated by reference; and the trihydrochloride form of DSG is disclosed in U.S. Pat. No. 5,162,581, incorporated by reference.

Other spergualin derivatives for use with anti-CD3 immunotoxin in a tolerance induction regimen include compounds disclosed in U.S. Pat. No. 4,658,058, U.S. Pat. No. 4,956,504, U.S. Pat. No. 4,983,328, U.S. Pat. No. 4,529,549; and EP 213,526, EP 212,606, all incorporated by reference.

The invention in a further preferred embodiment comprises the combined administration of an anti-CD3 immunotoxin according to the invention and still other spergualin analogs, such as compounds disclosed in U.S. Pat. No. 5,476,870 and EP 600,762, both incorporated by reference, e.g.,

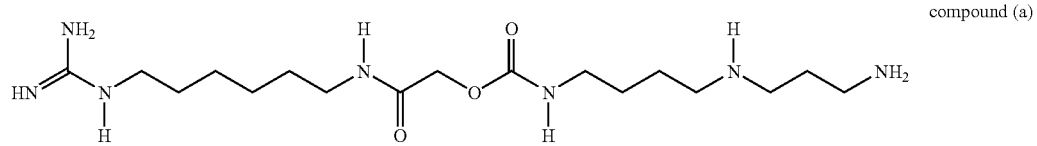

compound (a)

i.e. 2-[[[4-[[3-(Amino)propyl]amino]butyl]amino]carbonyloxy]-N-[6-[(aminoiminomethyl)-amino]hexyl]acetamide ("tresperimus") and its pharmaceutically acceptable addition salts with a mineral or organic acid; compounds disclosed in U.S. Pat. No. 5,637,613 and EP 669,316, both incorporated by reference, and, e.g.,

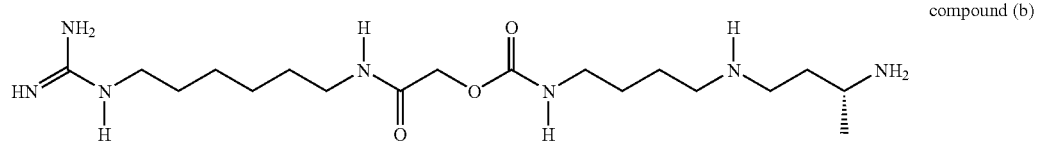

compound (b)

i.e. 2-[[[4-[[3(R)-(Amino)butyl]amino]butyl]amino carbonyloxy]-N-[6-[(aminoiminomethyl)amino]hexyl]acetamide tris(trifluoroacetate) and other pharmaceutically acceptable salts thereof. Pharmaceutically acceptable salts of the above compounds include salts with a mineral acid or an organic acid, including (with respect to mineral acids) hydrochloric, hydrobromic, sulfuric and phosphoric acid, and (with respect to organic acids) fumaric, maleic, methanesulfonic, oxalic and citric; compounds disclosed in U.S. Pat. No. 5,733,928 and EP 743,300, both incorporated by reference; compounds disclosed in U.S. Pat. No. 5,883,132 and EP 755,380, both incorporated by reference; and compounds disclosed in U.S. Pat. No. 5,505,715 (e.g., col. 4, I. 44-col. 5, I. 45), incorporated by reference.

By "combined administration" is meant treatment of the organ transplant recipient with both an anti-CD3 immunotoxin of the invention and the spergualin derivative or analog. Administration of the immunotoxin and the spergualin derivative or analog need not be carried out simultaneously, but rather may be separated in time. Typically, however, the course of administration of the immunotoxin and the spergualin related compound will be overlapping to at least some extent.

The total dose of the anti-CD3 immunotoxin is preferably given over 2-3 injections, the first dose preceding the transplant by the maximal time practicable, with subsequent injections spaced by intervals of, for example, about 24 h. The immunotoxin is preferably administered prior to transplant and at the time of and/or following transplant. In allotransplantation, administration of the anti-CD3 immunotoxin preferably precedes transplant surgery by about 2-6 h, whereas for xenotransplantation or living related allotransplantation, the first anti-CD3 immunotoxin injection may precede transplantation by as much as one week, see for example, Knechtle et al. [Transplantation 63:1 (1997)]. In a tolerance induction regimen, the immunotoxin treatment is preferably curtailed no later than about 14 days, and preferably on about day 7, or on day 5, or even on day 3, post-transplant.

The spergualin derivative or analog may be administered prior to transplant, at the time of transplant, and/or following transplant. The length of treatment either before or after transplant may vary. In a tolerance induction regimen, the treatment with spergualin derivative or analog compound is preferably withdrawn not later than about 120 days following transplant, and more preferably after about 60 days post-transplant, and more preferably after about 30 days, and even more preferably not later than 14, or even about 10 days, post-transplant. Thus, the term "combined administration" includes within its scope a treatment regimen wherein, for example, one or more doses of immunotoxin is/are administered prior to the transplant, followed by one or more doses commencing at around the time of transplant; together with administration of the spergualin derivative or analog also prior to and/or at the time of transplant, and typically continuing after transplant.

Corticosteroids such as methylprednisolone may be incorporated into the combined administration regimen. For example, steroid administration may commence prior to transplant, and may continue with one or more doses thereafter. The anti-CD3 immunotoxin of the invention is preferably provided in a dose sufficient to reduce the T-cell number in a patient by 2-3 logs. A total effective dosage to reduce the T-cell number in a patient by 2-3 logs in accordance herewith may be between about 50 μg/kg and about 10 mg/kg body weight of the subject, and more preferably between about 0.1 mg/kg and 1 mg/kg. A dosage regimen for an induction treatment with the spergualin derivative or analog may be between 1 and 10 mg/kg/day for 0-30 days, optimally, for example about 2.5 mg/kg/day for 15 days. Additional steroids may be administered at the time of the anti-CD3 immunotoxin injections, for example as a decreasing regimen of methylprednisone, such as 7 mg/kg on the day of the transplant surgery, 3.5 mg/kg at +24 h, and 0.35 mg/kg at +48 h. Alternatively, the steroid dosage may be held constant, for example treatment with 40 mg/kg of prednisone at the time of immunotoxin injection. It is understood that the exact amount and choice of steroid can vary, consistent with standard clinical practice.

In a preferred embodiment of the combination therapy of the invention, the immunotoxin of the combined therapy is DT90-bisFv(UCHT1) and is, in particular, an immunotoxin having the sequence of SEQ ID NO:19, 20, 17, 18, 27, 26, 49, 28, or 102. Said DT90-bisFv(UCHT1) is preferably co-administered with 15-deoxyspergualine, and especially, (–)-15-deoxyspergualin. In another aspect, said DT90-bisFv (UCHT1) is co-administered with the abovementioned compound (a). In a still further embodiment, said DT90-bisFv(UCHT1) is co-administered with the abovementioned compound (b).

In the practice of the above combination therapy and the other methods of this invention in the context of xenotransplantation, and especially where the transplant recipient is human, the donor cells, tissues or organs are preferably porcine, and are most preferably recruited from transgenic, e.g., human DAF expressing, pigs.

In another embodiment of the methods of the invention, the immunotoxin fusion proteins can be administered in vivo to a bone marrow recipient for prophylaxis or treatment of host-versus-graft disease through killing of host (i.e., a bone marrow transplant recipient) T cells.

As previously indicated, this invention also contemplates a method of prophylaxis or treatment of GVHD in a bone marrow transplant recipient.

In a further embodiment, the anti-CD3 immunotoxin of the invention can be administered to a subject in need thereof to treat still other T-cell mediated pathologies, such as T-cell leukemias and lymphomas. Clinical treatment of T-cell leukemias and lymphomas typically relies on whole body irradiation to indiscriminately kill lymphoid cells of a subject, followed by bone marrow replacement. An immunotoxin of the invention administered to a subject suffering from leukemia/lymphoma can replace whole body radiation with a selective means of eliminating T-cells.

In additional aspects of the invention, the immunotoxins of the invention may also be administered to a subject in vivo to treat T-cell-mediated autoimmune disease, such as systemic lupus erythematosus (SLE), type I diabetes, rheumatoid arthritis (RA), myasthenia gravis, and multiple sclerosis, by ablating populations of T cells in the subject.

The immunotoxin fusion protein can also be administered to a subject afflicted with an infectious disease of the immune system, such as acquired immune deficiency syndrome (AIDS), in an amount sufficient to deplete the subject of infected T-cells and thereby inhibit replication of HIV-1 in the subject.

Additionally, the immunotoxin fusion protein can be administered to subjects to treat conditions or diseases in instances in which chronic immunosuppression is not acceptable, e.g., by facilitating islet or hepatocyte transplants in subjects with diabetes or metabolic diseases, respectively. Diseases and susceptibilities correctable with hepatocyte transplants include hemophilia, αa1-antitrypsin insufficiencies, and hyperbilirubinemias.

In the methods of the invention, the subject is preferably human and the donor may be allogeneic (i.e. human) or xenogeneic (e.g., swine). The transplant may be an unmodified or modified organ, tissue or cell transplant, e.g., heart, lung, combined heart-lung, trachea, liver, kidney, pancreas, islet cell, bowel (e.g., small bowel), skin, muscles or limb, bone marrow, esophagus, cornea or neural tissue transplant.

For in vivo applications, the immunotoxin fusion protein will be administered to the subject in an amount effective to kill at least a portion of the targeted population of CD3-bearing cells (i.e. T-cells). In general, an effective amount of immunotoxin fusion protein will deplete a targeted population of T cells, i.e. in the lymph system and/or peripheral blood, by 1 or more logs, and more preferably by at least about 2 logs, and even more preferably by at least 2-3 logs. The most effective mode of administration and dosage regimen depends on the severity and course of the disease, the subject's health and response to treatment and the judgment of the treating physician. Thus the dosages of the molecules should be titrated to the individual subject. In general, a total effective dosage to reduce the T-cell number in a subject by 2-3 logs in accordance with the methods of the invention is about 10 μg/kg and about 10 mg/kg body weight of the subject, and more preferably between about 10 μg/kg and 600 μg/kg body weight of the subject based on toxin content over a 1-4 day period. The levels of CD3-bearing cells, and in particular, of T cells, in the treated subject's bone marrow, blood or lymphoid tissues, can be assayed by FACS analysis.

It is envisaged that, in the course of the disease state, the dosage and timing of administration may vary. Initial administrations of the composition may be at higher dosages within the above ranges, and administered more frequently than administrations later in the treatment of the disease.

Ex Vivo Applications

It is also within the scope of the present invention to utilize the immunotoxin fusion protein for purposes of ex vivo depletion of T cells from isolated cell populations removed from the body. In one aspect, the immunotoxin fusion protein can be used in a method for prophylaxis of organ transplant rejection, wherein the method comprises perfusing the donor organ (e.g., heart, lung, kidney, liver) prior to transplant into the recipient with a composition comprising a T-cell depleting effective amount of immunotoxin fusion protein, in order to purge the organ of sequestered donor T-cells.

In another embodiment of the invention, the immunotoxin fusion protein can be utilized ex vivo in an autologous therapy to treat T cell leukemia/lymphoma or other T-cell mediated diseases or conditions by purging subject cell populations (e.g., bone marrow) of cancerous or otherwise affected T-cells with immunotoxin, and reinfusing the T-cell-depleted cell population into the subject.

In particular, such a method of treatment comprises: recruiting from the subject a cell population comprising CD3-bearing cells (e.g., bone marrow); treating the cell population with a T-cell depleting effective amount of immunotoxin fusion protein; and infusing the treated cell population into the subject (e.g., into the blood).

A still further application of such an autologous therapy comprises a method of treating a subject infected with HIV.

According to still another embodiment of the invention, the immunotoxin fusion protein can be utilized ex vivo for purposes of effecting T cell depletion from a donor cell population as a prophylaxis against graft versus host disease, and induction of tolerance, in a subject to undergo a bone marrow transplant. Such a method comprises: providing a cell composition comprising isolated bone marrow and/or stem cell-enriched peripheral blood cells of a suitable donor (i.e. an allogeneic donor having appropriate MHC, HLA-matching); treating the cell composition with an effective amount of immunotoxin to form an inoculum at least partially depleted of viable CD3-bearing cells (i.e. T-cells); and introducing the treated inoculum into the subject.

The immunotoxin fusion protein may be incubated with CD3-expressing cells in culture at a concentration of, e.g., about 0.5 to 50,000 ng/ml in order to kill CD3-bearing cells in said culture.

In a further aspect, the above ex vivo therapeutic methods can be combined with in vivo administration of immunotoxin fusion protein, to provide improved methods of treating or preventing rejection in bone marrow transplant recipients, and for achieving immunological tolerance.

The in vivo and ex vivo methods of the invention as described above are suitable for the treatment of diseases curable or treatable by bone marrow transplantation, including leukemias, such as acute lymphoblastic leukemia (ALL), acute nonlymphoblastic leukemia (ANLL), acute myelocytic leukemia (AML), and chronic myelocytic leukemia (CML), cutaneous T-cell lymphoma, severe combined immunodeficiency syndromes (SCID), osteoporosis, aplastic anemia, Gaucher's disease, thalassemia, mycosis fungoides (MF), Sezany syndrome (SS), and other congenital or genetically-determined hematopoietic abnormalities.

In particular, it is also within the scope of this invention to utilize the immunotoxin fusion proteins as agents to induce donor-specific and antigen-specific tolerance in connection with allogeneic or xenogeneic cell therapy or tissue or organ transplantation. Thus, the immunotoxin can be administered as part of a conditioning regimen to induce immunological tolerance in the subject to the donor cells, tissue or organ, e.g., heart, lung, combined heart-lung, trachea, liver, kidney, pancreas, Islet cell, bowel (e.g., small bowel), skin, muscles or limb, bone marrow, esophagus, cornea or neural tissue.

Thus the present invention further contemplates a method of conditioning a subject to be transplanted with donor cells, or a tissue or organ. The method comprises the steps of (a) reducing levels of viable CD3-bearing (i.e. T cells) in the subject (i.e. in the peripheral blood or lymph system of the subject); (b) providing an inoculum comprising isolated hematopoietic cells (i.e. bone marrow and/or stem-cell enriched peripheral blood cells) of the donor treated with a T-cell depleting effective amount of immunotoxin; (c) introducing the inoculum into the subject; and thereafter, (d) transplanting the donor cells, tissue or organ into the subject.

The above method is preferably carried out in the absence of total body irradiation or total lymphoid irradiation and most preferably, in the absence of any radiation.

Example 1

Establishment of Tumors

The experimental design of the studies that give rise to the present invention was dictated by the goal of having an animal model as closely relevant to human in vivo tumor therapy as possible. In order to minimize the host killer cell immune response, bg/nu/xid strain of nude mice were used (Kamel-Reid and Dick (1988) *Science* 242:1706). The human T cell leukemia cell line, Jurkat, was chosen because of previous studies with this line and its relatively normal average complement of CD3 receptors (Preijers et al. (1988) *Scand. J. Immunol.* 27:553). The line was not cloned so that receptor variation among individual cells existed. A scheme was developed whereby well established tumors of constant mass equal to 0.1% of body weight (=4×10$^7$ cells) could be achieved 7 days after inoculation of Jurkat cells (see Dillman et al. (1988) *Cancer Res.* 15:5632). This required prior irradiation and inoculation with lethally irradiated helper feeder cells (see Dillman et al. (1988) *Cancer Res.* 15:5632).

Nude mice bg/nu/xid maintained in a semi-sterile environment are preconditioned with 400 cGy whole body $^{137}$CS γ radiation on day −7. On day 0, 2.5×10$^7$ Jurkat cells (human T cell leukemia CD3+, CD4+, CD5+) are injected subcutaneously with 1×10$^7$ HT-1080 feeder cells (human sarcoma) which have received 6000 cGy. Jurkat cells were passaged every other week in mice as subcutaneous tumors and dissociated by collagenase/dispase prior to inoculation. This cell population exhibits a 40% inhibition of protein synthesis after 5 hours exposure to 10$^{11}$ M anti-CD3-DT. Clones isolated from this population by infinite dilution exhibit varying sensitivity to anti-CD3DT (4 less sensitive, 3 more sensitive) corresponding to a 1.5 log variation in dose response curves. Immunotoxin treatment is given by intraperitoneal injection starting on day 7 when the tumor is visibly established. Evaluation takes place on day 37.

Example 2

Guinea Pig Studies

Immunotoxin toxicity studies were performed in guinea pigs, an animal (like humans) with a high sensitivity to diphtheria toxin (mice are highly resistant to diphtheria toxin). Therapy of CRM9 conjugates was set at ½ the guinea pig minimum lethal dose. In this study, minimum lethal dose (MLD) is defined as the minimum tested dose which results in both non-survivors and survivors over a 4 week evaluation period. All animals survive when a MLD is reduced by 0.5. MLD was evaluated in guinea pigs (300-1000 g) by subcutaneous injection. The following MLDs were found and are listed as µg of toxin/kg body weight; DT, 0.15; CRM9, 30; anti-CD5-DT (cleavable), 0.65; anti-CD5-CRM9 (non-cleavable), 150. Finally, the therapeutic efficacy of the immunotoxin treatment in producing tumor regressions was compared to graded doses of whole body irradiation which resulted in similar tumor regressions.

Example 3

Comparison of Immunotoxins

Several types of immunotoxins were compared in this study. They were synthesized as previously described by thiolating both the monoclonal antibody moiety and the toxin moiety and then crosslinking the bismaleimide crosslinkers (Neville et al. (1989) *J. Biol. Chem.* 264:14653). Purification was performed by, size exclusion HPLC columns and fractions containing 1:1 toxin:antibody mol ratios were isolated for these studies. Conjugates made with an acid-labile crosslinker bismaleimidoethoxy propane were compared with a non-cleavable, bismaleimidohexane. Conjugates made with this cleavable crosslinker have been shown to hydrolyze within the acidifying endosome releasing free toxin moieties with half-times of hydrolysis measured at pH 5.5 of 36 min (Neville et al. (1989) *J. Biol. Chem.* 264:14653).

The results of this study are tabulated in Table 2. Non-treatment groups such as group 10, groups treated with anti-CD5 immunotoxins (groups 5 and 6), and group 4 treated with a mixture of anti-CD3 and CRM9 did not show regression. The vascularized tumor nodules that weighed 20 mg on day 7 grew to between 1.5 to 7.8 g on day 37 and weighed between 7.9 and 11.6 on day 56. No late spontaneous regressions were noted. In contrast, group 1 consisting of treatment with anti-CD3-CRM9 non-cleavable conjugate (NC) given at 25 µg/kg on days 7, 8, and 9 showed only 1 tumor out of 6 by day 37. Some of the remaining animals were subject to autopsy and they failed to reveal residual tumor or even scaring. Tumors identified as regressed on day 37 by superficial inspection did not reappear during the course of the study (56 days).

TABLE 2

IMMUNOTOXIN AND RADIATION TREATMENT ON SUBCUTANEOUS HUMAN T CELL TUMORS (JURKAT) IN NUDE MICE

| Group | Treatment | Dose (intraperitoneal) | Animals Bearing Tumors At Day 37/Group Animals | % Tumor Regressions |
|---|---|---|---|---|
| 1 | Anti-CD3 – CRM9 (NC)[a] | 25 µg/kg. × 3d | 1/6 | 83 |
| 2 | Anti-CD3 – CRM9 (NC) Anti-CD5 – CRM9 (C) | 19 µg/kg. × 2d 19 µg/kg. × 2d | 1/4 | 75 |
| 3 | Anti-CD3 – CRM9 (C) | 25 µg/kg. × 3d | 2/4 | 50 |
| 4 | Anti-CD3 + CRM9 | 25 µg/kg. × 3d | 4/4 | 0 |
| 5 | Anti-CD5 – CRM9 (C) | 25 µg/kg. × 3d | 5/5 | 0 |
| 6 | Anti-CD5 – DT (NC) | 25 µg/kg. × 1d | 9/9 | 0 |
| 7 | γradiation $^{137}$Cs | 400 cGy | 2/2 | 0 |
| 8 | γradiation $^{137}$Cs | 500 cGy | 3/6 | 50 |
| 9 | γradiation $^{137}$Cs | 600 cGy | 0/2[b] | 100 |
| 10 | None | | 6/6 | 0 |

[a] Anti-CD3 refers to the monoclonal antibody UCHT1 and was purchased from Oxoid USA, Inc. Anti-CD5 refers to the monoclonal antibody T101 and was a gift from Hybritech (San Diego). NC and C refer, respectively, to non-cleavable and cleavable conjugates.
[b] These animals were evaluated on days 10 and 13 at the time of death from radiation sickness.

The cleavable crosslinker confers no therapeutic advantage to anti-CD3-CRM9 immunotoxins and may be less effective (group 3). Cleavable crosslinkers confer some advantage with anti-CD5-CRM9 conjugate in vitro (5) but had no effect in this in vivo system (group 5), and lacked significant potentiating effect when administered with anti-CD3-CRM9 (group 2). The cleavable crosslinker conferred a marked therapeutic advantage to anti-CD5 wild type toxin conjugates and tumor regressions were achieved. However, in these cases the guinea pig toxic dose was exceeded. A single dose on day 7 of cleavable anti-CD5-DT at 6 µg/kg produced 8/10 tumor regressions while a cleavable conjugate made with an irrelevant antibody (OX8) produced no regressions (4/4). However, this dose exceeded the guinea pig MLD by 9 fold. A rescue strategy was tried in which the above conjugate dose was given intravenously followed by DT antitoxin 4 hours later (also intravenously). The 4 hr rescue could not raise the MLD above 0.65 µg/kg. The 1 hr rescue could not raise the MLD above 0.65 µg/kg. The 1 hr rescue raised the MLD to 36 µg/kg, however, there were no tumor regressions in 10 mice receiving 21.5 µg/kg of the cleavable anti-CD5-DT conjugate.

In groups 7-9 increasing single doses of whole body radiation (102 cGy/min) were given to animals bearing 3×3×5 mm tumors. At 400 cGy no complete regressions occurred. At 500 cGy 50% complete tumor regressions occurred. At 600 cGy 100% regression was achieved as judged on day 10 and 13 when the animals died from radiation sickness. (Groups 7-9 did not receive prior radiation and tumor takes were less than 100%). It appears that the 75 µg/kg anti-CD3-CRM9 (NC) immunotoxin is equal in therapeutic power to between 500 and 600 cGy of radiation.

Example 4

Estimation of Cell Kill

The actual cell kill achieved by the radiation and the immunotoxin can be estimated by assuming radiation single hit inactivation kinetics along with a $D_{37}$ value for the radiation. A value for $D_{37}$ of 70-80 cGy with n=1.2-3 is not unreasonable for a rapidly dividing helper T cell. $D_{37}$ is the dose of radiation which reduces the fraction of surviving cells to 1/e as extrapolated from the linear portion of the log survivors vs. dose curve and n is the intercept at 0 dose (Anderson and Warner (1976) in *Adv. Immunol.*, Academic Press Inc., 24:257). At a dose of 550 cGy the fraction of surviving cells is calculated to be about $10^3$. Since a majority of tumors completely regress at this dose we estimate that both therapies are producing an approximate 3 log kill. (The remaining cells, $4 \times 10^7 \times 10^3 = 4 \times 10^4$ cells apparently cannot maintain the tumor, i.e., the in vivo plating efficiency is low, a fairly typical situation in the nude mouse xenograft system.) The reliability of this 3 log kill estimate has been verified by determining the tissue culture plating efficiency by limiting dilution of 7 day established Jurkat tumors (following dispersal) and tumors exposed 18 hours earlier in vivo to 600 cGy. Plating efficiencies were 0.14 and $1.4 \times 10^4$, respectively. (Plating efficiency is the reciprocal of the minimum average number of cells per well which will grow to form one colony.

It should be emphasized that with high affinity holo-immunotoxins the cell kill is inversely proportional to the target cell number. This presumably occurs because receptors are undersaturated at tolerated doses and free conjugate concentration falls with increasing target cell burden (Marsh and Neville (1987) *Ann. N.Y. Acad. Sci.* 507:165; Yan et al. (1991) *Bioconjugate Chem.* 2:207). To put this in perspective, the tumor burden in this study is almost equal to the number of T cells in a mouse ($\approx 10^8$). It can be expected that a tolerated dose of anti-CD3-CRM9 immunotoxin can achieve an in vivo 3 log depletion of a normal number of CD3 positive T cells.

Example 5

Cell Depletion in Rhesus Monkeys Induced by FN18-CRM9

FN18-CRM9 Conjugate

The monoclonal antibody FN18 is the monkey equivalent of the human anti-CD3 (UCHT1) and is known to bind the same CD3 receptor epitopes (E and y) as bound by the human CD3 antibody and is the same isotype as the human CD3 antibody. Thus, in terms of the parameters relevant for predicting successful T cell depletion, the present CD3-CRM9 conjugate and FN18-CRM9 are expected to have the same activity.

Administration

Conjugates can be administered as an I.V. bolus in a carrier consisting of 0.1 M $Na_2SO_4$ + 0.01 M phosphate buffer, pH 7.4. The dose schedule is every other or third day for about 3 days. The total dose is preferably from 50 to 200 micrograms of toxin per kg of body weight.

The actual dose of FN18-CRM9 used was varied between 0.167-1.13 of the minimum lethal dose (MLD) in guinea pigs. Since the estimation of the MLD was performed in an animal lacking an immunotoxin target cell population (guinea pigs), the true MLD of FN18-CRM9 and anti-CD3-CRM9 is expected to be higher in monkeys and humans than in guinea pigs.

T Cell Kill

Helper T cell (CD4+ cells) numbers in peripheral blood fell dramatically after the initial administration of FN18-CRM9 in two rhesus monkeys. T cell counts began to rise by day 4 (sampled just prior to the second dose of FN18-CRM9). On day 5 in monkey 8629, CD4+ cells were depressed below the limit of detection (<50 cells/mm$^3$). Cells remained below or equal to 200/mm$^3$ out to day 21. This low level of CD4+ cells is associated with profound immunodeficiency in humans and in monkeys (Nooij and Jonker (1987) Eur. J. Immunol. 17:1089-1093). The remarkable feature of this study is the long duration of helper T cell depletion (day 21) with respect to the last administration of immunotoxin (day 4) since intravenously administered immunotoxins were cleared from the vascular system with half-lives<9 hours (Rostain-Capaillon and Casellas (1990) Cancer Research 50:2909-2916), the effect outlasting circulating immunotoxin. This is in contrast to T cell depletion induced by unconjugated anti-CD3 antibodies (Nooij and Jonker (1987) Eur. J. Immunol 17:1089-1093).

In monkey 1WS the second dose of conjugate only appeared to result in a diminished rate of CD4+ cell recovery. However, CD4+ cells were still fewer than normal at day 21. The blunted response of monkey 1WS to the second dose of immunotoxin was found to be due to a preexisting immunization of this animal to the toxin. Monkey 1WS had a significant pre-treatment anti-diphtheria toxin titer as revealed by a Western blot assay. This titer was markedly increased at day 5, indicative of a classic secondary response. In contrast, monkey 8629 had no detectable pre-treatment titer and only a trace titer by day 5 and a moderate titer by day 28.

The specificity of FN18-CRM9 toward T cells can be seen by comparing the is total white blood cell (WBC) count in the same two monkeys. WBCs fell, but only to 45% of baseline value on day 2 compared to 6% of baseline values for the CD4+ T cell subset. Most of the fall in WBC values can be accounted for by the T cell component of the WBC population (≈40%). However, B cells are initially depleted after FN18-CRM9 although these cells recover more quickly. FN18 is an IgG, isotype and as such is known to bind to Fc$_{II}$ receptors present on B cells and macrophages with low affinity. The FN18-CRM9 depletion of B cells indicates that significant interactions between the Fc portion of the FN18 antibody and B cells is taking place.

The peripheral T cell depletion induced by unconjugated FN18 at a dose known to produce immunosuppression 0.2 mg/kg/day (Nooij and Jonker (1987) Eur. J. Immunol. 17:1089-1093) was compared to the immunotoxin FN18-CRM9 administered at ⅕th the FN18 dose. Peripheral CD4+ T cell depletion is more pronounced and more long-lasting with the conjugate. The demonstration that FN18-CRM9 reduces peripheral helper T cell subset (CD4+) to levels less than or equal to 200 cell/mm$^3$ for a period as long as 21 days demonstrates that this immunotoxin and its anti-human analogs are effective immunosuppressive reagents.

The demonstration that FN18-CRM9 is a potent agent for inducing T cell depletion in non-human primates demonstrates that an anti-human homolog of FN18-CRM9, UCHT1-CRM9 (Oxoid USA, Charlotte, N.C.) for example, is a potent agent for inducing T cell depletion in humans.

The Fc binding region of anti-TCR/CD3 monoclonals may or may not be needed to induce T cell depletion when the anti-TCR/CD3 monoclonals are conjugated to CRM9. The Fc$_{II}$ binding regions can be removed, for example, by forming the conjugates with F(ab')$_2$ derivatives as is indicated in the literature (Thorpe et al. (1985) J. Nat'l. Cancer Inst. 75:151-159). In addition, anti-TCR/CD3 IgA switch variants such as monoclonal antibody T3. A may be used (Ponticelli et al. (1990) Transplantation 50:889-892). These avoid rapid vascular clearance characteristic of F(ab')$_2$ immunotoxins. F(ab')$_2$ and IgA switch variants of anti-TCR/CD3-CRM9 immunotoxins are therefore derivative anti-TCR/CD3 immunotoxins. These derivatives will avoid the B cell interaction noted and can increase specificity. However, IgG$_{2a}$ a switch variants will maximize T cell activation through the Fc$_I$, receptor and may be useful in certain situations where T cell activation aids immunotoxin induced toxicity.

General methods to make antibodies lacking the Fc region or to make antibodies which are humanized are set forth in Harlow and Lane, Antibodies: A Laboratory Manual, Cold Spring Harbor Laboratory, Cold Spring Harbor, N.Y., 1988. Thus, as used in the claims, antibody can mean the entire antibody or any portion of the antibody sufficient for specific antigen or receptor binding.

Example 6

T Cell Depletion and Immunosuppression in Monkeys Using the Immunotoxin Anti-CD3-CRM9

CRM9 is a diphtheria toxin (DT) binding site mutant and forms the basis of the anti-T cell immunotoxin anti-CD3-CRM9. This immunotoxin has been constructed against human and rhesus T cells and has shown above to kill 3 logs of human T cells in a nude mouse xenograft system. The present example demonstrates a 2 log kill of T cells in rhesus monkey lymph nodes that is also shown to produce prolongation of skin allograft rejection in monkeys.

Humans are immunized against diphtheria toxin by exposure to DPT vaccines in childhood. This long lasting immunity may interfere with the efficacy of DT based immunotoxins. Many monkeys are immunized against DT by natural exposure to toxin producing Corynebacterium. The present method addresses any potential interference of pre-existing DT antibodies with the activity of the present immunotoxins.

ELISA

ELISA assays were performed in order to determine the levels of anti-DT titers existing in 9 individuals in a population ages 27 to 55. There were 3 individuals with titers of 1:100 (low) and 6 with titers of 1:1000 (moderate).

Rhesus monkeys were screened by the same assay and a 1:1000 titered monkey was selected.

Administration of Non-Toxic Diphtheria Toxin Mutant

Monkeys were treated by I.V. route 5 min prior to the immunotoxin dose with a 100 fold excess of CRM197 over the CRM9 content of the immunotoxin to be administered. Just prior to administering CRM197, a H1 histamine blocking agent such as Benadryl or Tagevil was given I.V. to minimize any possibility of an anaphylactic reaction (for Benadryl 4 mg/kg). No histaminic reaction was detected.

Anti-CD3-CRM9 was given at a total dose between 0.1 and 0.2 mg/kg (toxin weight) in 3 equally divided doses (approximately 0.033 mg/kg) on 3 consecutive days. In these monkeys, the total dose of immunotoxin was 0.1 mg/kg.

Table 2 shows a comparison of the efficacy of anti-CD3-CRM9 in monkeys by comparing the decrease in the lymph node T/B cell ratio (a measure of lymph node T cell depletion) and the immunosuppressive effect of the immunotoxin as judged by prolongation of mismatched skin graft survival. Effects on the survival of skin grafts is a clear indicator of the general effect a given treatment has on the subject's immune system.

The monkey with the preexisting anti-DT titer that was pretreated with CRM197 shows the same level of T/B cell inversion as in the negative titered monkey. Skin graft survival was significantly prolonged over the titered monkey treated without CRM197. The failure to achieve a prolongation of graft survival equal to the negatively titered monkey is likely due to the lower weight of this monkey which causes T cells to repopulate faster, in this case 3-4 days faster, due to the larger thymic T cell precursor pool in younger animals. Age related effects such as these can be compensated for by modification of dosage levels and timing of administration.

TABLE 3

Efficacy of Anti-CD3-CRM9 With and Without CRM197 In Rhesus Monkeys With Positive and Negative Anti-Diphtheria Toxin Titers.

| Monkey | Weight kg | Anti-DT Titer | Treatment | Post Treatment* Lymph node T/B Cell Ratio | Day (s) of Skin Graft Survival |
|---|---|---|---|---|---|
| historical controls | 4-7 | N/A | None | 2.1-2.4+ | 9.5 ± 08$ |
| B65 | 5.1 | neg | anti-CD3 | 1.8 | 12, 12 |
| 8838 | 5.1 | neg | anti-CD3-CRM9 | 0.14xx | 19, 20 |
| M93 | 5.1 | 1:1000 | anti-CD3-CRM9 | 0.57 | 11, 12 |
| C81 | 1 | 1:1000 | CRM197 + anti-CD3-CRM9 | 0.2 | 1415 |

*All monkeys received the same dose of immunotoxin 0.1 mg/kg total in divided doses on day 0, 1 and 2. Lymph node sampled on day 3. CRM197 when given in 100 fold excess over CRM9 content.
+In this study untreated animals show this lymph node T/B ratio
$Historical controls at TNO, Rijswijk
xxAnti-CD3 given at the same mol. dose as anti-CD3-CRM9

Example 7

Immunotoxin UCHT1-CRM9 for the Treatment of Steroid Resistant Graft-Versus-Host Disease Treatment protocols for this type of disease can be expected to last a year, with Patients being followed for at least 5 years.

Characterization of UCHT1-CRM9 and CRM197

UCHT1-CRM9 is a covalent 1:1 conjugate of anti-human CD3 IgG1 monoclonal antibody and CRM9. The conjugate is synthesized, purified, sterile filtered and assayed for concentration, biological efficacy toward target cells and non-target cell toxicity by standardized culture assays. The method of synthesis, purification assay are identical to that used for FN18-CRM9 which was used in the pre-clinical monkey studies described in Examples 5-7.

CRM9 and CRM197 are produced by the Biotechnology Unit, NIH and purified by the Cooperating Facility. UCHT1 is produced in mouse ascites fluid and is purified by affinity chromatography over Protein A Sepharose. The synthesis, purification and storage of UCHT1-CRM9 is performed in a dedicated secure area. UCHT1-CRM9 is purified in 2 mg lots which are pooled and stored at 4° C. Shelf life is documented to be five months at full biological potency but does not exceed 4 months for this study. Preferably, most of the immunotoxin is used within 3 months of synthesis.

Patient Population

The patient population consists of individuals suffering from steroid resistant GVHD whose prognosis is poor. Patients are assayed for anti-CRM9 (anti-DT) titers and antibodies to murine immunoglobulin. Patients having anti-CRM9 titers of 1:1000 and below are treated according to the present protocol. Patients who have a history of receiving murine immunoglobulins or who exhibit positive anti-Ig titers may require special consideration.

Dosage of CRM9 Immunotoxin and Non-Toxic Mutant

UCHT1-CRM9 is administered at a dose which is ¹/₁₀ or less of the estimated minimum lethal dose (MLD) in a T lymphopenic patient. The MLD is expected to be at least 0.15 mg/kg (CRM9 content) based on the MLD of 0.15 mg/kg of IgG1-CRM9 in guinea pigs which lack a target cell population for the IgG1. (The presence of target cells in humans raises the MLD by providing a sink for the immunotoxin.) The optimal dose schedule has been found in monkeys to be administration on 3 consecutive days in 3 equally divided doses, and this schedule can be used throughout the treatment period. This permits administration of the total dose before any rise in pre-existing antitoxin titers due to a secondary response. In addition, the initial repopulation from the thymus is also eliminated, thus, further lowering the total T lymphocyte pool. Therefore, a total of 0.0125 mg/kg in three equally divided doses is given to the patient. This dose does induces T cell depletion in monkeys so that monitoring of T cell subsets and signs and symptoms of GVHD is relevant at the lowest dose. For the administration of this dose patients with anti-CRM9 titers of 1:100 or less will be treated. This permits pretreatment doses of CRM197 at 0.33 mg/kg or ¹/₁₀ the dose easily tolerated in monkeys. A second dosage group can include patients selected for antitoxin titers of 1:330 or less to whom CRM197 will be given at 1.0 mg/kg. A third dosage group can include patients with 1:1000 antitoxin titers or less will be given CRM197 at 3.3 mg/kg, a dose expected to be tolerable in humans, because it is easily tolerated by monkeys (see Example 7). The monkey MLD data should be very similar to humans on a per weight basis. However, GVHD patients are expected to be more like guinea pigs, because they have a smaller target cell population compared to non-GVHD patients.

Dose escalation can be tested by increasing the dose by a factor of 1.5. The following table exemplifies such a dose escalation test. For example three patients are used in each dosage group. There is a 3 to 4 week delay between each patient so that any late toxicity is detected before a dosage group is completed:

| Patient # | CRM Dose each day mg/kg | Total Dose mg/kg | Week Ending |
|---|---|---|---|
| 1,2,3 | 0.00417 | 0.0125 | 12 |
| 4,5,6 | 0.00636 | 0.019 | 24 |
| 7,8,9 | 0.0083 | 0.028 | 36 |
| 10,11,12 | 0.0125 | 0.042 | 48 |

Assuming each patient weighs on the average 70 kg, the first dosage group will consume 2.6 mg of the CRM9 immunotoxin, and will be supplied as a pool of two 2 mg batches. The second group will consume 3.9 mg and will also be supplied as 2 pooled batches. The third group will require 5.9 mg and will be supplied as three pooled batches. The fourth group will require 8.9 mg and will be supplied as three pooled batches and an additional two pooled batches.

Administration

Prior to administering CRM197 a H1 histamine blocking agent such as Benadryl or Tagevil is given I.V. to minimize any possibility of an anaphylactic reaction (for Benadryl 4 mg/kg). The CRM197 is administered I.V. in a 5 mg/ml sterile filtered solution in phosphate buffered saline pH 7.4 (PBS) over a 5 min time period. The immunotoxin is then given I.V. at 0.2 mg/ml over 2 min time period in a sterile filtered solution of 0.90 mM sodium sulfate and 10 mM sodium phosphate pH 7.4.

Measurements of Biological Parameters

The following parameters can be measured at various intervals during treatment (as exemplified by the schedule below):

A Cytokines, TNF alpha, gamma IFN, IL-6

B Routine clinical chemistries

C WBC, Hct, diff; lymphocyte subsets CD3, CD4, CD8, CD2, CD16, CD20

D Body Weight

E Immune function assays. ELISA assays of serum to monitor antibody responses to UCHT1 (primary response) and CRM9 (secondary response). ELISA assays to monitor antibody responses to polio and DPT reimmunizations done at 1 year following bone marrow transplantation.

| (before IT)Day 0 | A, B, C, D, E | Also A 2 hrs post |
|---|---|---|
| Day 1 | A, C, D | |
| Day 2 | A, C, D | |
| Day 3 | A, B, C, D | |
| Day 4 | C, D | |
| Day 7 | A, C, D | |
| Day 10 | B, C | |
| Day 14 | A, C, D | |
| Day 21 | C, D | |
| Day 28 | A, B, C, D, E | |
| Day 45 | C, D | |
| Day 60 | B, C, D, E | |

Example 8

An Anti-CD3 Single-Chain Immunotoxin with a Truncated Diphtheria Toxin Decreases Inhibition by Pre-Existing Antibodies in Human Blood The present Example examines the effect of human serum with pre-existing anti-DT antibodies on the toxicity of UCHT1-CRM9, an immunotoxin directed against CD3 molecules on T-lymphocytes. Sera with detectable anti-DT antibodies at 1:100 or greater dilutions inhibited the immunotoxin toxicity. Experiments with radiolabeled-UCHT1-CRM9 indicate that anti-DT antibodies partially block its binding to the cell surface as well as inhibit the translocation from the endosome to the cytosol. The inhibitory effect could be adsorbed using a full-length DT mutant or B-subfragment. A C-terminal truncation mutant could not adsorb the inhibitory effect, suggesting that the last 150 amino acids contain the epitope(s) recognized by the inhibitory antibodies.

Therefore, an anti-CD3 single-chain immunotoxin, sFv-DT390, was made with a truncated DT. The $IC_{50}$ of sFv-DT390 was $4.8 \times 10^{-11}$ M, 1/16 the potency of the divalent UCHT1-CRM9. More importantly, sFv-DT390 toxicity was only slightly affected by the anti-DT antibodies in human sera. "sFv" and "scUCHT1" both are single chain antibodies containing the variable region.

Mutated full-length and truncated diphtheria toxin (DT) molecules are used for making immunotoxins. These immunotoxins show strong cytotoxic effects to their target cells, and some of them have already been used in clinical trials (1-7). Previously, an immunotoxin directed against the CD3E molecule of the T-cell receptor complex, a pan T-cell marker was constructed. This construct is made with a monoclonal antibody of mouse-origin, UCHT1, and a binding site mutant of diphtheria toxin (DT), CRM9 (8). The immunotoxin, UCHT1-CRM9, is capable of regressing established xenografted human T-cell (Jurkat) tumors in nude mice (9). A rhesus monkey analog of UCHT1-CRM9, FN18-CRM9 was capable of not only depleting circulating T-cells but also depleting resident T-cells in the lymph nodes. This immunotoxin also delayed skin allograft rejection as compared to antibody treatment and non-treatment controls.

In contrast with ricin and *Pseudomonas exotoxin* (PE) based immunotoxins, there is a potential problem using UCHT1-CRM9, or other DT-based immunotoxins, in the treatment of human diseases. Most people have been immunized against DT. Therefore these people have a pre-existing anti-DT antibody titer which could potentially inhibit or alter the efficacy of these immunotoxins. This limitation also occurred in rhesus monkey studies. FN18-CRM9 could deplete T cells in the blood, but to a much lesser extent in animals with anti-DT antibodies, and the T cells repopulated several days earlier compared to those monkeys without anti-DT titers. In order to overcome this antibody mediated inhibition, the first examination of the effect and the mechanism of human sera containing anti-DT antibodies on UCHT1-CRM9 toxicity was done.

A DT point-mutant, a truncation mutant and DT-subfragments were used in an attempt to neutralize the anti-DT effect in human sera. Based on the neutralization data, a single-chain immunotoxin was constructed with a C-terminal deletion mutant of DT which is expected to bypass the inhibitory effect of the pre-existing anti-DT antibodies.

Cells.

Jurkat cells (ATCC) were maintained in RPMI 1640 supplemented with 10% fetal calf serum, 25 mM sodium bicarbonate and 50 µg/ml of gentamycin sulfate.

Serum and Adsorbing Molecules.

Goat anti-DT serum was provided by Dr. Randall K Holmes (USUHS, Bethesda, Md.). Human serum samples were provided by Dr. Henry McFarland (NINDS, NIH, Bethesda Md.). CRM197, an A-subfragment mutant (Gly 52 to Glu) of DT (see FIG. 1A), with no enzymatic activity (10) is available from Biocine-IRIS (Siena, Italy). MSPΔ5, a truncation mutant (amino acid 385) of DT with an additional 5 amino acids at the C-terminus was provided by Dr. Richard Youle (NINDS, NIH, Bethesda Md.). Purification of the DT B-subfragment has been described (11). Immunotoxins-UCHT1-CRM9 synthesis has been described (12).

The recombinant immunotoxin, sFv-DT390, was generated in two phases. First the coding sequences for the variable light ($V_L$) and variable heavy ($V_H$) chain regions of the UCHT1 antibody were amplified by a two step protocol of RT-PCR using primers based on the published sequence (13). The 5' $V_L$ primer added a unique NcoI restriction enzyme site while the 3' $V_H$ primer added a termination codon at the J to constant region junction and an EcoRI site. The $V_L$ region was joined to the $V_H$ region by single-stranded overlap extension and the two regions are separated by a $(Gly_4Ser)_3$ (SEQ ID NO: 105) linker that should allow for proper folding of the individual variable domains to form a function antibody binding site (14). Second, genomic DNA was isolated from a strain of *C. diphtheriae* producing the DT mutant CRM9

C7($\beta^{h\ tox-201\ tax-9\ h'}$) as described (15). This DNA was used for PCR. The 5' primer was specific for the toxin gene beginning at the signal sequence and added a unique NdeI restriction site. The 3' primer was specific for the DT sequence terminating at amino acid 390 and added an NcoI site in frame with the coding sequence. The PCR products were digested with the appropriate restriction enzymes and cloned into the E. coli expression plasmid pET-17b (Novagen, Inc., Madison, Wis., USA) which had been linearized with NdeI and EcoRI. The resulting plasmid was used to transformed E. coli BL21/DE3 cells. Cells were grown to an $OD_{590}$ of 0.5, induced with 0.5 M IPTG (Invitrogen, San Diego, Calif., USA) and incubated for an additional 3 hours. The sFv-DT390 protein was isolated in the soluble fraction after cells were broken with a French Press and the lysate subjected to centrifugation at 35,000×g.

Protein Synthesis Inhibition Assay.

Inhibition assays were performed as described (12) with the following modifications. Immunotoxins were incubated for 30 minutes with the indicated serum sample or leucine free medium at room temperature prior to addition to cells. In some experiments the serum was pre-incubated for 30 minutes with an adsorbing molecule at the given concentrations to bind the antibodies. The immunotoxin/serum mixture was incubated with Jurkat cells ($5 \times 10^4$ cells/well in 96 well plate) for 20 hours. A 1 hour pulse of [$^3$H]-leucine (4.5 µCi/ml) was given before cells were collected onto filters with a Skatron harvester. Samples were counted in a Beckman scintillation counter. Each experiment was performed in 4 replicates. Results were calculated into a mean value, and recorded as a percentage of control cells.

Serum Antibody Detection.

Anti-DT antibodies were detected in human serum by ELISA. CRM9 (10 µg/ml) was adsorbed to Costar 96-well EIA/RIA flat bottom plates (Costar, Cambridge, Mass., USA) for 2 hours and then washed in phosphate buffered saline (PBS) containing 0.1% Tween 20. Each well was then incubated with PBS containing 3% gelatin to prevent non-specific binding of antibodies to the plastic. Serum samples were diluted in PBS containing 0.1% Tween 20 and 0.3% gelatin prior to addition to the plate. After 1 hour incubation, the wells were washed as above, and incubated for an additional hour with protein A/G-alkaline phosphatase (1:5,000; Pierce, Rockford, Ill., USA). Wells were washed, and phosphatase substrate (Pierce) was added following the manufacturer's directions. After 30 minutes color development was stopped with NaOH and the optical density (OD) was measured with a kinetic microplate reader Molecular Devices Corporation, Palo Alto, Calif., USA). Each sample was performed in triplicate. Results are presented as O.D. values and antibody titers.

Endocytosis Assay.

UCHT1-CRM9 was iodinated using the Bolton-Hunter reagent (NEN Dupont, Wilmington, Del., USA) as described (16). Jurkat cells were washed twice with binding medium (RPMI 1640 supplemented with 0.2% bovine serum albumin, 10 mM Hepes (pH 7.4) and without sodium bicarbonate). Cells ($1.5 \times 10^6$) were incubated for 2 hours on ice with $^{125}$I-UCHT1-CRM9 ($1 \times 10^{-9}$ M) that had been pre-incubated with serum or binding medium. Unbound antibody was removed by washing the cells twice in PBS (pH 7.4) with centrifugation and resuspension. Duplicate samples were incubated for 30 minutes on ice or at 37° C. One sample from each temperature point was centrifuged at 800×g to separate the total cell associated (pellet) from the exocytosed or dissociated counts (supernatant). Both fractions were counted in a Beckman a γ-counter. To determine the amount of internalized immunotoxin, cells from the second sample at each temperature were incubated in low pH medium (binding medium containing 10 mM morpholinoethanesulfonic acid, all of which was titrated to pH 2.0 with HCl) for 5 minutes to dissociate the surface bound $^{125}$I-immunotoxin (17). Samples were centrifuged at 800×g to separate the internalized (pellet) from the membrane bound (supernatant). Both fractions were counted in a Beckman γ-counter (Beckman, Fullerton, Calif., USA).

Serum with Anti-DT Antibodies Inhibits UCHT1-CRM9 Toxicity.

Since humans are immunized against DT, the presence of anti-DT antibodies in the serum was determined by ELISA (Table 4). In a limited sample population, 80% of the serum samples had an anti-DT antibody titer of 1:100 or above. The vaccination status of the donors was not available. To determine the effect of these antibodies on UCHT1-CRM9 toxicity, the immunotoxin was pre-incubated with different concentrations of serum and the toxicity of the mixture was assayed (Table 4). Serum samples without a significant ELISA O.D. (2 fold above background) were incapable of affecting UCHT1-CRM9 toxicity at high concentrations of serum (1:10). However, serum samples with a positive ELISA result could neutralize the cytotoxic effect at 1:10 dilution, and those with a high ELISA O.D. (7-11 fold above background) inhibited toxicity even at a 1:100 dilution. Similar results were seen in assays conducted with monkey serum samples.

TABLE 4

Human serum with anti-DT antibodies inhibits the toxicity of UCHT1-CRM9 and the inhibition correlates with the anti-DT titer

| | ELISA | | Protein Synthesie[b] (% control) | | |
|---|---|---|---|---|---|
| Sample | O.C. (X ± S.D.) | Titer | 1:10 | 1:100 | 1:1,000 |
| 10010 | 0.738 ± 0.017 | 1:750 | 97 ± 3 | 79 ± 8 | 2 ± 0 |
| 10011 | 0.568 ± 0.048 | 1:500 | 104 ± | 13 ± 2 | 2 ± 0 |
| 10012 | 0.491 ± 0.025 | ND[c] | 96 ± 3 | 19 ± 2 | 2 ± 0 |
| 10013 | 0.411 ± 0.052 | 1:500 | 105 ± 8 | 7 ± 1 | 2 ± 0 |
| 10014 | 0.390 ± 0.047 | 1:500 | 96 ± 2 | 7 ± 0 | 2 ± 0 |
| 10015 | 0.353 ± 0.008 | 1:250 | 125 ± 6 | 6 ± 4 | 2 ± 0 |
| 10019 | 0.359 ± 0.019 | 1:250 | 101 ± 7 | 6 ± 1 | 2 ± 0 |
| 10016 | 0.141 ± 0.015 | 1:100 | 22 ± 1 | 3 ± 0 | 2 ± 0 |
| 10017 | 0.100 ± 0.006 | <1:100 | 4 ± 0 | 3 ± 0 | 2 ± 0 |
| 10018 | 0.071 ± 0.001 | <1:100 | 2 ± 0 | 2 ± 0 | 2 ± 0 |
| Goat | 1.450 ± 0.013 | 1:10$^5$ | | 102 ± 19 | 104 ± 3 |

[a]ELISA was performed in triplicate for each serum sample as described under "Materials and Methods." The O.D. values were derived from 1:100 dilutions and presented as a mean value ± SD. The background value was 0.060 ± 0.02. titers are recorded as the highest serum dilution that showed a positive reaction in ELISA.
[b]UCHT1-CRM9 ($2 \times 10^{-10}$) was incubated with different dilutions of serum for 30 min. The mixture was then added to cells as described under "Materials and Methods." Four replicates were performed for each sample. Data are presented as a mean value ± S.C.in percentage of the control counts. UCHT1-CRM9 inhibited protein synthesis to 2.0% of controls. The goat anti-DT serum could be diluted to 1:10,000 and still completely inhibited the toxicity of UCHT1-CRM9.
[c]ND, not done Sera do not Inhibit Endocytosis of UCHT1-CRM9.

The inhibitory effect of serum on UCHT1-CRM9 toxicity could be due to prevention of the immunotoxin binding to the cell surface or the endocytosis of UCHT1-CRM9 into the cell. Endocytosis assays were conducted using $^{125}$I-UCHT1-CRM9 to determine if either of these processes were affected by anti-DT antibodies present in sera. The results indicate that the presence of serum (goat anti-DT or human) reduces as much as 80% of the immunotoxin counts binding to the cell surface (Table 5). While this is a significant reduction in binding, limiting 90% of input immunotoxin (one log less UCHT1-CRM9) in toxicity assays reduces protein synthesis to <25% of controls (see FIG. 2). In contrast, the inhibitory effect of serum containing anti-DT antibodies is 100%. Therefore the effect of the anti-DT antibodies is not all at the level of inhibition of binding to the cell surface. The pre-incubation of $^{125}$I-UCHT1-CRM9 for 2 hours on ice and subsequent washing at room temperature resulted in 18 to 25% of the total cell associated counts internalized (Table 5). After incubation for 30 minutes at 37° C., there is a doubling of internalized counts both with and without serum, indicating that the same percentage of labeled immunotoxin is endocytosed. The identical dilutions of serum were incubated with non-labeled UCHT1-CRM9 and used in protein synthesis inhibition assays. The results demonstrate that the ratio of immunotoxin to serum used was capable of completely inhibiting the toxicity (Table 5), although the endocytosis of UCHT1-CRM9 was not affected.

TABLE 5

Inhibition of UCHT1-CRM9 toxicity by serum does not correlate with inhibition of endocytosis.

| Serum Sample | Time (37° C.) | % Bound | % of Bound internalized | Protein Synthesis (% Control) |
|---|---|---|---|---|
| — | 0 | 100 | 23.6 | N.D.$^a$ |
| — | 30 | 100 | 58.8 | 3 ± 1 |
| Human | 0 | 20 | 18.1 | N.D.$^a$ |
| Human | 30 | 19 | 35.9 | 105 ± 5 |
| — | 0 | 100 | 25.3 | N.D.$^a$ |
| — | 30 | 100 | 54 | 3 ± 1 |
| Goat | 0 | 37 | 24.4 | N.D.$^a$ |
| Goat | 30 | 33 | 50.7 | 92 ± 14 |

[$^{125}$I]-UCHT1-CRM9 (2 × 10–9 M) was incubated with medium or anti-DT serum (1:4 dilution of human sample 10010 or a 1:1,000 dilution of goat serum; Table 4) for 30 minutes at room temperature. This mixture was added to Jurkat cells (1.5 × 106) for 2 hours on ice (final concentration of [$^{125}$I]-UCHT1-CRM9 was 1 × 10–10). The cells were then washed and endocytosis assays performed as described in Materials and Methods. The % Bound value represents the cell associated counts divided by the cell associated counts without serum. Non-labeled UCHT1-CRM9 was incubated with the above dilutions of sera and the resulting mixture was used in protein synthesis inhibition assays. The results shown are representative of two independent assays.
n.d.: not done.

The Inhibitory Effect of Anti-DT Antibodies can be Removed by Adsorption.

To prevent the inhibitory effect of serum as well as gain insight into the mechanism by which serum inhibits toxicity, experiments were designed to adsorb the protective anti-DT antibodies from the serum. The serum (a pool of all human sera with positive anti-DT ELISA or goat anti-DT) was pre-incubated for 30 minutes with increasing concentrations of CRM197 (an A-chain mutant of DT with no enzymatic activity), MSPΔ5 (a truncation mutant missing the last 150 amino acids) and the purified A- and B-subfragments of DT (FIG. 1A). The adsorbed serum was then incubated with UCHT1-CRM9 in protein synthesis inhibition assays. CRM197, the full length DT-like construct, was capable of completely adsorbing the protective antibodies from both goat (FIG. 1B) and pooled human serum (FIG. 1C). The B-subfragment of DT is also capable of complete adsorption, however ~100 fold more is required. The A-subfragment of DT had little or no effect on either serum, although the serum samples were demonstrated to contain antibodies reactive to both the A- and the B-subfragments by Western Blot analysis. Of interest were the results seen with MSPΔ5, the truncation mutant. Adsorption of goat serum with MSPΔ5 gave a dose dependent removal of the serum's protecting effect (FIG. 1B). However, this adsorption could not bring toxicity down to levels obtained when CRM197 or the B-subfragment was used.

In contrast to the results observed with the goat serum, MSPΔ5 had little effect on pooled human serum (FIG. 1C). These results suggest that the pre-existing anti-DT antibodies important for the protecting effect in human serum are mainly directed against the last 150 amino acids of DT.

sFv-DT390 is Relatively Resistant to Inhibition by Anti-DT Antibodies Present in Human Sera.

Having observed that the epitope(s) recognized by the antibodies important for protection lay in the C-terminal 150 amino acids, a single-chain immunotoxin was generated with the first 390 amino acids (out of 535) of DT. Position 390 was chosen for 2 reasons: first, the 3 dimensional structure of DT suggested that this position was an external point on the molecule away from the enzymatic domain (18), and second, fusion toxins have been generated with longer DT subfragments with no reports of serum effects (19). The DNA encoding the first 390 amino acids of DT was ligated to DNA encoding the anti-CD3εsFv ($V_L$ linked to $V_H$ using a (Gly$_4$Ser)$_3$ (SEQ ID NO:105) linker sequence). The predicted molecular weight for the fusion protein is 71,000 Daltons and has been confirmed by Western Blot analysis of both in vitro transcribed and translated protein as well as protein isolated from E. coli using goat anti-DT antibodies. The toxicity of sFv-DT390 protein, isolated from E. coli strain BL21/DE3, was compared to UCHT1-CRM9 in protein synthesis inhibition assays (FIG. 2A]). The IC$_{50}$ (concentration required to inhibit protein synthesis to 50% of controls) of sFv-DT390 was $4.8 \times 10^{-11}$ M compared to $2.9 \times 10^{-12}$ M for UCHT1-CRM9, a 16-fold difference. To demonstrate the specificity of the sFv-DT390 construct, competition experiments were performed using increasing concentrations of UCHT1 antibody as competitor (FIG. 2B). The results showed that approximately ⅛ antibody is needed to compete the sFv-DT390 toxicity to 50% as compared to UCHT1-CRM9. The antibody was capable of totally competing toxicity of both constructs thereby showing their specificity. The immunotoxins were then subjected to protein synthesis assays in the presence of increasing dilutions of serum (Table 6).

UCHT1-CRM9 toxicity was completely inhibited with a 1:10 dilution of the human sera but at a 1:100 dilution toxicity was equivalent to controls without serum. In contrast, the sFv-DT390 immunotoxin is only partially inhibited with the 1:10 dilution of the human sera and the 1:100 dilution no effect on the toxicity. Both immunotoxins are completely inhibited by goat anti-DT serum (1:1,000 dilution). These results indicate that the sFv-DT390 immunotoxin partially evades the pre-existing anti-DT antibodies present in most human sera.

These results indicate that the pre-existing anti-DT antibodies present in human serum inhibit the toxicity of the immunotoxin UCHT1-CRM9. This inhibition of toxicity was also observed with goat anti-DT serum, however less goat serum was needed to completely inhibit toxicity. The experiments were designed in such a way to mimic the in vivo situation. The peak concentration of circulating immunotoxin currently being tested in animal models is $1 \times 10^{-9}$ M. The immunotoxin concentration incubated with the 1:10 dilution of human serum was $1 \times 10^{-10}$ M, thus approximating in vivo conditions. The inhibition of toxicity correlates with the serum antibody levels as determined by ELISA (Table 5), indicating that sera with higher anti-DT titers have a stronger inhibitory effect. Similarly, the goat anti-DT serum which gave the highest ELISA value could be diluted 10,000 times and still completely inhibited UCHT1-CRM9 toxicity. Since this correlation exists, there is no indication that any other component of the serum inhibits the toxicity of UCHT1-CRM9.

Furthermore, the data show that a titer of 1:100 dilution is necessary for an inhibition of the immunotoxin toxicity. A construct in which the first 486 amino acids of DT were fused to interleukin-2, DAB$_{486}$IL-2, was used in lymphoid malignancy patients. A partial response to $DAB_{486}IL-2$ was observed in several patients who had a anti-DT titer below 1:100 dilution prior to the treatment.

Intoxication of cells by immunotoxins can be subdivided into four general stages: 1) specific binding to the cell surface, 2) endocytosis into the cell, 3) translocation of enzymatic domain of the toxin out of the endosome and 4) enzymatic inactivation of the target molecule. The results presented indicate that, while the amount of immunotoxin reaching the cell surface is lower in the presence of serum, the same percentage of bound immunotoxin is endocytosed. Taking into account the reduced amount of immunotoxin bound to the cell, the amount of endocytosed immunotoxin should intoxicate the cells to below 25% of controls. However, the immunotoxin had no effect on protein synthesis in the presence of serum containing anti-DT antibodies. Since the A-subfragment of DT could not adsorb the protective effect of serum while the B-subfragment could, the effect of serum is not likely to be at the level of inhibiting enzymatic activity of the toxin. Therefore, the anti-DT antibodies probably affect the translocation of the A-subfragment into the cytosol.

CRM197, B-subfragment, and MSPΔ5 could adsorb the protecting anti-DT antibodies from the goat and rhesus monkey sera. However, among the 3 DT mutants, MSPΔ5 could not prevent the UCHT1-CRM9 toxicity in the presence of the human sera, showing a difference in the anti-DT antibody repertoire among humans, goat and rhesus monkeys. This difference does not seem to be due to immunization routes, because monkeys used in the present study were not immunized for DT and presumably acquire the antibodies after a natural infection with toxigenic strains of C. diphtheriae. There have been reports showing that rhesus monkeys and humans shared a similar antibody repertoire (21), but the present results suggest that the effect of antibodies from the host for whom immunotoxin treatment is intended should be useful.

To overcome the blocking effect of the pre-existing anti-DT antibodies in human sera, there are basically two pathways existing. One is to neutralize the antibodies with non-toxic DT mutants, and the other is to modify the DT structure used for making immunotoxin (3). The antibody neutralization pathway has been tested in monkey studies of FN18-CRM9 treatment as described above.

The present results showed that although antibodies against both A- and B-subfragments existed in human sera, MSP5 could not neutralize the pre-existing protective anti-DT antibodies, and therefore could not prevent the inhibition of the cytotoxicity of UCHT1-CRM9. However, it did block the inhibitory effect of the goat and monkey sera. This prompted the construction of the present recombinant immunotoxin, sFv-DT390. The $IC_{50}$ of sFv-DT390 is $4.8 \times 10^{-11}$ M, 1/16 as potent as UCHT1-CRM9. Like many other single-chain constructs, sFv-DT390 is monovalent as compared to immunotoxins generated with full length, bivalent antibodies. The reduced toxicity in sFv-DT390 could be explained primarily on this affinity difference. Immunotoxins generated with purified F(ab)' fragments of antibodies also show an in vitro loss in toxicity (generally a 1.5 log difference) when compared to their counterparts generated with full length antibodies (22). The toxicity of sFv-DT390 is comparable to that reported for DAB486IL-2 (23). From the present data some advantages of sFv-DT390 are expected. First, sFv-DT390 is only 1/3 of the molecular weight of UCHT1-CRM9. The molar concentration of sFv-DT390 will be 3 times higher than that of UCHT1-CRM9 if the same amount is given (for example, 0.2 mg/kg). Therefore, their difference in potency could be reduced to approximately 5 times. Second, in an in vitro experiment (Table 6), the same molar concentration of sFv-DT390 and UCHT1-CRM9 was used for serum inhibition test, although the former is only 1/16 potent compared to the latter. The pre-existing anti-DT antibodies in human sera could only partially block the toxicity of sFv-DT390 while the effect of UCHT1-CRM9 was completely blocked. Thus, sFv-DT390 is expected to bypass the anti-DT antibodies in in vivo situations while UCHT1-CRM9 cannot. Third, sFv-DT390 contains only the variable region of UCHT1, and is expected to have less immunogenicity in human anti-mouse antibody (HAMA) responses than the native murine antibody UCHT1. Finally, the production cost of sFv-DT390 is much lower than that of UCHT1-CRM9. Based on these reasons, sFv-DT390, or others with similar properties, are expected to be useful in the treatment of T-cell mediated diseases in humans, especially in anti-DT positive individuals and in patients who need repeated treatments. To obtain evidence supporting this assumption, it is only necessary to construct a rhesus monkey analog of sFv-DT390, and test it in monkey models as described in previous examples.

TABLE 6

Anti-DT antibodies present in human sera have reduced effect on sFv-DT390 toxicity.

| | | Protein synthesis (% Control) | | | | | |
|---|---|---|---|---|---|---|---|
| | ELISA value | UCHT1CRM9 | | | sFv-DT390 | | |
| Serum Sample | (±S.D.) | 1:10 | $1:10^2$ | $1:10^3$ | 1:10 | $1:10^2$ | $1:10^3$ |
| 10012 | 0.491 ± 0.025 | 119 ± 24 | 8 ± 2 | $ND^a$ | 47 ± 9 | 21 ± 8 | ND |
| Pooled | 0.331 ± 0.015 | 108 ± 37 | 7 ± 1 | $ND^a$ | 49 ± 7 | 16 ± 7 | ND |
| Goat | 1.450 ± 0.013 | ND | ND | 94 ± 21 | ND | ND | 8 ± 11 |

$^a$Not done
UCHT1CRM9 or sFv-DT390 ($2 \times 10^{-9}$M) was incubated with the indicated dilutions of serum for 30 min. The mixture was then added to cells as described under "Materials and Methods." The final concentration of immunotoxin on cells was $1 \times 10^{-10}$M. Four replicates were performed for each sample. Data are presented as a mean value ± S.D. in percentage of the control counts. UCHT1-CRM9 inhibited protein synthesis to 50% of controlswhile the sFv-DT390 inhibited protein synthesis to 18% of controls. The ELISA value was determined using a 1:100 dilution of serum. The results are representative of two independent experiments.

Example 9

Expression and Characterization of A Divalent Chimeric Anti-Human CD3 Single Chain Antibody Murine anti-CD3 monoclonal antibodies (mAbs) are used in clinical practice for immunosuppression. However, there are two major drawbacks of this treatment: the associated cytokine release syndrome and human anti-mouse antibody response. To overcome these side effects, a chimeric anti-human CD3 single chain antibody, scUCHT1 was generated. It is an IgM variant of the UCHT1 described in Example 9. scUCHT1 consists of the light and heavy variable chain binding domains of UCHT1 and a human IgM Fc region ($CH_2$ to $CH_4$). The method used was reported by Shu et al. (37) and is further described below. The following data show that the engineered chimeric anti-CD3 single chain antibody (scUCHT1) will be useful in clinical immunosuppressive treatment.

Oligonucleotide Primers and DNA Amplification.

Figure 3:
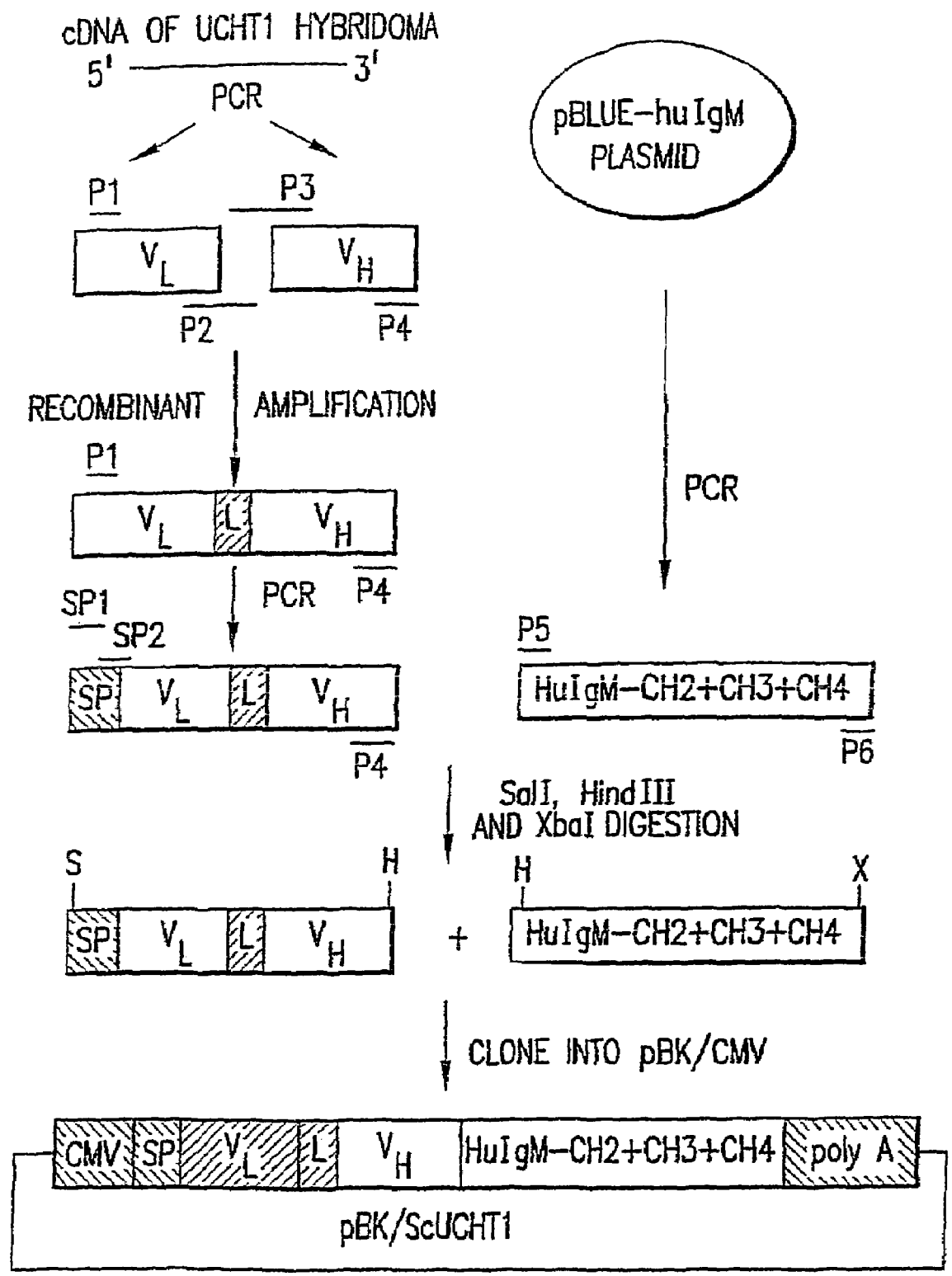
FIG. 3 shows the schematic flow sheet for generation of the single chain antibody scUCHT1 gene construct. PCR: polymerase chain reaction; L: linker; SP: signal peptide. P1 to P6, SP1, and SP2 are primers used in PCR, and listed in Table 2.

Primers used for the antibody engineering are listed in Table 7, and the primer sequences are based on published data (13). The procedures of cloning scUCHT1 is schematically depicted in FIG. 3. mRNA isolated from UCHT1 hybridoma cells (provided by Dr. P. C. Beverley, Imperial Cancer Research Fund, London was reverse transcribed into cDNA. The $V_L$ and $V_H$ regions of UCHT1 were amplified with polymerase chain reaction (PCR) from the cDNA using primer pairs P1, P2 and P3, P4 respectively. Primers P2 and P3 have a 25 bp complementary overlap and each encoded a part of a linker peptide $(Gly_4Ser)_3$ (SEQ ID NO: 105). The single chain variable fragment ($V_L$-linker-$V_H$) was created by recombinant amplification of $V_L$ and $V_H$ using primers P1 and P4. A mouse kappa chain signal sequence was added at the $V_L$ 5'-end by PCR, first with primers SP2 and P4, and then with primers SP1 and P4. The human IgM Fc region ($CH_2$ to $CH_4$) was amplified from the plasmid pBlue-huIgM (kindly provided by Dr. S. V. S. Kashmiri, National Cancer Institute, Bethesda This gene fragment was about 1.8 kb. The $V_L$-linker-$V_H$-CH2 region which is important for antigen recognition was confirmed by sequence analysis. Finally, the single chain variable fragment and the human IgM Fc region were cloned into plasmid pBK/CMV (Stratagene, La Jolla, Calif., USA). Using the generated pBK/scUCHT1 plasmid as template, an in vitro transcription-translation assay yielded a product of 75 kDa, the expected size.

Expression in COS-7 and SP2/0 Cells.

The gene fragment encoding scUCHT1 was then cloned into an expression vector pLNCX (36). The scUCHT1 gene construct was introduced into COS-7 cells with a calcium-phosphate method (32), and introduced into SP2/0 myeloma cells by electroporation (33). Cells transfected were selected with 500 µg/ml G418 (GIBCO/BRL, Gaithersburg, Md., USA) in DMEM medium. The drug resistant transfectants were screened for scUCHT1 secretion by an anti-human IgM ELISA technique. Transfectants secreting scUCHT1 were cloned by limiting dilution.

Figure 4:
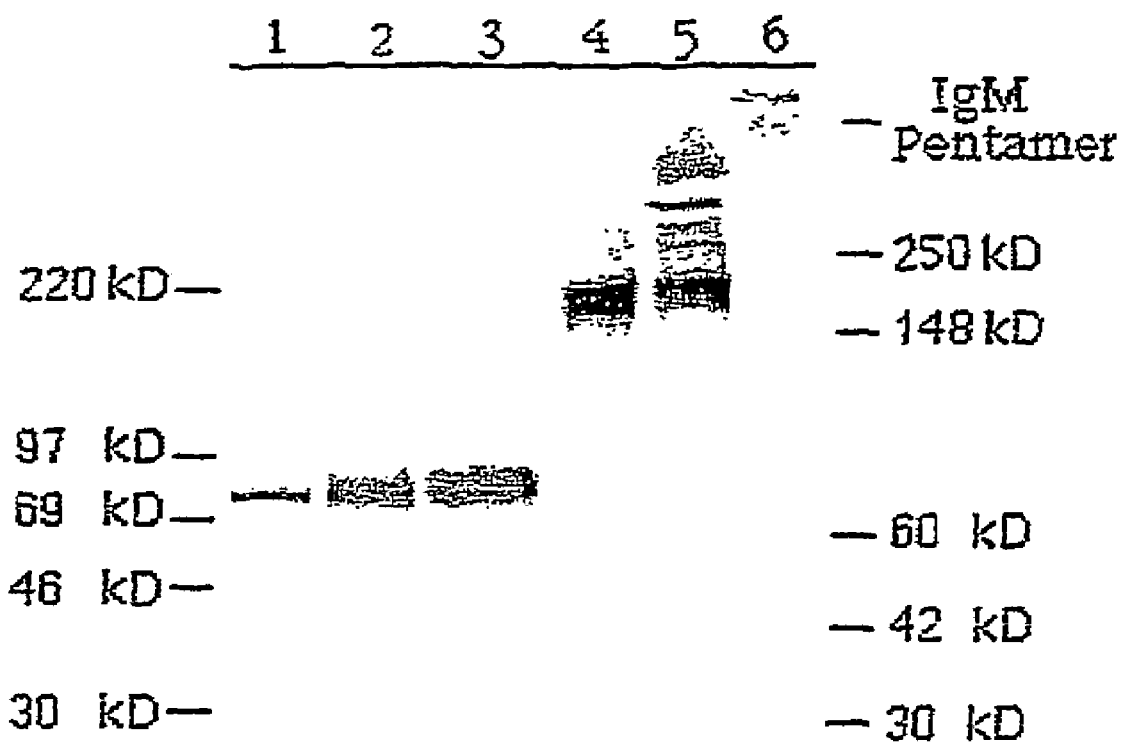
FIG. 4 shows the Western blotting analysis of the single chain antibody scUCHT1. scUCHT1 was immunoprecipitated, and separated on 4-20% SDS/PAGE gradient gel. After transferring to Problott™ membrane, scUCHT1 was visualized by an anti-human IgM antibody labeled with phosphatase. scUCHT1 secreted was mainly a dimeric form. Lane 1-3 representing electrophoresis under reducing conditions, and 4-6 non-reducing conditions. Lane 1 and 6 are human IgM; lane 1: IgM heavy chain. The light chain is not visible, because the anti-IgM antibody is directed at the heavy chain; lane 6: IgM pentamer is shown as indicated by the arrow. Lane 2 and 4 scUCHT1 from COS-7 cells; 3 and 5 scUCHT1 from SP2/0 cells.

Two stable clones, COS-4C10 and SP2/0-7C8, which could produce about 0.5 mg/ml scUCHT1 in culture medium, were selected for further evaluation. The culture supernatant of COS-4C10 and SP2/0-7C8 cells was analyzed by immunoblotting using anti-human IgM antibody (FIG. 4). Human IgM antibody was included as a control in the analysis. Under reducing conditions, scUCHT1 produced by COS-7 and SP2/0 cells had a similar electrophoretic mobility to that of the control human IgM heavy chain (75 kDa). Under non-reducing conditions, scUCHT1 from COS-7 cells appeared as a single band of approximately 150 kDa, which was thought to be a homodimer of the single chain antibody. SP2/0 cells mainly produced a protein of similar size with some higher molecular weight products.

In constructing scUCHT1, the domain orientation of sFv, $V_H$-$V_L$, which Shu et al. used to $V_L$-$V_H$ orientation, was changed so that the heavy chain constant domains were linked to the $V_H$ domain. In mammalian cells, secretion of immunoglobulin molecules is mediated by light chain, and free light chain is readily secreted (38). However, free heavy chain is generally not secreted (39). In a bacterial expression system, the yield of secreted sFv with a $V_L$-$V_H$ domain orientation was about 20-fold more than that obtained with a $V_H$-$V_L$ domain orientation (40). It was reasoned that $V_L$ at the NH2-terminal position and $V_H$ inked to heavy chain constant region in scUCHT1 construct might enhance the secretion of this immunoglobulin-like molecule in mammalian cells. In fact scUCHT1 was efficiently produced by both COS-7 and SP2/0 cells. Hollow fiber culture should increase its production.

TABLE 7

Sequences of oligonucleotide primers used for PCR amplification

| Primers | Sequences 5'　　　　　　　　3' | | RE sites |
|---|---|---|---|
| P1(UCHT1 VL5) | GACATCCAGATGACCCAGACC | (SEQ ID NO:2) | |
| P2(UCHT1 VL3) | CCTCCCGAGCCACCGCCTCCGCTGCCTCCGCCTCCTTTTATCTCCAGCTTG(T)GTC(G)CC | (SEQ ID NO:3) | |
| P3(UCHT1 VH5) | GCAGCGGAGGCGGTGGCTCGGGAGGGGGAGGCTCGGAGGTGCAGCTTCAGCAGTCT | (SEQ ID NO:4) | |
| P4(UCHT1 VH3) | GC<u>AAGCTT</u>GAAGACTGTGAGAGTGGTGCCTTG | (SEQ ID NO:5) | Hind III |
| P5(HuIgM-CH2) | GTCTCTTCA<u>AAGCTT</u>ATTGCC(T)GAGCTGCCTCCCAAA | (SEQ ID NO:6) | Hind III |
| P6(HuIgM-CH4) | GC<u>ATCTAGA</u>TCAGTAGCAGGTGCCAGCTGTGT | (SEQ ID NO:7) | Xba I |
| SP1 (Signal 1) | CG<u>GTCGAC</u>ACCATGGAGACAGACACACTCCTGTTATGGGTACTGCTGCTCTGGGTTCCA | (SEQ ID NO:8) | Sal I |
| SP2 (Signal 2) | GTACTGCTGCTCTGGGTTCCAGGTTCCACTGGGGACATCCAGATGACCCAG | (SEQ ID NO:9) | |

Moreover, scUCHT1, the IgM-like molecule, has a secretory tailpiece with a penultimate cysteine (Cys 575) which is involved in polymerization and also provides retention and degradation of IgM monomers (41-43). Replacing the Cys 575 with serine might also greatly improve the yield.

scUCHT1 secreted from COS-7 cells was shown to be a divalent form by immunoblotting, suggesting a disulfide bond linkage of two monovalent molecules. The disulfide bond is likely situated between the CH2 and CH3 regions, where the Cys 337-Cys 337 disulfide bond is thought to exist. Cys 337 is believed to be sufficient for assembly of IgM monomers, and was neither sufficient nor necessary for formation of polymers. However, Cys 575 was necessary for assembly of IgM polymers, and Cys 414 was not required for formation of IgM monomers or polymers (44). This divalent form of the single chain antibody should increase its binding affinity. While scUCHT1 produced from SP2/0 cells was mainly in the divalent form, a small fraction of the antibody had a higher molecular weight, nearly comparable to that of the human IgM pentamer, the natural form of secreted human IgM.

Western Blotting Analysis of scUCHT1.

scUCHT1 was precipitated from the culture supernatant using goat anti-human IgM-Agarose (Sigma, St. Louis, Mo., USA), and separated on 4-20% SDS-PAGE gradient gel under reducing and non-reducing conditions. The separated proteins were transferred to ProBlott™ membrane (Applied Biosystems, Foster City, Calif., USA) by electroblotting at 50 volts for 1 hour. The membrane was blocked and incubated with alkaline phosphatase labeled goat anti-human IgM antibody (PIERCE, Rockford, Ill., USA) following the manufacturer's instruction. Color development was carried out with substrate NBT/BCIP (PIERCE).

Purification of scUCHT1.

Culture supernatant was mixed with anti-human IgM-Agarose, and incubated at 4° C. with shaking overnight, and then the mixture was transferred to a column. The column was washed with washing buffer (0.01 M Na-phosphate, pH 7.2, 0.5 M NaCl) until the OD280 of flow-through was <0.01. scUCHT1 was eluted with elution buffer (0.1 M glycine, pH 2.4, and 0.15 M NaCl). The fractions were neutralized with 1 M Na-phosphate (pH 8.0) immediately, and then concentrated and dialyzed against PBS.

Competitive Binding Assay.

Figure 5:
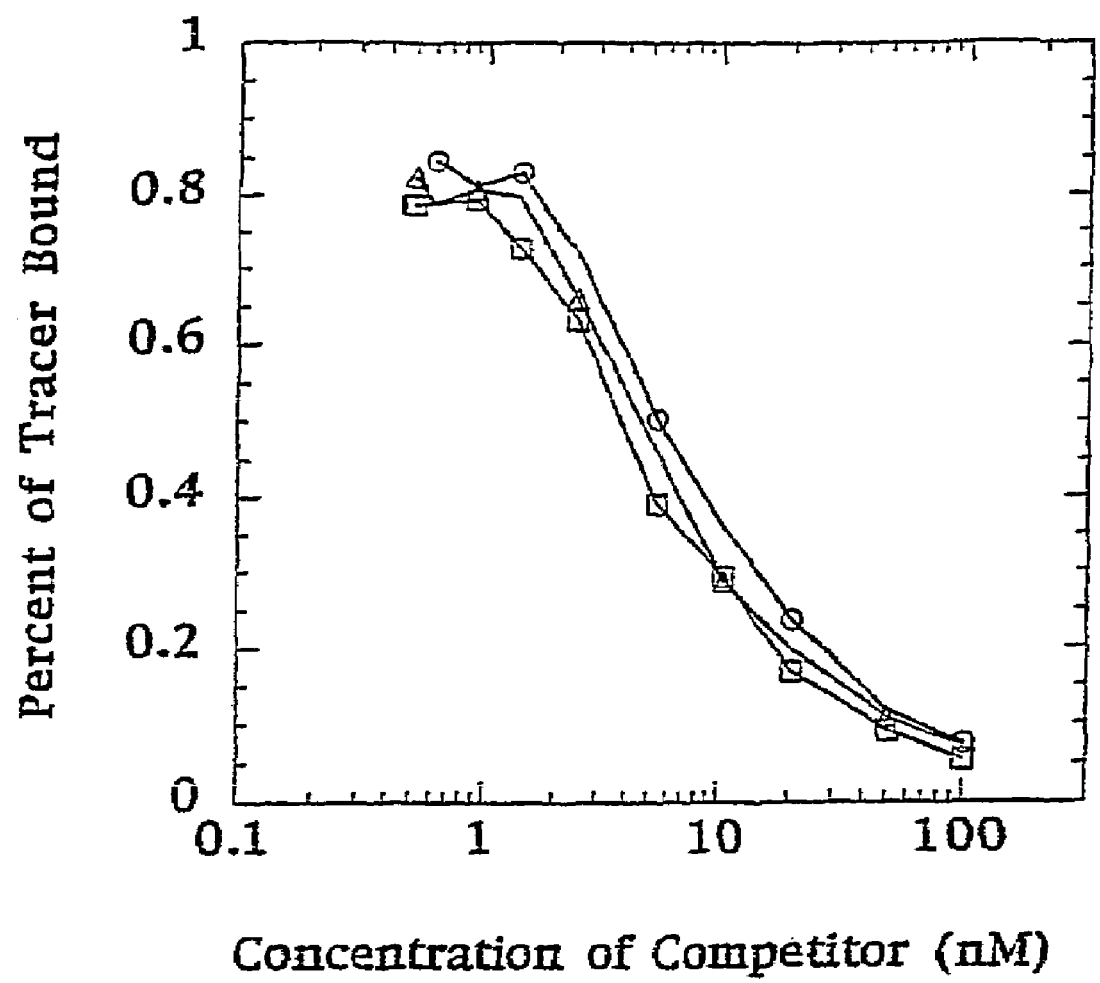
FIG. 5 shows that scUCHT1 had the same specificity and affinity as its parental antibody UCHT1. In the competition assay, $^{125}$I-UCHT1 was used as tracer in binding Jurkat cells. scUCHT1 from COS-7 (□) and SP2/0 cells (Δ), or unlabeled UCHT1 (○) with indicated concentrations were included as competitor. Results were expressed as a percentage of the $^{125}$I-UCHT1 bound to cells in the absence of competitors.

The parental antibody UCHT1 was iodinated using Bolton-Hunter Reagent (NEN, Wilmington, Del., USA) as described previously (34). The $^{125}$I-labeled UCHT1 was used as tracer and diluted with DMEM medium to 0.3-0.6 nM. UCHT1 and the purified scUCHT1 from COS-7 and SP2/0 transfectant cells were used as competitors. Human CD3 expressing Jurkat cells were suspended in DMEM medium ($2\times10^7$/ml). 50 µl of such cell suspension ($1\times10^6$) was incubated with 50 µl diluted tracer and 50 ml diluted competitors on ice for 2 hours. Afterwards, cells were pelleted, and counted in a gamma counter. Results were expressed as a percentage of the $^{125}$I-UCHT1 bound to cells in the absence of competitors (FIG. 5).

scUCHT1 from both COS-7 and SP2/0 cells could specifically inhibit the binding of $^{125}$I-UCHT1 to Jurkat cells in a dose dependent way. As the concentration of the competitors (UCHT1, scUCHT1 from COS-7 and SP2/0 cells) increased from 1 to 100 nM, the tracer (1251 iodinated UCHT1) bound to Jurkat cells decreased from 80% to nearly 0%. No significant difference was observed among the affinity curves of UCHT1 and scUCHT1 from COS-7 and SP2/0 cells. This indicates that the engineered antibody scUCHT1 has nearly the same affinity as UCHT1. Moreover, scUCHT1 contains human IgM constant region, and is expected be less immunogenic than UCHT1. The degree of its immunogenicity might vary due to the murine variable region of scUCHT1. Humanized variable regions by CDR-grafting or human variable regions can be used to further reduce its immunogenicity (31).

T-Cell Proliferation Assay.

Figure 6:
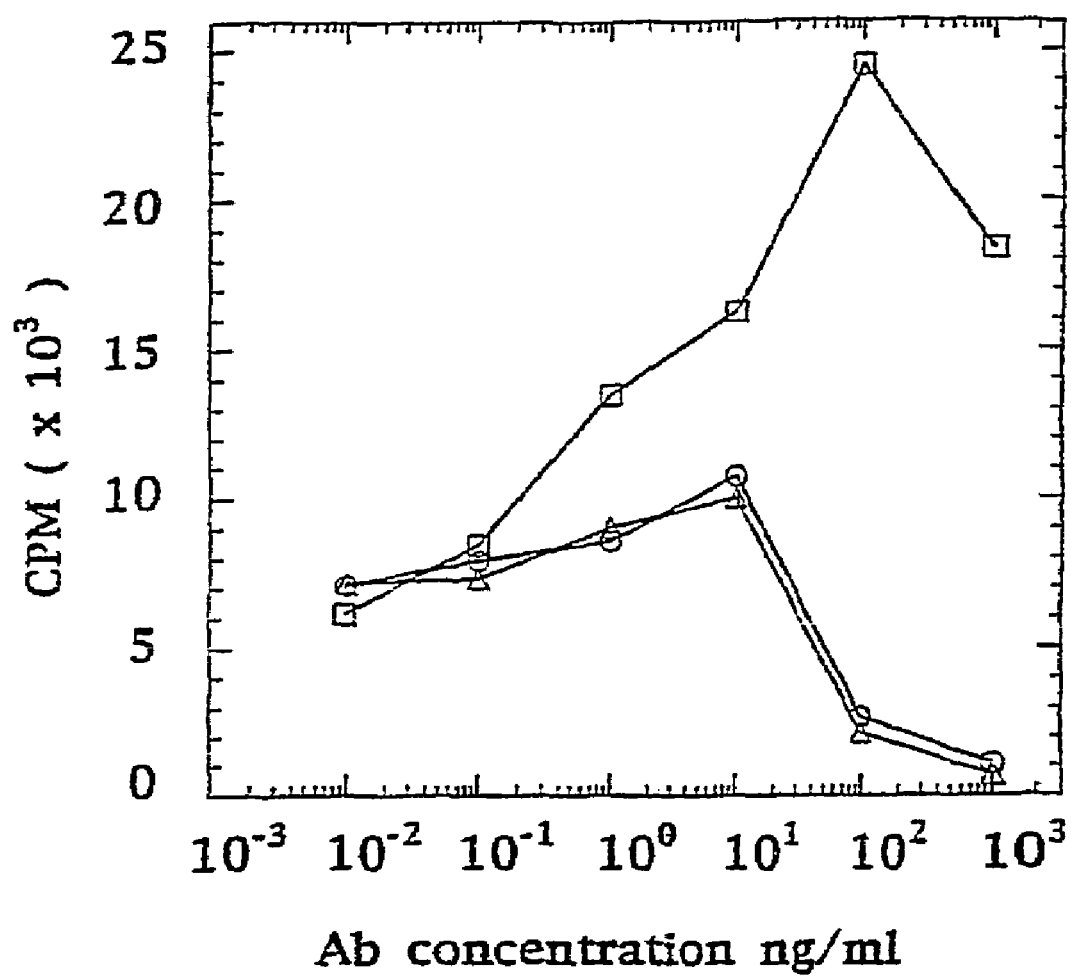
FIG. 6 shows that scUCHT1 did not induce human T cell proliferation response. scUCHT1 from COS-7 (Δ) and SP2/0 (○) cells and UCHT1 (□) were added to human PBMCs at indicated concentrations and T cell proliferation was assayed by [3H]thymidine incorporation. UCHT1 induced a vigorous proliferation response. On the contrary, scUCHT1 had little effect at any doses.

T-cell proliferation in response to UCHT1 and scUCHT1 was tested on human PBMCs from a healthy donor (FIG. 6). Human peripheral blood mononuclear cells (PBMCs) were isolated from blood of a healthy adult by density centrifuge over Ficoll-Hypaque gradient (34). The PBMCs were resuspended in RPMI 1640 supplemented with 10% FCS and aliquoted to 96-well U-bottom plates at $5\times10^4$ cells/well. Increasing amounts of anti-CD3 antibodies (UCHT1, scUCHT1) were added. After 72 hours of culture at 37° C. in a humidified atmosphere containing 5% $CO_2$, 1 µCi [$^3$H] thymidine (NEN) was added to each well. 16 hours later, cells were harvested and [$^3$H]thymidine incorporation was counted in a liquid scintillation counter.

The parental antibody UCHT1 started to induce proliferation at 0.1 ng/ml, and peaked at 100 ng/ml. A small drop in CPM was observed as the concentration increased to 1,000 ng/ml. However, [$^3$H]thymidine incorporation in PBMCs incubated with scUCHT1 was only slightly increased in the range of 0.1-10 ng/ml, and when the concentration was higher than 10 ng/ml, the incorporated counts decreased and were close to 0 counts at 1,000 ng/ml.

Measurement of TNF-α and IFN-γ.

TNF-α and IFN-γ productions of human PBMCs induced by UCHT1 and scUCHT1 were measured with ELISA. $4\times10^5$ PBMCs were cultured with serial dilutions of anti-CD3 antibodies (UCHT1, scUCHT1) in 96-well flat-bottom plates in RPMI 1640 supplemented with 10% FCS. Supernatant was collected at 36 hours for TNF-α and 72 hours for IFN-γ after the start of the culture (35). TNF-α and IFN-γ were measured with ELISA kits (Endogen Inc. Cambridge, Mass., USA) following the manufacturer's instruction.

Figure 7A:
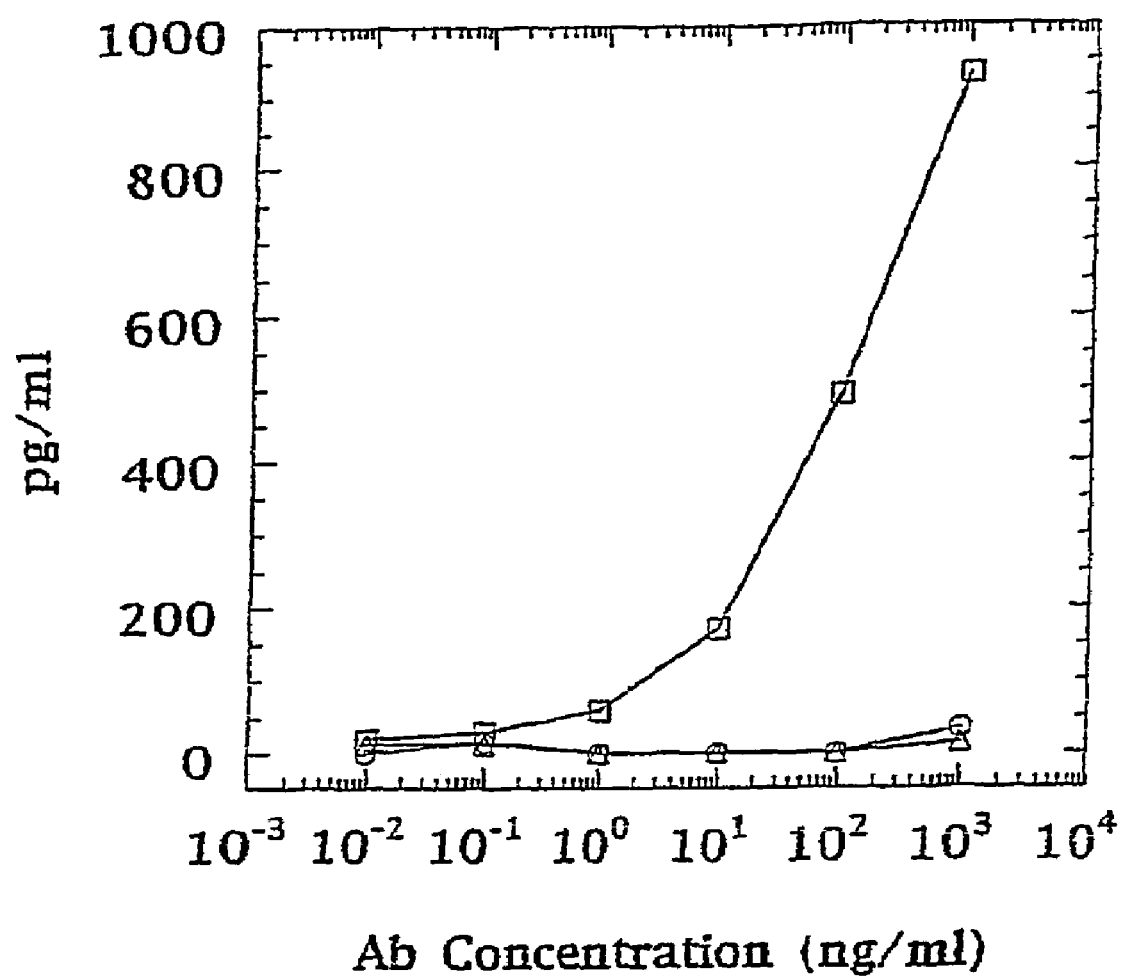
FIG. 7a shows that UCHT1 and scUCHT1 had little effect on TNF-α secretion, and scUCHT1 from both COS-7 (Δ) and SP2/0 (○) cells and UCHT1 (□) were added to cultures of human blood mononuclear cells. Culture supernatant was harvested and used for ELISA determination of TNF-α and IFN-γ as described in materials and methods.
Figure 7B:
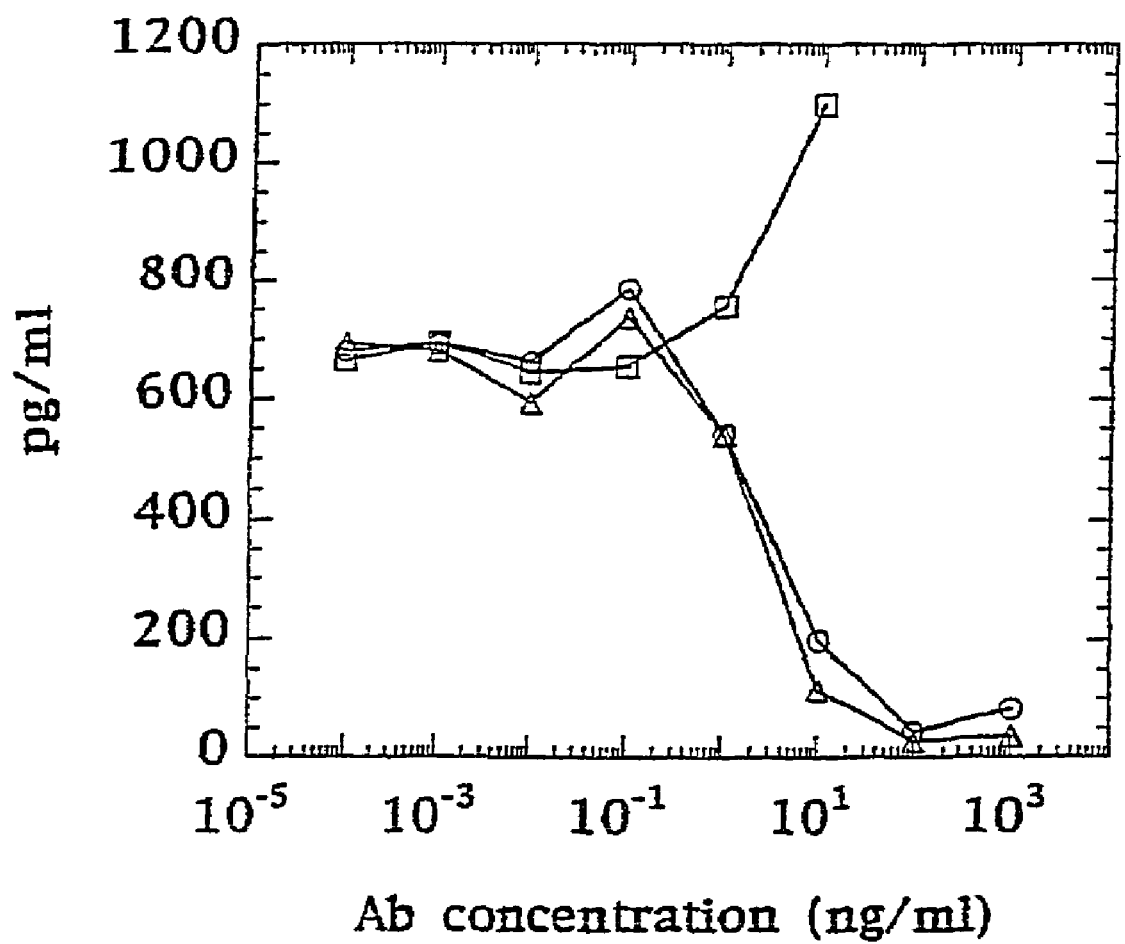
FIG. 7b shows that UCHT1 and scUCHT1 inhibited the basal production of IFN-γ. scUCHT1 from both COS-7 (Δ) and SP2/0 (○) cells and UCHT1 (□) were added to cultures of human blood mononuclear cells. Culture supernatant was harvested and used for ELISA determination of TNF-α and IFN-γ as described in materials and methods.

The native antibody UCHT1 induced production of both TNF-α and IFN-γ in a dose dependent way (FIGS. 7a and 7b). Higher concentration of UCHT1 induced higher production of TNF-α and IFN-γ. On the contrary, scUCHT1 did not induce secretion of TNF-α at any concentration (FIG. 7a), and inhibited IFN-γ production when its concentration was higher than 0.1 ng/ml (FIG. 7b). At the time of supernatant harvesting, the PBMCs cultured with UCHT1 and scUCHT1 were also checked with trypan blue exclusion test. Cells were shown to be alive in both situations. In TNF-α and IFN-γ ELISA assays, an unrelated human IgM was included and it did not affect the TNF-α and IFN-g production.

Measurement of Possible Complement Binding by scUCHT1

Divalent scUCHT1 failed to bind detectable quantities of complement. This feature is an advantage in treating patients with a foreign protein in that it will minimize immune complex disease.

Anti-CD3 mAbs can induce T cell activation and proliferation both in in vitro and in vivo situations (45). Crossinglinking of anti-CD3 antibody between T cells and FcR expressing cells is an essential step in this process (46). T cell activation therefore reflects an efficient interaction of the mAb with a human FcR. Previous data of in vitro study indicated that T cell activation resulted in increased production of TNF-α, IFN-γ, and IL-2 (24). Human IgG Fc receptors (FcγR I, FcγR II, FcγR III) are distributed on human monocytes, T, B lymphocytes, and NK cells (47). FcγR I and FcγR II can recognize both mouse and human IgG. In accordance with the above observation, UCHT1 was potent in induction of T cell proliferation and TNF-α and IFN-γ release. Human IgM Fc receptor (FcμR) was reported to be present mainly on a small fraction of B lymphocytes, NK cells, and possibly a helper subset of T lymphocytes (47, 48). Pentamer form of IgM and an intact $CH_3$ domain are required for optimal binding to FcμR. Monomeric or dimeric subunits of IgM are less efficient in binding to FcμR (49, 50). Cross-linking of IgM to FcμR on T cells inhibited the mitogen-induced T cell proliferation, and FcμR may function as a negative signal transducing molecule (51, 52).

Therefore, it can specifically bind to human CD3 molecule and FcμR. It is conceivable that scUCHT1 can cross-link human B and T cells, and possibly T and T cells. In an in vitro assay, scUCHT1 from both COS-7 and SP2/0 cells had little effect in the T cell proliferation assay at low concentrations (below 10 ng/ml), and became inhibitory as the concentration increased. In accordance with these results, scUCHT1 did not induce TNF-α production and even inhibited the basal yield of IFN-γ.

The present chimeric anti-CD3 single chain antibody scUCHT1 possesses high human CD3 binding specificity and affinity, and does not induce T cell proliferation and cytokine release. Moreover, it has a human IgM Fc fragment, which should decrease the possibility of inducing human anti-mouse antibody response. Thus, scUCHT1 can be used for clinical immunosuppressive treatment.

Example 10

Cloning the Full-Length of DT Gene for the Construction of DTM2

Corynebacteriophage beta (*C. diphtheriae*) tox 228 gene sequence was from genebank. (*Science* 221, 885-858, 1983). The sequence is 2220 bp. There are 300 bp of 5' untranslated region (1 to 300) including the promoter sequence around (−180 to −10), 1682 of coding region (301-1983) including signal peptide (301 to 376), A chain (377 to 955) and B chain (956 to 1983), and 3' untranslated region (1984 to 2220).

The full-length DT was amplified in two fragments. The pelB leader sequence (ATG AAA TAC CTA TTG CCT ACG GCA GCC GCT GGA TTG TTA TTA CTGCGCT GCC CAA CCA GCG ATG GCC 3') (SEQ ID NO:10) was added to the 5' end of the DT coding sequence to all the constructs during polymerase chain reaction by primer EcosignalDT-1 and EcosignalDT-2. The upstream fragment of 311 bp (from position 301 to 546 bp) was amplified by oligo EcosignalDT-2 and p546R with CRM9 DNA as a template and the downstream fragment of 1471 bp was amplified by p514S and p1983R with the DTM1 DNA as template. Then, the combined PCR product of full-length DT was amplified with primer EcosignalDT-1 and p1983% As a result, the amplified DT coding sequence (position 376 to 1983 bp) acquired the pelB leader sequence added to the 5' end and contains the two mutant sites [(508 Ser to Phe) and (525 Ser to Phe)] as DTM1 does.

Primers:

```
EcosignalDT-1 5' ATG AAA TAC CTATTG CCT ACG GCA GCC GCT      (SEQ ID NO:11)
GGA TTG TTA TTA CTC GCT GCC CAA 3'

EcosignalDT-2 5' GGA TTG TTA TTA CTC GCT GCC CAA CAA GCG     (SEQ ID NO:12)
ATG GCCGGC GCT GAT GATGTT GTT GAT TC 3' p546R:  5' CGGTACTATAAAACTCTTTCCAATCATCGTC 3'               (SEQ ID NO:13)

p514S:  5' GACGATGATTGGAAAGAGTTTTATAGTACCG 3'               (SEQ ID NO:14)

p1983R: 5' AGATCTGTCGA/CTCATCAGCTTTTGATTTCAAAAAATAGCG 3'.   (SEQ ID NO:15)
```

A mutant residue was introduced at position 52. The glycine (GGG) at position 52 wild type DT was substituted by glutamic acid (GAG). The two primers p546R and p514S carried the mutant codon (GGG to GAG). The PCR products of these two primers contained the substituted codon (GAG) instead of codon GGG. The jointed double stranded DNA of the two fragments (1683 bp) were cloned into pET 17b by restriction site NdeI and BamHI.

The data show that anti-human blocking antibodies are specifically directed at the toxin C-terminus. Although a specific sequence derived from the UCHT1 VLVH regions is described, anyone skilled in the art could make sequence variations in VLVH domains which can be designed to increase the affinity of the sc-anti-CD3-antibody conferring a more favorable therapeutic ratio to fusion immunotoxins using this derivative. Such modifications are within the scope of the present teaching. The disadvantage of the monovalent antibody VLVH construct, is that it has a lower affinity for T cells compared to the chemically coupled conjugate which utilizes a divalent antibody.

These are believed to be the first instances of a sc anti-CD3 antibodies. IgM was chosen since very few B cells or macrophages contain IgM Fc receptors. (Binding of immunotoxin to cells other than T cells reduces the specificity of the anti-T cell immunotoxin and this situation is purposefully avoided). However, using a bacterial expression system no carbohydrate is attached to the antibody which also eliminates Fc receptor binding. Thus, substituting other human IgG constant domains would be a routine modification.

Figure 8:
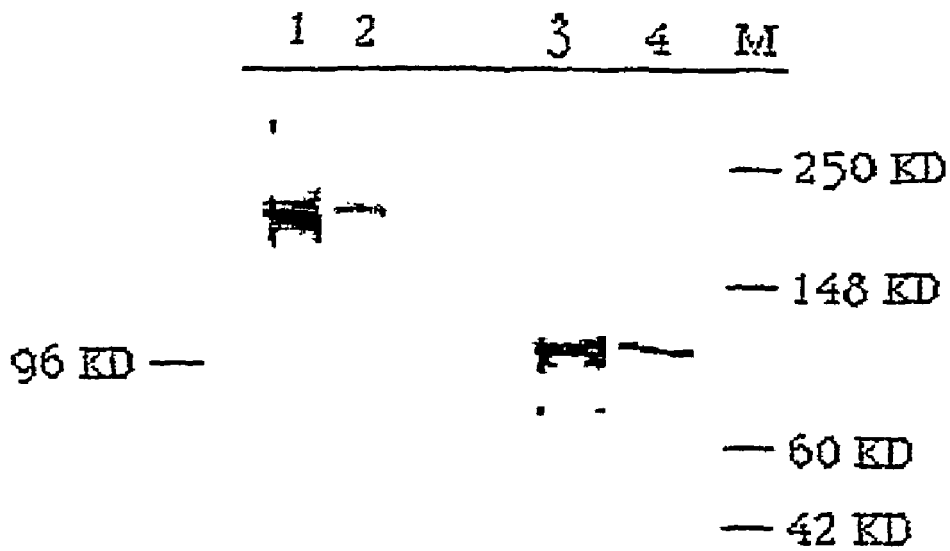
FIG. 8 shows a Western blot showing the secreted scUCHT1 immunotoxin.
Figure 9A:
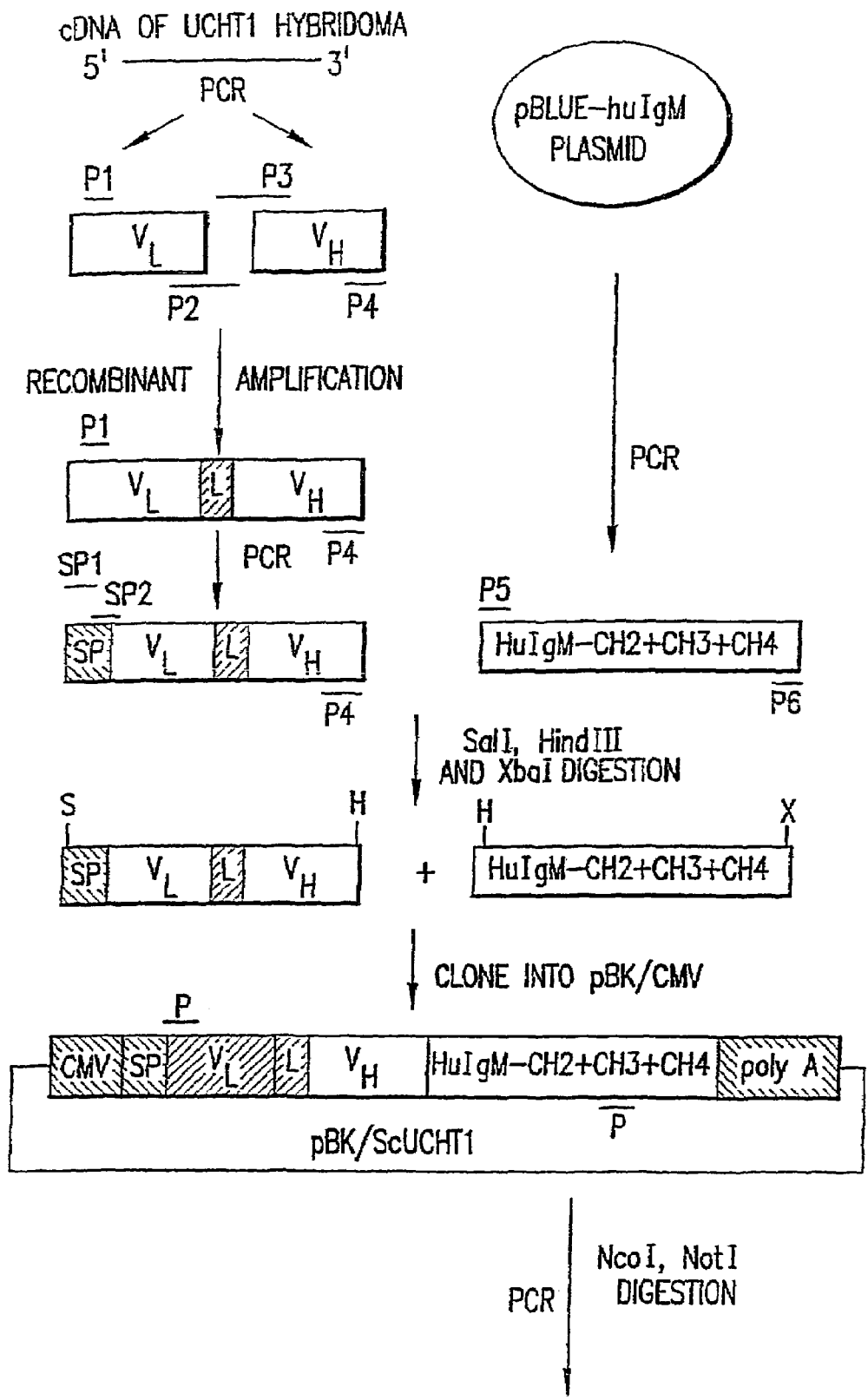
FIG. 9 shows a schematic flow sheet for generating the divalent immunotoxin fusion protein construct.
Figure 9B:
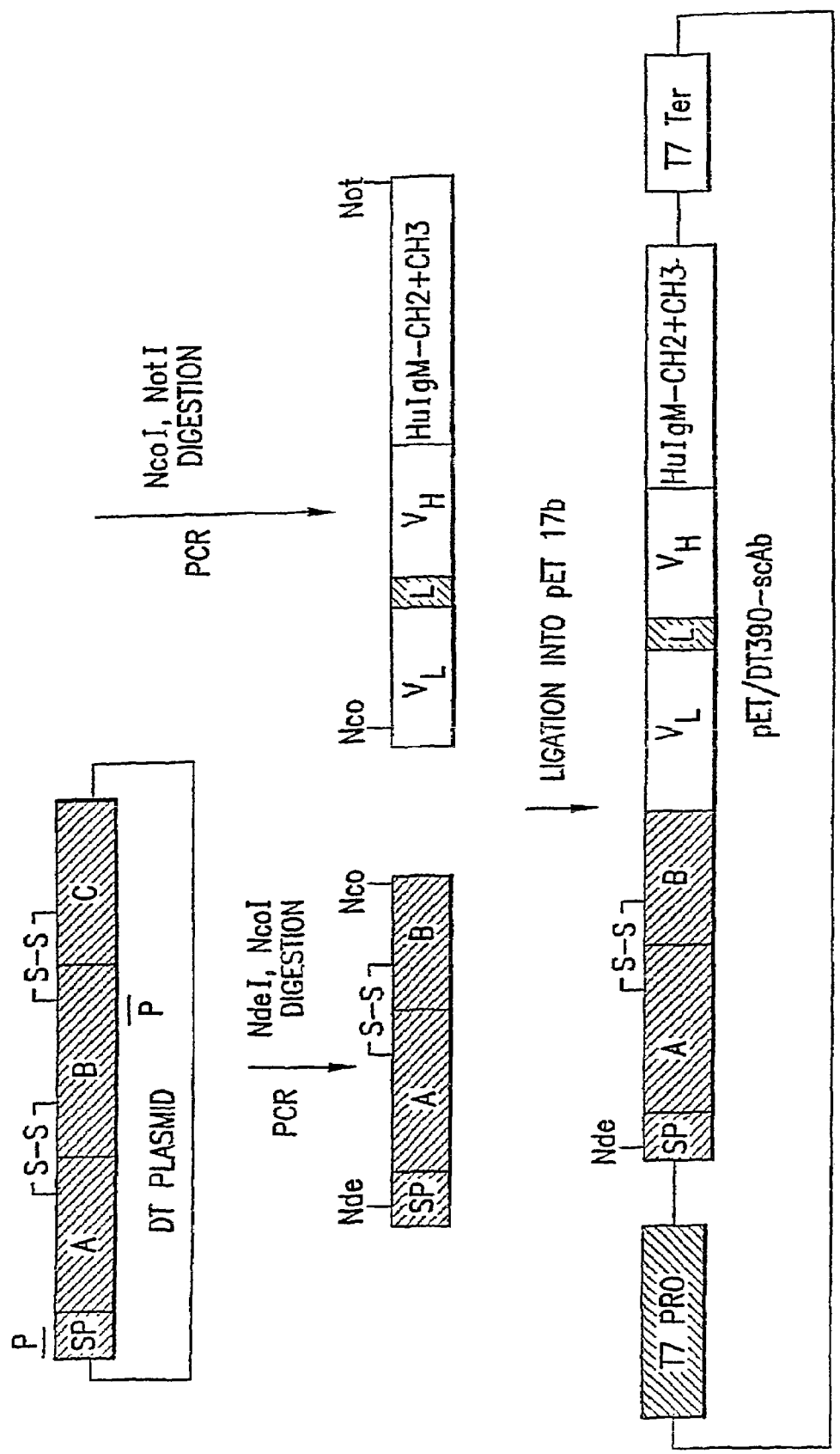

A variety of divalent fusion protein immunotoxins are provided. These have been expressed in *E. coli*, and Western blots of reduced and non-reduced SDS gels confirm that most of the immunotoxin is secreted as the dimeric (divalent) species (FIG. 8). The position of the toxin has been varied in an attempt to minimize stearic hindrance of the divalent antibody site, yet provide the best interactions with the CD3 receptor to facilitate toxin translocation across the membrane. FIG. 9 shows a clone expressing divalent immunotoxin fusion proteins. The clone producing this consists of a clone constructed by using the single chain antibody followed by a stop codon and the single chain immunotoxin, all under one promoter (Better et al. *Proc. Natl. Acad. Sci.* 90:457-461, January 1993). After secretion and oxidation of the interchain disulfide, 3 species are present: sc divalent antibody, divalent fusion immunotoxin, and a divalent sc antibody containing only one toxin. This species is isolated by size separation. The advantage of this species is that stearic hindrance to the divalent antibody domains is limited by the presence of only one toxin domain. Other variations are routine to construct given the methods described herein and in the art. Those diagramed are considered to be the most likely to exhibit divalent character. Numerous orientations of toxin relative to antibody domains can be made and many are expected to be effective.

In addition, the length of the toxin C-terminus has been varied to provide optimization between two competing functions. The numbers after DT refer to the number of amino acid residues counting the amino terminus of the toxin A chain as 1. The full length toxin is called DTM1 and was provided by Dr. Richard Youle NINDS, NIH (Nicholls et al. *J. Biol. Chem.* 268(7):5302-5308, 1993). It has point mutations S to F at positions 508 and 525. This full length toxin mutant has the essential mutation of CRM9, S to F at 525 which reduces binding to the DT receptor by 34 logs without abolishing the translocation function. The other mutation S to F at 508 has been added because of previous restrictions on cloning mutant DT that can revert to wild type toxin with a minimum lethal dose of 0.1 microgram/kg by means of a single base pair reversion. Other mutations can be routinely made in the C terminus to perform this function (Shen et al. *J. Biol. Chem.* 269(46):29077-29084, 1994). They are: F530A; K526A; N524A; V523A; K516A Y514A. A clone having a single point mutation in DT reducing toxicity by 10-100 fold can be made providing that the clone contains an antibody fragment fusion protein, because chemical conjugation of antibody to DT has been shown to reduce systemic wild type toxin toxicity by 100 fold (Neville et al. *J. Biol. Chem.* 264(25):14653-14661, 1989). Therefore, the present invention provides a full length mutant DT sequence with the 525 S to F mutation alone as well as those listed above. These same mutations are also contemplated for the B chain mutant site in DTM2 and can be made similarly. Previous data with chemical conjugation has shown that the longer the C-terminus the better the translocation function (Colombatti et al. *J. Biol. Chem.* 261 (7):3030-3035, 1986). However, the shorter the C-terminus the less effect of circulating anti-toxin blocking antibodies. Since patients have different levels of blocking antibodies which can be measured (see toxicity assay in), the optimal immunotoxin can be selected for individual patients. scUCHT1 fusion proteins with DTM1 and DT483, DT390 and DT370 have been cloned and expressed in *E. coli*. Each of these variations as well as the divalent scUCHT1 fusion proteins using each of these toxin domains are provided.

The present invention provides an improvement on CRM197 (a non-toxic toxin mutant described in U.S. Ser. No. 08/034,509, filed Sep. 19, 1994) referred to herein as DTM2. DTM2 has the same mutation as CRM197 plus two mutations in the C-terminus which block binding (see sheet and FIG. 8). This is expected to reduce the likelihood of immune complex disease which could result when CRM197 becomes bound to cells and then is further bound by circulating antitoxin. Kidneys are particularly susceptible. DTM2 cannot bind to cells thereby lessening the possibility of tissue damage. In addition DTM2 is made for high level production by including the pelB secretory signal for production in *E. coli* or a iron-independent mutated promoter DT sequence cloned from CRM9 DNA for production in *C. diphthleriae*. The essential feature of *DTM2* is the S to F mutation at 525 and the G to E mutation at 52, and a construct containing these two mutations is provided.

All of the constructs reported here can be expressed in *E. coli* using pelB signal sequences or other appropriate signal sequences. Expression can also be carried out in *C. diphtheriae* using appropriate shuttle vectors (Serwold-Davis et al. *FEMS Microbiol. Letters* 66:119-14, 1990) or in protease deficient strains of *B. subtilis* and using appropriate shuttle vectors (Wu et al. *Bio. Technol.* 11:71, January 1993).

Example 11

Thymic Injection and Tolerance Induction in Primates

Without thymic treatment, rhesus monkey renal allografts reject at a mean of 7 days. Renal allografts in rhesus monkeys (age 2-5 years; 2-3 kg body weight) were performed. The experimental protocol consisted of first selecting MHC class I disparate rhesus monkey donors and recipients. Donor lymphocytes were injected into the recipient thymus gland 7 days prior to renal allografting from the same donor. Recipients received the immunotoxin of the present invention by intravenous injection. Renal allografts were performed and recipients underwent native nephrectomy.

Immunotoxin

Techniques for preparing anti-CD3-CRM9 (where the antibody is directed at the human T-cell receptor complex "CD3") have previously been described. See U.S. Pat. No. 5,167,956 and D. Neville et al., 89 P.N.A.S. USA 2585-2589 (1992). A hybridoma secreting UCHT1 was kindly provided by Dr. Peter Beverly, Imperial Cancer Research Fund, and was grown in ascites fluid and purified over immobilized Protein A. This is an IgG1.

FN18, also an IgG1, is the rhesus analog of UCHT1 and shares with it the property of being a T-cell mitogen in the presence of mixed mononuclear cells. FN18 was produced in hollow fiber and purified over Protein A. The strain of *C. diphtheriae* used for production of CRM9, CRM9 C7($\beta^h$ tox-201 tox-9 h') was obtained from R. Holmes, Uniformed Services University of Health Sciences, Bethesda, Md. See also V. Hu et al., 902 Biochimicia et Biophysica Acta 24-30 (1987).

Antibody-CRM9 was recovered from the supernatant of 30 liter fermentation runs under careful control of iron concentration. See S. L. Welkos et al., 37 J. Virol. 936-945 (1981). CRM9 was purified by membrane concentration, ammonium sulfate precipitation and chromatography over DEAE. See S. Carroll et al., 165 Methods In Enzymology 68 (1988).

Large scale purification of immunotoxin was accomplished by HPLC size exclusion chromatography on MODcol (1266 Andes Blvd., St. Louis, Mo. 63132) 2"×10" column packed with Zorbax (DuPont Company) GF-250 5 μm, 150 Å. Fractions containing 1:1 toxin:antibody mol ratios were isolated for these studies. immunotoxins were synthesized as previously described by thiolating both the monoclonal antibody moiety and the toxin moiety and then crosslinking with bismaleimidohexane. See D. Neville et al., 264 J. Biol. Chem. 14653-14661 (1989). CRM9 was nicked and the monomer (Carroll et al.) was isolated by the MODcol column described above prior to thiolation.

While CRM9 is a presently preferred mutant diphtheria toxin protein, other preferred embodiments include diphtheria mutants with a mutation in the DT binding region, such as DT390 (see example 9), should also be suitable (as the concept behind the immunotoxin is to replace the normal binding function with the antibody provided T-cell binding function, with minimal conformational change).

T-Cell Ablation

Monoclonal antibody FN18 (specific for rhesus monkey T lymphocytes) coupled to the immunotoxin CRM9 was used to deplete peripheral blood T-cells to levels below 200 cells/M13 in adult rhesus monkeys (measured six days after the injection). Some modest B cell depletion occurred. Following depletion, complete T-cell recovery takes about three to four weeks in a juvenile rhesus monkey model using this agent. Surprisingly, notwithstanding this fast recovery, donor T-cells injected into the thymus still were not impaired in their ability to produce tolerance.

Four monkeys received 0.2 mg/kg of immunotoxin, in three divided doses (24 hours apart from each other). Another monkey received 0.133 mg/kg immunotoxin in two divided doses (24 hours apart from each other), and the other monkey received 0.1 mg/kg in two divided doses (24 hours apart from each other). Two days after the last dose of immunotoxin, all monkeys except the last had at least 80% (actually greater than 99%) depletion of T cells both in the peripheral blood and in the lymph nodes. The lowest dose used in the last monkey reduced, but did not substantially eliminate either peripheral blood or lymph node lymphocytes.

Lymphocytes

Lymphocytes to be donated are preferably pooled from axillary and cervical lymph nodes of a single donor. The nodes are harvested, strained through a mesh to separate the lymphocytes, diluted with saline, and then injected. Alternatively, a representative "cocktail" of lymphocytes from several primates other than the donor, at least one of which turns out to be the same haplotype as the likely donor, should also work (if the donor is not available early enough).

Transplantation

Table 8 summarizes the outcome of renal transplants performed following thymic injection of donor lymph node lymphocytes (mixture of T and B cells) combined with immunotoxin therapy. Cells injected intrathymically consisted of the pooled axillary and inguinal lymph node lymphocytes in the numbers listed.

TABLE 8

Renal Allograft Survival by Treatment Group*

| Monkey | Intrathymic injection | FN18-CMR9 | Survival (days) |
|---|---|---|---|
| T4T | none | none | 5 |
| X9X | none | none | 7 |
| 1FE | none | none | 7 |
| H7C | 10.6 × 108 donor lymphocytes | none | 1 |
| W7C | 9.1 × 108 donor lymphocytes | none | 1 |
| 93023 | 7.0 × 108 donor lymphocytes | 0.2 mg/kg | >517 |
| 92108** | 1.9 × 108 donor lymphocytes | 0.2 mg/kg | 181 |
| POJ | 7.5 × 108 donor lymphocytes | 0.2 mg/kg | >340 |
| POF | normal saline | 0.2 mg/kg | >368 |
| PIP | normal saline | 0.2 mg/kg | >250 |
| W7D | none | 0.2 mg/kg | 51 |
| POG | none | 0.2 mg/kg | 84 |
| PIN | none | 0.2 mg/kg | >165 |
| X3J | none | 0.2 mg/kg | >117 |

*FN18-CRM9 was given on day −7, −6, −5 at a total dose of 0.2 mg/kg, i.v. Lymphocytes and saline were injected intrathymically on day −7.
**(acute rejection 40 days after skin graft)

Two monkeys died of pneumonia, one at 39 days and the other at 13 days. A third monkey died at 8 days of complications stemming from a urine leak. At autopsy, none of these three monkeys had any evidence of renal transplant rejection, either grossly or histologically.

Monkey #93023, which received the intrathymic injection and immunotoxin seven days prior to renal transplantation, had normal renal function more than 180 days post-transplant. A renal biopsy of his transplanted kidney at 100 days showed no evidence of rejection.

Surgical Procedures

Preferred surgical procedures include partial median sternotomy for exposure of the thymus and injection of donor lymphocytes into the thymus gland; inguinal and axillary lymphadenectomy to procure donor lymphocytes; laparotomy for procurement of the left kidney from kidney donors; and a second laparotomy for renal transplantation and native right nephrectomy. All of these procedures are performed under general anesthesia as outlined below. Serial blood draws are performed under ketamine and xylazine anesthesia as outlined below.

Thymic injection is performed through a midline chest incision beginning at the sternal notch extending down to the midportion of the sternum. The sternum is divided and retracted to expose the underlying thymus gland. The thymus gland is injected with donor lymphocytes and the sternum reapproximated and the soft tissue closed.

Donor nephrectomy is performed under general anesthesia through an upper midline incision in the abdomen. The retroperitoneal attachments of the left kidney are divided, the ureter is ligated and divided near the bladder, and the left renal artery and vein are dissected free. The left renal artery and vein are ligated adjacent to the aorta and inferior vena cava, and the kidney excised and flushed on the back table with preservation solution.

The recipient operation for renal transplantation is performed by making a midline abdominal incision under general anesthesia. The distal aorta and inferior vena cava are dissected free. The vena cava is clamped proximally and distally near its bifurcation and the donor renal vein anastomosed end-to-side to the recipient inferior vena cava using running 7-0 proline suture. The aorta is cross-clamped proximally and distally just proximal to its bifurcation and the donor renal artery anastomosed end-to-side to the aorta using running 8-0 proline. A ureteroneocystostomy is then performed by making an anterior cystotomy and anastomosing the spatulated tip of the donor ureter to the bladder mucosa using B-0 proline suture. The cystotomy is then closed. The abdomen is then closed.

Lymphadenectomy is performed through an approximately 2 cm groin incision for inguinal lymphadenectomy and a similar length incision for axillary lymphadenectomy. The lymph nodes are excised and bleeding points cauterized. The skin is then closed with running 4-0 nylon suture.

It should be appreciated that kidney transplants are merely an example application. The invention should be suitable for use with a wide variety of organs (e.g. liver, heart, lung, pancreas, pancreatic islets and intestine).

In sum, surprisingly immunotoxins known to severely deplete T-lymphocytes will selectively deplete the host lymphocytes, without interfering with the donor T lymphocytes ability to cause tolerance. Further, the extreme level of depletion caused by this immunotoxin facilitates induction of tolerance.

Example 12

Anti-CD3-CRM9 Immunotoxin Promotes Tolerance in Primate Renal Allografts

The ability of thymic injection and transient T lymphocyte depletion to permit development of donor-specific tolerance to rhesus monkey renal allografts was investigated. For T cell ablation, the immunotoxin FN18-CRM9, was used that depletes T cells from both the lymph node and blood compartments (see Example 5 and Neville et al. J Immunother 1996 (In press)). FN18-CRM9 is composed of an anti-rhesus monkey CD3 monoclonal antibody (mAb), FN18 (Neville et al., 1996), and a binding site mutant of diphtheria toxin, CRM9 (Neville et al. Proc Natl Acad Sci USA; 89:2585-2589 (1992)). Compared to other anti-T cell agents used in clinical and experimental transplantation, FN18-CRM9 produces more effective killing of T cells, and this was the rationale for its choice as an agent to promote transplantation tolerance. Anti-CD3-CRM9 alone successfully delayed graft rejection. T cell depletion with anti-CD3-CRM9 combined with thymic injection prolonged graft survival to >150 days in five of five recipients and induced donor-specific tolerance in four of five recipients. Donor skin grafts were accepted long-term, whereas third party skin grafts were promptly rejected. These results are unique in their reliable induction of donor-specific tolerance as confirmed by skin grafting in a non-human primate model. This approach to tolerance reasonably correlates to induction of tolerance in humans.

MHC Typing and Donor-Recipient Selection.

Donor-recipient pairs were selected based on maximizing MHC disparity. This was based on pre-transplant cytotoxic T lymphocyte (CTL) and mixed lymphocyte reaction (MLR) analysis (Derry H, Miller R G. Fathman C G, Fitch F W, eds. New York: Academic Press, 510 (1982) and Thomas et al. Transplantation, 57:101-115 (1994)), analysis of MHC class I differences by one-dimensional isoelectric focusing (1-D IEF) (Watkins et al. Eur J Immunol; 18:1425-1432 (1988)), and evaluation of MHC class II by PCR-based analysis.

Flow Cytometry.

Two×$10^5$ lymphocytes obtained from peripheral blood or inguinal, axillary, or mesenteric lymph nodes were stained with FITC-labeled FN18 or isotype control antibody. Cells were subjected to flow cytometry on a Benton Dickenson FACSCAN.

Animals and Surgical Procedures.

Outbred male juvenile rhesus monkeys (ages 1 to 3 years), virus free, were used as donors and recipients. Surgical procedures were performed under general anesthesia, using ketamine, 7 mg/kg, i.m., and xylazine, 6 mg/kg, i.m. induction, and inhalation with 1% halothane to maintain general anesthesia. Post-operatively, monkeys received butorphanol, 0.25 mg/kg, i.v., and aspirin, 181 mg, p.o., for pain control. Thymic injection was performed via a limited median sternotomy to expose the thymus gland. Seven days before renal transplantation, each lobe of the thymus was injected with donor lymphocytes suspended in 0.75 to 1.0 ml normal saline using a 27 gauge needle. Donor lymphocytes were procured from the inguinal, axillary, and mesenteric lymph nodes of the donor, counted and resuspended in normal saline for injection. Heterotopic renal transplants were performed using the donor left kidney. Following transplantation, the recipient underwent native nephrectomy. Graft function was monitored by measuring serum creatinine. Rejection was diagnosed by rise in serum creatinine to >0.07 mol/L, no evidence of technical problems, such as urine leak or obstruction at autopsy, and histologic confirmation. Monkeys were killed with a lethal dose of sodium pentobarbital if they rejected their kidney, and were autopsied. To test for tolerance, full thickness skin grafts were placed using ventral abdominal skin from donors placed onto the dorsal upper back of recipients. Grafts were evaluated daily by inspection.

Immunosuppression.

FN18-CRM9 was chemically conjugated and purified as described (Neville et al. 1996). It was administered intravenously at a dose of 0.2 mg/kg in 3 divided daily doses starting 7 days prior to renal transplantation. No additional immunosuppressive drugs were given to any of the monkeys, and monkeys were not isolated from environmental pathogens.

Figure 10A:
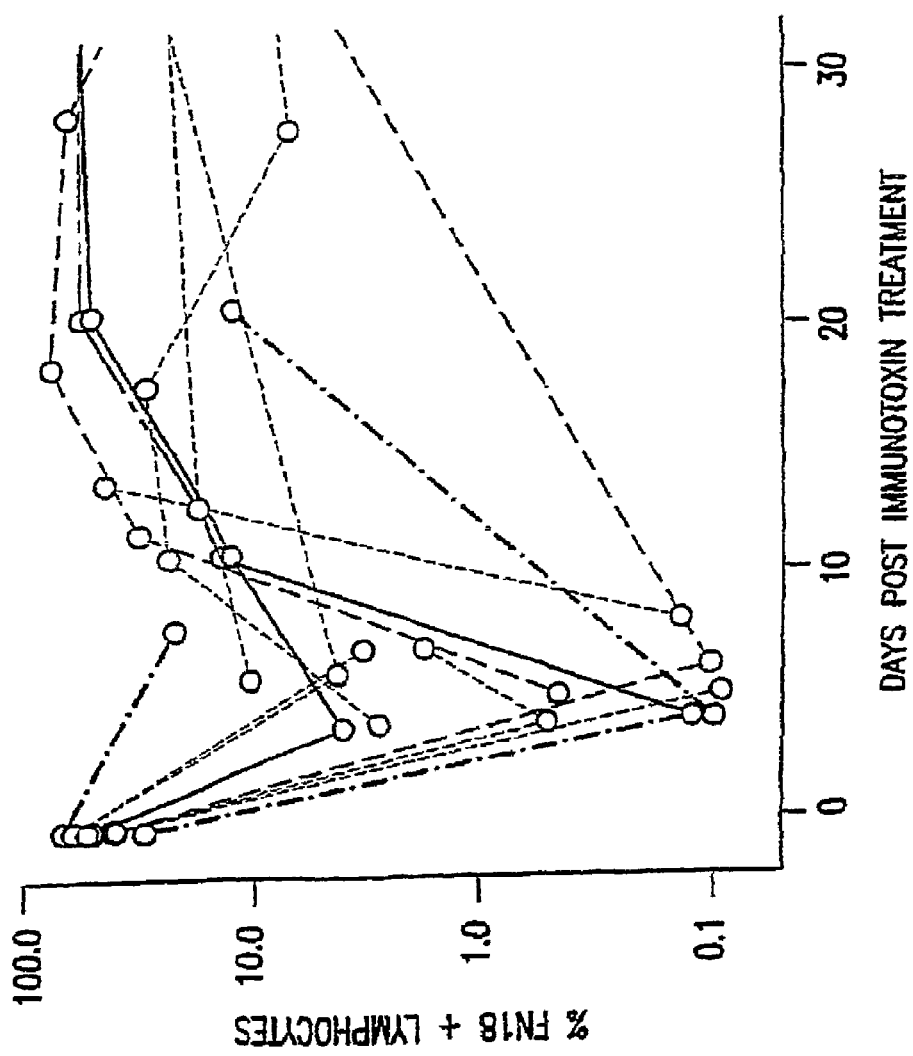
FIG. 10a shows CD3+ cell depletion and recovery in peripheral blood following immunotoxin treatment. Days refer to days after the first dose of immunotoxin.
Figure 10B:
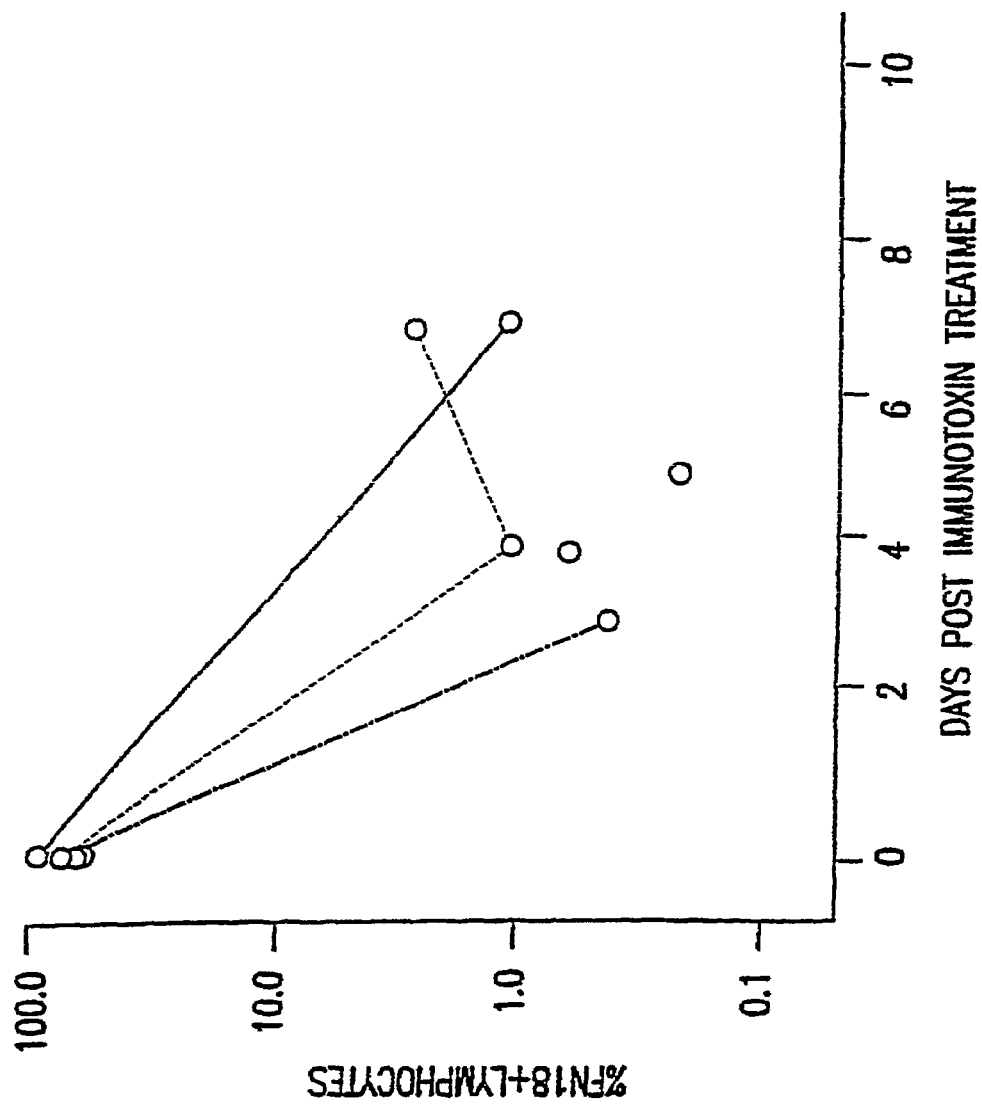
FIG. 10b shows CD3+ cell depletion in lymph nodes following immunotoxin treatment.

The effect of FN18-CRM9 on rhesus peripheral blood lymphocytes and lymph node lymphocytes is summarized in FIGS. 10a and 10b. In addition to causing transient T cell depletion from the peripheral blood, FN18-CRM9 depleted lymph node lymphocytes almost completely at the dose given and when measured 04 days after the third dose of drug. Absolute leukocyte counts did not change significantly with treatment. Recovery times were variable, but in general peripheral blood T lymphocytes returned toward baseline levels 2 to 4 weeks following treatment. Recovery rates varied between individual monkeys.

Untreated monkeys acutely rejected their allografts (n=3) within one week (Table 8). Monkeys receiving lymphocytes intrathymically but no anti-CD3-CRM9 developed hyperacute rejection within 24 hours (Table 8) with the typical histologic features of hemorrhage, infarction, and a dense neutrophil and lymphocyte infiltrate. Three of three recipients treated with donor lymphocytes intrathymically and anti-CD3-CRM9 had long-term graft survival (Table 8). One monkey (92108) rejected its kidney 40 days after a donor and third party skin graft were placed to test for donor-specific tolerance. This monkey rejected its third party skin graft at 10 days and a lymphocyte infiltrate in the donor skin graft developed with rejection of the renal allograft 40 days later. The other two recipients of donor lymphocytes and anti-CD3-CRM9 were successfully skin grafted from the donor with survival of these skin grafts for more than 100 days, but rejection of third party skin grafts at 10 days. All biopsies of their renal allografts showed an interstitial infiltrate but no evidence of glomerular or tubular infiltrates or injury. Two monkeys receiving normal saline injections in the thymus in combination with anti-CD3-CRM9 became tolerant of their renal allografts. Both of these monkeys rejected a third party skin graft at 10 days and have had long-term survival of donor skin grafts. The results of all skin grafts are summarized in Table 9. Renal biopsies of long-surviving tolerant recipients demonstrated focal interstitial mononuclear infiltrates without invasion or damage of tubules or glomeruli. Monkeys treated with anti-CD3-CRM9 alone developed late rejection in two cases at day 54 and day 88 and the histology of their kidneys at autopsy demonstrated a dense lymphocytic infiltrate. In two other cases, long-term unresponsiveness was observed (Table 8) to >127 days and >79 days. The thymuses of the two monkeys which rejected their grafts were markedly decreased in size at autopsy compared to age-matched controls prior to treatment, but a small thymic remnant was identified.

The data demonstrate that anti-CD3-CRM9 is a potent, new immunosuppressive agent which is capable of inducing tolerance in outbred MHC class I and class II disparate rhesus monkeys. This attribute distinguishes it from other currently known immunosuppressive agents, such as antithymocyte globulin, cyclosporine, or monoclonal antibodies which have more limited efficacy or safety in tolerance induction in large mammals or which require more cumbersome strategies (Powelson et al., Transplantation 57: 788-793 (1994) and Kawai et al., Transplantation 59: 256-262 (1995)). The degree of T cell depletion produced by 3 doses of the drug is more complete than that achieved by a longer course of anti-lymphocyte globulin, which generally depletes to a much lesser degree (Abouna et al., Transplantation 59: 1564-1568 (1995) and Bourdage J S, Hamlin D M, Transplantation 59:1194-1200 (1995)). Unlike OKT3, an activating antibody which does not necessarily kill T lymphocytes, anti-CD3-CRM9 is a lytic therapy with a more profound effect on T cells than OKT3 and better potential for tolerance induction. Its efficacy may be in part related to its ability to deplete T cells in the lymph node compartment, as well as in peripheral blood, since the majority of potentially alloreactive T cells reside in the lymph node compartments. The T cell depletion produced by anti-CD3-CRM9 is more complete than that achieved by any other known pharmacologic means, including total lymphoid irradiation, and it avoids the toxic side effects of radiation. Following treatment with the anti-CD3-CRM9, the thymus decreases markedly in size, although thymic cortex and medullary structures are still apparent. Anti-CD3-CRM9 appears to be safe and well tolerated in rhesus monkeys. No significant adverse drug effects were encountered. About half of the monkeys were treated with intravenous fluids for 3 to 5 days following administration to prevent dehydration. No infections were encountered in these experiments and only routine perioperative antibiotic prophylaxis was used at the time of renal transplantation and thymic injection. Cytokine release syndrome was not seen and monkeys did not develop febrile illness following drug administration.

The induction of tolerance in monkeys receiving thymic injection of either donor lymphocytes or normal saline in conjunction with anti-CD3-CRM9 suggests that thymic injection may provide an adjunct to tolerance induction using T cell depletion with anti-CD3-CRM9. Presumably, CD3+ lymphocytes present in the donor lymphocyte inoculum are also killed by the drug administered to the recipients. This would leave donor B cells to express donor MHC class I and class II in the recipient thymus. Rodent studies would suggest that it is the presence of one or both of these antigens that is crucial to promoting thymic tolerance (Goss J A, Nakafusa Y, Flye M W, Ann Surg 217: 492-499 (1993); Knechtle et al., Transplantation 57: 990-996 (1994) and Oluwole et al., Transplantation 56: 1523-1527 (1993)). Of even more interest is the observation that normal saline injected into the thymus in conjunction with anti-CD3-CRM9 produced tolerance in two of two recipients. Surprisingly, the success of this approach suggests that immunotoxin rather than thymic injection is crucial. Alternately, non-specific disruption of thymic integrity may contribute The observation that two of four recipients treated with anti-CD3-CRM9 alone became tolerant suggests that transient depletion of T cells by the drug is crucial in promoting tolerance. In rodents, transplant tolerance can be achieved by concomitant administration of donor antigen and anti-T-cell agents (Qin S et al., J Exp Med 169: 779-794 (1989); Mayumi H, Good R. A., J Exp Med 1989; 169: 213-238 (1989); and Wood M L et al., Transplantation 46: 449-451 (1988)), but this report demonstrates donor-specific tolerance using T cell specific therapy alone. The depletion of T cells from the lymph node compartment by anti-CD3-CRM9 may be crucial in promoting its efficacy as a tolerance inducing agent and differentiate it from anti-CD3 mAb alone which depletes the peripheral blood CD3 cells, but has a weaker effect on the lymphoid tissues (Hirsch et al., J Immunol 140: 3766-3772 (1988)).

These experiments using an outbred, MHC incompatible non-human primate model provide a rationale for tolerance strategies in human organ transplantation. The results are unique in offering a simple, reliable, and safe approach to tolerance in a model immunologically analogous to human solid organ transplantation. An anti-human CD3 immunotoxin (e.g., scUCHT1-DT390 and anti-CD3-CRM9) has been constructed and has T cell killing properties similar to FN18-CRM9 (see Examples 9 and 11 Neville 1992 and Neville 1996). The preliminary results reported here have broad implications for tolerance in humans.

In summary, immunotoxin treatment alone leads to marked prolongation of graft survival in 100% of the cases to date. Eliminating the thymic manipulation did not alter the success rate. No other drug or treatment regimen comes close to achieving these results in primates.

TABLE 9

Skin Graft Results

| Monkey | Interval after kidney transplant | skin survival (days) | 3rd party Donor skin survival (days) |
|---|---|---|---|
| 93023 | 182 | 10 | >367 |
| 92108 | 140 | 1040 | (and renal allograft rejection) |
| POF | 147 | 10 | >221 |
| POJ | 188 | 10 | >152 |
| PIP | 176 | 10 | >74 |

Example 13

Immunotoxin Alone Induces Tolerance

Depletion of mature T cells can facilitate stable acceptance of MHC mismatched allografts, especially when combined with donor bone marrow infusion. Although ATG and anti-T cell mAbs eliminate recirculating cells, residual T cells in lymphoid tissue have potential to orchestrate immune recovery and rejection. Unlike pure antibodies, CD3-immunotoxin (CD3-IT) can destroy cells following direct binding and intracellular uptake without limitations of immune effector mechanisms. Thus, CD3-IT may have superior immunosuppressive activity. The action of CD3-IT in rhesus monkey kidney transplant recipients was examined.

The present example of CD3-IT is a conjugate of IgG1 mAb anti-rhesus CD3 epsilon (FN18) and a mutant diphtheria toxin CRM9 (FN18-CRM9). The B chain of CRM9 diphtheria toxin bears a mutation that markedly reduces binding to diphtheria toxin receptors, allowing specificity to be directed by anti-CD3.

CD3-IT was administered to 3-5 kg normal male rhesus monkey allograft recipients at a dose of 67 μg/kg on days-1 and 33 μg/kg on days +0 and +1 without additional immunosuppressive drugs. Recipient-donor combinations were selected to be incompatible by MLR and multiple DR allele mismatches; and all were seronegative for CRM9-reactive antibody to diphtheria toxin. Three groups received CD3-IT: (1) alone (n=3), (2) in combination with day 0 infusion of donor bone marrow DR$^-$CD3$^-$ (n=3), (3) or with donor bone marrow and 200 cGy lymphoid irradiation given on days-1 and 0 (n=3).

Kidney allograft survival was remarkably prolonged. With CD3-IT alone, graft survival time was 57, 51, and 44 days. In combination with donor bone marrow infusion, graft survival was >400, 124, and 36 days. CD3-IT, lymphoid irradiation, and donor bone marrow resulted in graft survival of >300, 143, and 45 days. Both the 36 or 45 day graft losses were from hydronephrosis without evidence of rejection. Peripheral blood T cell counts fell selectively by 2 logs, and time to 50% recovery was 20-60 days. The peripheral blood CD3+CD4/CD8 ratio increased 2-6 fold before adjusting to baseline by 3 weeks. B cell/T cell ratios in lymph nodes were elevated >40-fold on day 5-7, reflecting a 1-2 log reduction in circulating and fixed tissue T cell compartments. LN CD4/CD8 ratios were normal at 5-7 days, but CD45RA+CD4 and CD28-CD4 cell subsets increased >1 log while CD28+ CD8 cells decreased by >1 log, suggesting functional subset changes.

Anti-donor MLR responses became reduced uniformly, but specific unresponsiveness was seen only in the donor bone marrow-treated group. Peripheral blood microchimerism was detectable by allele specific PCR after donor bone marrow-infusion. These studies show CD3-IT to be an unusually effective and specific immunosuppressive agent in non-human primate transplantation and provides clinical tolerance induction strategies applicable to transplantation in humans.

Example 14

Immunotoxin Plus Short Term Immunosuppressant Drugs Induces Tolerance in Monkeys in Models Simulating Human Cadaveric Donors The efficacy of IT in prolonging allograft survival was evaluated in a model that stimulates transplantation of organs from cadaveric donors in humans. Rhesus monkey donor-recipient pairs were selected on the basis of MHC class I and II disparity. Monkeys were given anti-CD3-CRM9 immunotoxin 0.2 mg/kg iv in three divided daily doses starting on the day of the renal allograft (group 1). In group 2, recipients also received methylprednisolone 125 mg iv daily for 3 days and mycophenolate mofetil 250 mg po daily for 3 days starting on the day of the transplant. Rejection was monitored by serum creatinine levels and confirmed histologically.

| Graft Survival (days) | | |
| --- | --- | --- |
| Group 1 (IT alone) | Group 2 (IT + MMF + methylprednisolone) | Group 3 (untreated) |
| 79 | >90 | 5 |
| 57 | >75 | 7 |
| 51 | >60 | 7 |
| >124 | | |
| >102 | | |

The short burst of intensive anti-T cell therapy given at the time of the transplant appears to be well tolerated and to reliably result in long-term allograft survival. The mRNA cytokine profile of graft infiltrating cells obtained from renal transplant biopsies in this protocol suggests that IL-2 and γ-IF (TH$_1$ associated) are present in measurable levels and IL-4 and 10 (TH$_2$ associated) are detected at much lower levels. These results in a non-human primate model provide a strategy that can be applied to human organ transplant recipients who would benefit substantially from independence from maintenance immunosuppressive drugs.

A second group of rhesus monkeys undergoing mismatched renal transplantation received anti-CD3-CRM9 (IT) 18 hours pretransplant, 0.067 mg/kg and 0.033 mg/kg on days 0 and +1. Group 1 received only IT, n=. Group 2, n=7, received in addition to IT deoxyspergualin (DSG) IV 2.5 mg/kg/day and solumedrol (SM), 7, 3.5 and 0.33 mg/kg IV during the IT administration. DSG was continued from 4 to up to 14 days. Plasma samples were tested by ELISA for cytokine release syndrome by measuring pre and post transplant plasma IL-12 and INF gamma levels.

| Graft Survival (days) | |
| --- | --- |
| Group 1 (IT alone) | Group 2 (IT + DSG + SM) |
| 10-57 n = 6 (rejections) | >155-200 n = 4 |
| | 28-45 n = 3 (rejections) |
| | 2 deaths from non-rejection causes |

Figure 15:
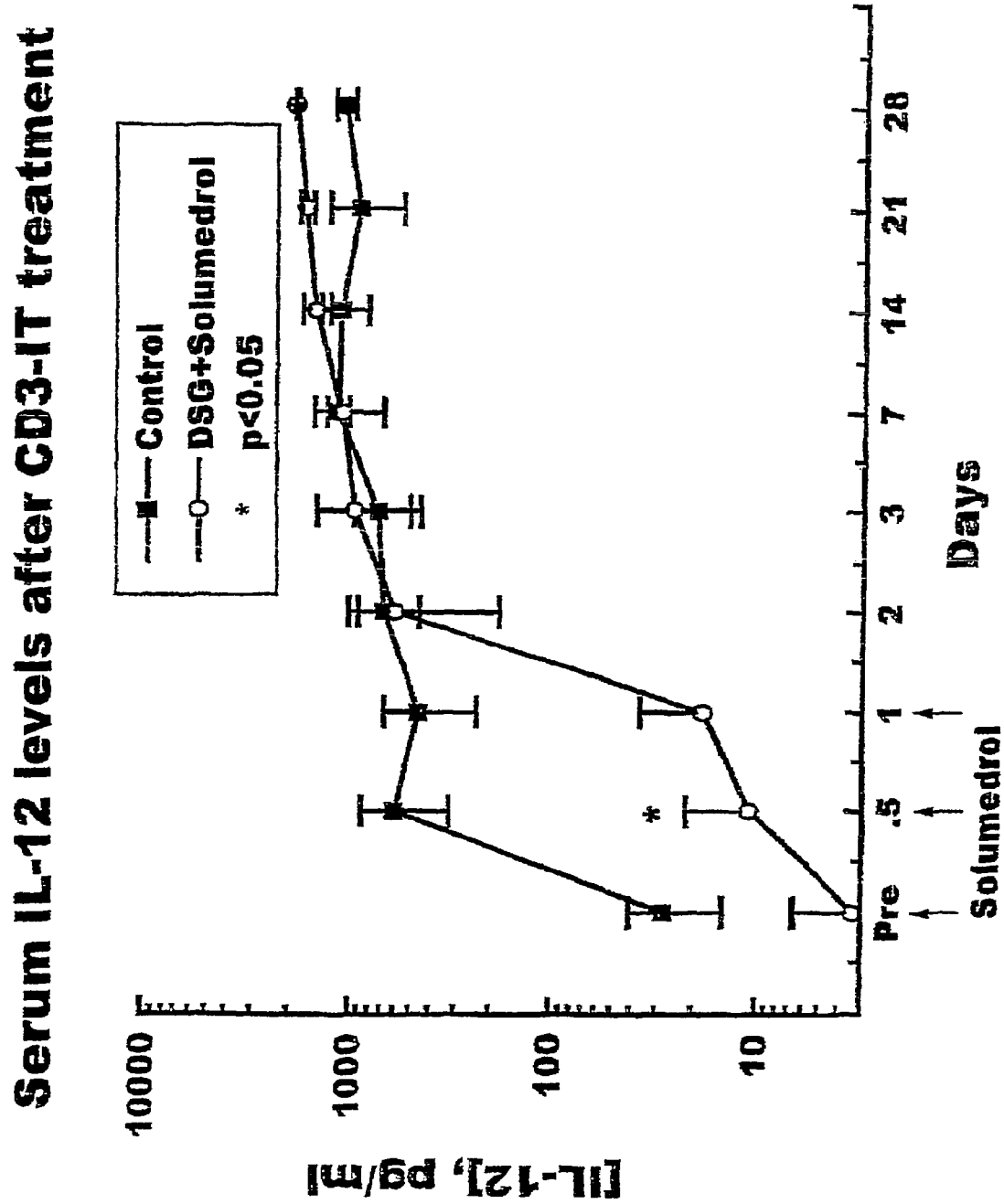
FIG. 15 shows the rise in serum IL-12 following FN18-CRM9 immunotoxin treatment in post kidney transplant monkeys with and without treatment with DSG (deoxyspergualin) and solumedrol.
Figure 16:
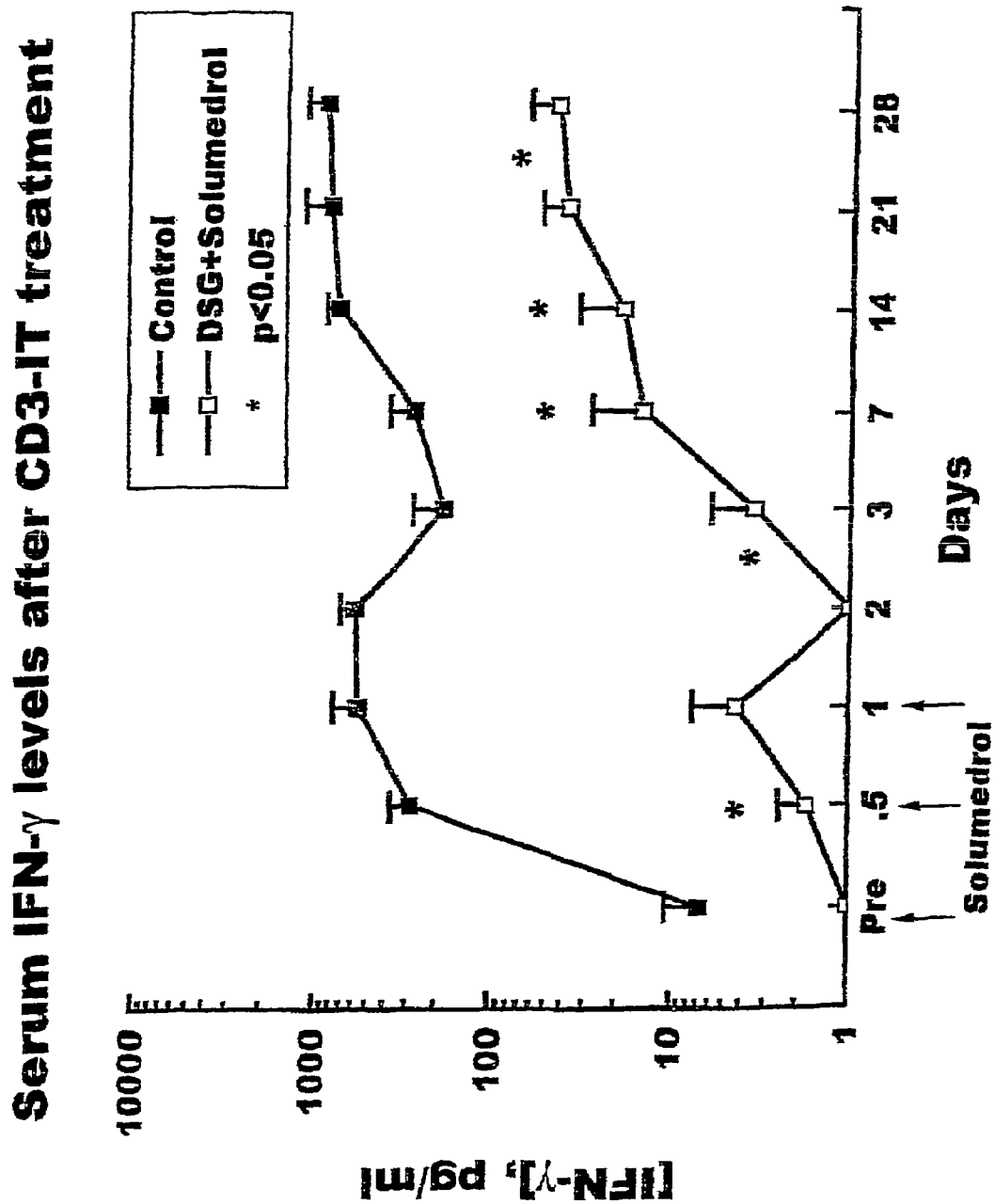
FIG. 16 shows the rise in serum IFN-gamma following FN18-CRM9 immunotoxin treatment in post kidney transplant monkeys with and without treatment with DSG and solumedrol. The treatment dramatically attenuates the rise of IFN-gamma.
Figure 17:
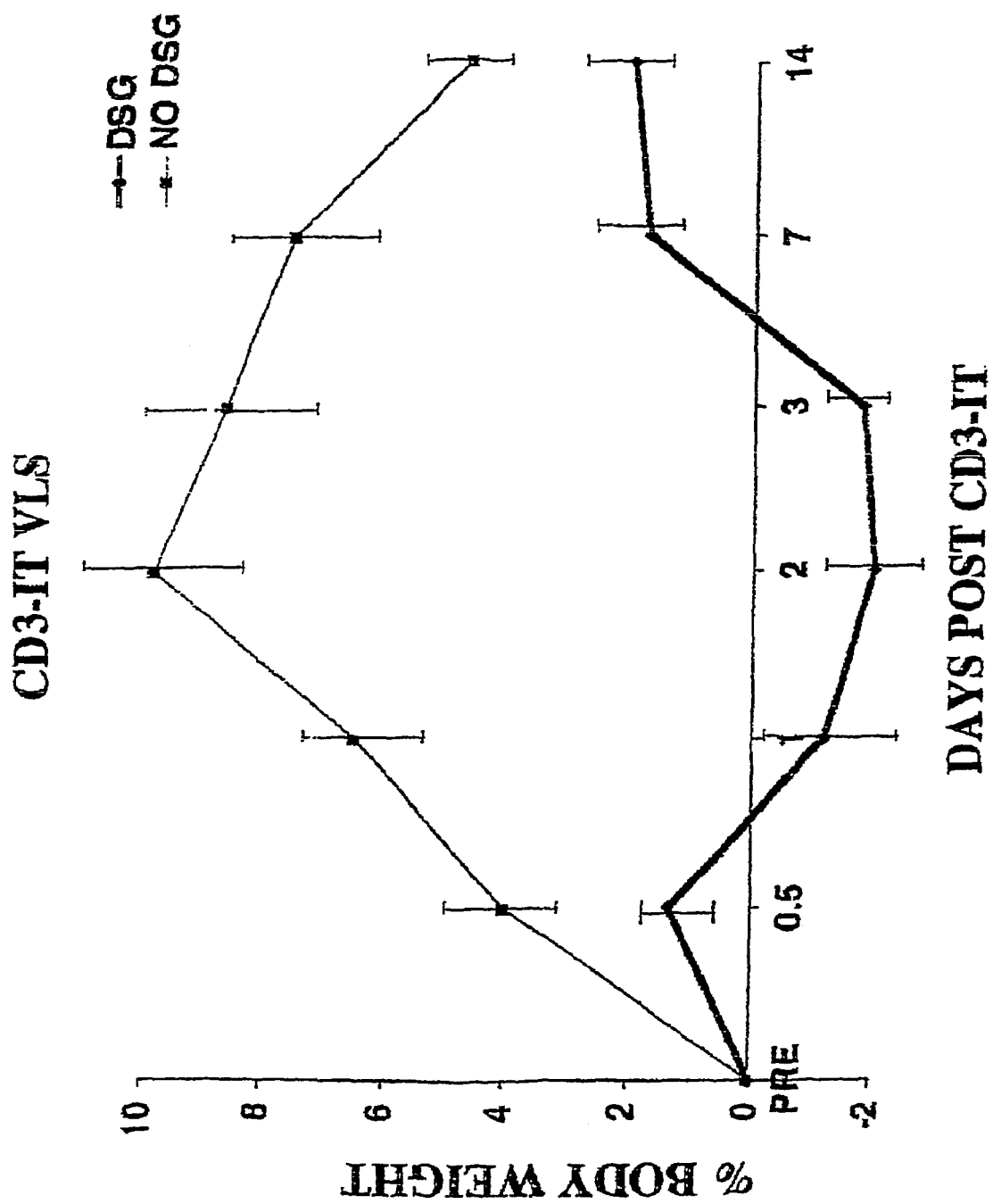
FIG. 17 shows that DSG and solumedrol treatment in the peritransplant period following immunotoxin suppresses weight gain, a sign of vascular leak syndrome related to IFN-gamma elevation.
Figure 18:
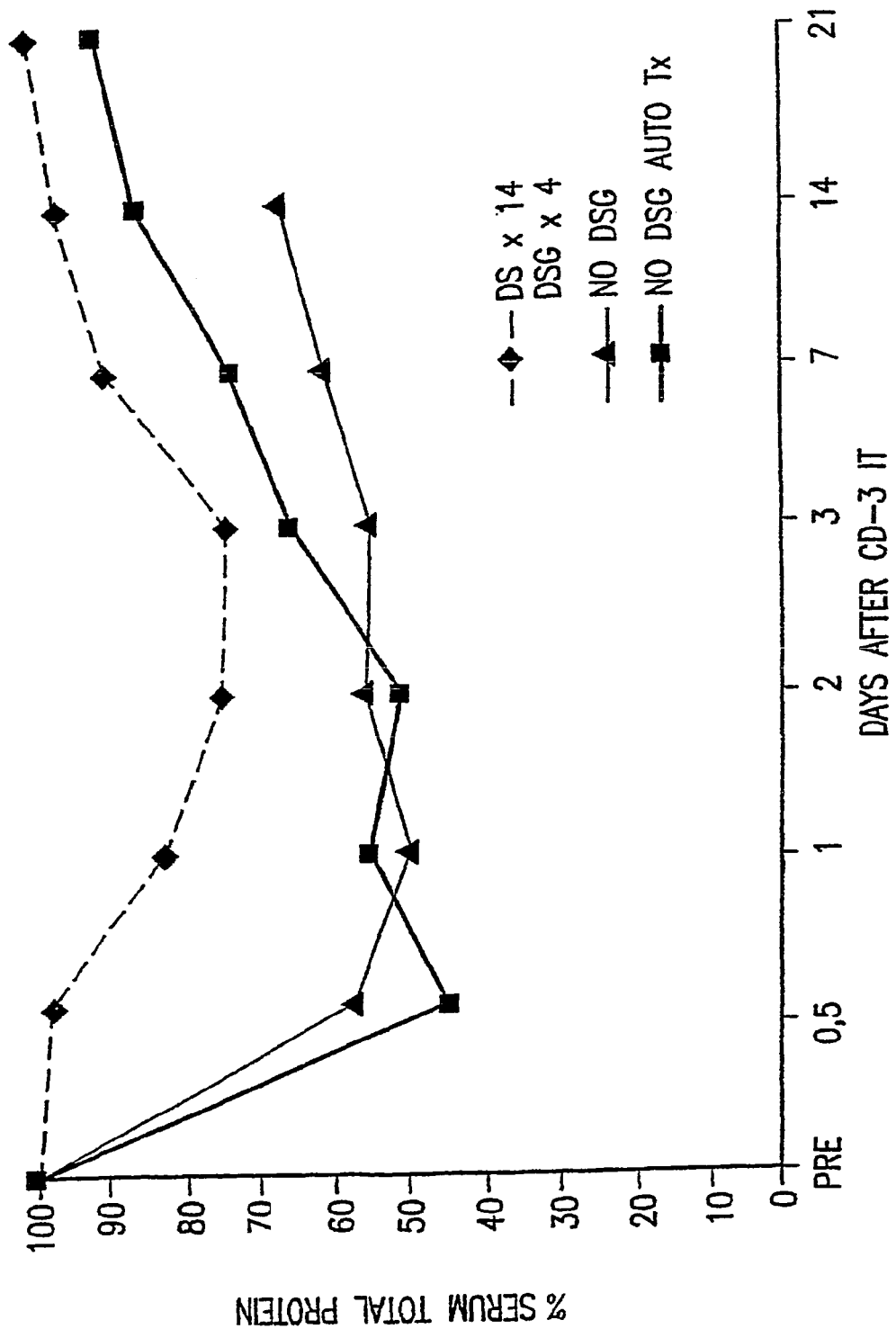
FIG. 18 shows that DSG and solumedrol treatment in the peritransplant period following immunotoxin suppresses hypoproteinemia, a sign of vascular leak syndrome related to IFN-gamma elevation.

IT, Group I, (or rhesus anti-CD3 an antibody alone) elevated both IL-12 and INF-8 gamma DSG and solumedrol appear to block IL-12 induced activation of INF-gamma by a mechanism that may be associated with NF-kappa/beta (see FIGS. 15-16). This treatment is found to eliminate peritransplant weight gain (FIG. 17) and serum hypoproteinemia (FIG. 18), both signs of vascular leak syndrome, which in this study is associated with early graft rejection. This peritransplant treatment regimen can provide a rejection-free window for tolerance induction applicable to cadaveric transplantation.

It takes over 24 hours for IT to exert most of its lymph node T cell killing effects. Therefore, IT cadaveric transplantation protocols (protocols in which organ transplantation occurs generally within 6 hours of initial therapy and not longer than 18 hours) benefit substantially from peritransplant supplemental short term immunosuppressant agents to minimize peritransplant T cell responses to the new organ as shown by the above data Example 15

Cloning of DT390-bisFv(UCHT1)

DT390-sFv(UCHT1) was generated as follows. The sequence for diphtheria toxin was PCR amplified from the beginning of the signal sequence (with the addition of the restriction site, NdeI) to amino acid 390 (with the addition of the restriction site, NcoI, added in-frame) using genomic DNA isolated from *Corynebacterium diphtheriae* C7 ($\beta^{h\ tox-201\ tox-9\ h'}$). The variable light ($V_L$) and variable heavy ($V_H$) chain regions of the antibody UCHT-1 were PCR amplified by a two-step protocol of reverse-transcriptase PCR using primers based on the published sequence (Shalaby, et al, 1992) or conserved antibody sequence. The 5' $V_L$ primer added an in-frame NcoI restriction site while the 3' $V_H$ primer added a stop codon at the J to constant region junction and an EcoRI restriction site (this primer sequence based on conserved J-C$_{kappa}$ sequences). The $V_L$ region was linked to the $V_H$ region by single-stranded overlap extension and the two domains are separated by a (Gly$_4$Ser)$_3$ (SEQ ID NO:105) linker. The $V_L$-(G$_4$S)$_3$-$V_H$ is an example of an sFv. The DT390 NdeI to NcoI DNA fragment was subcloned 5' of the sFv NcoI to EcoRI DNA fragment in the plasmid pET17b (NdeI/EcoRI)(Novagen) to generate signal-sequence-DT390-sFv(UCHT1'). This construct does differ in amino acid sequence in the $V_H$ framework region from UCHT1 (see FIG. 20), and this fact is represented by the prime symbol (').

However, a single chain antibody with these same discrepancies had identical binding activity as the parental antibody UCHT1. Construct 1, DT390-sFv(UCHT1') was expressed in *Escherichia coli* and was the basis for all further constructs.

The next construct did not contain the *C. diphtheriae* signal sequence. The DNA coding sequence for native DT (sequence without signal peptide) was PCR amplified from amino acids 1 through 390 with the addition of an NdeI restriction site at the 5' end and an NcoI restriction site at the 3' end. This DNA fragment was subcloned 5' of the sFv NcoI to EcoRI DNA fragment in the plasmid pET15b (NdeI/EcoRI)(Novagen). This construct, Construct 2, (His-throm) DT390-sFv(UCHT1') had 6 histidine amino acid residues in a $NH_2$ terminal sequence to facilitate purification on nickel columns using commercial resins as well as a thrombin cleavage site supplied by the pET15b vector. The plasmid pDTM-1 contains the native DT sequence (with mutations downstream of amino acid 500) under the control of the T7 promoter in pET11d (Novagen). The plasmid pDTM-1 was digested with XbaI (located in the plasmid 5' of the DT start) and ClaI (located at position 864 of native DT) and subcloned into pET15b+ (His-throm)DT390-sFv(UCHT1') also digested with XbaI and ClaI. The resulting construct, Construct 3, (Met)DT390-sFv(UCHT1'), contains no extraneous sequences with the exception of a NcoI restriction site between DD390 and the sFv domain. These two constructs were expressed in a rabbit reticulocyte coupled transcription and translation system. The two resultant proteins were shown to have identical toxicity on Jurkat cells in a standard 20-hour protein synthesis inhibition assay. Construct 4 is generated under certain conditions in *E. coli* from Construct 3 by proteolytic removal of the amino-terminal Met residue.

To generate a bivalent construct, two linkers were designed to separate the individual sFv domains, Table 11. The first, CHB1, is a flexible linker peptide from *Trichoderma reesi* cellobiohydrolase I and was used successfully to generate a bivalent bispecific sFv. See Mallender and Voss, 1994, which is incorporated herein in its entirety for the CHB1 structure and uses. The CHB1 linker was used to generate Construct 5. The second bivalent construct uses the $(Gly_4Ser)_3$ (SEQ ID NO: 105) linker between the individual sFv domains, Construct 6. In the case of the $(Gly_4Ser)_3$ (SEQ ID NO: 105) linker, the 3' sequence of the $V_H$ region within the first sFv was corrected to the published sequence, however, the identical region of the second sFv was unchanged (see FIG. 20). This fact is noted as bisFv(UCHT1*) Constructs 5 and 6 were made with an amino histidine tag.

Figure 22:
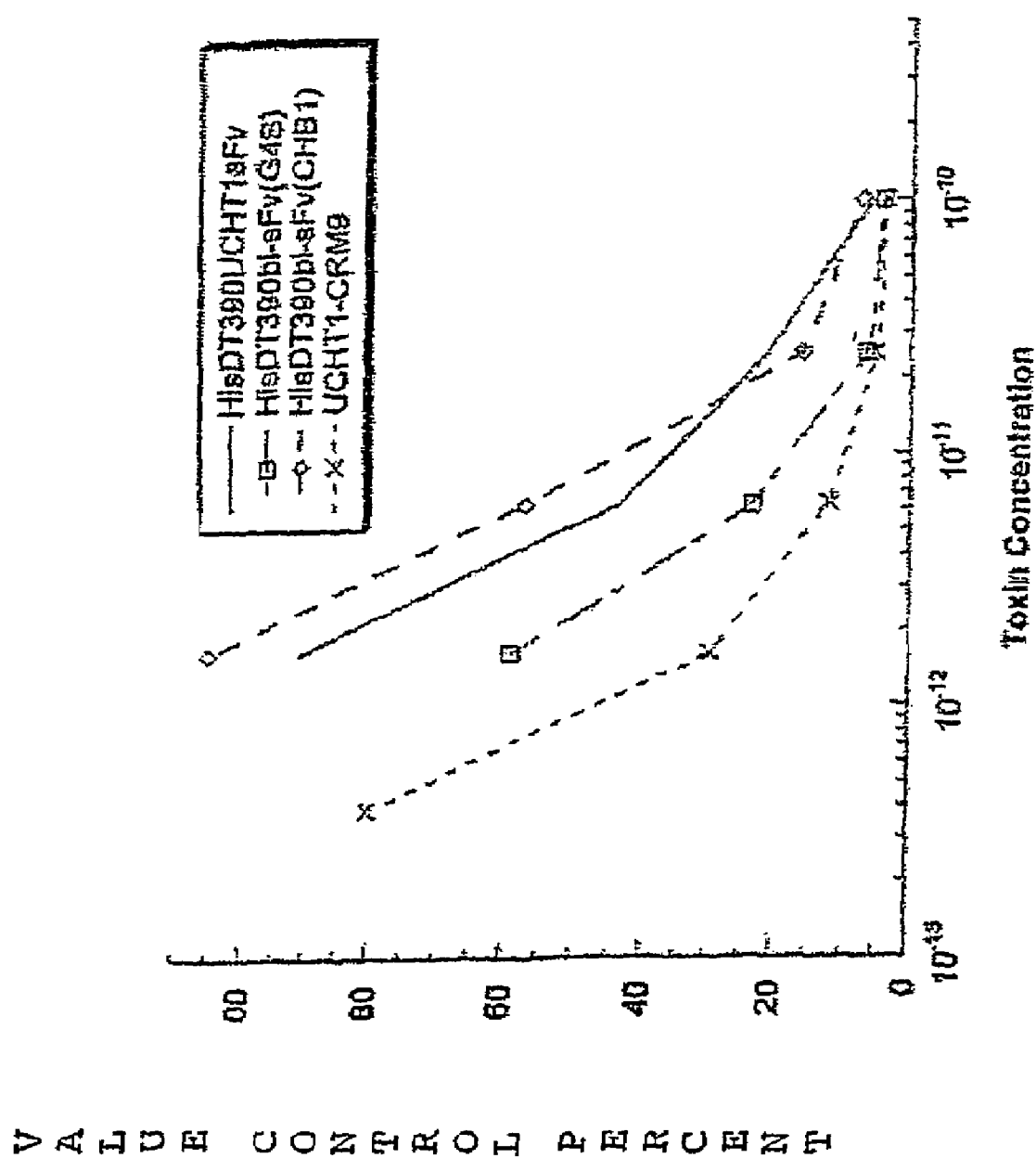
FIG. 22 shows the average results of three independent 20-hour protein synthesis inhibition assays using Jurkat cells and increasing concentrations of immunotoxin constructs: (His-throm)DT390-sFv(UCHT1), (His-throm)DT390-bisFv(UCHT1)(G4S), (His-throm)DT390bisFv(UCHT1)(CHB1), and UCHT1-CRM9. The results indicate that (His-throm)DT390-bisFv(UCHT1)(G4S) has increased toxicity as compared to a similar construct having the CHB1 linker or no linker between the sFvs.
Figure 32:
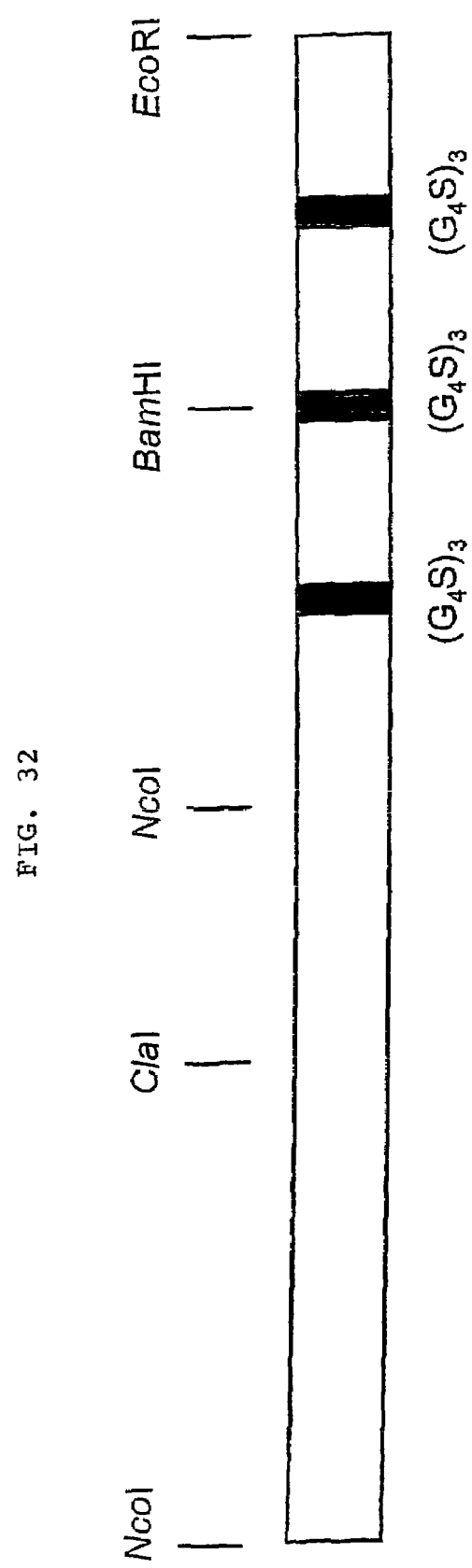
FIG. 32 shows a schematic of DT390-bisFv(UCHT1) and its unique restriction enzyme sites. The depicted clone exists in pET17b with the diphtheria toxin signal sequence, in pET17b with the pelB signal sequence, in pSRαNeo with a mouse Igκ secretion signal, and in pPIC9K and pPICZa with the alpha mating factor secretion signal.

The two constructs, Constructs 5 and 6, were used in an in vitro transcription and translation system. The resulting proteins were quantitated by Western Analysis using CRM9 as a standard. These two constructs were tested for their toxicity on Jurkat cells in a 20-hour protein synthesis inhibition assay, FIG. 22. Construct 5 (CHB1) demonstrated toxicity equivalent to (His-throm)DT390-sFv(UCHT1'), Construct 2. On the other hand, the Construct 6 (G4S) construct showed increased toxicity as compared to Construct 2. All subsequent work has been conducted with the DT390-bisFv(UCHT1*)(G4S) linker configuration. A schematic picture of the DT390-bisFv (UCHT1)(G4S) is shown in FIG. 32.

TABLE 10

Additional Amino Acids and Signal Sequences to the Coding Sequence of Immunotoxin Plasmid Constructs based on UCHT1 sFvs.

| Construct Number Name | Signal Sequence | Expression System | Vector |
|---|---|---|---|
| 1. DT390-sFv(UCHT1') | *C. diphtheria* | *E. coli* | pET17b |
| 2. (His-throm)DT390-sFv(UCHT1') | | *E. coli* | pET15b |
| 3. (Met)DT390-sFv(UCHT1') | | *E. coli* | pET15b |
| 4. DT390-sFv(UCHT1') | | *E. coli* | pET15b |
| 5. (His-throm)DT390-bisFv(UCHT1*) (CHB1) | | *E. coli* | pET15b |
| 6. (His-throm)DT390-bisFv(UCHT1*) (G4S) | | *E. coli* | pET15b |
| 7. (Met)DT390-bisFv(UCHT1) | | *E. coli* | pET15b |
| 8. DT390-bisFv(UCHT1) | | *E. coli* | pET15b |
| 9. (Met)DT390-bisFv(UCHT1*) | | *E. coli* | pET15b |
| 10. (Ala)DT390-sFv(UCHT1*)His | kappa | CHO | pSRαNeo |
| 11. (Ala)dmDT390-sFv(UCHT1*) | kappa | CHO | pSRαNeo |
| 12. (Ala)dmDT390-bisFv(UCHT1*) | kappa | CH0 | pSRαNeo |
| 13. (Ala)dmDT390-bisFv(UCHT1*) | alpha-mating | Pichia | pPICZα |
| 14. dmDT390-bisFv(UCHT1*) | alpha-mating | Pichia | pPICZα |
| 15. (TyrValGluPhe)dmDT390-bisFv(UCHT1*) | alpha-mating# | Pichia | pPIC9K |
| 16 (Met)DT389-sFv(UCHT1) | | *E. coli* | pET15b |
| 17. DT389-sFv(UCHT1) | | *E. coli* | pET15b |

Construct residues in parentheses are amino-terminal residues not appearing in wild type toxin but present in the mature protein.
Kappa signal sequence used is shown in SEQ ID NO: 25.
Alpha-mating factor signal sequence is shown in SEQ ID NO: 29 and is terminated after the Kex2 cleavage site except for alpha-mating# which contains GluAlaGluAla following Kex2.

TABLE 11

Linker sequence of DT390-bisFv(UCHT1) constructs.

| Construct | Amino Acid Sequence | Reference: |
|---|---|---|
| DT390-bisFv(UCHT1*) (CHB1) | PGGNRGTTRPATSGSSPGPTNSHY (SEQ ID NO: 42) | Mallender and Voss (71) |
| DT390-bisFv(UCHT1*) (G4S) | GGGGSGGGGSGGGGS (SEQ ID NO: 43) | Johnson and Bird (14) |

Example 16

Cloning DT390sFv(UCHT1') for CHO Cell Expression

Figure 23:
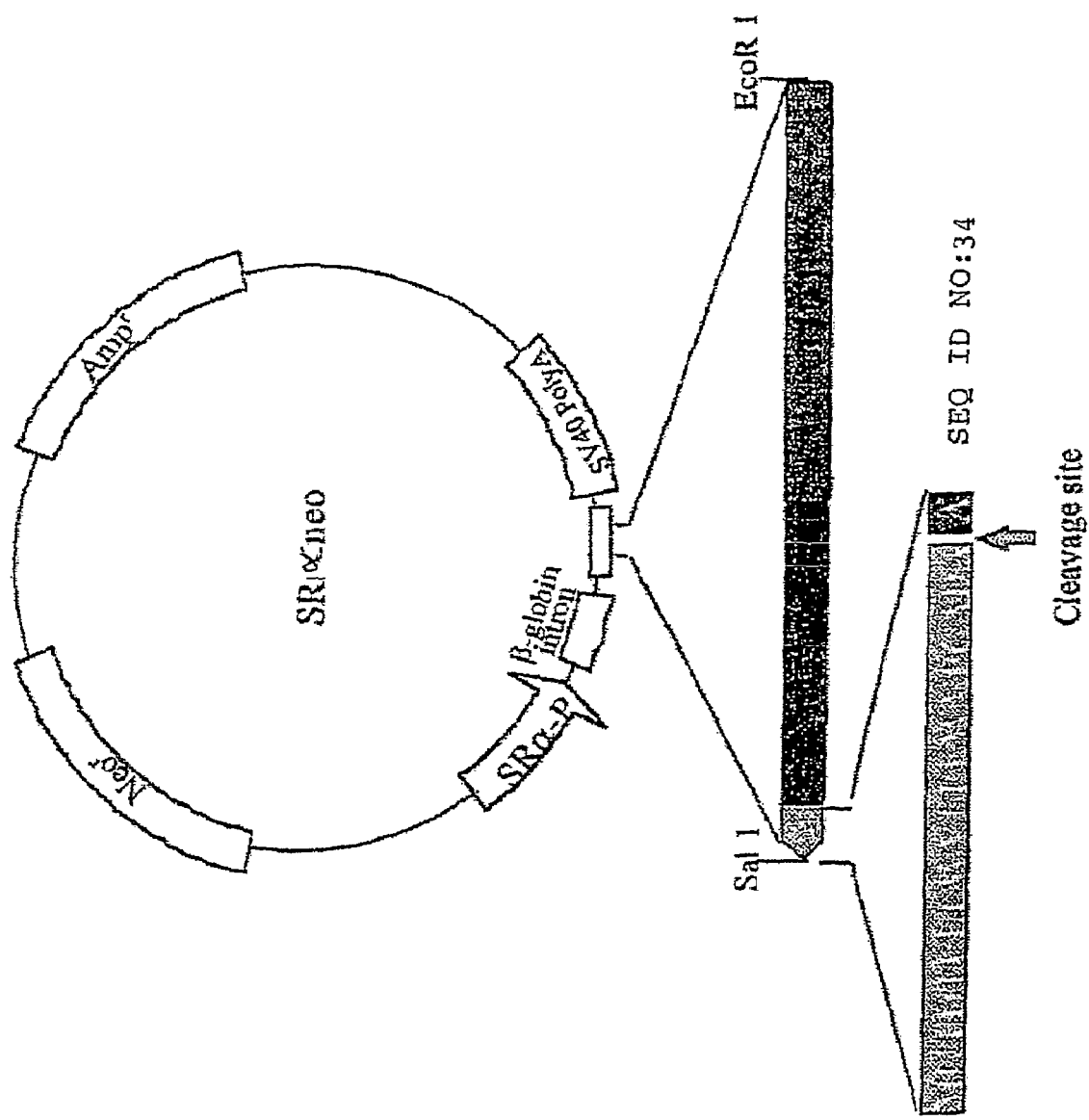
FIG. 23 shows a schematic representation of the vector used for CHO cell expression of sp-DT390-sFv(UCHT1). PCR was performed on DT390-sFv(UCHT1) with primers sp2 and 3'DT-his, and the product was purified by agarose gel electrophoresis and used as a template for the second PCR with sp1 and 3'DT-his. The second PCR product was digested by Sal 1 and EcoR 1, and then inserted into vector SRα-Neo.

Recombinant immunotoxin, DT390-sFv(UCHT1), was constructed according to Example 15. To facilitate secretion of the immunotoxin from CHO cells, a mouse κ-immunoglobulin signal peptide (METDTLLLWVLLLWVPGADAA) (SEQ ID NO:25) (see Schechter et al. (72)) was used to replace the signal peptide of DT, creating sp-(Ala)DT390-sFv (UCHT1')). The cleavage site for this signal peptide is between the C-terminal alanine and the preceding alanine, generating an additional alanine residue at the amino-terminus of the DT domain. This was done to insure efficient processing which has not been observed with a kappa signal peptide juxtaposed with glycine, the first amino acid of mature DT. This was done by a two-step PCR using pfu polymerase (Stratagene, La Jolla, Calif., USA) and the following three primers: sp1, cgg gat cca GTC GAC atg gag aca gac aca ctc ctg tta tgg gtactgctgctctgggttcca (SEQ ID NO:44); sp2, gtactgctgctctgggttcca ggt gcc gac gct gct ggc gct gat gat gtt gtt gat (SEQ ID NO:45); and 3'DT-his, ata GAA TTC TTA gtg gtg gtg gtg gtg gtg tga gaa gac tgt gag agt ggt gcc tt (SEQ ID NO:46). Primers sp1 and sp2 contained a Sal 1 site (upper case) for the signal peptide, overlapped sequences (underlined), and sequence homologous to the 5' end of DT (italics). Primer 3'DT-his had an EcoR1 site (upper case), a stop codon (bold), sequence for a His-tag, and sequence complementary to the 3' end of DT. First, PCR was performed on DT390-sFv (UCHT1') with primers sp2 and 3'DT-his. This product was purified by agarose get electrophoresis and was then used as template for the second PCR with sp1 and 3'DT-his. The second PCR product was digested by Sal 1 and EcoR 1, and then inserted into vector SRα-Neo (FIG. 23) generating Construct 10, (Ala)dmDT390-sFv(UCHT1')His.

Example 17

High Level Recombinant Immunotoxin Production by CHO Cells

Figure 24:
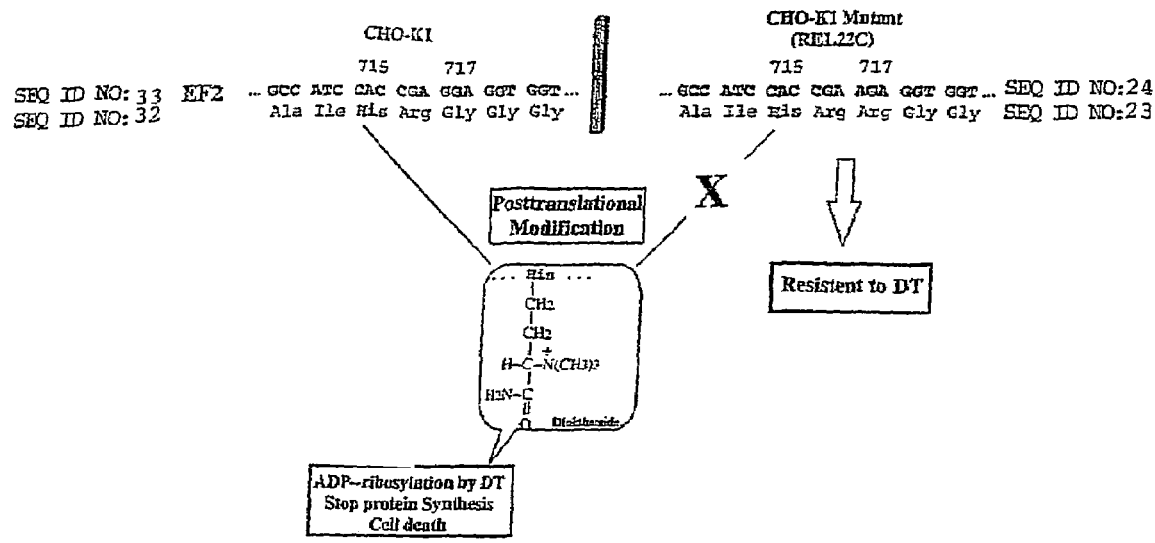
FIG. 24 shows the mechanism DT resistance in the CHO-K1 RE 1.22c cell line, as selected by Moehring & Moehring (73). The resistant cells have a G-to-A point mutation in the first position of codon 717 of both copies of the EF-2 gene, which prevents posttranslational modification and results in DT resistance.

To improve recombinant immunotoxin production a DT resistant cell line, CHO-K1 RE 1.22c, as selected by Moehring & Moehring (73), was used. Moehring & Moehring (73) is incorporated herein by reference in its entirety for the method of selecting the CHO-K1 RE 1.22c cell line. The resistant cells have a G-to-A point mutation in the first position of codon 717 of both copies of the EF-2 gene. The mechanism for DT resistance is summarized in FIG. 24.

Wild-type CHO (CHO-K1) cells were transfected with Construct 10. Three weeks after transfection very few colonies survived (four separate transfections). SDS-PAGE gel and Western blotting did not detect the presence of the immunotoxin protein in the culture medium from these colonies. Cells from each well were then pooled after trypsin treatment and cultured to full confluence in separate T-25 flasks. The target protein was still not detected. Mutant CHO (CHO-K1 RE 1.22c) cells transfected with the construct survived to form colonies which covered about 50% of the area of each culturing well. When the culturing medium was analyzed by SDS-PAGE gel and western blotting, the target protein was detected in three quarters of the transfections. When the cells were pooled after trypsinization and cultured to full confluence in separated T-75 flasks, the accumulation of the immunotoxin protein in the culturing medium of one T-75 flask reached approximately 5 μg/ml in 48 hrs. The mutant cells in the presence of the immunotoxin did not show an obvious difference in cell morphology and growth as compared to those transfected with the vector alone.

Example 18

Identification of Glycosylation Sites

Protein sequence analysis revealed two potential N-glycosylation sites in the DT moiety of the immunotoxin. One such site is located at position 16 in the catalytic domain (A chain) and the other at position 235 in the trans-membrane domain (B chain). The immunotoxin expressed by CHO cells migrated slower than that expressed in bacteria, indicating an increase in molecular weight, and formed two distinct bands in non-reducing gels. CHO cells modify proteins post-translationally and bacteria do not. This increase in molecular weight of the target protein was likely caused by glycosylation, particularly N-glycosylation. The CHO expressed immunotoxin was treated with PNGase F, which cleaves the bond between the asparagine residue of the protein and the first residue of the carbohydrate chain, to determine whether the immunotoxin expressed in CHO is N-glycosylated. After the treatment, CHO expressed immunotoxin migrated, in SDS-PAGE, as one band identically as the bacterial expressed product. These results indicate that the slower migrating bands represent glycosylated molecules.

When the transfected cells were grown in the presence of tunicamycin (which inhibits core glycosylation of proteins in the ER (Elbein (74)) at concentrations of at least 6 μg/ml, only one band, migrating coincident with non-glycosylated protein, was observed. At high concentrations of tunicamycin, cell growth was reduced, and, consequently, accumulation of immunotoxin in the culturing media was also reduced. With decreasing concentrations of tunicamycin the ratio of glycosylated to non-glycosylated molecules increased. At concentrations of 0.125 μg/ml or less, all immunotoxin molecules were glycosylated.

Example 19

Introduction of Mutations into N-Linked Glycosylation Sites of Bacterial Plasmid pET17b+ DT390-sFv(UCHT1)His To mutate glycosylation sites in DT390, several conservative amino acid changes were selected based on their size, polarity and codon preference. These were introduced in vitro into a bacterial pET17b plasmid that carried the DT390-sFv (UCHT1')His insert, and the mutated plasmids were tested to determine if these changes attenuated DT toxicity. The selected changes were: Asn to Gln at position 235 (235Gln), Asn to Ala at position 235 (235Ala), Thr to Ala at position 237 (237Ala), Asn to Ala at position 16 (16Ala), and Ser to Ala at position 18 (18Ala). The sequence surrounding these mutations and the oligonucleotides that were used to generate the mutations are shown in FIG. 25.

The following general method, as modified from "MORPH Plasmid DNA Mutagenesis Procedure" from 5 PRIME-3 PRIME, INC., was used to introduce the selected changes into pET17b. First oligonucleotides were synthesized which were complimentary to pET17b plasmid insert glycosylation sites (FIG. 25). The sequence of these oligonucleotides was slightly modified to accommodate the necessary amino acid change as well as incorporating a novel restriction enzyme site (FIG. 25). The double-stranded plasmid DNA target (methylated) was denatured at 100° C. The mutagenic oligonucleotide (non-methylated and phosphorylated) was annealed to the target DNA. The mutagenic oligonucleotide: target plasmid template was incubated for two hours at 37° C. with T4 DNA polymerase and T4 DNA ligase, which produced a non-methylated replacement strand containing the mutation. The reaction mixture, which consisted of mutagenized plasmid DNA (original methylated template strand and non-methylated replacement strand) and non-mutagenized target plasmid DNA (both strands methylated), was incubated with DpnI restriction enzyme for 30 minutes to destroy non-mutagenized plasmid DNA target. The DpnI digested DNA was transformed into $E.\ coli$ (mut$^S$ strain) by electroporation and plated on selective medium. The colonies were screened for mutants by restriction digest with an appropriate restriction enzyme.

Of the mutants identified by restriction digest, certain mutants were selected for sequencing to check the sequence in the region of the mutation site. DT390-sFv(UCHT1')His was translated from plasmid DNA using a coupled reticulocyte lysate transcription/translation system and the resulting proteins were checked in a Jurkat cell protein synthesis assay for toxicity. The toxicity of all the mutants selected for sequencing was similar to the non-mutated molecules. Two mutations, 18Ala and 235Ala, were selected to be introduced into the target molecule simultaneously to remove both potential glycosylation sites in DT390-sFv(UCHT1')His. The same methodology was used except that two oligonucleotides, each containing sequence coding for one of the mutations, were annealed to the plasmid DNA. Selected colonies were screened for both new restriction sites. The presumptive double mutant was sequenced to check the mutation sites. Recombinant protein was synthesized from plasmid DNA as before, and the resulting protein was checked in a protein synthesis assay for toxicity.

Example 20

Introduction of Mutations into Vector SRα-Neo for Expression in Mammalian Cells

Mutations 18Ala and 235Ala, which remove potential N-glycosylation sites, were introduced into plasmid SRα-Neo-sp-DT390-sFv(UCHT1')His to use for expression in CHO cells. SRα-Neo was made by incorporating a neomycin resistance into the vector Srα (Takebe et al., 1988 (77)), which utilizes the SV40 promoter, and also by incorporating a downstream globin intron enhancer. In order to introduce mutations into both glycosylation sites of SRα-Neo-spDT390-sFv(UCHT1)His the technique described in Example 19 was used. Selected colonies were screened for both new restriction sites. The presumptive double mutant (dm) was sequenced to check the sequence in the region of the mutation sites.

When a mutant immunotoxin gene, (Ala)dmDT390-sFv(UCHT1')His, which had mutations at the two potential N-glycosylation sites, was expressed in CHO K1 RE1.22c, only one protein band, which migrated at the position of the bacterial expressed immunotoxin, was detected. This indicated that N-linked glycosylation had been blocked by the double mutation. The His tag when then removed generating Construct 11, (Ala)dmDT390-sFv(UCHT1).

DT has a proteolytic furin cleavage site between the catalytic (A-chain) and trans-membrane (B-chain) domains. Fragments of nicked DT are held together by a disulfide bond between the A and B-chains. Under reducing conditions, fragments of nicked DT were separated and migrated as two bands in SDS-PAGE. Reducing SDS-PAGE revealed that some of the CHO expressed dm and wild type immunotoxins were cleaved, thereby generating A-chain and B-chain-sFv fragments. These data indicated that in wild-type spDT390-sFv(UCHT1')His both A and B chains were glycosylated. However, not all A chains were glycosylated. This glycosylation pattern was also demonstrated in non-reducing SDS-PAGE by the presence of two slower migrating bands, of unequal intensities, the top one being fainter.

A protein synthesis assay showed that the CHO expressed immunotoxin had a lower toxicity ($IC_{50}=4.8\times10^{-10}$) than expected (at least $4.8\times10^{-11}$, Thompson et al., 1995). However, when the CHO expressed immunotoxin was treated with PNGase to remove the N-linked oligosaccharide chains, the toxicity increased more than two logs with an $IC_{50}=4.3\times10^{-12}$. Mutations at the two N-glycosylation sites had the same effect as PNGase treatment: the mutant immunotoxin had an $IC_{50}=4.1\times10^{-12}$. The single mutant in the B chain did not suffer a large loss in toxicity, indicating that the B chain glycosylation was responsible for most of the toxicity attenuation.

Example 21

CHO Cell Cloning for High Level Expression (Ala)dmDT390-bisFv(UCHT1*)

The pSRα-Neo+(Ala)dmDT390-sFv(UCHT1)His construct was used to generate (Ala)dm-bisFv(UCHT1*), Construct 12, for CHO cell expression. This construct was digested with ClaI and EcoRI to release the sFv segment and the resulting vector DNA was purified. The bisFv(UCHT1) segment was purified from the construct, pET15bDE+(His-throm)DT390-bisFv(UCHT1), which had been digested with ClaI and EcoRI. The DNA fragments were ligated to generate the construct pSRα-Neo+(Ala)dmDT390-bisFv(UCHT1*). Plasmid DNA from this construct was transfected into CHO cells (CHOVE1.22RC) using Superfect (Qiagen) according to the manufacturer's directions. After 24-hours, cells were transferred to a 10-cm style dish in the presence of complete medium (Ham's F-12 supplemented with 10% fetal calf serum and antibiotics) and 500 mg/ml G418. After two weeks individual colonies were isolated using cloning cylinders. Individual cell lines were tested for DT390-bisFv(UCHT1) production and the cell line with the best production per cell number seeded was expanded. That cell line is designated (Ala)dmDT390-bisFv(UCHT1*) clone E4.

Example 22

Production and Purification of (Ala)dmDT390-bisFv(UCHT1*) from CHO Cells

Prior to purification, several factors were analyzed in order to optimize production. A growth curve was completed using the E4 cell line. Cells growing in Ham's F-12 supplemented with 10% FCS and 500 mg/ml G418 were trypsinized, washed, and seeded at various densities in CHO-S-SFM II medium supplemented with 250 mg/ml G418. The cell number was determined (Table 12).

TABLE 12 dmDT390-bisFv(UCHT1*) Clone E4 Growth in CHO-S-SFM II Medium.

| Seeding Density | Cell Count at 24-hour | Cell Count at 48-hour |
|---|---|---|
| $2 \times 10^5$ | $3.6 \times 10^5$ | $8 \times 10^5$ |
| $4 \times 10^5$ | $7 \times 10^5$ | $15.8 \times 10^5$ |
| $6 \times 10^5$ | $9.4 \times 10^5$ | $23 \times 10^5$ |
| $8 \times 10^5$ | $12 \times 10^5$ | $33.4 \times 10^5$ |
| $10 \times 10^5$ | $17 \times 10^5$ | $47.6 \times 10^5$ |
| $10 \times 10^{5*}$ | $12.2 \times 10^5$ | $24.2 \times 10^5$ |

*Cells in were seeded in Ham's F-12 medium supplemented with 500 mg/ml, after 2-hours, cells were washed twice with HBSS and CHO-S-SFM II medium supplemented with 250 mg/ml added.

The supernatants from these time points were also analyzed. Western blot analysis indicated that, there was an increase in immunoreactive material with seeding density (5 second exposure). There was also an increase in breakdown products at 48-hours production (20 second exposure). These data also demonstrated the ability to grow seed cells in growth medium (Ham's F-12 supplemented with 10% FCS and 500 mg/ml G418) and, subsequently, to change to production medium (CHO-S-SFM II supplemented with 250 mg/ml G418).

Another factor examined was the medium in which the cells were grown. The media, which are commercially available from Gibco, are specifically designed for protein production in CHO cells. The first medium, CHO-S-SFM II, is a low protein content medium of <0.1 mg/ml (mostly transferrin and albumin) while the second, CD, is a chemically defined medium containing no exogenous protein. Cells growing in Ham's F-12 supplemented with 10% FCS and 500 mg/ml G418 were trypsinized, washed, and seeded at $1 \times 10^6$ cells/ml in the appropriate media After 24-hours, the cell supernatants were analyzed by ELISA. The cells produced 1.2 mg/ml in CHO-S-SFM II medium but only 0.3 mg/ml in CD medium. Subsequent purifications have been conducted using the CHO-S-SFM II medium to attain a greater production level.

The first batch purification of (Ala)dmDT390-bisFv(UCHT1*) utilized two columns: 1) DEAE-Fast Flow Sepharose (Pharmacia) to concentrate the dmDT390-bisFv(UCHT1*) and 2) a Protein-L Plus (Pierce) for affinity chromatography. Cells from the CHO cell line E4 expressing (Ala)dmDT390-bisFv(UCHT1*) were seeded in three T-175 flasks at $7 \times 10^6$ cells per flask. After two days, cells were washed twice with HBSS, and 45 ml CHO-S-SFM II medium supplemented with 250 mg/ml G418 was added. After 24-hours, the cell supernatant was harvested. Cells were washed with 5 ml HBSS per flask and pooled with culture supernatant. A count of the cells remaining in the flask revealed an average of $33 \times 10^6$ cells per flask.

The cells and debris were first spun down for 10 minutes at 10,000×g. The cells were then concentrated 100× through an Amicon 10 K membrane and diluted four times with water (1.5 ml to 6 ml). The resulting cell solution was applied to a 1.5 cm² DEAE fast flow sepharose column equilibrated with 20 mM Tris-Cl pH 8.0 (1 cm diameter column). The column was washed with 4 ml 20 mM Tris-Cl pH 8.0 and eluted with 9 ml 0.5 M NaCl/20 mM Tris-Cl pH 8.0 (collected as 2-4.5 ml fractions). The fractions were pooled and concentrated to 480 ml and 120 ml of 3 M NH$_4$SO$_4$ was added. This solution was applied to a 3 cm² Protein L-Plus column equilibrated with 0.6 M NH$_4$SO$_4$/20 mM Tris-Cl pH 8.0 (1.5 cm diameter column) which was washed with 4 ml 0.6 M NH$_4$SO$_4$/20 mM Tris-Cl pH 8.0 and eluted with 20 mM Tris-Cl pH 8.0 collecting 1 ml fractions.

Figure 26:
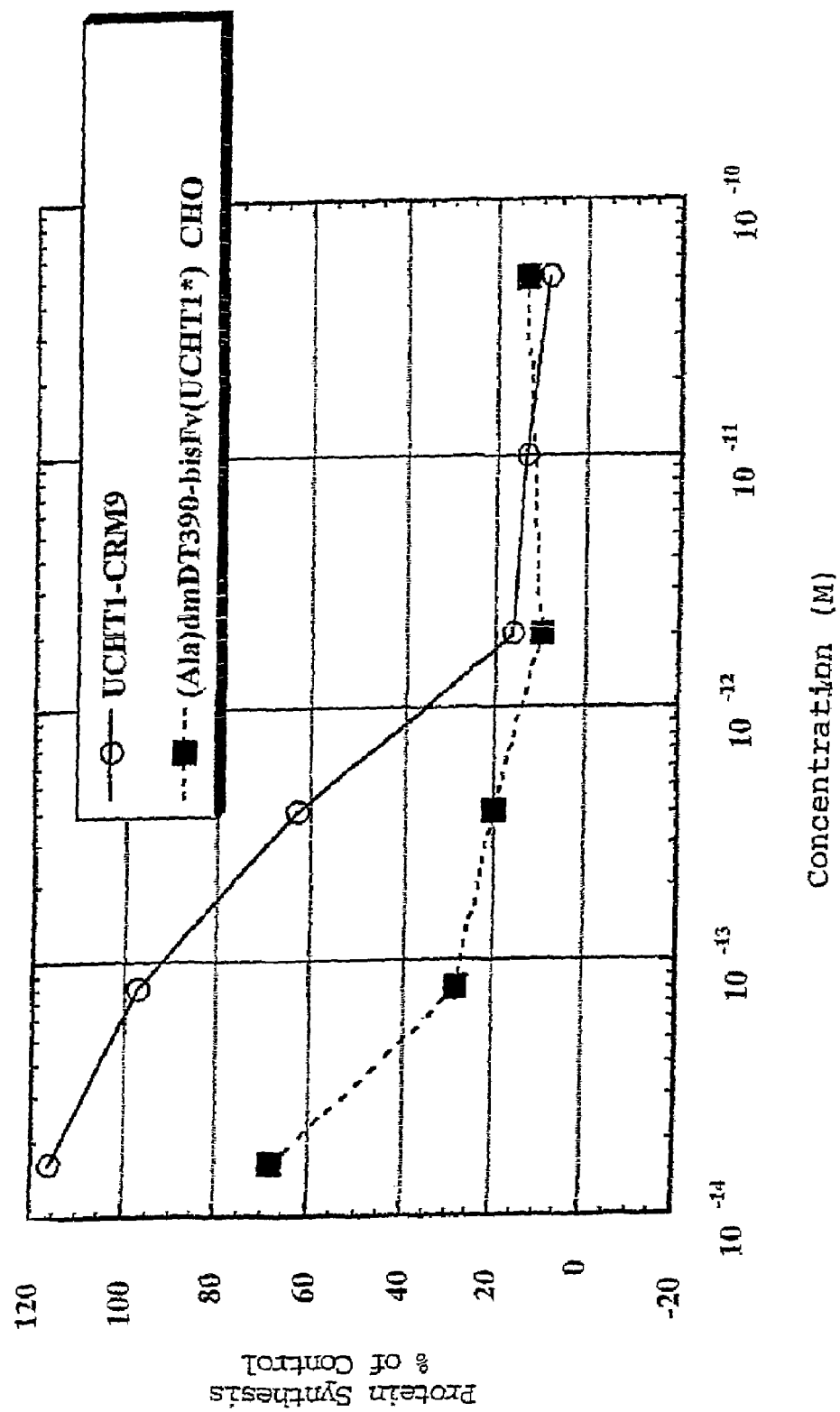
FIG. 26 shows the results of a protein synthesis inhibition assay using Jurkat cells and comparing the inhibition by various concentrations of (Ala)dmDT390-bisFv(UCHT1*) expressed by CHO cells and UCHT1-CRM9. In this experiment, no thiophilic column purification step was used.

Samples taken from various steps within the purification procedure were analyzed. Samples were separated by electrophoresis on a polyacrylamide gel and analyzed by Western blotting or by staining with Coomassie Blue. Western Blot analysis revealed that 75% of the starting (Ala)dmDT390-bisFv(UCHT1*) was lost during the concentration using the Amicon membrane. Western Blot analysis also revealed that a small amount of (Ala)dmDT390-bisFv(UCHT1*) was lost in the "flow-through" and wash of the Protein-L-Plus column (Pierce Chemical Co., Rockford, Ill.). This loss is eliminated by limiting the application volume to one half of the protein L column. The Coomassie Blue stained gel demonstrated that the proteins eluted from the DEAE column had an identical profile as the proteins found in the starting material. The early fractions eluted from the Protein-L-Plus column were slightly contaminated with a protein of molecular weight between 46 and 69 kD. By fraction 4 this contaminating protein became a minor protein in the sample. Fractions 4 and 5 were pooled and quantitated by Western blot analysis using CRM9 as a standard. Quantification determined the pooled sample to contain 31.5 µg/ml of (Ala)dmDT390-bisFv(UCHT1*). Similar results were obtained by Western blot analysis using the polyclonal goat anti-DT serum. Using the predicted molar extinction coefficient ($E_{0.1\%\ at\ 280\ nm}=1.63$), based on the amino acid sequence (MW 96,305 calculated from sequence), the sample was determined to contain $3.0 \times 10^{-7}$ M of (Ala)dmDT390-bisFv(UCHT1*). The purified (Ala)dmDT390-bisFv(UCHT1*) was compared to UCHT1-CRM9 immunotoxin (chemical conjugate) in a standard 20-hour protein synthesis inhibition assay. The results of one assay are shown in FIG. 26.

A second purification scheme eliminated the concentration step and increased the yield by substituting a thiophilic column for the protein L column. Thiophilic resin (Clontech) contains thioether groups bound to agarose. These thioether groups have an affinity for proteins containing exposed disulfide bonds in the presence of high concentrations of sulphate ion.

Cells were seeded day 1 with $2.5 \times 10^6$ cells/T175 flask (3 flasks). On day 4, the cells were washed with 2×HBSS and CHO-S-SFM II+G418 was added (30 ml/flask). On days 5, 6, and 7, the supernatants were harvested and CHO-S-SFM II+G418 was added (30 ml/flask).

The supernatants from days 5 and 6 contained 1.5 and 3.1 mg/ml of dmDT390-bisFv(UCHT1*) respectively. Eighty ml of the 3.1 mg/ml material (supernatant day 6) was purified on DEAE Sepharose as described above with the following exceptions: 1) the elution was with 10 ml of 0.5 M Na$_2$ SO$_4$ pH 7.0 with 30 mM Pi and 2) this material was applied directly to a 0.6 ml thiophilic resin column which was washed with 5 column volumes of 0.5 M Na$_2$ SO$_4$ and eluted with 0.4 ml fractions of 30 mM NaPi pH 7. The total yield was calculated to be 95%.

The gels revealed that an albumin contaminant from the media and other media derived proteins of molecular weight >>100,000 kD were still present in low amounts. Optionally, a sizing step can be used to further purify the material as needed. See Neville et al. 1996 (69), which is incorporated herein by reference in its entirety for the sizing step.

Example 23

Cloning (Ala)dmDT390-bisFv(UCHT1*) for *Pichia pastoris* Production

Initial attempts to produce DT390 constructs in *Pichia* were not successful.

To determine whether an AT-rich region in the DNA sequence of the DT390 domain can induce early termination of transcript, RT-PCR was carried out. Total RNA was purified from different clones (GS115 host strain, K3 clone containing the sp(killer)-DT390-sFv-CH2 gene, L5 clone containing the sp(alpha)-DT390-sFv gene, and A10 clone containing the sp(alpha)-DT390-sFv-CH2 gene). The term "sp(alpha)" refers to the alpha mating factor signal peptide, and the term "sp(killer)" refers to *Kluyveromyces lactis* killer toxin signal peptide. Complementary DNA (cDNA) was synthesized from the total RNA preparations by using reverse transcriptase and oligo d(T) primer, and then PCR product was synthesized from this cDNA by priming with 5' AOX1 and 3' AOX1 primers. If a DT390 related construct is fully transcribed in *Pichia*, two bands of PCR product should be amplified because the entire construct is placed between the AOX1 gene promoter and the AOX1 gene terminator. However, the results indicated that only one band of PCR product corresponding to the AOX1 gene transcript could be amplified, suggesting that the AT-rich region in the DNA sequence of the DT390 domain induced early termination.

To express (Ala)dmDT390-bisFv(UCHT1*) in *Pichia pastoris* the DNA sequence of (Ala)dmDT390, containing three AT-rich regions, was rebuilt so that the AT-rich regions would not induce early termination of the mRNA transcript during transcription (FIG. 28). The percentage of AT sequence in the AT-rich regions starting at the 5' end of the DNA was 65.63, 69.23 and 63.83%, respectively. After rebuilding the dm DT390 sequence the AT content in these regions was decreased to 44.50, 48.86 and 49.18%, respectively. Rebuilding of the 5' AT-rich region (nucleotides 960-1170) was not sufficient to achieve translation, nor was rebuilding of 960-1170 plus 660-780. See FIG. 28. Only when all three regions were rebuilt did translation occur. The rebuilt DNA was made by PCR technique using techniques known in the art.

Figure 29:
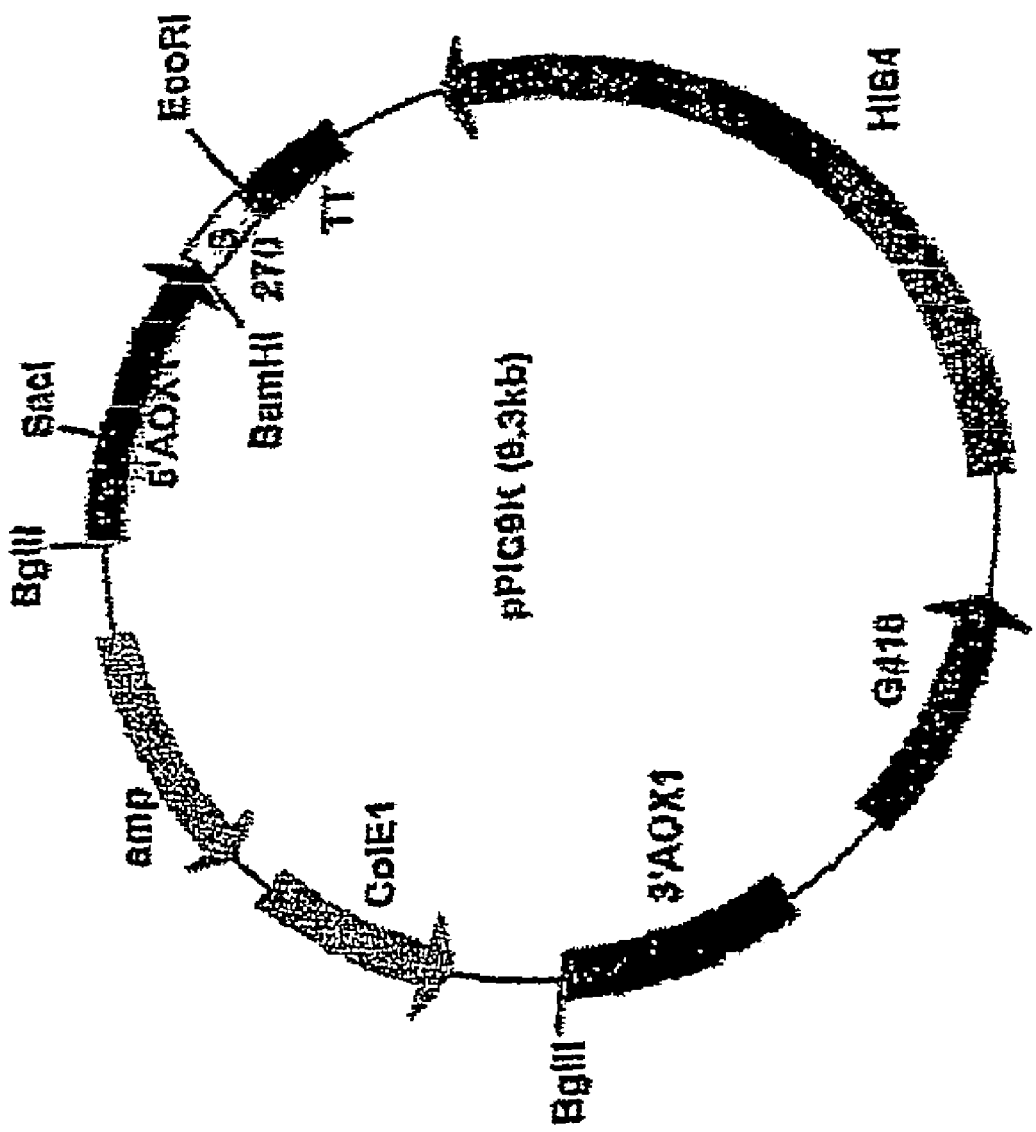
FIG. 29 shows a map of pPIC9K (9.3 kb) vector and cleavage site in prepro-alpha-mating factor. The gene of (Ala)dmDT390-bisFv(UCHT1*) was inserted into EcoRI site in pPIC9K vector.
Figure 30:
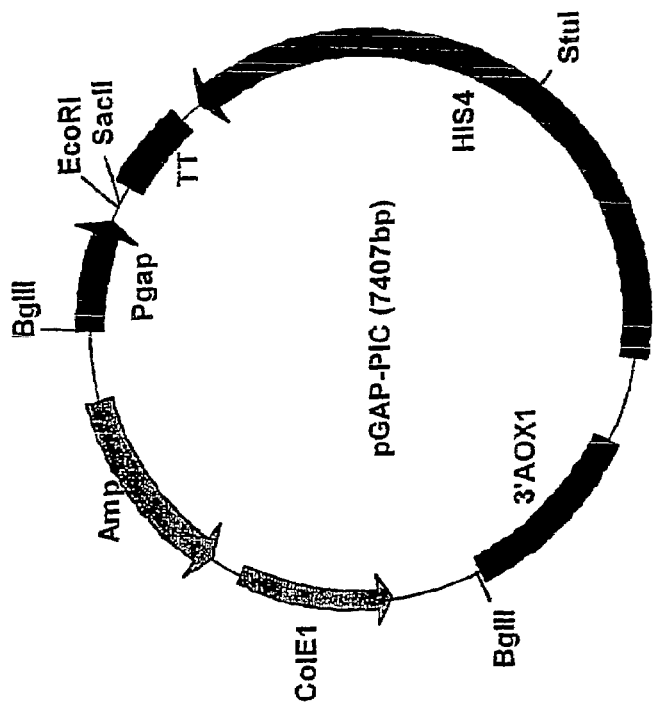
FIG. 30 shows a map of pGAP-Pic (7.4 kb) vector and mutated site on mEF2 gene. The mEF2 gene was inserted into EcoRI and SacII site in pGAP-PIC vector mutated yeast EF-2 gene from S. cerevisiae was made by site-directed mutagenesis.

The following *Pichia* vectors were used for transformation: pPIC9K vector (Invitrogen, Carlsbad, Calif.) (FIG. 29), pGAP-PIC (FIG. 30), and pPICZa (Invitrogen, Carlsbad, Calif.). The following *Pichia* strain was used: *Pichia pastoris* KM71 strain with a genotype of aox1D::SARG4 His4 Arg4 and a phenotype of Mut$^S$ His$^-$.

pPIC9K was used as the initial *Pichia* expression vector. This vector has two selectable markers, the HIS4 gene and the G418 resistant gene, and contains a prepro-α-mating leader sequence. This signal sequence promotes the secretion of dmDT390-bisFv(UCHT1*), encoded by the rebuilt DNA described above, into the medium. The signal peptide also contains a Kex2 endopeptidase specific site (KR) and a spacer amino acid sequence (EAEA) which may or may not be further cleaved by Ste13 endopeptidase. After cleavage, the resulting protein has either 8 (EAEAYVEF) (SEQ ID NO:47), 6 (EAYVEF) (SEQ ID NO:48) or 4 (YVEF) (SEQ ID NO:49) additional amino acids at the N-terminus of (Tyr-ValGluPhe)dmDT390-bisFv(UCHT1*) Construct 15. The tyrosine and valine residues were from the pPIC9K vector. The glutamate and phenylalanine residues came from the EcoRI restriction enzyme site used for insertion of the dmDT390-bisFv(UCHT1*) gene.

Another vector, pPICZa zeocin (Invitrogen) was used to produce (Ala)dmDT390-bisFv(UCHT1*) identical in composition to the product produced in CHO cells. (Ala) dmDT390-bisFv(UCHT1*) was inserted into the AOX1 gene as was done with the PIC9K vector and was preceded by the α-mating factor signal sequence up to the Kex2 cleavage site. The product from this vector lacked the additional amino terminus amino acids, YVEF (SEQ ID NO:49), but contained an A (Ala) at the 5' terminus Construct 13. A construct lacking the 5' Ala was also produced, Construct 14. In both construct 13 and 14, the alpha mating factor signal peptide was truncated at the main Kex2 cleavage site. This insured that additional EA residues would not be present in the 5' region.

Example 24

Factors Influencing the Expression Level of (Ala)dmDT390-bisFv(UCHT1) and its Stability Cell density affected expression levels. When methanol induction started, the expressed amount of dmDT390-bisFv (UCHT1*) was dependent on the cell density of the culture. As cell density increased, the expression level of (Ala) dmDT390-bisFv(UCHT1*) also increased. This increase in expression could be because Clone # 16 is a Mut$^S$ strain and Mut$^S$ cultures metabolize methanol poorly, implying that their oxygen consumption is very low. Low consumption of oxygen allows high cell density culture in a flask or a fermenter. Generally, the major limitation in increasing cell density in a fermenter culture of Mut$^+$ strains is low oxygen transfer rate because of the high oxygen consumption associated with methanol metabolism.

Medium also affects cell density and expression level. Cell density is higher when yeast extract and peptone are added to the medium and the protein of interest production is also increased 4-fold. However, this medium contains many extraneous proteins that complicate the purification process.

The gene copy number is likely to affect expression. Clone #16 was selected on YPD agar containing G418 (4 mg/ml), so this clone may have multiple copies of the gene of interest. The level of resistance to G418 in *Pichia* roughly depends on the number of integrated kanamycin resistance genes. The gene copy number is likely to be important in improving the expression level.

When a protein is secreted into the medium, the pH of the medium is important for optimal growth. Since the B chain translocation domain of (Ala)dmDT390-bisFv(UCHT1*) is very sensitive to low pH, the pH of the medium for the methanol induction phase can affect the toxicity of (Ala) dmDT390-bisFv(UCHT1*). For expression of dmDT390-bisFv(UCHT1*), Clone #16 was cultivated at three different pH conditions (pH 6.0, 6.5 and 7.0). In this pH range, there was no significant difference in the toxicity of (Ala) dmDT390-bisFv(UCHT1*). However, purification at pH 6.5 resulted in an unstable product with respect to the reproducibility of in vitro toxicity assays.

During the methanol induction phase, the medium pH was maintained at either pH 6.0, 6.5 or 7.0. Neutral proteases can attack and degrade expressed (Ala)dmDT390-bisFv (UCHT1*). To inhibit neutral protease in the medium, casamino acids were supplemented to a final concentration of 1%. When casamino acids were supplemented, expressed (Ala)dmDT390-bisFv(UCHT1*) was 2-3 fold higher. In addition, 3 mM PMFS, a protease inhibitor, can be added to the medium during methanol induction, and (Ala)dmDT390- bisFv(UCHT1*) has also been expressed in the protease A deficient strain SMD1168 to minimize proteolytic degradation.

The methanol level was optimized because the Mut$^S$ strain utilizes methanol poorly and high levels of methanol are toxic to the Mut$^S$ strain. When methanol was added to 0.5% or 1.0% of the final concentration, there was not a significant difference between the amount of protein produced. To optimize induction time, samples were taken from *Pichia* culture every 24 hrs after methanol induction. Expression levels peaked 48 hrs after methanol induction, and there was no increase in expression level after 48 hrs.

Clone #16 was analyzed by PCR-RFLP to find out whether it contained the mEF-2 gene in its genome. It was thought that Clone #16 should have the mEF-2 gene because diphtheria toxin is also toxic to *Pichia pastoris* if its catalytic domain is translocated to the cytosol Interestingly, Clone #16 lacked the mEF-2 gene, based on PCR-RFLP analysis. This fact suggests that the mEF-2 gene product is not required for resistance to the toxicity of (Ala)dmDT390-bisFv(UCHT1*) expressed in *Pichia*, and the secretory pathway in *Pichia* must be strictly isolated from the cytosol compartment. The toxin translocation process is pH-dependent and translocation occurs between pH 5-6. The pH in the secretory pathway is not favorable for the translocation process.

Overexpression of protein disulfide isomerase from *S. cerevisiae*, as generally described in Robinson et al, 1994 (78) and U.S. Pat. No. 5,773,245, increases the expression of (Ala)dmDT390-bisFv(UCHT1*) in the *Pichia* double transformant.

Example 25

Two-Step Purification of dmDT390bisFv(UCHT1*) from *Pichia*

A two-step purification method was used at pH 7.0. Anion exchange and protein L affinity chromatography were used to purify (TyrValGluPhe)dmDT390-bisFv(UCHT1*) produced from Clone #16 incubated in a *Pichia* 4 L fermenter. A DEAE sepharose column was used as an anion exchanger, and the *Pichia* culture supernatant was dialyzed against 20 mM Bis-Tris buffer (pH 7.0) three times before loading. One hundred ml of dialyzed material was loaded onto the DEAE sepharose column (10 ml of bed volume, 1.5 cm×5.7 cm), which had been equilibrated with 20 mM Bis-Tris buffer (pH 7.0). This pH was chosen to minimize DEAE binding of (TyrValGluPhe)dmDT390-bisFv(UCHT1*) breakdown products. The calculated pI of the breakdown products were: bisFv (UCHT1), 7.22; and B-chain-390-bisFv(UCHT1), 6.02; compared to intact dmDT390-bisFv(UCHT1*), pI=5.55. Following loading, the column was washed with three bed volumes of 20 mM Bis-Tris buffer (pH 7.0) and then eluted by a linear gradient from 0 to 500 mM NaCl in 170 ml of 20 mM Bis-Tris buffer (pH 7.0). Each fraction (10 ml) was collected immediately after loading the sample until the gradient reached 500 mM NaCl. Fractions #10 and #11 contained (TyrValGluPhe)dmDT390-bisFv(UCHT1*). These two fractions were pooled and concentrated to less than 1 ml by using a Centriplus (cutoff size 30,000) concentrator. The concentrated material was used as the starting material for the protein L affinity column. One part 3M $(NH_4)_2SO_4$ was added to four parts of the concentrated material. The prepared sample was applied to a protein L column (3 mL 1 cm×3.8 cm) equilibrated with binding buffer (600 mM $(NH_4)_2SO_4$ and 20 mM Tris-Cl, pH 8.0). The column was washed with 4.5 ml of binding buffer and eluted with 20 mM Tris-Cl (pH 8.0). The first fraction (7 ml) was collected immediately after loading the sample and then 10 fractions (0.75 ml) were collected. Fractions #5 and #6 were pooled, and the protein concentration of (TyrValGluPhe)dmDT390-bisFv(UCHT1*) was estimated by using a calculated sequence based extinction coefficient ($E_{0.1\% \text{ at } 280 \text{ nm}}$=1.63). The estimated concentration of (TyrValGluPhe)dmDT390-bisFv(UCHT1*) was 31.9 µg/ml (total 47.9µ of (TyrValGluPhe)dmDT390-bisFv(UCHT1*)). The concentration step prior to the protein L step was preferred in view of the relatively low affinity of (TyrValGluPhe)dmDT)T390-bisFv(UCHT1*) for protein L, even in the presence of 0.6 M $(NH_4)_2SO_4$ To avoid run through of (TyrValGluPhe)dmDT390-bisFv(UCHT1*), the preferred application volume was less than the protein L column volume. Reduced gels indicated that more than 95% of the (TyrValGluPhe)dmDT390-bisFv(UCHT1*) was nicked between the DT A and B chains. This compares with 15-25% for CHO expressed material harvested at 24 hours of medium incubation.

Using a two-step purification method at pH 8.0 from a flask culture, constructs generated with pPICZa were purified. *Pichia* culture containing 5 µg/ml of construct was dialyzed against 20 mM Tris-Cl buffer (pH 8.0) three times before loading onto a DEAE Sepharose column (1 ml of bed volume, 1.0 cm×1.3 cm) equilibrated with 20 mM Tris-Cl buffer (pH 8.0). Following loading, the column was washed with 1.5 bed volumes of 20 mM Tris-Cl buffer (pH 8.0) and then step eluted with 5 bed volumes of 2M NaCl and 20 mM Tris-Cl (pH 8.0). The eluted fraction containing the protein of interest, 1.18 ml, was used as starting material for the protein L purification.

The starting material for the protein L column was diluted with 3M $(NH_4)_2SO_4$. One part of 3M $(NH_4)_2SO_4$ was added to four parts of the eluted material from the DEAE column. The prepared sample was applied to a protein L column (3 ml, 3 cm×1.3 cm) equilibrated with binding buffer (600 mM $(NH_4)_2SO_4$ and 20 mM Tris-Cl, pH 8.0). The column was washed with 1.5 ml bed volumes of binding buffer and eluted with 5 bed volumes of 20 mM Tris-Cl (pH 8.0). The protein of interest was concentrated in the volume fractions 9.25 ml to 11.5 ml following the start of the 20 mM Tris elution buffer.

Example 26

Toxicity of Purified Material from *Pichia*

Figure 27:
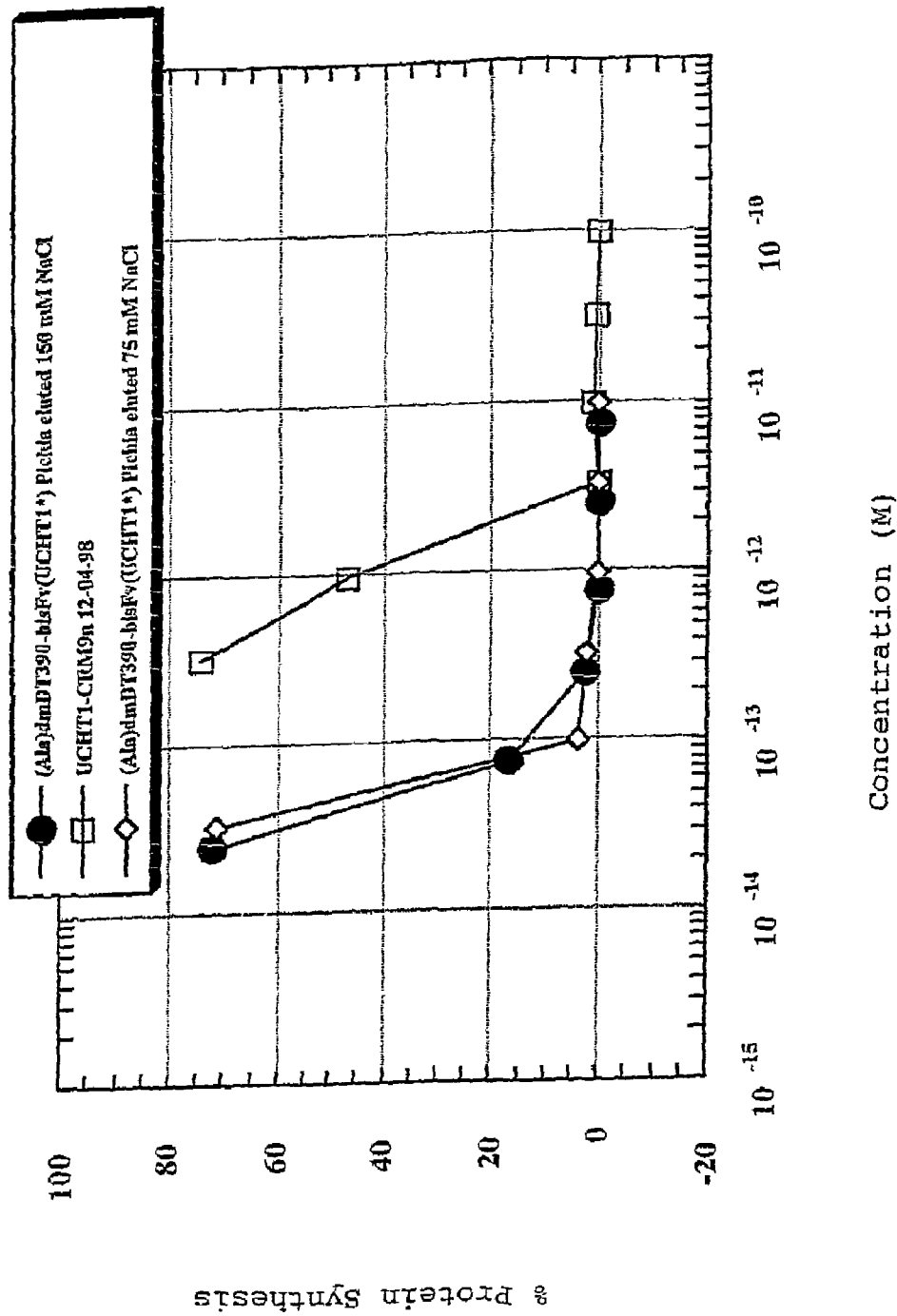
FIG. 27 shows the results of a protein synthesis inhibition assay using Jurkat cells and comparing the inhibition by various concentrations of (Ala)dmDT390-bisFv(UCHT1*) expressed by Pichia and UCHT1-CRM9. In this experiment, the (Ala)dmDT390-bisFv(UCHT1*) was further purified by a thiophilic column followed by DEAE Separose with elutions at 75 mM and 150 mM NaCl followed by a Protein L column.

Purified (TyrValGluPhe)dmDT39O-bisFv(UCHT1*) proteins were tested for toxicity on Jurkat cells. The construct having YVEF (SEQ ID NO: 49) at the amino-terminus exhibited a 3-fold greater toxicity than that of the chemical conjugate, UCHT1-CRM9. This toxicity is approximately 10-fold lower than that of purified (Ala)dmDT390-bisFv(UCHT1*) expressed in CHO cells as shown in FIG. 26. This is likely to reflect the extra charged amino acids present at the amino-terminus. When these amino acids were removed, toxicity increased to 20 and 22-fold greater than the chemical conjugate. See FIG. 27. This value is close to that observed for CHO produced material. The absence of casamino acids as an inhibitor of proteolysis was probably not a major factor in lowering toxicity. When these were included in flask cultures of the Clone #16 material, toxicity remained at 3-fold greater than the chemical conjugate.

Example 27

Estimation of Efficiency of Purification from *Pichia*

Table 13 indicates the relative amounts of protein recovered from each purification step. It is clear from these results that the low overall recovery was a consequence of loss during the concentration step prior to protein L affinity step.

TABLE 13

Recovery of dmDT390-bisFv(UCHT1*) from Pichia culture.

| Purification step | total volume & protein of interest | yield |
|---|---|---|
| supernatant from fermenter culture (pH 6.5) | 100 ml & 700 µg | 100.0% |
| DEAE column | 20 ml & 400 µg | 57.1% |
| Protein L affinity column | 1.5 ml & 90.0 µg (47.9 µg) | 12.9% |

( ): calculated value by extinction coefficient at 280 nm.

Example 28

Figure 31:
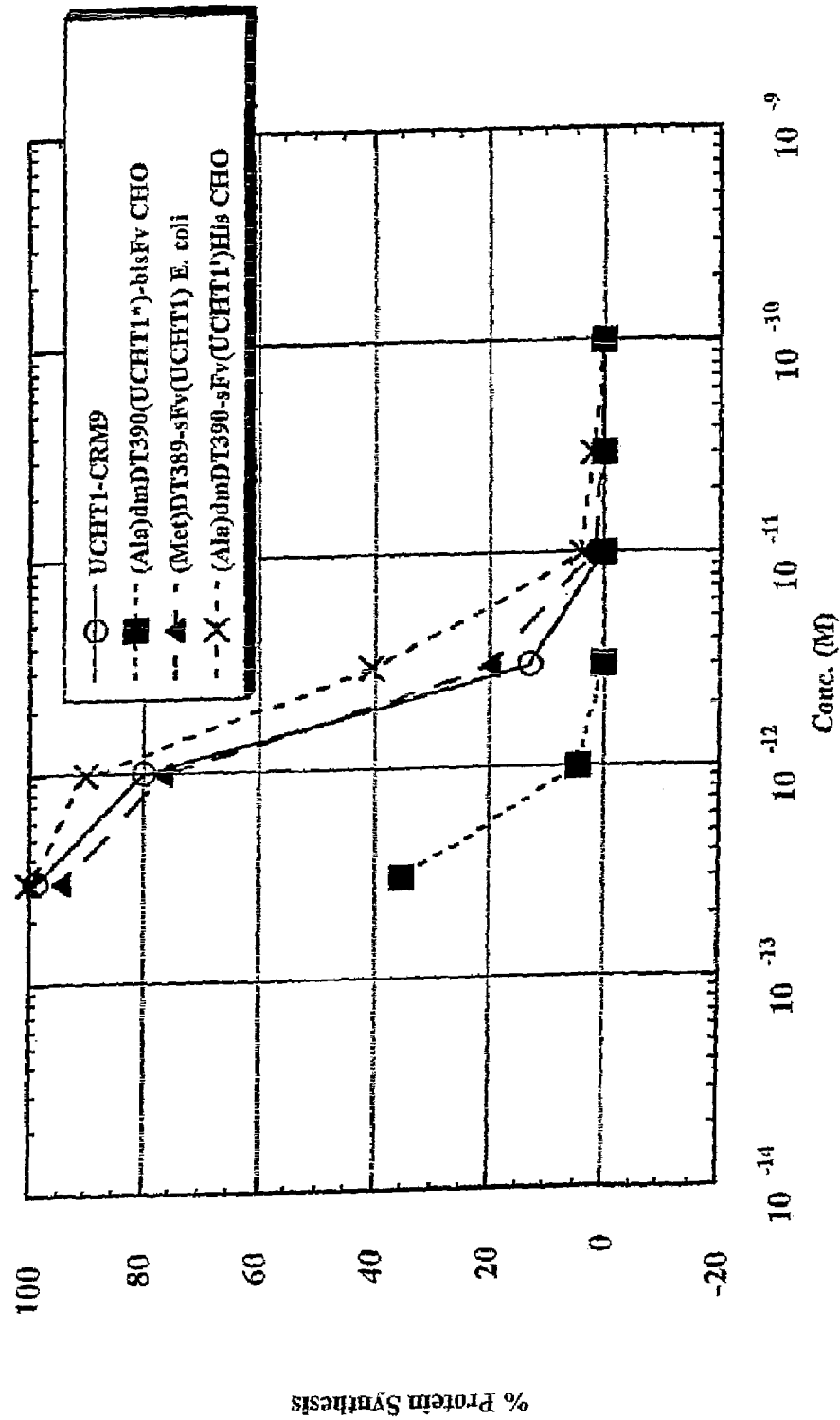
FIG. 31 shows the results of a 22 hour protein synthesis assay that compares the relative toxicity of (Ala)dmDT390-bisFv(UCHT1*) from CHO cells with DT-sFv constructs from E. coli and CHO cells and the chemical conjugate UCHT1-CRM9.

Binding and Toxicity of DT390-bisFv(UCHT1) and Other Related Fusion Immunotoxins FIG. 21 summarizes the toxicity data and binding data for a variety of DT390 mono and bisFv(UCHT1) constructs. These constructs were built in an attempt to maximize toxicity and to explore the variables that regulate anti-CD3 immunotoxin toxicity. Although the relative toxicity at 5 hours reflects the rate of entry of toxin into the cytosol compartment from an initial wave of endocytosis rather than the final toxicity of a cell exposed to a constant concentration of immunotoxin over the assay period, all toxicity data represented in FIG. 21 and FIG. 31 were derived from 20 hour assays on Jurkat cells. FIG. 31 compares the relative toxicity of (Ala) dmDT390-bisFv(UCHT1*) and its C-terminal His tag derivative from CHO cells, (Met)DT389sFv (UCHT1) refolded from *E. coli* and the chemical conjugate. The mono-sFv construct is equal in toxicity to the chemical conjugate while the (Ala)dmDT390-bisFv(UCHT*1) construct maintains a 10-fold increase in toxicity over the chemical conjugate.

Binding was determined either by competition of the construct over a 100 fold concentration range with a UCHT1-FITC tracer at 5 nM or by exposing cells to graded concentrations of construct (0.5-50 nM), washing and applying a second anti-DT-FITC Ab. Both methods gave similar values. The relevant parameter may be binding to a subset of receptors that have different binding attributes, are in a different state, and are being rapidly internalized.

Immunotoxin toxicity is regulated by at least four separate processes: binding, internalization, intracellular routing, and translocation. As an oversimplification one usually considers toxicity to be the product of the first and last steps. The binding data suggest that the mono-sFv and bisFv(UCHT1) constructs have very high translocation efficiencies compared to the chemical conjugate. The minimal amount of DT B chain domain to necessary to achieve translocation efficiency equal to the native toxin was evaluated. Because the C-terminus of the B-chain contains the most antigenic epitopes for toxin-blocking antibody production, there is an advantage to using the minimum B-chain sequence. Constructs increasing the DT sequence length within the immunotoxin were created. Starting with DT390, sequence encoding 20 amino acids was added or subtracted from the construct. Increasing concentrations of immunotoxin prepared in an in vitro transcription and translation system were tested in a 20-hour protein synthesis assay. The results show that there is no advantage to including sequence beyond DT390. Both DT350 and DT370 were non-toxic.

Furthermore, the effect of spacers between the DT390 and the bis Fv moiety was assessed. Constructs containing (Gly$_4$Ser)-n were generated in the context of pSRα-Neo+ dmDT390-bisFv(UCHT1*). CHO cells were transfected and stable producing cell lines were established. Cell supernatants were quantitated for immunotoxin by Western blot analysis. The insertion of between one and four G4S spacers between the DT390 moiety and the bisFv(UCHT1) moiety result in no improvement in toxicity.

Example 29

Factors Determining In Vivo T Cell Killing

Dose response curves of toxin induced inhibition of protein synthesis follow single hit inactivation kinetics of the form $S=e^{-kc}$ where S is the fraction of surviving cells. The exponent k is a lumped constant that includes the translocation efficiency and the binding of the immunotoxin to the cell and c is the local free concentration of immunotoxin. Using a hypothetical dose response curve for two different immunotoxins differing by 10-fold in their IC-50 and plotting the data as log S versus linear concentration, the 10-fold difference in IC-50 appears as a 10-fold difference in the slope of the survival curve. At any given dose the fraction of survivors for the steeper curve is equal to the fraction of survivors of the shallow curve to the $10^{th}$ power. Therefore, when choosing between various anti-T cell immunotoxins, it should be emphasized that differences in IC-50 by only 2 or 3 fold can have very large effects on the extent of T cell depletion (Neville D M and Youle RJ (75); Hudson T H and Neville D M (76)).

The lumped constant k contains a saturable binding term which will decrease the slope of the survival curve as the free concentration of immunotoxin approaches the dissociation constant, $k_d$, of the T cell/immunotoxin binding reaction, which in our case does not appear to be less than $1 \times 10^{-8}$ M. In this case the exponent $-kc$ becomes $(k_1)(nk_2c)/(1+k_2c)$ where $k_2=1/k_d$. Another factor that will blunt the killing curve is depletion of the immunotoxin by an excess of binding sites. 0.1 mg/kg of toxin in a volume of 50 ml (5% by volume of 1 kg) gives an initial concentration of $3.3 \times 10^{-8}$ M and corresponds to an input of 1.7 nanomoles. At $10^{10}$ T cells per kg and 50,000 receptors per cell, two molecules of immunotoxin per receptor are present. Assuming a $k_d$ of $10^{-8}$ M, 36% of the input immunotoxin will be bound. This is not an appreciable depletion of the immunotoxin free concentration. However, if input is decreased by a factor of 0.3, (equivalent to an in vivo dose of 30 mg/kg) 100% of the input would be bound based on a simple non-iterative calculation This fact may account for a blunting of T cell killing in vivo at low input concentrations compared to that expected from protein synthesis assays where the cell density per bathing fluid volume is 400-fold lower than that in the in vivo situation.

Example 30

Cloning of DT389-scFv(UCHT1)

Figure 33:
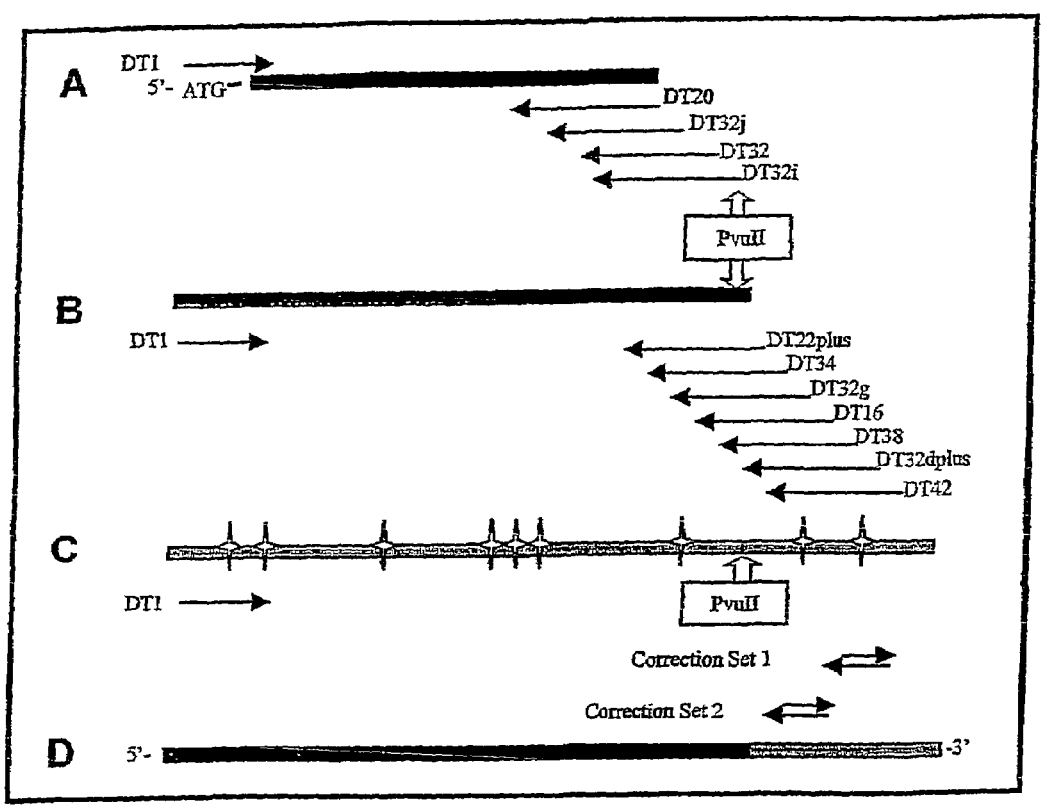
FIG. 33 shows a schematic of construction of the diphtheria toxin gene fragment encoding DT389 from ATCC culture clone #67011. The gene was encoded by two separated fragments in the plasmid. The first 0.8 kb was generated in a single PCR reaction (2A) and extended with three additional 3' oligos (2B).

The DT389 fragment was cloned using plasmid DNA encoding full length diphtheria toxin prepared from ATCC culture #67011: JM109 cells carrying insert PDγ2 in vector PEMBL8+ (European Patent Application No: 87201239.8, which is incorporated herein by reference in its entirety). Standard PCR methods, using DT1 (5'-TATAC-CATGGGCGCTGATGATGTTGTTGAT-3' (SEQ ID NO:50)) and DT20 (5'-ACTGCCCACGCCGCATAGT-TAGC-3' (NONCODING) (SEQ ID NO:51)) as 5' and 3' oligos respectively, were successful in generating 0.8 kb of the 1.3 kb DT fragment of interest. The remaining fragment, though present as a separate open reading frame in the parental plasmid, could not be amplified by standard PCR methods. Successful generation of the 3' end was accomplished through a direct synthesis scheme entailing a series of stepwise PCR reactions to extend the 5' fragment (FIG. 33). The sequences of three 3' oligos, DT32j (5'-TTGCGCAACG TTTACTGCCCACGCCGCATAGTTAGCCC-3' (SEQ ID NO:52)), DT32(5'-CGCTATCGATAACTTGCG-CAACGTTTACTGCCC-3' (SEQ ID NO:53)) and DT32I (5'-GCAGTTGTCTTTTCCAAATTAT CAGCTGTTTCGCTATCGATAAC-3' (SEQ ID NO:54)), hybridizing to the noncoding strand were used with the 5' coding-strand oligo DT1 (used as 5' oligo throughout) and their positions are indicated in FIG. 33. The PvuII restriction site in DT321 is indicated by underlining. Initial PCR conditions entailed 25-cycle hot start (94° C., 2 min) reactions with Pfu polymerase and cycling parameters of 94° C. 45 sec; 62-65° C. 45 sec; 72° C. 1 min-1 min 40 sec. The first 3 additional rounds of PCR extended the original base fragment past a unique PvuII restriction site. This fragment was subcloned and verified as error-free by DNA sequence analysis. The subcloned DNA then served as a template for seven sequential rounds of PCR amplification using the following 3' primers in conjunction with DT1 5' primer: DT22plus (5'

(5'-AAAAGACAACTGCTGCTCTTTC GATACTTCCTG-GTATCGG-3' (SEQ ID NO:62))) and Correction Set 2 used to correct bp 1308 (DT32plus and DT31H (5'-AAGTAGT-TCATAATTCGTATAATC GTCCCGCGTATTCTCCG-3' (SEQ ID NO:63))). The cycling parameters were: 95° C. 2 min; followed by 14 cycles of: 95° C. 30 sec; 55° C. 1 min; 68° C. 8 minutes. Once corrected, the 3' end was spliced back onto the mutation-free original 5' PvuII fragment by restriction enzyme digestion. The complete DT389 fragment was cloned as an NcoI-BamHI fragment into a pLitmus plasmid containing the UCHT1-scFv gene.

UCHT-1 mAb variable regions were cloned from hybridoma cells. Genes encoding murine anti-CD3 Fv were amplified by RT-PCR from UCHT-1 hybridoma cell RNA (Beverley and Callard, 1981(83)). Oligonucleotide primers based on the sequence of UCHT-1 and consensus primers described for cloning antibody variable regions (Orlandi et al., 1989 (84)) were used for this purpose. Briefly, PCR primers IM34A (5'-GCGGATCCGACATCCAGATGACCCAGACCACC-3' (SEQ ID NO:64) (shown with the BamHI site underlined)) and IM-34B (5'-CC TCTAGAAGCCCGTTTGATTTCCAGCTTGGT-3' (SEQ ID NO:65) (shown with the XbaI site underlined)) were used to amplify the $V_L$ region. Primers IM-61(5'-CC GTCGACGAGGTGCAGCTCCAGCAGTCT-3' (SEQ ID NO:66) (shown with the XbaI site underlined)) and IM-34C (5'CCAAGCTTTCATGAGGAGACGGT GACCGTG-GTCCC-3' (SEQ ID NO:67) (shown with the HindIII site underlined)) were used to amplify the $V_H$ fragment. The amplified fragments were subcloned into *E. coli* plasmid vectors using TA Vector (Invitrogen, Carlsbad, Calif.) and their DNA sequences determined.

```
GCTACCGATA CCAGGAAGTA TCGAAAGAGCAGCAG TTGTCTTTTCC-3',        (SEQ ID NO:55))

DT34 (5'-GAACGGCACCGTCTGCAATGCCCATTACGCTACCGATACC              (SEQ ID NO:56))

AGGAAGTATCGAAAGAG-3',

DT32g (5'-ACTATCTCTTCTGTATTGTGGTGAACGGCACCGTCTGCAATG-3',     (SEQ ID NO:57))

DT16 (5'-CAACCATTAAAGACGATAAAGCTATTGATTGTGCCACTATCTCTTCTG-3', (SEQ ID NO:58))

DT38 (5'-CTACAAAATTATA TGCAGCGAAACCAATATCAACTAGCT             (SEQ ID NO:59))

CTCCTACCAATGGAATAGCTTGAGCAACCATTAAAGACGAT-3',

DT32dplus (5'-CGATTATACGAATTAT GAACTACTTGAAA                  (SEQ ID NO:60))

TAAATTGATAATACTCTCTACAAAATTATATGCAGCG-3',

DT42 (5'-GCGAATTCGGATCCACCGGCGGAAGCAAATGGTTGCGTTTTAT          (SEQ ID NO:61))

GCCCCGGAGAATACGCGGGACGATTATACGAATTATGAAC-3'.
```

In spite of the proof-reading activity of the Pfu polymerase (Stratagene), mutations were observed and the overall yield was inconsistent following the first three amplification reactions. Therefore, the last four remaining reactions (DT16 onwards) were performed with AmpliTaq (Perkin-Elmer); cloned; and sequenced. Plasmid DNA with the fewest number of mutations served as the template for the subsequent round of PCR amplification.

Two rounds of site directed mutagenesis were required to correct the synthesized portion between the PvuII site and the 3' end using Stratagene QuikChange Site-Directed Mutagenesis Kit (Stratagene Cloning Systems, La Jolla, Calif.; catalog #200518). The following two oligo sets were used: Correction Set 1 used to correct bp 1106 (DT22plus and DT31 C For generation of the single chain Fv construct, the peptide sequence used to link the $V_L$ and $V_H$ regions consisted of a flexible Gly-Ser repeat $(Gly_3Ser)_4$ (SEQ ID NO:104). This linker, created by PCR using overlapping oligonucleotides, joined the 3-prime end of $V_L$ with the 5 prime end of $V_H$. A six amino acid connector sequence including a Bam HI restriction site was added to the 5-prime end of the Fv fragment by PCR, and two termination codons and a BglII site were added at the 3' end. The connector sequence thus contains the six amino-acid linker sequence ASAGGS (SEQ ID NO:37), where GS denotes the position of the BamHI site. The complete nucleic acid sequence of the DT389-scFv-(UCHT1) including restriction sites and deduced amino acid sequence is shown in FIG. 35. The nucleic acid sequence is provided as SEQ ID NO:40, and the deduced amino acid sequence is provided as SEQ ID NO:38. A comparison of amino acid sequences for DT 389-sFv(UCHT1) and DT390-sFv (UCHT1) is shown in FIG. 34.

The final DT390-sFv(UCHT1) construct was subcloned into the pET15b expression plasmid and transformed into BL21 cells. The native *Corynebacterium diphtheriae* signal peptide was not included in the construct as production of insoluble protein as inclusion bodies was desired. Initiation of translation was at an introduced ATG codon immediately preceding the glycine codon which encoded the first amino acid of the mature protein.

The plasmid used for expression, pET15 (Novagen), has an IPTG-inducible lac promoter; host cells are *E. coli* BL21 (λDE3) cells. A selected clone was grown in 5 liter batches (Bioflo 3000 fermentor) (New Brunswick Scientific, Inc., Edison, N.J.) of LB broth containing 100 ug/ml ampicillin. A 100 ml overnight LB-amp culture was centrifuged once and resuspended in fresh LB-ampicillin prior to the inoculation of the fermenter culture. Cells were grown at 37° C. and induced with 1 mM IPTG final concentration once growth was in the range of OD6 M 0.6 to 0.8. The induction was allowed to proceed for 2.5-3 hours, bacteria were collected by centrifugation and the pellet stored at −80° C. until use.

The DT389-scFv(UCHT1) immunotoxin fusion protein was purified from *E. coli* inclusion. Briefly, inclusion bodies were prepared from approximately 20-30 g cell pellet through a series of cell homogenization and buffer/detergent washes. The washed inclusion body protein was solubilized with 6M guanidine under reducing conditions (0.3M DTE, dithioerythreitol) (Sigma, St. Louis, Mo.). Refolding was carried out at 8° C. by rapid 100-fold dilution of the sample into refolding buffer containing 8 mM oxidized glutathione (GSSG) (Sigma, St. Louis, Mo.). These conditions were later modified to 0.65 M DTE and 0.9 mM GSSG, as used successfully to refold a DT390-anti mouse CD3 immunotoxin (Vallera et al., 1996 (85)).

Figure 36A:
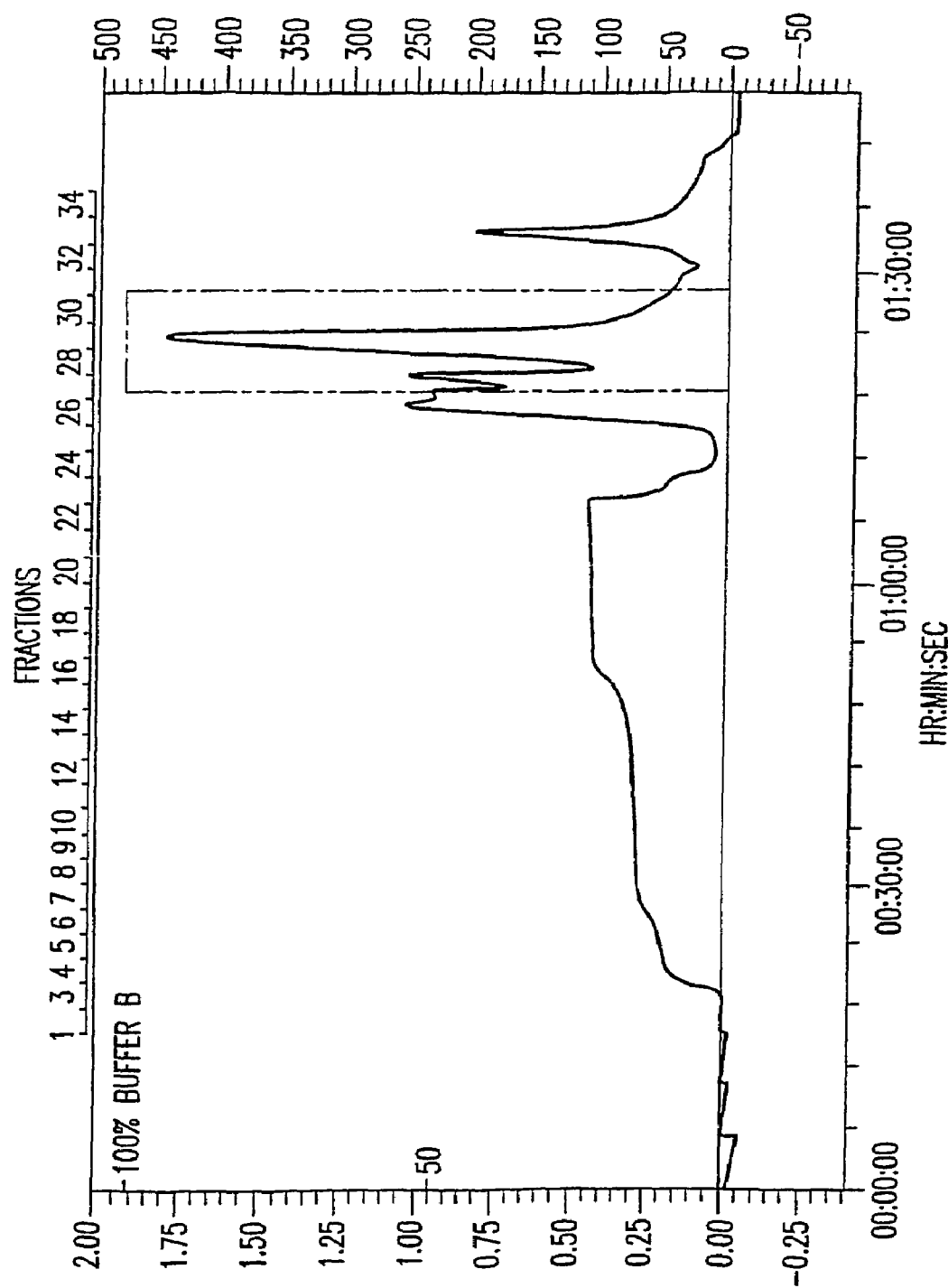
FIG. 36a shows the results with an FFQ 0.28M NaCl isocratic gradient. Fractions 28/29 were subsequently diluted 5× in 20 mM Tris pH 7.4.
Figure 36B:
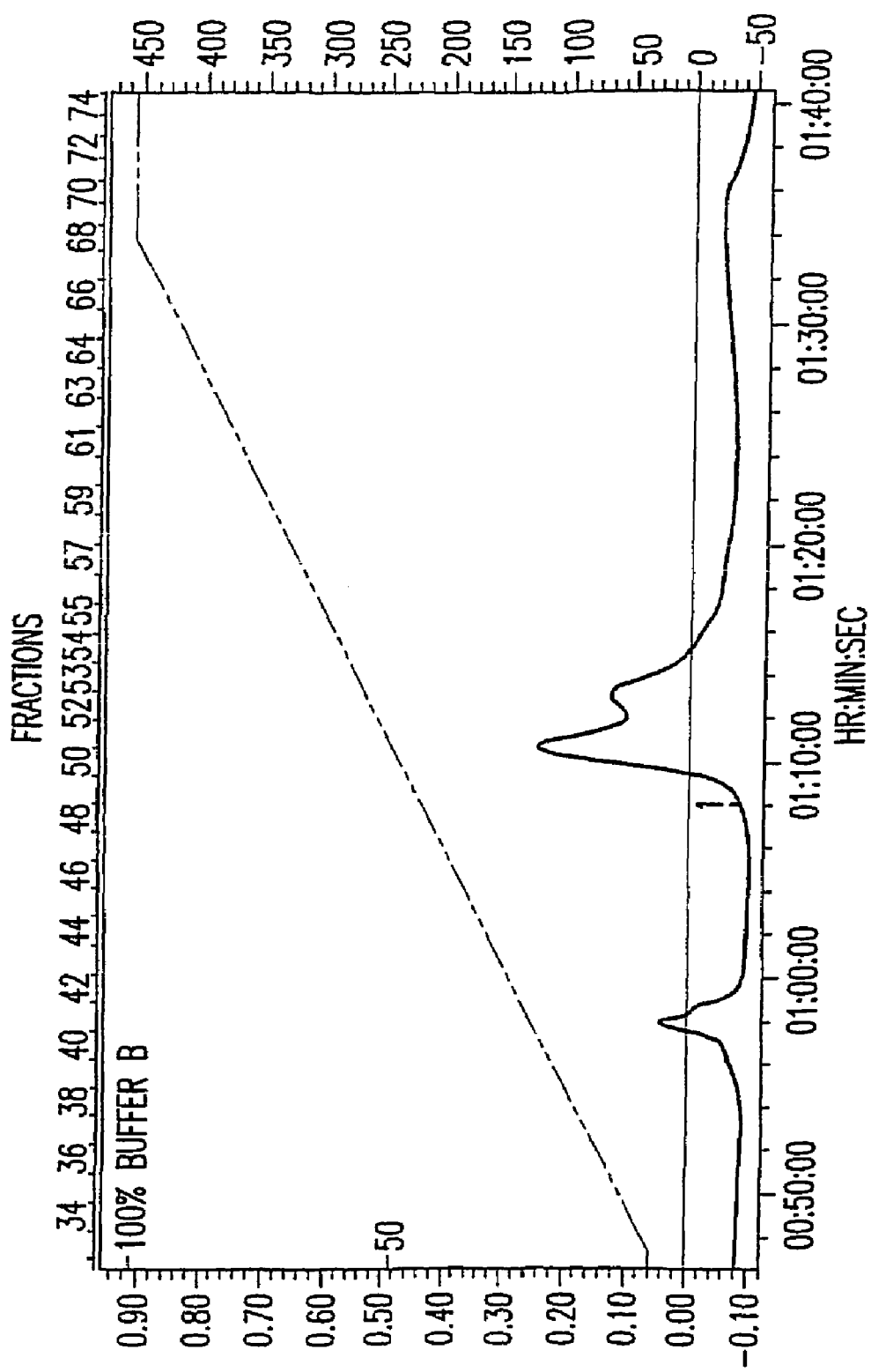
FIG. 36b shows the results of fraction 28/29 run on a mono Q5 column with a linear gradient from 0 to 0.28M NaCl.

Protein refolding continued without stirring for 48-72 hr at 8° C. The sample was dialyzed into 20 mM Tris-HCl pH 7.4, 100 nM urea Following concentration via an Amicon tangential flow 30,000 Mr cut off membrane (Amicon, Lexington, Mass.), two rounds of anion exchange chromatography were performed using 20 mM Tris-HCl pH 7.4 as column start and equilibration buffer. See FIG. 36. First, a 0.28 M NaCl step elution from a 10 ml Pharmacia Fast flow Q (FFQ) column (Pharmacia, Piscataway, N.J.) was performed. See FIG. 36A. The fractions were analysed by 10% SDS-PAGE under reducing conditions. Fractions were pooled based on the SDS-PAGE analysis and further chromatography carried out on a 5 ml BioRad Q5 column (BioRad, Richmond Calif.) eluted with a 0-0.28 M NaCl gradient (70 ml). See FIG. 36B. Fractions were again analysed by SDS-PAGE. The pre-FFQ column material, the FFQ eluted pooled fractions 28/29 (FIG. 36A), and fractions 42, 51, 52, 53, 54, and 55 from the Q5 column (FIG. 36B) were compared to high molecular weight markers (Amersham, Arlington Heights, Ill.) on SDS-PAGE gels stained with BluePrint (Life Technologies, Gaithersburg, Md.). The major peak in each fraction had an Mr of about $66 \times 10^{-3}$.

The major peak from the Q5 column separation was dialyzed into PBS; sterile filtered; and subjected to in vitro characterization. Specifically, the native molecular weight of DT389-scFv(UCHT1) was determined by gel filtration on Sephacryl S200 column calibrated with Bio-Rad molecular weight standards (β-amylase 200 kD; alcohol dehydrogenase 150 kD; bovine serum albumin 66 kD; carbonic anhydrase 29 kD; cytochrome c 12.4 kD). Essentially all of the protein migrated near the position of bovine serum albumin (66 kD). The material eluted as a single monomeric peak with an apparent molecular weight of in the region of 70 kDa, which is close to the BSA calibration standard. This actual molecular weight agrees well with the calculated value from the amino acid sequence of DT389-scFv(UCHT1) (69359 Da). There appeared to be essentially no aggregated material as assayed by size exclusion column chromatography.

Example 31

MTS Assay

Specific toxicity towards a $CD3^+$-expressing human Jurkat T-cell line was demonstrated using an MTS assay three days after addition of immunotoxin to the cells. The MTS assay measures lactate dehydrogenase (LDH) enzymatic activity, which is directly proportional to the number of viable cells present. The cell lines used for negative controls for non-specific toxicity are the human $CD3^-$ Ramos B-cell line and the U937 monocytic cell line.

The number of viable cells at the time of test compound addition was compared to the number of viable cells present 3 days (72 hrs) post compound addition. The cell viability was determined by the tetrazolium derivative MTS (3(4,5-dimethylthiazol-2-yl)-5-(3-carboxymethoxyphenyl)-2H-tetrazolium, inner salt) which is converted by LDH in viable cells in the presence of the electron coupling agent, phenazine methosulfate (PMS), to a water-soluble formazan derivative. The absorbance at 490 nm of the formazan derivative is proportional to the number of viable cells.

The assay was performed as follows:

Day 0: The cells were plated at $2 \times 10^4$ cells per well in 100 uL of culture medium with the addition of 100 units/mL of penicillin and 100 ug/nL streptomycin (MTS Medium).

Day 1: The immunotoxins were prepared in MTS medium in serial 3-fold dilutions and added in 100 μL to the plated cells.

Day 4: The experiment was terminated by addition of 10 μl of a working solution comprised of 19 parts of 2 mg/ml MTS: 1 part of 0.92 mg/ml PMS in 2.5 phosphate buffered saline and read at OD490 4 hours later.

Data were plotted as a percent of control cell value, i.e., growth in the absence of immunotoxin. The $IC_{50}$ is calculated using the Excel Forcast function, which has been shown to provide very comparable $IC_{50}$s to the "Sigmoidal fit" of Origin 5.0. The $IC_{50}$ and standard deviations of the anti-CD3 immunotoxins measured in the 3 day MTS assay are shown in Table 14. The data presented in Table 14 show selective toxicity for the $CD3^+$ Jurkat cell line; an $IC_{50}$ for killing CD3-Ramos or U937 cells was not attained in these experiments with 4-5-logs higher concentration of the immunotoxins.

TABLE 14

$IC_{50}$ determinations for cell killing in a 2 day toxicity assay (MTS) for four anti-CD3 immunotoxins

| Immunotoxin | $IC_{50}$ ± SD Jurkat (CD3+) | $IC_{50}$ Ramos; U937 (CD3−) |
|---|---|---|
| DT389-sFv(UCHT1) | 0.24 ± 0.071 pM | >14 nM |
| DT390-bisFv(UCHT1) | 0.031 ± 0.011 pM | >1 nM |
| UCHT1-CRM9 | 0.68 ± 0.11 pM | >17 nM |

Figure 37:
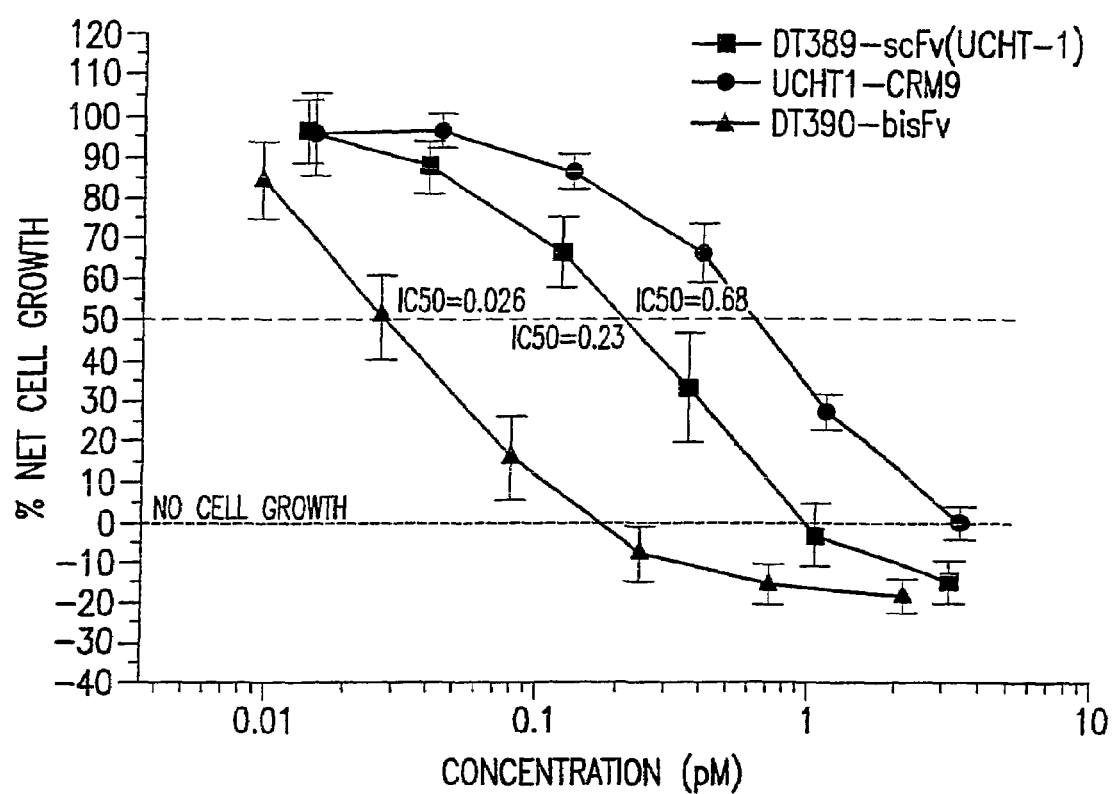
FIG. 37 shows the cytotoxic effect of the anti-CD3 immunotoxins (DT389-sFv(UCHT1); UCHT1-CRM9; and DT390-bisFv(UCHT1)) on net growth of Jurkat (CD3+) cells as assayed in the MTS assay. The mean and standard deviation for the data reported in Table 14 are plotted. This graph plots the mean and standard deviation from seven determinations.

The relative order for the potencies of the anti-CD3 immunotoxins is: DT390-bisFv(UCTH1) is 10-fold more potent than DT389-scFv(UCHT1), which is ~3-fold more potent than UCHT1-CRM9. Little or no effect of any of the anti-CD3 immunotoxins was observed on the CD3-Ramos or U937 cell lines at concentrations exceeding the $IC_{50}$ for potency on Jurkat cells by more than 3-logs for DT389-scFv (UCHT1) or more than 4-logs for DT390-bisFv(UCHT1). At high concentrations, the proteins clearly reduce the viable cell number below the starting cell number and, therefore, behave as cytotoxic agents. See FIG. 37.

Example 32

Gene Optimization for *Pichia* Expression

To increase expression of (Ala)dmDT390-bisFv (UCHT1*), additional rebuilding was performed as compared to Example 23. Specifically, four minor AT rich regions in the bisFv domain were rebuilt along with two minor AT rich regions in the DT390 domain still left after the rebuilding work described in Example 23. The second rebuilding work was carried out to change the DNA sequence of these AT rich regions. The expression level was improved after DNA rebuilding in the bisFv domain. The sequence of the twice rebuilt (Ala)dmDT390-bisFv(UCHT1*) is provided as SEQ ID NO:102.

Two factors were considered for criteria of which regions to rebuild. One factor was an AT rich region, which has more than 64% AT content. The other was preferred codon usage. Each species has preferred codons for efficient protein translation. Codon optimization can increase expression level by 2-10 fold or even higher. Table 15 shows the frequency of codon usage in highly expressed *P. pastoris* genes. Sreekrishna (1993) has analyzed these data from AOX1, AOX2, dihydroxy acetone synthetase 1 and 2, and glyceraldehydes phosphate dihydrogenase genes. A preferred codon was defined as a codon that was used 30% or more in the above listed proteins. For example, there are 6 synonymous codons encoding leucine. In this case, TTG is the preferred codon and the others are non-preferred codons. Based on these criteria, the preferred codons for *P. pastoris* were determined. FIG. 38 shows how to determine the regions that are to be rebuilt. The star indicates a non-preferred codon. The double underlining in the line of amino acids indicates AT-rich regions, which are still left in the gene of interest after the rebuilding work described in Example 23. The underlining in the reb line indicate regions that were rebuilt.

Ten regions were rebuilt by PCR. The gene of interest was divided into three parts—the DT region, and two sFv regions. See FIG. 39. In rebuilding the DNA sequence of DT390, three major fragments were made by PCR. PCR was done three times to make a first fragment by using three individual 3' primers and one 5' primer. Each primer has a DNA sequence for rebuilding and/or restriction enzyme sites. Second and third fragments also were made by similar method. After PCR, each fragment was ligated by using compatible cohesive ends or unique enzyme sites.

Coomassie-stained SDS-PAGE gels showed that expression level was increased by DNA rebuilding. The samples were taken from the culture of different clones in shake flasks. A control sample was taken from the culture of a clone before DNA rebuilding. Expression level was increased 4-5 times by DNA rebuilding.

FIG. 40 shows the method used to select expression strain pJHW#1. Expression strain, pJHW#1 was obtained by double transformation. GS115 strain was used as the host strain. It was transformed with plasmid, DT390-bisFv in pPICZa Linearized DNA was integrated into AOX1 locus by a single crossover. The resulting transformant has at least one copy of the gene of interest. Transformants selected on zeocin medium were screened to obtain the highest transformant expression by shake flask culture. Among these transformants, opr#4-3 clone was selected. This clone was used as the host strain for a second transformation. The opr #4-3 clone was transformed with plasmid, DT390-bisFv in pPIC9K. Linearized DNA was integrated into either 5' AOX1 regions by a single crossover. The resulting transformants had at least 2 copies of the gene of interest. Among double copy transformants, pJHW#1 strain was selected. This clone was used as an expression strain for fermentation.

To obtain a single copy clone, GS115 strain was transformed with plasmid, DT390-bisFv in pPIC9K, having the gene of interest and a His4 selectable maker. Transformants were selected on histidine-deficient agar plate. Among these transformants, pJHW#2 clone was selected by comparison of the expression level in a shake flask culture and used as an expression strain for fermentation to compare the expression

TABLE 15

Frequency of codon usage in highly expressed *P. pastoris* genes (Sreekrishna, 1993)

| codon | aa | fraction | codon | aa | fraction | codon | aa | fraction | codon | aa | fraction |
|---|---|---|---|---|---|---|---|---|---|---|---|
| TTT | phe | 0.19 | TCT | ser | 0.47 | TAT | tyr | 0.12 | TGT | cys | 0.83 |
| TTC | phe | 0.81 | TCC | ser | 0.37 | TAC | tyr | 0.88 | TGC | cys | 0.17 |
| TTA | leu | 0.09 | TCA | ser | 0.07 | TAA | stop | 0.80 | TGA | stop | 0.00 |
| TTG | leu | 0.52 | TCG | ser | 0.03 | TAG | stop | 0.20 | TGG | trp | 1.00 |
| CTT | leu | 0.18 | CCT | pro | 0.39 | CAT | his | 0.13 | CGT | arg | 0.18 |
| CTC | leu | 0.03 | CCC | pro | 0.04 | CAC | his | 0.88 | CGC | arg | 0.00 |
| CTA | leu | 0.03 | CCA | pro | 0.57 | CAA | gln | 0.66 | CGA | arg | 0.00 |
| CTG | leu | 0.15 | CCG | pro | 0.00 | CAG | gln | 0.34 | CGG | arg | 0.01 |
| ATT | ile | 0.56 | ACT | thr | 0.50 | AAT | asn | 0.13 | AGT | ser | 0.04 |
| ATC | ile | 0.44 | ACC | thr | 0.43 | AAC | asn | 0.87 | AGC | ser | 0.02 |
| ATA | ile | 0.00 | ACA | thr | 0.05 | AAA | lys | 0.21 | AGA | arg | 0.79 |
| ATG | met | 1.00 | ACG | thr | 0.03 | AAG | lys | 0.79 | AGG | arg | 0.01 |
| GTT | val | 0.50 | GCT | ala | 0.60 | GAT | asp | 0.32 | GGT | gly | 0.74 |
| GTC | val | 0.41 | GCC | ala | 0.29 | GAC | asp | 0.68 | GGC | gly | 0.03 |
| GTA | val | 0.04 | GCA | ala | 0.10 | GAA | glu | 0.42 | GGA | gly | 0.22 |
| GTG | val | 0.05 | GCA | ala | 0.00 | GAG | glu | 0.58 | GGG | gly | 0.00 |

*Underlined letters indicate *P. patoris*-preferred codon.

level between single copy clone (pJHW#2) and double copy clone (pJHW#1) in the fermentor.

Example 33

Optimization of Fermentation Conditions for *Pichia* Expression

Fermentation has three distinct phases. During the first phase, the glycerol batch phase, which continues until glycerol in the starting media is completely consumed, complete consumption was monitored by the dissolved oxygen level (DO level). During the second phase, the glycerol fed-batch phase, high cell density was attained, as the expression level is dependent on cell density in the culture. The last phase is the methanol induction phase. In this phase, most of the protein of interest was produced. Methanol level in the culture was maintained at 0.15% by a methanol controller. The fermentation parameters and starting media as shown in Table 16 were used. 50% glycerol solution or glucose solution was supplemented into the culture for phase II as a carbon source. 10% casamino acid solution, which plays a role as a natural protease inhibitor and nitrogen source, was fed at the start of methanol induction.

TABLE 16

Fermentation parameters and recipe of fermentation medium

| Fermentation parameters | Starting Medium (10 L): 4% glycerol 1% casamino acid 1% yeast extract 2% peptone 0.34% YNB (without amino acids and ammonium sulfate) 1% ammonium sulfate 0.435% PTM1 salt solution 0.01% Antiform 289 (Sigma A-5551, St. Louis, MO) 50% glycerol solution: 50% (w/v) glycerol & 0.6% PTM1 Methanol solution: 12 ml PTM1 per liter of methanol 10% casamino acid |
|---|---|
| Fermentation media | temperature: 28° C. dissolved oxygen: >25% pH: 7.0 or pH shift (3.5 to 7.0) agitation: 800 rpm aeration: 1 vvm vessel pressure: 3 psi |

Figure 41:
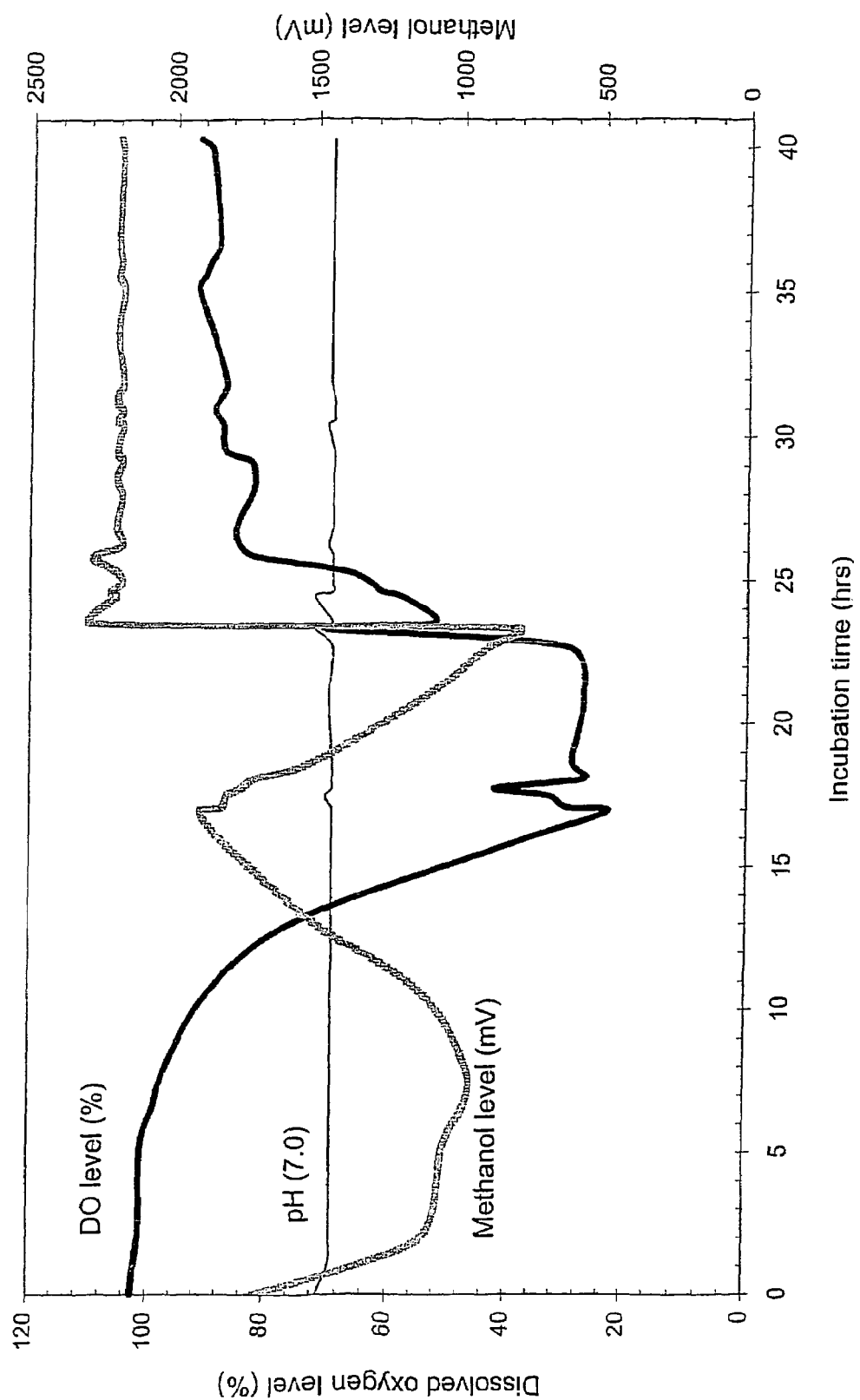
FIG. 41 shows trends of all parameters for fermentation using the standard protocol. Percentages of dissolved oxygen, methanol level; and pH are plotted over the incubation time course.

Trends of all parameters for fermentation are shown in FIG. 41, using the standard protocol. DO level is decreased as cell density starts to increase. The first DO peak indicates complete consumption of glycerol in the starting media Glycerol or glucose feeding was started at this time. Glycerol or glucose feeding rate was controlled by DO level. The DO level was maintained to 30% during glycerol fed-batch phase for complete consumption of added glycerol or glucose. The solid line indicates the trend of methanol level in the culture. The methanol sensor can detect methanol and ethanol. Actual methanol feeding was initiated after the appearance of a second DO peak, so the peak of methanol before addition of methanol indicates that ethanol was produced during phase 1 and 2. Even though ethanol production was increased until the end of phase 1, maintaining the culture to a limited growth state could decrease ethanol level to basal level. The methanol detector produced the voltage signal based on methanol concentration. In this run, 2200 mV was corresponding to 0.15% methanol and this value was used as the set point of the methanol controller to maintain 0.15% methanol in the fermentor for whole period of methanol induction. Expression of recombinant (Ala)dmDT390-bisFv(UCHT1*) was detectable on a Coomassie-stained gel from starting glycerol feeding, indicating that expression may be initiated from start of phase 2 or end of phase 1. The AOX1 promoter was leaky in the presence of glycerol, so protein expression was initiated before methanol induction.

The graph in FIG. 42 shows the expression pattern in five different fermentation runs with pJHW#1 clone having a double copy of the gene of interest. In a normal condition without addition of protease inhibitors during methanol induction, expression level of (Ala)dmDT390-bisFv (UCHT1*) started to decrease after 7 hours of methanol induction. These data indicate that some proteases were secreted from *Pichia* cells or entered the medium by lysis of *Pichia*. It was determined that 3 mM PMSF (phenylmethylsulfonyl fluoride) and 5 mM EDTA ((ethylenedinitrilo)-tetraacetic acid) could help to increase expression level in shake flask cultures by inhibiting protease activity. In this run, adding 5 mM EDTA decreased the expression level. When adding 1 mM PMSF for methanol induction, expression level was slightly increased and maintained a similar expression level for next 11 hours. In this run, the pH was maintained to 3.5 before methanol induction, and then was changed to 7.0 during methanol induction. Also, 1 mM PMSF was added. The pH shifting appears to reduce other proteins secreted from *Pichia*. Expression level at 3 mM PMSF was tested. As shown in FIG. 42, expression level was gradually increased up to 15 mg/L for 20 hours of methanol induction. In the Mut$^+$ strain, maintaining 25% of DO level is important since considerable oxygen is required for metabolizing methanol. So oxygen enrichment was employed to maintain 25% of DO level for methanol induction.

Even though many reports regarding expression of heterologous protein in *Pichia* pointed out that copy number of the gene of interest in a transformant is critical to determine an expression level, that issue is still controversial. Sometimes, the expression level was not correlated to copy number or decreased by increasing copy number. To determine the effect of copy number in expression of (Ala)dmDT390-bisFv (UCHT1*) in *Pichia*, expression level in the fermentor under best condition described above was compared using a single copy clone and a double copy clone.

Coomassie-stained SDS-PAGE gels showed that expression level was higher in the single copy clone than the double copy clone. Expression strain, pJHW#2 consumed methanol 1.5 times more than pJHW#1 strain during methanol induction. The expression level of (Ala)dmDT390-bisFv (UCHT1*) in the single copy clone was about 30 mg/L.

Example 34

Three-Step Purification of dmDT390-bisFv(UCHT1*) from *Pichia*

Three-step chromatography was employed to purify (Ala) dmDT390-bisFv(UCHT1*) as rebuilt the second time. Thiophillic adsorption and Poros HQ 50 ion exchange chromatography were used to concentrate of the protein of interest. Protein L affinity chromatography was used to polish the protein of interest. Thiophillic resin, can interact with thiol group in proteins under high salt condition (500 mM $Na_2SO_4$) was developed for purification of the antibody.

A 10 L fermentor run (New Brunswick BioFlo 4500; Edison, N.J.) using strain pJHW#1 harvested after 19 hours of methanol induction was performed.

Prior to applying the sample to the thiophillic resin (Clonetech, Palo Alto, Calif.) column (600 ml bed volume, packed in 10 cm×550 cm column), solid sodium sulfate and 1 M Tris buffer (pH 8.0) were added to the supernatant to final concentration of 500 mM and 20 mM, respectively. After loading the sample to the column equilibrated with binding buffer (500 mM Na$_2$SO$_4$ and 20 mM Tris, pH 8.0), the column was washed with 3 bed volumes of binding buffer. And then the protein of interest was eluted with elution buffer (5% glycerol and 20 mM Tris, pH 8.0). Most of the protein of interest should be in first three bed volume fraction. The sample volume was reduced from 10 L to 1.8 L. The sample obtained from thiophillic adsorption was diafiltrated against 5% glycerol and 20 mM Tris (pH 8.0) by using a hollow fiber concentrator (polysulfone, cutoff size: 10 kd, surface area: 680 cm$^2$; Spectrum Laboratories, Inc.) and exchanging 5 volumes of sample. The diafiltrated sample was applied to Poros HQ 50 (Applied Biosystems; Foster City Calif.) column (20 ml bed volume, packed in 2.6 cm×20 cm column) equilibrated with binding buffer (5% glycerol and 20 mM Tris, pH 8.0). The protein of interest was eluted with a 20 bed volume gradient from 0 to 500 mM NaCl in binding buffer. One quarter bed volume fraction was collected immediately after starting the gradient elution. The protein of interest was in fraction # 14 to 29, as shown with Coomassie blue stained gels. The sample volume was reduced from 1.8 L to 80 ml. The sample was applied to Protein L Plus agarose (Pierce) column (54 ml bed volume, packed in 5 cm×20 cm column) equilibrated with binding buffer (600 mM (NH$_4$)$_2$SO$_4$, 5% glycerol, and 20 mM Tris, pH 8.0). This Protein L agarose can bind light chains of some immunoglobulins. The recombinant (Ala)dmDT390-bisFv(UCHT1*) could bind weakly to Protein L only under high salt conditions (600 mM (NH$_4$)$_2$SO$_4$, 5% glycerol, and 20 mM Tris, pH 8.0). It was easily eluted with low salt buffer. Loading volume should be less than one bed volume, because binding affinity was very low. The column was washed with 1.5 bed volume of binding buffer. Protein of interest was eluted with elution buffer (5% glycerol and 20 mM Tris, pH 8.0). Fractions #6 to 10 from Protein L affinity were pooled. The total yield of purified material was 52 mg, representing a 35% yield. NaCl and EDTA were added to a final concentration of 200 mM and 1 mM, respectively. Finally, the purified sample was tested for specific toxicity towards a human T cell line (Jurkat) of purified (Ala)dmDT390-bisFv(UCHT1*) and protein elution profile on HPLC equipped with GF-250 Zorbax column (Agilent Technologies) to assess size homogeneity in the absence of SDS. The concentration of (Ala)dmDT390-bisFv(UCHT1*) inhibiting protein synthesis 50% (IC$_{50}$) is $1\times10^{-13}$ M. This is 25-fold more potent than the standard chemical conjugate UCHT1-CRM9. The purified (Ala)dmDT390-bisFv(UCHT1*) runs as a single band on Zorbax GF250. A preceding shoulder of aggregated (Ala)dmDT390-bisFv(UCHT1*) was variably present and does not exceed 15% by area. An alternative polishing step instead of Protein L affinity is gel filtration using Superose 12 prep resin (Pharmacia) in a 5×30 cm column.

Example 35

Natural Selection of *Pichia* Strain

The diphtheria toxin (DT) and immunotoxin are not toxic to *Pichia* if they are outside the cell, because the *Pichia* cell, in contrast to mammalian cells, has a cell wall that exerts a physical barrier to the uptake of these proteins to the cytosol compartment. Nevertheless when it is expressed and secreted, the immunotoxin may be toxic to *Pichia*. In general, a gene of interest under control of the AOX1 promoter will be expressed in the methanol induction phase and the resulting gene product should transverse several compartments along the secretory pathway. During these processes, some of (Ala)dmDT390-bisFv(UCHT1*) may be leaked into cytosol or the catalytic domain of (Ala)dmDT390-bisFv(UCHT1*) may be translocated into cytosol. In this case, the immunotoxin would inhibit protein synthesis in *Pichia* because of ADP-ribosylation of EF-2 by the catalytic domain. To overcome this situation, *Pichia* may eliminate the gene of interest, reduce an amount of protein secreted by regulation at translational level or post-translational level or select a mutated EF-2 gene conferring resistance to DT. To find out how the expression pattern in *Pichia* cells was changed by the duration of methanol induction, *Pichia* cells were isolated from the culture taken at a different time points (0, 24 or 48 hours of methanol induction), and each isolated colony was tested if they could express (Ala)dmDT390-bisFv(UCHT1*) in a shake flask. The capacity of expressing (Ala)dmDT390-bisFv(UCHT1*) was reduced or abolished as methanol induction time was increased. Reduction or abolishment of capacity might be due to decreasing secretion efficiency or elimination of the gene of interest by the toxic selection pressure, (Ala)dmDT390-bisFv(UCHT1*). This result suggested that leakage of (Ala)dmDT390-bisFv(UCHT1*) or translocation of catalytic domain took place in the secretory pathway in a time dependent manner. Notably, expression level in each colony isolated at 24 hours of methanol induction varied. Some colonies have higher expression levels than that in colonies isolated before induction. Production of (Ala)dmDT390-bisFv(UCHT1*) in some colonies was decreased. This result indicated that the toxic selection pressure could be used for screening high-producing colonies.

A natural selection procedure was employed in which the pJHW#1 strain was used as the original strain for improving the expression level and colonies were recovered at 24 hours of methanol induction. Two rounds of selection procedure were carried out to obtain a high producing *Pichia* strain. In the first round, 168 colonies were tested for expression levels of (Ala)dmDT390-bisFv(UCHT1*) in test tube cultures and then the A54 strain was selected as the highest expressing strain In the second round with the A54 strain, 144 colonies were tested and the B 126 strain was selected. These two strains were used for a fermentation run. Expression levels, however, were not significantly increased in the fermentor compared to the original strain, pJHW#1, because there was a difference between test tube culture and fermentation.

Example 36

Production of a *Pichia* Strain with EF-2 Mutation

A mutated EF-2 strain was developed to improve expression levels of (Ala)dmDT390-bisFv(UCHT1*). Several procedures were employed to obtain a mutated EF-2 strain.

First, a mutated EF-2 strain was developed by transformation with a mutagenizing oligo having the sequence CCCTGCACGCCGATGCTATCCACAG A<u>A</u>G <u>A</u>GGAGGACAAGTCATTCCAACCATGAAG (SEQ ID NO:100). The oligomer contained two point mutations to change amino acid 701 from glycine to arginine. Mutagenizing oligo (56mer, 100 ug) was co-transformed to GS200 (Mut$^+$, His$^-$, Arg$^-$) strain with an Arg4 fragment. The arg4 gene with promoter was supplied by Jim Cregg of the Oregon Graduate Institute of Science and Technology from plasmid pYM30 and was released by digestion with Sph I and EcoR V and purified by a Qiagen kit. Approximately 1000 transformants were obtained. To screen for a mutated clone having mutation on amino acid 701 of EF-2, diagnostic PCR was performed. To do this PCR, a mutation-detecting primer was designed, having the sequence GCCGATGCTATCCACA-GAAGA (SEQ ID NO:101). By differential binding, it distinguished a difference on a DNA sequence between a normal gene and a mutated gene at amino acid 701. For the normal gene, the PCR product could not be produced because two DNA residues at 3' end were not matched, so that Taq polymerase could not extend. For the mutated gene, the primer could anneal perfectly with the DNA sequence of mutated gene, so Taq polymerase could produce a PCR product. The first 1,200 colonies screened by this PCR method failed to find a mutated colony. (In the above PCR assay AA 701 mutated EF-2 from S. cerevisiae served as a positive control. This mutated gene had been made previously with the intent of introducing it into Pichia. However, Pichia thus transformed had a very slow growth rate and produced the protein of interest at low levels.)

Second, a mutated EF-2 strain was developed by transformation with a partial fragment containing a conserved region of EF-2 gene and a mutation on amino acid 701. The DNA sequence of the partial fragment is shown in FIG. 43. This fragment has 513 bp and a mutation of amino acid 701 of EF-2 from glycine to arginine. The partial fragment was co-transformed to GS200 strain with the Arg4 gene fragment. The first 2400 transformants screened failed to find a mutated EF-2 strain by diagnostic PCR.

Third, a mutated EF-2 strain was developed using spheroplast transformation with a partial fragment of mutated EF-2 and Arg4 fragment in the presence of wild type DT. In the above methods, there was no selection step against wild type DT. DT is not toxic to intact *Pichia* cells because the cells have a cell wall, which plays a role as a physical barrier. Only spheroplast cells of *Pichia* are sensitive to wild type DT. A double transformation was employed. First of all, the partial fragment of mutated EF-2 was transformed to GS200 strain by electroporation. Electroporated cells were then cultivated overnight to allow expression of the mutated EF-2 inside the cells. Cultivated cells were used for making spheroplasts. The resulting spheroplasts were treated with wild type DT (200 μg/ml) and Arg4 fragment (10 μg) for 1 hour and transformed by $CaCl_2$ and PEG. However, only a small number of transformants of normal colony size were obtained and there was no mutated strain. In addition, there were 100 or more microcolonies obtained. One hundred of these were screened but the mutated strain was not detected.

Fourth, EF-2 mutated strain was developed using electroporation with a partial fragment of mutated EF-2 and Arg4 fragment in the presence of wild type DT. Spheroplast transformation was not efficient to obtain transformants in the presence of wild type DT. Electroporation with Arg4 fragment in the presence of excess wild type DT (110 μg per 55 μl) killed all transformants. During electroporation of *Pichia* with Arg4 DNA, pores on the membrane of *Pichia* transiently formed, and DNA entered the cell through these pores and integrated into genomic DNA of host strain. Simultaneously, wild type DT also entered through the pores and killed the cells. Fifty colonies were obtained by this procedure, all colonies had the normal EF-2 gene.

As the fifth method of making an EF-2 mutated strain, the 3' UTR of EF-2 gene was cloned for making a mutagenizing gene cassette. The previous results demonstrated that partial fragments of EF-2 gene were not long enough to efficiently integrate into the EF-2 locus. A 1 kb fragment was cloned from the 3' end of the partial fragment by PCR. In a Southern blot probed with 300 bp sequence of the conserved region in EF-2 gene, a 5-kb band was detected when genomic DNA was digested with EcoRI and SalI. According to this result, genomic DNA was completely digested with EcoRI and SalI enzymes, and then 4 to 6 kb DNA fragments were recovered by gel elution. DNA fragments recovered from gel elution were cloned between EcoRI and XhoI site in pET17b vector. The resulting 4-6-kb library DNA was used as a template DNA for PCR. The 5' primer that can anneal DNA sequence of conserved region and T7 terminator or T7 promoter primer as 3' primer was used to amplify the 3' UTR region. The resulting 1 kb PCR product was cloned into a pCR2.1 vector. DNA sequencing is used to confirm the DNA sequence of the PCR product. The cloned fragment contains the C-terminus of EF-2 and 3' UTR region. After sequencing the 3' UTR region, Arg4 or His4 selectable marker gene is introduced between the C-terminus and the 3' UTR region. This fragment is used for transformation to obtain a mutated EF-2 strain and resulting transformants can be easily detectable when it is transformed to the $Arg^-$ or $His^-$ strain.

Example 37

T Cell Depletion in tge600$^{+/-}$ Mice tge600 homozygous mice were obtained from Dr. Cox Terhorst, Beth Israel Hospital, Harvard Medical School, Boston, Mass. 02215. In this work the heterozygote strain of the mouse, tge600$^{+/-}$, was used (F1 of tg 600×C57BL/6J). These mice contain three copies of the complete human CD3e gene under the transcriptional regulation of their endogenous promoters and enhancers. The mice were injected with either (Met)DT389-sFv(UCHT1) or (Ala)dmDT390-bisFv (UCHT1*) derived from the CHO expression system as described above. A twice per day experimental dosing regimen was chosen because the immunotoxin with one sFv domain was observed to have a short half-life in mice (<6 hrs.) Accordingly, tge600$^{+/-}$ were treated with immunotoxin twice daily for four days by tail vein administration.

Approximately 16 hours after the final treatment, the lymph nodes and spleen were removed, and single cell suspensions were prepared from individual mice. Total cells were counted by chamber counts. The percentage of CD3 positive cells was assessed by two-color FACS analysis using a FITC-conjugated anti-human CD3 antibody (UCHT1-FITC) to measure human CD3 expression, phycoerythrin (PE)-conjugated anti-mouse CD3 antibody (500A2-PE) to measure expression of mouse CD3 and the appropriately stained isotype controls. Viaprobe (Pharmingen, San Diego, Calif.) was used to gate on the live cells. Gates were set to count the fraction of double positive (DP) events (huCD3$^+$ muCD3$^+$) for the isotype controls in non-treated animals and the fraction of DP events in treated animals. The fraction of DP isotype controls was subtracted from the fraction of DP events in treated animals, and the result, DP', multiplied by the total cell count. This was subtracted from the DP' cells in control animals. The result was divided by the DP' cells in control animals to give the fractional depletion in DP cells at each immunotoxin concentration. In non-treated animals 98-99% of the lymph node and spleen T cells were DP cells, the remaining being single positive muCD3$^+$.

Mean fractional lymph node and spleen T cell depletion values were calculated for each immunotoxin concentration. Spleens and lymph nodes from 3 to 9 animals were used to generate the means for each concentration. In both spleen and lymph node the mean depletion values from (Ala)dmDT390-bisFv(UCHT1*) immunotoxin are shifted to the left indicating higher potency. The data were fitted by probit analysis using a log transformation of the concentration scale using SPSS software (SPSS Inc., Chicago Ill.). In probit transformation, instead of regressing the actual proportion responding to the values of the stimuli, each of the observed proportions is replaced with the value of the standard normal curve below which the observed proportion of the area is found. Data points for (Met)DT389-sFv(UCHT1) or (Ala) dmDT390-bisFv(UCHT1*) immunotoxins were fitted alone or together to yield parallel curves with one regression coefficient. The regression model is Transformed Pi=A+B logXi where Pi is the observed proportion responding at dose logXi and B is the regression coefficient. The regression coefficient is related to the fractional depletion F by the empirical formula $F=X^B/X^B+(IC_{50})^B$.

Figure 44A:
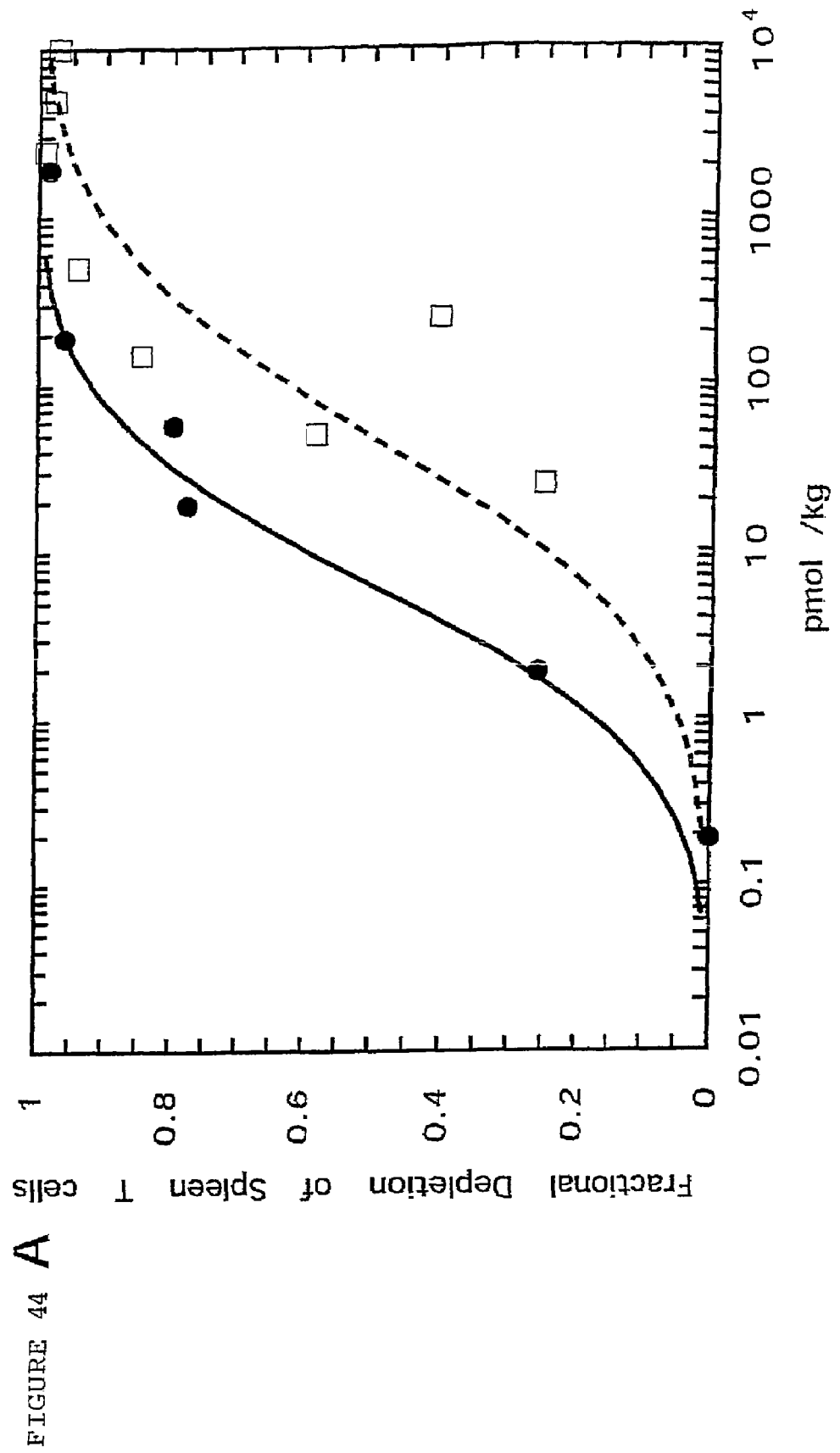
FIG. 44 shows in vivo T cell depletion induced by varying concentrations of single chain immunotoxins with one sFv or two sFvs in Tge600 heterozygote mice in spleen and lymph node.
Figure 44B:
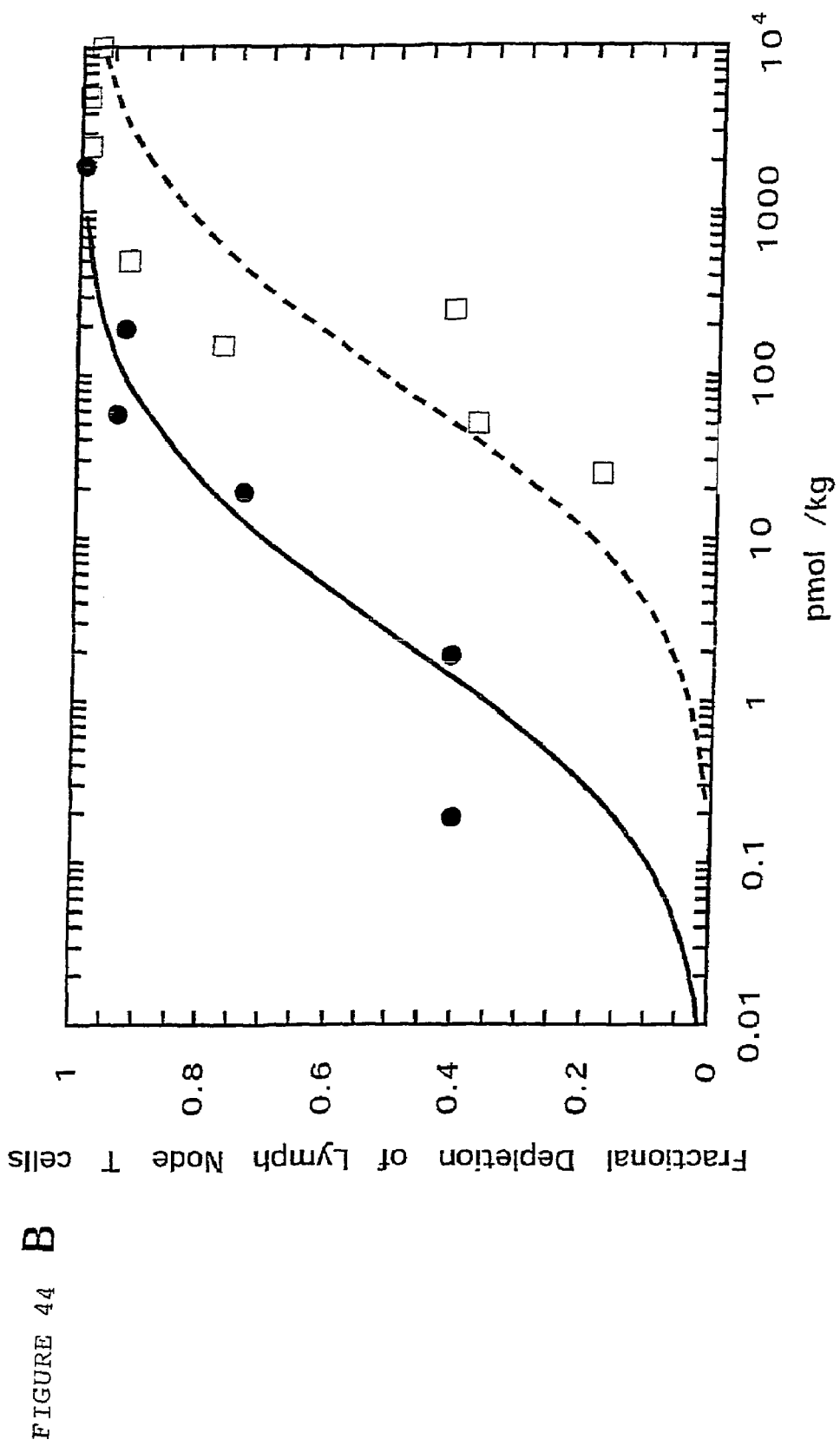

The spleen fit is shown in FIG. 44A and the lymph node fit in FIG. 44B. In both FIGS. 44A and 44B, the (Ala)dmDT390-bisFv(UCHT1*) fitted curves are the solid lines and the (Met) DT389-sFv(UCHT1) fitted curves are the dashed lines. For the spleen fit, 54 cases were available for (Met)DT389-sFv (UCHT1) and 39 cases for (Ala)dmDT390-bisFv(UCHT1*) immunotoxin, and the fits in FIG. 44A were performed individually. The regression coefficients are nearly identical and the curves are nearly parallel. When both cases are fitted together (93 cases), the changes are minimal. In the lymph node fit shown in FIG. 44B, both (Met)DT389-sFv(UCHT1) and (Ala)dmDT390-bisFv(UCHT1*) were fitted together (89 cases). The curves are more shallow compared to the spleen curves. This result is influenced by the lowest concentration mean value of the (Ala)dmDT390-bisFv(UCHT1*) immunotoxin that has a mean value of 0.4 as compared to 0 in the spleen. In both the spleen and lymph node, the (Ala) dmDT390-bisFv(UCHT1*) immunotoxin appears significantly more potent than the (Met)DT389-sFv(UCHT1) immunotoxin based on the probit model.

Example 38

Construction and Expression of Additional Immunotoxins

To generate immunotoxins with various truncations in DT, the toxin sequence in pDTM1, which contains two point mutations in the toxin binding domain (S508F and S525F), was used as template for PCR. A PCR primer was synthesized for the 5' end of DT and included an NcoI restriction site and an ATG codon. The 3' PCR primers were synthesized to correspond to the appropriate amino acid sequence and also contained an NcoI restriction site. PCR products from the individual reactions were cloned upstream of the UCHT1 sFv in pET-15b (Novagen, Inc., Madison, Wis.). All constructs were sequence-verified to encode the correct amino acid sequence. Note that the DT510 primer corrects the mutation in DTM1 back to the wild-type DT amino acid serine. However, the DT535 clone does contain the two mutations encoded by pDTM1. A variant construct, M-DT389-sFv, was produced. This construct was expressed in *E. coli* without a signal peptide and was refolded and purified from cytoplasmic inclusion bodies. This construct encoded an $NH_2$ terminal methionine residue. In addition to having one less DT residue, this construct also contained a 6 residue flexible linker (ASAGGS (SEQ ID NO:37)) between the DT moiety and the sFv moiety, and the sequence of the $V_L$-$V_H$-linker was changed to $(G_3S)_4$ (SEQ ID NO: 104).

The individual plasmid DNAs were amplified and isolated from *E. coli*. Plasmid DNA (0.6 mg) was used in a coupled in vitro transcription and translation system (Promega, Madison, Wis.) following manufacturer's instructions. The transcription/translation reaction mixture (1-2 ml) was separated on a SDS-polyacrylamide gel along with known amounts of purified CRM9 (a binding site mutant of DT). The proteins were transferred to Immobilon-P (Millipore, Bedford, Mass.) and analyzed by Western blot utilizing a goat anti-DT sera provided by Dr. Randell Holmes, Department of Microbiology, University of Colorado Health Sciences Center, Denver, Colo. 80220, USA. The primary antibody was detected with an HRP-labeled rabbit anti-goat antibody (Pierce, Rockford, Ill.), and bands were visualized by chemiluminescence. Films were scanned and the intensity of each band quantified using Scion Image software (Scion Corporation, Frederick, Md.). The value for each known amount of CRM9 was plotted to generate a standard curve from which the unknown values were calculated.

The Fab fragment of UCHT1 was prepared by papain digestion using cross-linked agarose-papain (Pierce) following manufactures directions. Contaminating Fc fragments and undigested UCHT1 were removed by absorption on to protein A Sepharose (Pierce). Fab was quantified by size exclusion HPLC GF-250 Zorbax and UV absorption and integration using a UCHT1 standard and a correction for MW reduction. The sFv and bisFv of UCHT1 were amplified by PCR, The template was DT390bisFv (described above), and the primers were chosen from the 5' end of $V_L$ and the 3' end of $V_H$. The PCR products were checked by gel electrophoresis, and the bands of sFv and bisFv of UCHT1 were cut out and extracted with QIAquik Gel Extraction Kit (Qiagen, Chatsworth, Calif.). The extracted DNA was digested with NdeI and EcoRI and cloned into expression vector pET17b (Novagen, Inc.) at NdeI and EcoRI sites. These were transformed into *E. coli* strain: BL21 (DE3)pLysS competent cells (Novagen, Inc). A single colony was cultured overnight. The overnight culture was re-cultured for 3-4 h with fresh medium to reach $OD_{600}$ of 0.6, after which IPTG, 1 mM, was added to induce expression. The bacterial pellet was harvested by centrifugation. Inclusion bodies were prepared by the method of Buchner et al., Anal Biochem 205:263-70, and solubilization of inclusion bodies and refolding of the protein was performed according to Vallera et al, Blood 88:2342-53.

The (sFv(UCHT1)-H-gCH3-h)2 minibody was constructed by PCR overlap extension. This construct was patterned on the flex minibody described by Hu et al., Cancer Res 56:3055-61. The sFv(UCHT1) template was DT390sFv. In the minibody, the sFv region is followed by the hinge region of human IgG1 (residue 216 to residue 229). These residues were amplified from a plasmid containing human IgG1 heavy chain (supplied by Dr. Syed Kashmiri, National Cancer Institute). In the hinge, residue C220 was changed to P (20) leaving C226 and C229 residues to form the interchain disulfide dimer. Between the hinge and gCH3, a flexible spacer, $(G_3S_2)_2$ (SEQ ID NO:121) was inserted following the construction of Hu et al, 56 Cancer Res. 565:3055-61. A histidine (h) tag of 6 residues was added at the carboxy terminus of gCH3 and a murine kappa signal peptide, MSVPTQVLGLLLLWLTDARC (SEQ ID NO:103), was placed 5' to the sFv. This gene was cloned into pBacPAK8 (Clontech, Palo Alto Calif.) and expressed in S9 cells at a level of 5 mg/ml as quantified by Coomassie staining using UCHT1 as a standard. Although the sFv of UCHT1 does not bind to Protein L Plus (Pierce) at pH 8.0 in PBS, it does bind in the presence of high salt. One volume of culture medium was mixed with 1.5 volume of 2.5 M glycine/5 M NaCl, pH 9.0 an applied to a 1 ml column volume of Protein-L plus equilibrated with 1.5 M glycine/3 M NaCl, pH 9.0. The column was washed with two column volumes of application buffer and eluted with 4 ml of 0.25 M glycine/HCl pH 2.5.

The construct was quantified by Coomassie staining of SDS gels using an Fab(UCHT1) standard.

The (sFv(UCHT1)-mCH$_2$-h)$_2$ minibody construct was made by using PCR amplification, a cloned single chain human IgM antibody construct. The sFv(UCHT1)-mCH$_2$-h construct was amplified by using 5' sFv and 3' CH2 primers. A 6 histidine residue tag was introduced to 3' end of CH2 domain. Following purification of the amplified sFv (UCHT1)-μCH$_2$-h fragment by gel elution and digestion with EcoRI and NotI, it was inserted between EcoRI and NotI site of pET17b vector (Novagen, Inc.). *E. coli* XL-1 Blue strain was used for all plasmid constructions. For expression in *Pichia pastoris*, pPICZα (Invitrogen, Carlsbad, Calif.) was used as the *Pichia* expression vector. The DNA sequence was confirmed by sequencing. KM71 was used as the host strain (Invitrogen). Maximum secretion of the anti-CD3 minibody could be obtained at 4 days after methanol induction in 1% yeast extract, 2% peptone, 100 mM potassium phosphate, pH 6.0, 1.34% yeast nitrogen base, $4 \times 10^{-5}$% biotin, 1% methanol plus 1% casaminoacids to retard proteolysis. Western blots from non-reducing and reducing gels probed with polyclonal anti human IgM (Life Technologies, Bethesda, Md.) confirmed the disulfide dimmer, which accounted for 75% of the secreted material. Partial purification was achieved by absorbing contaminating proteins on DEAE Sepharose at pH 8.5 and applying the flow through to Protein L agarose (Pierce) in the presence of 1.5 M glycine and 3 M NaCl, pH 8.9 and eluting with saline buffered phosphate diluted 1:3 in water. The construct was quantified by Coomassie staining of SDS gels using an Fab(UCHT1) standard.

The gene for the human serum albumin (HSA)-sFv (UCHT1) fusion construct codes from 5' to 3' the 609 residues of human serum albumin precursor variant A followed by a 6 residue flexible linker (ASAGGS (SEQ ID NO:37)) and then the sFv moiety of sFv(UCHT1) used in DT389-sFv. The fusion was performed by PCR overlap extension. This gene was cloned into the pHIL D2 vector (Invitrogen) under the AOX1 promoter and expressed as a secreted form in *Pichia pastoris* GS115. HSA-sFv(UCHT1) was purified from the supernatant by ammonium sulphate precipitation, followed by cation exchange chromatography on a Bio-Rad S2 column at pH 6.0, where the protein was in the unbound fraction. HSA-sFv(UCHT1) was quantified by Lowry protein assay using an HSA standard.

Recombinant immunotoxins, such as dmDT390-sFv (His6), were produced from stably transfected DT resistant CHO cell lines by means of the pSRα-neo vector. The notation dm refers to the double mutation removing the potential N-glycosylation sites at positions 16-18 in the DT A chain and positions 235-237 in the DT B chain. The signal peptide used in CHO expression contained an additional terminal alanine to optimize the cleavage process at an ala-ala junction and therefore added an ala residue to the DT NH2 terminus. This construct is now called Ala-dmDT390-sFv (after removal of the C terminal His 6 tag). For CHO cell expression of the single chain construct, DT390 was removed at the NcoI site from the DT390sFv plasmid for *E. coli* expression, and replaced by sp-dmDT390 yielding on expression Ala-dmDT390bisFv. The production of the disulfide-linked immunotoxins (Ala-DT390-sFv-H-γCH3-h)$_2$ and (Ala-DT390-sFv-μCH2-h)$_2$ was performed in CHO cells as described above, except that the glycosylation sites were not removed by mutation. These constructs were treated with N-glycosidase prior to toxicity assays under conditions that removed all detectable glycosylated forms. M-DT389-sFv was expressed in *E. coli* and purified from cytoplasmic inclusion bodies by the methods of Buchner et al, Anal Biochem. 205: 263-70, and solubilization of inclusion bodies and refolding of the protein was performed according to Valerra et al., Blood 88:2342-53. The protein was purified by anion exchange chromatography yielding a single band on SDS gels. Routine quantification was by Lowry protein assay calibrated by mass spectrometry.

Example 39

Optimization of the Anti-Human CD3 Immunotoxin DT389-sFv(UCHT1) N-Terminal Sequence to Yield a Homogeneous Protein The production and regulatory approval processes for biopharmaceuticals require detailed characterization of potential products. Therapeutic proteins should preferably be homogeneous, although limited, reproducible heterogeneity may be tolerated. Mass spectroscopy and N-terminal sequencing by Edman degradation revealed that the diphtheria toxin-based DT389-scFv(UCHT1) immunotoxin molecule expressed in *E. coli* and purified following refolding was heterogeneous at the N-terminus, containing species both with (60%) and without (40%) the initiator methionine. Similar results were obtained with refolded, active material and inclusion bodies, produced at the laboratory scale and larger batches from high density fermentation. In an attempt to generate an N-terminally homogeneous molecule, a panel of seven N-terminal variants was designed, based on the specificity of bacterial methionine aminopeptidase (MAP) (Ben-Bassat, Bioprocess Technol. 12:147-59) (1991); Ben-Bassat et al. J. Bacteriol. 169:751-757; Gonzales and Robert-Baudouy, Microbiol. Revs. 18:319-344). The first residue immediately after the methionine has been shown to be the most important factor in efficiency of cleavage by MAP. In general, peptides with smaller amino acids (e.g. glycine, alanine, proline and serine) at this position constituted better substrates for MAP. In contrast, peptides with larger amino acids such as phenylalanine, leucine, methionine, glutamic acid, arginine or lysine, following the methionine, were poor substrates for MAP. Variable cleavage of methionine was observed when the intermediate-sized amino acids isoleucine, valine, cysteine and threonine were present at this position in the sequence. Mutants of DT389-scFv(UCHT1) were designed as good or poor substrates based on these data, and relatively conservative amino acid changes from the native diphtheria toxin sequence were chosen. See Table 17.

These mutants were cloned and expressed in *E. coli* and inclusion body protein which was then subjected to N-terminal sequence analysis. A pET15b (Novagen)-derived plasmid encoding DT389-scFv(UCHT1) was mutagenized using the QuikChange kit (Cat. # 200518-5, Stratagene). Complementary mutagenic primer pairs from Sigma/Genosys were designed based on the recommendations in the kit to generate the seven different N-terminal mutants described in Table 17. *E. coli* strain DH10B used for cloning was from Gibco/BRL (#18297-010). The new mutant clones were verified by automated DNA sequencing, on an ABI373A sequencer and transformed into the *E. coli* strain BL21(DE3) for expression. *E. coli* BL21 (DE3) strain for protein expression was obtained from Novagen (Cat. #69450-4).

Overnight cultures (3 ml) of the N-terminal mutants, grown at 37° C., in Luria-Bertani (LB) medium, containing 100 μg/ml ampicillin (Sigma), were collected by centrifugation and resuspended in 3 ml of fresh medium then inoculated into 300 ml cultures of the same medium. The cultures were grown until the OD$_{600}$ reached 0.58-0.69, at which point protein expression was induced with IPTG (1 mM. After 2.5 hr of induction at 37° C., the cultures were collected by centrifugation. Decanted pellets were stored at −80° C. until use. The inclusion body preparation protocol defined by Vallera et al., Blood 88:2342-2353, was followed, with the exception that volumes were scaled down. Final inclusion body pellets were resuspended in 8M Urea/0.1M Tris pH 8.0 and stored at −20° C. Resuspension volumes ranged from 24 mL, dependent upon the volume of the final inclusion body pellet.

Proteins were subjected to SDS-PAGE under reducing conditions, transferred to PVDF membrane which was then stained with Coomassie Blue. Specifically, the 8M Urea/ 0.1M Tris pH 8.0 inclusion body suspensions were thawed and aliquots mixed with SDS-PAGE reducing sample buffer (2×). The samples were heated at 90° C. for 8 min, loaded onto a minigradient Tris-glycine 4-20%, 1 mm, gel (Novex) and electrophoresed at 200 V for 70 min. After electrophoresis, the gel was soaked in transfer buffer (10 mM 3-[cyclohexylamino]1-propanesulfonic acid, 10% methanol, pH 11.0) for 8 min to reduce the amount of Tris and glycine. During this time, a PVDF membrane was immersed in 100% methanol for a few seconds and then soaked in transfer buffer. The gel, sandwiched between a sheet of PVDF membrane, two sheets of filter paper (Whatman 3 MM Chr) and two porous foam pads, was assembled into a grid cassette, mounted into the Bio-Rad blotting apparatus and electroblotted for 80 min at 200 mA in transfer buffer. During transfer the blotting tank was magnetically stirred and cooled by vertical insertion of an ice block. After transfer, the PVDF membrane was washed in twice-distilled water for 5 min, stained with 0.1% Coomassie Blue in 50% methanol for 1 min and then destained in 50% methanol, 5% acetic acid until the background became clear (3 to 5 min) at room temperature. The membrane was finally rinsed in twice-distilled water for 5 to 10 min and stored in a wet state at −20° C.[5]. Stained bands corresponding to immunotoxin proteins at about 70 kDa were excised from the membrane and destained with two portions of 500 µl methanol. The excised membrane was cut into strips of about 5×1 mm, filled into a modified HP-biphasic sequencer column and mounted into the protein sequencer. Proteins were analyzed on an HP G1000A protein sequencer system (Hewlett-Packard). Molecular weight (MW) markers were from Pharmacia (LMW, Cat# 17-0615-01). The major protein band in each preparation displayed an apparent molecular weight of 70 kDa, consistent with the predicted molecular weight of these immunotoxins. These major 70 kDa bands were excised from PVDF blots and subjected to N-terminal sequencing by Edman degradation. DNA sequencing was carried out by automated sequencing on an ABI373XL, with the T7 promoter primer, using the manufacturers reagents.

Three of the mutants, N2, N3 and N4, yielded a 100% homogeneous amino acid sequence. See Table 17. In contrast, the original DT389-scFv(UCHT1) protein and four variant proteins, N1, N5, N6 and N7 yielded two sequences which differed by the presence or absence of the N-terminal methionine at varying ratios. The N-terminal sequences of the three homogeneous clones were MLADD (SEQ ID NO:106), MLDD (SEQ ID NO:107), where the methionine was completely retained, and SADD (SEQ ID NO:108), where the methionine was completely removed. Of the homogeneous proteins N2 (final sequence=SADD (SEQ ID NO:108) has the most conservative change from the native diphtheria toxin sequence (a single G>S mutation). The other two homogeneous proteins N3=MLADD (SEQ ID NO:106) and N4=MLDD (SEQ ID NO: 107) contain respectively, a non-conservative mutation (G>L in N3) and an amino acid deletion (G) combined with a substitution of A>L (N4). In addition, both N2 and N3 retain the introduced initiation methionine which is not present in the native diphtheria toxin sequence, it being a secreted protein. Thus, using a rational mutagenesis approach, three N-terminally homogeneous variants of DT389-scFv(UCHT1), with minimal amino acid sequence changes have been identified.

TABLE 17

N-terminal heterogeneity observed with N-terminal variants of DT389-scFv(UCHT1) constructed to produce homogeneous N-terminal sequences. Mutants were designed according to published specificity of bacterial methionine aminopeptidase using relatively conservative substitutions of the native diphtheria toxin amino-terminus. SP denotes the signal peptide of the native toxin which is a secreted protein. N-terminal sequence data was determined from inclusion body protein by Edman degradation following SDS-PAGE and transfer to PVDF membrane.

| Construct | Encoded Sequence | Predicted MAP Substrate | Sequence (s) Detected | Initial yield (pM) | Ratio |
|---|---|---|---|---|---|
| Native DT | SPGADD (SEQ ID NO:109) | N/A | GADD (SEQ ID NO:110) | N/A | — |
| DT389-scFv(UCHT1) | MGADD (SEQ ID NO:111) | 0 | MGADD (SEQ ID NO:111) | 12 | 60% |
|  |  |  | -GADD (SEQ ID NO:110) | 8 | 40% |
| N1 | MAADD (SEQ ID NO:112) | 0 | -AADD (SEQ ID NO:113) | 7 | 82% |
|  |  |  | MAADD (SEQ ID NO:112) | 1.5 | 18% |
| N2 | MSADD (SEQ ID NO:114) N.D. | 0 | -SADD (SEQ ID NO:108) | 9 | 100% |
| N3 | MLADD (SEQ ID NO:106) N.D. | — | MLADD (SEQ ID NO:106) | 14 | 100% |

TABLE 17-continued

N-terminal heterogeneity observed with N-terminal variants of DT389-scFv(UCHT1) constructed to produce homogeneous N-terminal sequences. Mutants were designed according to published specificity of bacterial methionine aminopeptidase using relatively conservative substitutions of the native diphtheria toxin amino-terminus. SP denotes the signal peptide of the native toxin which is a secreted protein. N-terminal sequence data was determined from inclusion body protein by Edman degradation following SDS-PAGE and transfer to PVDF membrane.

| Construct | Encoded Sequence | Predicted MAP Substrate | Sequence (s) Detected | Initial yield (pM) | Ratio |
|---|---|---|---|---|---|
| N4 | ML-DD SEQ ID NO:107) N.D. | — | MLDD (SEQ ID NO:107) | 22 | 100% |
| N5 | MGSDD (SEQ ID NO:115) | 0 | MGSDD (SEQ ID NO:115) | 25 | 74% |
|   |   |   | -GSDD (SEQ ID NO:122) | 9 | 26% |
| N6 | MGGDD (SEQ ID NO:116) | 0 | MGGDD (SEQ ID NO:116) | 30 | 94% |
|   |   |   | -GGDD (SEQ ID NO:118) | 2 | 6% |
| N7 | MGVDD SEQ ID NO:117) | 0 | MGVDD (SEQ ID NO:117) | 20 | 80% |
|   |   |   | -GVDD (SEQ ID NO:119) | 5 | 20% |

Throughout this application various publications are referenced by numbers within parentheses. Full citations for these publications are as follows. Also, some publications mentioned herein above are hereby incorporated in their entirety by reference. The disclosures of these publications in their entireties are hereby incorporated by reference into this application in order to more fully describe the state of the art to which this invention pertains.

While the foregoing invention has been described in some detail for purposes of clarity and understanding, it will be appreciated by one skilled in the art from a reading of this disclosure that various changes in form and detail can be made without departing from the true scope of the invention and appended claims.

It is emphasized that this abstract is provided to comply with the rules requiring an abstract that will allow a searcher or other reader to quickly ascertain the subject matter of the technical disclosure. It is submitted with the understanding that it will not be used to interpret or limit the scope or meaning of the claims.

REFERENCES

1. Nicholls, P. J., Johnson, V. G., Andrew, S. M., Hoogenboom, H. R., Raus, J. C. and Youle, R. J. (1993) *J Biol Chem* 268, 5302-5308.
2. Neville, D. J. (1987) Ann NY Acad Sci 507, 155-1643.
3. Williams, D. P., Parker, K, Bacha, P., Bishai, W., Borowski, M., Genbauffe, F., Strom, T. B. and Murphy, J. R. (1987) Protein Eng 1, 493-498
4. Johnson, V. G. and Youle, R. J. (1989) J Biol Chem 264, 17739-17744
5. Kreitman, R. J., Chaudhary, V. K., Waldmann, T. A., Hanchard, B., Cranston, B., FitzGerald, D. J. and Pastan, I. (1993) Leukemia 7, 553-562
6. Murphy, J. IL (1988) Cancer Treat Res 37, 123-124
7. Laske, D. W., Ilercil, O., Akbasak, A., Youle, R. J. and Oldfield, E. H. (1994) J Neurosurg 80, 520-526
8. Neville, D. J., Scharff, J. and Srinivasachar, K. (1992) J of Controlled Release 24, 133-141
9. Neville, D. J., Scharff, J. and Srinivasachar, K. (1992) Proc Natl Acad Sci U S A 89, 2585-2589
10. Giannini, G., Rappuoli, R. and Ratti, G. (1984) Nucleic Acids Res 12, 4063-4069
11. Chang, T. M. and Neville, D. M. J. (1977) J Biol Chem 252, 1505-1514
12. Neville, D. J., Srinivasachar, K, Stone, R. and Scharff, J. (1989) J Biol Chem 264, 14653-14661
13. Shalaby, M. R., Shepard, H. M., Presta, L., Rodrigues, M. L., Beberley, P. C. L., Feldman, M. and Carter, P. (1992) J Exp Med 175, 217-225
14. Johnson, S. and Bird, R. E. (1991) in Methods in Enzymol, pp. 88-98, Academic Press, Inc., San Diego, Calif.
15. Grimont, F. and Grimont, P. A. D. (1991) in Nucleic acid techniques in bacterial systematics, pp. 252, E. A. G. Stackebrandt M. John Wiley and Sons, LTD, West Sussex, England
16. Esworthy, R. S. and Neville, D. M. J. (1984) J Biol Chem 258, 11496-11504
17. Pelchen-Matthews, A., Armes, J. E., Griffiths, G. and Marsh, M. (1991) J Exp Med 173, 575-578
18. Choe, S., Bennett, M. J., Fujii, G., Curmi, P. M., Kantardjieff, K. A., Collier, R. J. and Eisenberg, D. (1992) Nature 357, 216-222
19. LeMaistre, C. F., Meneghetti, C., Rosenblum, M., Reuben, J., Parker, K., Shaw, J., Deisseroth, A., Woodworth, T. and Parkinson, D. R. (1992) Blood 79, 2547-2554
20. Platanias, L. C., Ratain, M. J., O'Brien, S., Larson, R. A., Vardiman, J. W., Shaw, J. P., Williams, S. F., Baron, J. M., Parker, K. and Woodworth, T. G. (1994) LeukLymphoma 14, 257-262
21. Higashi, K., Asada, H., Kurata, T., Ishikawa, K, Hayami, M., Spriatna, Y., Sutarman, Y. and Yamanishi, K. (1989) J Gen Virol 70, 3171-3176
22. Youle, R. J. and Neville, D. M. J. (1982) J Biol Chem 257, 1598-1601

23. Williams, D. P., Snider, C. E., Strom, T. B. and Murphy, J. R. (1990) J Biol Chem 265, 11885-11889
24. Parlevliet et al. (1992) Transplant Int; 5:234-246.
25. Cosimi et al. (1981) Transplantation; 32:535-9.
26. Jaffers et al. (1986) Transplantation; 41:572-8.
27. Abramowicz et al. (1989) Transplantation; 47:606-8.
28. Burns et al. (1982) J Immunol; 129:1451-7.
29. Parren et al. (1991) Res Immunol; 142:749-63.
30. Waid et al. (1991) Transplant Proc; 23:1062-5.
31. Khazaeli et al. (1994) J Immunotherapy; 15:42-52.
32. Chen C and Okayama H. (1987); Mol Cell Biol 7:2745-52.
33. Slavin-Chiorini et al. (1993) Int J Cancer; 53:97-103.
34. Rigaut K D, Scharff J E, Neville D M Jr. (1995) Eur J Immunol; 25:2077-82.
35. Woodle E S, Thistlethwaite J R, Jolliffe L K, et al. (1992) J Immunol; 148:2756-63.
36. Miller A D, Rosman G J. (1989) BioTechniques 7:980-90.
37. Shu L M, Qi C F, Schlom J, Kashmiri S V S (1993) Proc Natl Acad Sci USA; 90:7995-9.
38. Mosmann T R, Williamson A R (1980) Cell; 20:283-92.
39. Capon D J, Chamow S M, Mordenti J, et al. (1989) Nature 337:525-31.
40. Anand N N, Mandal S, MacKenzie C R, et al. (1991) J Bio Chem 266:21874-9.
41. Sitia R, Neuberger M, Alberini C M, et al. (1990) Cell; 60:781-90.
42. Alberini C M, Bet P, Milstein C, Sitia R. (1990) Nature 347:485-7.
43. Fra A M, Fragioli C, Finazzi D, Sitia R, Alberini C M (1993) The EMBO Journal; 12:4755-61.
44. Wiersma E J, Shulman M J (1995); 154:5265-72.
45. Smith K G, Austyn J M, Hariri G, Beverley P C, Morris P J (1986) Eur J Immunol; 16:478-86.
46. Tax W J, Hermes F F, Willems R W, Capel P J, Koene R A (1984) J Immunol; 133:1185-9.
47. Lynch, RG, Sandor M., Metzger H, ed. Washington D.C.: American Society for Microbiology 1990:305-34.
48. Moretta I, Webb S R, Grossi C E, Lydyard M, Cooper M D. (1977) J Exp Med; 146: 184-200.
49. Ferrarini M, Moretta L, Mingari M C, Tonda P, Pernis B. (1976) Eur J Immunol; 6:520-1.
50. Mathur A, Lynch R G, Kohler G (1988); J Immunol; 140:143-7.
51. Pricop L, Rabinowich H, Morel Pa., Sulica A, Whiteside T L, Herberman R B (1993) J Immunol; 151:3018-29.
52. Emara M, Sanfilippo F (1992) Cell Immunol; 144:143-54.
53. Glu M, Gordon V M, Fitzgerald D J, Leppla S (1996) Infect. and Immun.; 64(2):524-527.
54. Kuan C T, Pastan I (1996) Proc. Natl. Acad. Sci. USA, 93:974-978, 1996.
55. Francisco J A, Kiener Pa., Moran-Davis P, Ledbetter J A, Siegall C B (1996) J. Immunol.; 157:1652-1658.
56. Kaczorek M, Delpeyroux F, Chenciner N, Streeck R (1983) Science; 221:855
57. Shen W H, Choe S, Eisenberg D, Collier R J (1994). Biol. Chem.; 469(46):29077-29084.
58. Muhlrad D, Hunter R, Parker R (1992) Yeast; 8:79-82.
59. Madshus I H, Stenmark H, Snadvig K, Olsnes S (1991) J. Biol. Chem.; 266(26):17446-53.
60. Federal Register, Notices, May 7, 1986), Appendix F-II-B, p. 16971.
61. Perkins S J, Nealis A S, Sutton B J, Feinstein A (1991) J. Mol. Biol., 221:1345-1366.
62. Theuer, CP, Kreitman R J, FitzGerald D J, Pastan I (1993) Cancer Res., 53:340-347.
63. Kihara A, Pastan I (1994) Cancer Res., 54:5154-5159.
64. Chaudry G J, Fulton R J, Draper R K (1993) J. Biol. Chem., 268(13):9437-9441.
65. Schmidt M, Hynes Nebr., Groner B, Wels W (1996) Int. J. Cancer, 65:538-546.
66. Better M, Bernhard S L, Lei S P, Fishwild D M, Lane J A, Carroll S F, Horwitz A H (1993) Proc. Natl. Acad. Sci USA, 90:457-461.
67. Thompson J, Hu H, Scharff J, Neville, Jr. D (1995) J. Biol. Chem., 24:28037-28041.
68. Ma S, Thompson J, Hu H, Neville, Jr. D (1996) Scand. J. Immunol. 43:134-139.
69. Neville, Jr. D, Scharff J, Hu H, Rigaut K, Shiloach J, Singerland W, Jonker M (1996) J. Immunotherapy 19(2): 85-92.
70. Knechtle S, Vargo D, Fechner J, Zhai Y, Wang J, Hanaway M, Scharff J, Hu H, Knapp L, Watkins D, Neville, Jr. D (1997) Transplantation 63(6):1-6.
71. Mallender and Voss, (1994), J. Biol. Chem. 269:199-206.
72. Schechter et al. (1980) Ann. N.Y. Acad. Sci. 343: 218-231.
73. Moehring & Moehring (1979) Somat. Cell Genet. 5:453-468.
74. Elbein, A. D. (1983) Methods Enzymol. 98, 135-154.
75. Neville D M and Youle R J (1982) Immunol. Rev. 62:75-91.
76. Hudson T H and Neville D M (1985) J. Biol. Chem. 260: 2675-80.
77. Takebe et al. (1988) Mol Cell Biol. 8: 466-72.
78. Robinson A S, Hines V, Wittrup K D (1994) Biotechnology 12:381-84.
79. Perentesis J P, Genbauffe F S, Veldman S A, Galeotti C L, Livingston D M, Bodley J W, Murphy J R. Expression of diphtheria toxin fragment A and hormone-toxin fusion proteins in toxin-resistant yeast mutants. Proc Natl Acad Sci USA. 1988 November; 85(22):8386-90.
80. Simpson et al. (1999) FEBS Lett. 459: 80-84.
81. Chen J Y, et al. (1985) Diphtheria toxin-resistant mutants of *Saccharomyces cerevisiae*. Mol Cell Biol. 5:3357-60.
82. Brake A J, Merryweather J P, Coit D G, Heberlein U A, Masiarz F R, Mullenbach G T, Urdea Miss., Valenzuela P, Barr P J. (1984) Alpha-factor-directed synthesis and secretion of mature foreign proteins in *Saccharomyces cerevisiae*. Proc Natl Acad Sci USA. 81:4642-6.
83. Beverley P C, Callard R E (1981) Distinctive functional characteristics of human "T" lymphocytes defined by E rosetting or a monoclonal anti-T cell antibody. Eur. J. Immunol. 11:329-34.
84. Orlandi R, Gussow D H, Jones P T, Winter G (1989) Cloning immunoglobulin variable domains for expression by the polymerase chain reaction. Proc Natl Acad SciUSA. 86:3833-37.
85. Vallera D A, Panoskaltsis-Mortari A, Jost C, Ramakrishnan S, Eide C R, Kreitman R J, Nicholls P J, Pennell C, Blazar B R (1996) Anti-graft-versus-host disease effect of DT390-anti-CD3sFv, a single-chain Fv fusion immunotoxin specifically targeting the CD3 epsilon moiety of the T-cell receptor. Blood. 88:2342-53.
86. Buchner et al., Anal Biochem 205:263-70.
87. Hu et al., Cancer Res 56:3055-61.
88. Ben-Bassat, Bioprocess Technol. 12:147-59) (1991).
89. Ben-Bassat et al. J. Bacteriol. 169:751-757.
90. Gonzales and Robert-Baudouy, Microbiol. Revs. 18:319-344.
91. Sreekrishna, K. 1993. Strategies for optimizing protein expression and secretion in the methylotropic yeast *Pichia pastoris*. (In) Industrial Microorganisms: Basic and Applied Molecular Genetics. Ef R. H. Baltz, G. D. Hegeman and P. L. Skatrud. American Society for Microbiology, Washington, D.C., pp. 119-126.

What is claimed is:

1. A nucleic acid encoding an anti-T cell immunotoxin fusion protein, comprising, from the amino terminus, a truncated diphtheria toxin moiety, a connector, and two single chain Fvs of the variable region of a UCHT1 antibody, wherein the two single chain Fvs comprise VL, L, VH, L, VL, L, VH, wherein L is a Gly-Ser linker, wherein the diphtheria toxin moiety contains the first 390 amino acids of the native toxin, wherein VL and VH are the variable light and heavy domains of the anti-CD3 antibody UCHT1, and wherein the nucleic acid comprises the nucleic acid sequence of SEQ ID NO:30.

2. A nucleic acid encoding an anti-T cell immunotoxin fusion protein, comprising, from the amino terminus, a truncated diphtheria toxin moiety, a connector, and two single chain Fvs of the variable region of a UCHT1 antibody, wherein the two single chain Fvs comprise VL, L, VH, L, VL, L, VH, wherein L is a Gly-Ser linker, wherein the diphtheria toxin moiety contains the first 390 amino acids of the native toxin, wherein VL and VH are the variable light and heavy domains of the anti-CD3 antibody UCHT1, and wherein the nucleic acid comprises the nucleic acid sequence of SEQ ID NO: 102.

* * * * *

SEQUENCE LISTING

<160> NUMBER OF SEQ ID NOS: 122

<210> SEQ ID NO 1
<211> LENGTH: 3476
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 1

```
aaaaaaaagc cgccgaagc gggctttatt accaagcgaa gcgccattcg ccattcaggc      60
tgcgcaactg ttgggaaggg cgatcggtgc gggcctcttc gctattacgc cagctggcga    120
aaggggatg tgctgcaagg cgattaagtt gggtaacgcc agggttttcc cagtcacgac     180
gttgtaaaac gacggccagt ccgtaatacg actcacttaa ggccttgact agagggaaga    240
tctggatgca ttcgcgcgca cgtacggtct cgaggaattc ctgcaggata tcgtggatcc    300
aagcttcacc atgggagacg tcaccggttc tagaacctag ggagctctgg tacccactag    360
tgagtcgtat tacgtaaccg caggtaaaag gcatattttt cgcgtgtcat ggctagtaaa    420
taacaccggt gtcatttaga gtcagggaaa gacaatgaaa acgaagaaa gccaccgggc     480
ggcaacccga tgactttcgc ttatcaccca gcacacacct gggagaaatc acggtcatga    540
gtttacagac tcatgcgcag aatgcgcaca ctaaaacacc tacccgcgtc gagcgcgacc    600
gtggtggact ggacaacacc ccagcatctg ccagtgaccg cgacctttta cgcgatcatc    660
taggccgcga tgtactccac ggttcagtca cacgagactt taaaaaggcc tatcgacgca    720
acgctgacgg cacgaactcg ccgcgtatgt atcgcttcga gactgatgct ttaggacggt    780
gcgagtacgc catgctcacc accaagcagt acgccgccgt cctggtcgta gacgttgacc    840
aagtaggtac cgcaggcggt gaccccgcag acttaaaccc gtacgtccgc gacgtggtgc    900
gctcactgat tactcatagc gtcgggccag cctgggtggg tattaaccca actaacggca    960
aagcccagtt catatggctt attgaccctg tctacgctga ccgtaacggt aaatctgcgc   1020
agatgaagct tcttgcagca accacgcgtg tgctgggtga gcttttagac catgacccgc   1080
actttttccca ccgctttagc cgcaaccgt tctacacagg caaagccccct accgcttatc  1140
gttggtatag gcagcacaac cgggtgatgc gccttggaga cttgataaag caggtaaggg   1200
atatggcagg acacgaccag ttcaacccca ccccacgcca gcaattcagc tctggccgcg   1260
aacttatcaa cgcggtcaag acccgccgtg aagaagccca agcattcaaa gcactcgccc   1320
aggacgtaga cgcggaaatc gccggtggtc tcgaccagta tgacccggaa cttatcgacg   1380
gtgtgcgtgt gctctggatt gtccaaggaa ccgcagcacg cgacgaaaca gcctttagac   1440
atgcgcttaa gactgccacc gcttgcgcc agcaaggcca acgcctgaca gacgcagcaa   1500
tcatcgacgc ctatgagcac gcctacaacg tcgcacacac ccacggcggt gcaggccgcg   1560
acaacgagat gccacccatg cgcgaccgcc aaaccatggc aaggcgcgtg cgcgggtatg   1620
tcgcccaatc caagagcgag acctacagcg gctctaacgc accaggtaaa gccaccagca   1680
gcgagcggaa agccttggcc acgatgggac gcagaggcgg acaaaaagcc gcacaacgct   1740
ggaaaacaga ccccgagggc aaatatgcgc aagcacaaag gtcgaagctt gaaaagacgc   1800
accgtaagaa aaaggctcaa ggacgatcta cgaagtcccg tattagccaa atggtgaacg   1860
atcagtattt ccagacaggg acagttccca cgtgggctga ataggggca gaggtaggag   1920
```

```
tctctcgcgc cacggttgct aggcatgtcg cggagctaaa gaagagcggt gactatccgg      1980
acgtttaagg ggtctcatac cgtaagcaat atacggttcc cctgccgtta ggcagttaga      2040
taaaacctca cttgaagaaa accttgaggg gcagggcagc ttatatgctt caaagcatga      2100
cttcctctgt tctcctagac ctcgcaaccc tccgccataa cctcaccgaa ttgtgggcca      2160
tcgccctgat agacggtttt tcgccctttg acgttggagt ccacgttctt taatagtgga      2220
ctcttgttcc aaactggaac aacactcaac cctatctcgg gctattcttt tgatttataa      2280
gggattttgc cgatttcggc ctattggtta aaaatgagc tgatttaaca aaaatttaac       2340
gcgaatttta acaaaatatt aacgtttaca atttaaatat ttgcttatac aatcttcctg      2400
tttttggggc ttttctgatt atcaaccggg gtaaatcaat ctaaagtata tatgagtaaa      2460
cttggtctga cagttaccaa tgcttaatca gtgaggcacc tatctcagcg atctgtctat      2520
ttcgttcatc catagttgcc tgactccccg tcgtgtagat aactacgata cgggagggct      2580
taccatctgg ccccagtgct gcaatgatac cgcgagaccc acgctcaccg gctccagatt      2640
tatcagcaat aaaccagcca gccggaaggg ccgagcgcag aagtggtcct gcaactttat      2700
ccgcctccat ccagtctatt aattgttgcc gggaagctag agtaagtagt tcgcagtta      2760 atagtttgcg caacgttgtt gccattgcta caggcatcgt ggtgtcacgc tcgtcgtttg      2820
gtatggcttc attcagctcc ggttcccaac gatcaaggcg agttacatga tcccccatgt      2880
tgtgcaaaaa agcggttagc tccttcggtc ctccgatcgt tgtcagaagt aagttggccg      2940
cagtgttatc actcatggtt atggcagcac tgcataattc tcttactgtc atgccatccg      3000
taagatgctt ttctgtgact ggtgagtact caaccaagtc attctgagaa tagtgtatgc      3060
ggcgaccgag ttgctcttgc ccggcgtcaa cacgggataa taccgcgcca catagcagaa      3120
ctttaaaagt gctcatcatt ggagaacgtt cttcggggcg aaaactctca aggatcttac      3180
cgctgttgag atccagttcg atgtaaccca ctcgtgcacc caactgatct tcagcatctt      3240
ttactttcac cagcgtttct gggtgagcaa aaacaggaag gcaaaatgcc gcaaaaaagg      3300
gaataagggc gacacggaaa tgttgaatac tcatactctt cctttttcaa tattattgaa      3360
gcatttatca gggttattgt ctcatgagcg gatacatatt tgaatgtatt tagaaaaata      3420
aacaaatagg ggttccgcgc acatttcccc gaaaagtgcc acctgacgta gttaac         3476
```

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 2

```
gacatccaga tgacccagac c                                                21
```

<210> SEQ ID NO 3
<211> LENGTH: 58
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 3

```
cctcccgagc caccgcctcc gctgcctccg cctcctttta tctccagctt gtgtcgcc        58
```

<210> SEQ ID NO 4
<211> LENGTH: 56
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 4
gcagcggagg cggtggctcg ggaggggggag gctcggaggt gcagcttcag cagtct    56

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 5
gcaagcttga agactgtgag agtggtgcct tg    32

<210> SEQ ID NO 6
<211> LENGTH: 37
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 6
gtctcttcaa agcttattgc ctgagctgcc tcccaaa    37

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 7
gcatctagat cagtagcagg tgccagctgt gt    32

<210> SEQ ID NO 8
<211> LENGTH: 59
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 8
cggtcgacac catggagaca gacacactcc tgttatgggt actgctgctc tgggttcca    59

<210> SEQ ID NO 9
<211> LENGTH: 51
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 9
gtactgctgc tctgggttcc aggttccact ggggacatcc agatgaccca g    51

<210> SEQ ID NO 10

```
<211> LENGTH: 67
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 10
atgaaatacc tattgcctac ggcagccgct ggattgttat tactgcgctg cccaaccagc      60
gatggcc                                                               67

<210> SEQ ID NO 11
<211> LENGTH: 54
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 11
atgaaatacc tattgcctac ggcagccgct ggattgttat tactcgctgc ccaa            54

<210> SEQ ID NO 12
<211> LENGTH: 59
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 12
ggattgttat tactcgctgc ccaacaagcg atggccggcg ctgatgatgt tgttgattc       59

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 13
cggtactata aaactctttc caatcatcgt c                                    31

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 14
gacgatgatt ggaaagagtt ttatagtacc g                                    31

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence:/note =
      synthetic construct
<220> FEATURE:
<221> NAME/KEY: misc_feature
<222> LOCATION: 11
<223> OTHER INFORMATION: Note: n can be a or c

<400> SEQUENCE: 15
```
agatctgtcg ntcatcagct tttgatttca aaaaatagcg 40

<210> SEQ ID NO 16
<211> LENGTH: 637
<212> TYPE: PRT
<213> ORGANISM: Artificial Sequence
<220> FEATURE:
<223> OTHER INFORMATION: Description of Artificial Sequence:/Note = synthetic construct

<400> SEQUENCE: 16

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

```
Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu Pro Trp Asp Ile Gln Met Thr Gln Thr Thr
385                 390                 395                 400

Ser Ser Leu Ser Ala Ser Leu Gly Asp Arg Val Thr Ile Ser Cys Arg
                405                 410                 415

Ala Ser Gln Asp Ile Arg Asn Tyr Leu Asn Trp Tyr Gln Gln Lys Pro
            420                 425                 430

Asp Gly Thr Val Lys Leu Leu Ile Tyr Tyr Thr Ser Arg Leu His Ser
        435                 440                 445

Gly Val Pro Ser Lys Phe Ser Gly Ser Gly Ser Gly Thr Asp Tyr Ser
    450                 455                 460

Leu Thr Ile Ser Asn Leu Glu Gln Glu Asp Ile Ala Thr Tyr Phe Cys
465                 470                 475                 480

Gln Gln Gly Asn Thr Leu Pro Trp Thr Phe Ala Gly Gly Thr Lys Leu
                485                 490                 495

Glu Ile Lys Arg Gly Gly Gly Gly Ser Gly Gly Gly Gly Ser Gly Gly
            500                 505                 510

Gly Gly Ser Glu Val Gln Leu Gln Gln Ser Gly Pro Glu Leu Val Lys
        515                 520                 525

Pro Gly Ala Ser Met Lys Ile Ser Cys Lys Ala Ser Gly Tyr Ser Phe
    530                 535                 540

Thr Gly Tyr Thr Met Asn Trp Val Lys Gln Ser His Gly Lys Asn Leu
545                 550                 555                 560

Glu Trp Met Gly Leu Ile Asn Pro Tyr Lys Gly Val Ser Thr Tyr Asn
                565                 570                 575

Gln Lys Phe Lys Asp Lys Ala Thr Phe Thr Val Asp Lys Ser Ser Ser
            580                 585                 590

Thr Ala Tyr Met Glu Leu Leu Ser Leu Thr Ser Glu Asp Ser Ala Val
        595                 600                 605

Tyr Tyr Cys Ala Arg Ser Gly Tyr Tyr Gly Asp Ser Asp Trp Tyr Phe
    610                 615                 620

Asp Val Trp Gly Gln Gly Thr Thr Leu Thr Val Phe Ser
625                 630                 635

<210> SEQ ID NO 17
<211> LENGTH: 896
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 17

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
```

-continued

```
                65                  70                  75                  80
Val Val Lys Val Thr Tyr Pro Gly Leu Thr Lys Val Leu Ala Leu Lys
                    85                  90                  95
Val Asp Asn Ala Glu Thr Ile Lys Lys Glu Leu Gly Leu Ser Leu Thr
                    100                 105                 110
Glu Pro Leu Met Glu Gln Val Gly Thr Glu Phe Ile Lys Arg Phe
                    115                 120                 125
Gly Asp Gly Ala Ser Arg Val Val Leu Ser Leu Pro Phe Ala Glu Gly
                130                 135                 140
Ser Ser Ser Val Glu Tyr Ile Asn Asn Trp Glu Gln Ala Lys Ala Leu
145                 150                 155                 160
Ser Val Glu Leu Glu Ile Asn Phe Glu Thr Arg Gly Lys Arg Gly Gln
                    165                 170                 175
Asp Ala Met Tyr Glu Tyr Met Ala Gln Ala Cys Ala Gly Asn Arg Val
                180                 185                 190
Arg Arg Ser Val Gly Ser Ser Leu Ser Cys Ile Asn Leu Asp Trp Asp
                    195                 200                 205
Val Ile Arg Asp Lys Thr Lys Thr Lys Ile Glu Ser Leu Lys Glu His
                210                 215                 220
Gly Pro Ile Lys Asn Lys Met Ser Glu Ser Pro Asn Lys Thr Val Ser
225                 230                 235                 240
Glu Glu Lys Ala Lys Gln Tyr Leu Glu Glu Phe His Gln Thr Ala Leu
                    245                 250                 255
Glu His Pro Glu Leu Ser Glu Leu Lys Thr Val Thr Gly Thr Asn Pro
                260                 265                 270
Val Phe Ala Gly Ala Asn Tyr Ala Ala Trp Ala Val Asn Val Ala Gln
                    275                 280                 285
Val Ile Asp Ser Glu Thr Ala Asp Asn Leu Glu Lys Thr Thr Ala Ala
                290                 295                 300
Leu Ser Ile Leu Pro Gly Ile Gly Ser Val Met Gly Ile Ala Asp Gly
305                 310                 315                 320
Ala Val His His Asn Thr Glu Glu Ile Val Ala Gln Ser Ile Ala Leu
                    325                 330                 335
Ser Ser Leu Met Val Ala Gln Ala Ile Pro Leu Val Gly Glu Leu Val
                340                 345                 350
Asp Ile Gly Phe Ala Ala Tyr Asn Phe Val Glu Ser Ile Ile Asn Leu
                355                 360                 365
Phe Gln Val Val His Asn Ser Tyr Asn Arg Pro Ala Tyr Ser Pro Gly
370                 375                 380
His Lys Thr Gln Pro Phe Leu Pro Trp Asp Ile Gln Met Thr Gln Thr
385                 390                 395                 400
Thr Ser Ser Leu Ser Ala Ser Leu Gly Asp Arg Val Thr Ile Ser Cys
                    405                 410                 415
Arg Ala Ser Gln Asp Ile Arg Asn Tyr Leu Asn Trp Tyr Gln Gln Lys
                420                 425                 430
Pro Asp Gly Thr Val Lys Leu Leu Ile Tyr Tyr Thr Ser Arg Leu His
                435                 440                 445
Ser Gly Val Pro Ser Lys Phe Ser Gly Ser Gly Ser Gly Thr Asp Tyr
                450                 455                 460
Ser Leu Thr Ile Ser Asn Leu Glu Gln Glu Asp Ile Ala Thr Tyr Phe
465                 470                 475                 480
Cys Gln Gln Gly Asn Thr Leu Pro Trp Thr Phe Ala Gly Gly Thr Lys
                    485                 490                 495
```

```
Leu Glu Ile Lys Gly Gly Gly Ser Gly Gly Gly Ser Gly Gly
                500                 505                 510

Gly Gly Ser Glu Val Gln Leu Gln Gln Ser Gly Pro Glu Leu Val Lys
            515                 520                 525

Pro Gly Ala Ser Met Lys Ile Ser Cys Lys Ala Ser Gly Tyr Ser Phe
            530                 535                 540

Thr Gly Tyr Thr Met Asn Trp Val Lys Gln Ser His Gly Lys Asn Leu
545                 550                 555                 560

Glu Trp Met Gly Leu Ile Asn Pro Tyr Lys Gly Val Ser Thr Tyr Asn
                565                 570                 575

Gln Lys Phe Lys Asp Lys Ala Thr Leu Thr Val Asp Lys Ser Ser Ser
            580                 585                 590

Thr Ala Tyr Met Glu Leu Leu Ser Leu Thr Ser Glu Asp Ser Ala Val
            595                 600                 605

Tyr Tyr Cys Ala Arg Ser Gly Tyr Tyr Gly Asp Ser Asp Trp Tyr Phe
            610                 615                 620

Asp Val Trp Gly Ala Gly Thr Thr Val Thr Val Ser Ser Gly Gly Gly
625                 630                 635                 640

Gly Ser Gly Gly Gly Gly Ser Gly Gly Gly Gly Ser Asp Ile Gln Met
                645                 650                 655

Thr Gln Thr Thr Ser Ser Leu Ser Ala Ser Leu Gly Asp Arg Val Thr
            660                 665                 670

Ile Ser Cys Arg Ala Ser Gln Asp Ile Arg Asn Tyr Leu Asn Trp Tyr
            675                 680                 685

Gln Gln Lys Pro Asp Gly Thr Val Lys Leu Leu Ile Tyr Tyr Thr Ser
            690                 695                 700

Arg Leu His Ser Gly Val Pro Ser Lys Phe Ser Gly Ser Gly Ser Gly
705                 710                 715                 720

Thr Asp Tyr Ser Leu Thr Ile Ser Asn Leu Glu Gln Glu Asp Ile Ala
                725                 730                 735

Thr Tyr Phe Cys Gln Gln Gly Asn Thr Leu Pro Trp Thr Phe Ala Gly
            740                 745                 750

Gly Thr Lys Leu Glu Ile Lys Gly Gly Gly Ser Gly Gly Gly Gly
            755                 760                 765

Ser Gly Gly Gly Gly Ser Glu Val Gln Leu Gln Gln Ser Gly Pro Glu
770                 775                 780

Leu Val Lys Pro Gly Ala Ser Met Lys Ile Ser Cys Lys Ala Ser Gly
785                 790                 795                 800

Tyr Ser Phe Thr Gly Tyr Thr Met Asn Trp Val Lys Gln Ser His Gly
                805                 810                 815

Lys Asn Leu Glu Trp Met Gly Leu Ile Asn Pro Tyr Lys Gly Val Ser
            820                 825                 830

Thr Tyr Asn Gln Lys Phe Lys Asp Lys Ala Thr Leu Thr Val Asp Lys
            835                 840                 845

Ser Ser Ser Thr Ala Tyr Met Glu Leu Leu Ser Leu Thr Ser Glu Asp
850                 855                 860

Ser Ala Val Tyr Tyr Cys Ala Arg Ser Gly Tyr Tyr Gly Asp Ser Asp
865                 870                 875                 880

Trp Tyr Phe Asp Val Trp Gly Gln Gly Thr Thr Leu Thr Val Phe Ser
                885                 890                 895

<210> SEQ ID NO 18
<211> LENGTH: 896
```

```
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 18

Met Gly Ala Asp Asp Val Val Asp Ser Ser Lys Ser Phe Val Met Glu
 1               5                  10                  15

Asn Phe Ser Ser Tyr His Gly Thr Lys Pro Gly Tyr Val Asp Ser Ile
             20                  25                  30

Gln Lys Gly Ile Gln Lys Pro Lys Ser Gly Thr Gln Gly Asn Tyr Asp
         35                  40                  45

Asp Asp Trp Lys Gly Phe Tyr Ser Thr Asp Asn Lys Tyr Asp Ala Ala
     50                  55                  60

Gly Tyr Ser Val Asp Asn Glu Asn Pro Leu Ser Gly Lys Ala Gly Gly
 65                  70                  75                  80

Val Val Lys Val Thr Tyr Pro Gly Leu Thr Lys Val Leu Ala Leu Lys
                 85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380
```

-continued

```
His Lys Thr Gln Pro Phe Leu Pro Trp Asp Ile Gln Met Thr Gln Thr
385                 390                 395                 400

Thr Ser Ser Leu Ser Ala Ser Leu Gly Asp Arg Val Thr Ile Ser Cys
                405                 410                 415

Arg Ala Ser Gln Asp Ile Arg Asn Tyr Leu Asn Trp Tyr Gln Gln Lys
            420                 425                 430

Pro Asp Gly Thr Val Lys Leu Leu Ile Tyr Tyr Thr Ser Arg Leu His
        435                 440                 445

Ser Gly Val Pro Ser Lys Phe Ser Gly Ser Gly Ser Gly Thr Asp Tyr
    450                 455                 460

Ser Leu Thr Ile Ser Asn Leu Glu Gln Glu Asp Ile Ala Thr Tyr Phe
465                 470                 475                 480

Cys Gln Gln Gly Asn Thr Leu Pro Trp Thr Phe Ala Gly Gly Thr Lys
                485                 490                 495

Leu Glu Ile Lys Gly Gly Gly Ser Gly Gly Gly Ser Gly Gly
                500                 505                 510

Gly Gly Ser Glu Val Gln Leu Gln Gln Ser Gly Pro Glu Leu Val Lys
            515                 520                 525

Pro Gly Ala Ser Met Lys Ile Ser Cys Lys Ala Ser Gly Tyr Ser Phe
        530                 535                 540

Thr Gly Tyr Thr Met Asn Trp Val Lys Gln Ser His Gly Lys Asn Leu
545                 550                 555                 560

Glu Trp Met Gly Leu Ile Asn Pro Tyr Lys Gly Val Ser Thr Tyr Asn
                565                 570                 575

Gln Lys Phe Lys Asp Lys Ala Thr Leu Thr Val Asp Lys Ser Ser Ser
            580                 585                 590

Thr Ala Tyr Met Glu Leu Leu Ser Leu Thr Ser Glu Asp Ser Ala Val
        595                 600                 605

Tyr Tyr Cys Ala Arg Ser Gly Tyr Tyr Gly Asp Ser Asp Trp Tyr Phe
    610                 615                 620

Asp Val Trp Gly Ala Gly Thr Thr Val Thr Val Ser Ser Gly Gly Gly
625                 630                 635                 640

Gly Ser Gly Gly Gly Gly Ser Gly Gly Gly Gly Ser Asp Ile Gln Met
                645                 650                 655

Thr Gln Thr Thr Ser Ser Leu Ser Ala Ser Leu Gly Asp Arg Val Thr
            660                 665                 670

Ile Ser Cys Arg Ala Ser Gln Asp Ile Arg Asn Tyr Leu Asn Trp Tyr
        675                 680                 685

Gln Gln Lys Pro Asp Gly Thr Val Lys Leu Leu Ile Tyr Tyr Thr Ser
    690                 695                 700

Arg Leu His Ser Gly Val Pro Ser Lys Phe Ser Gly Ser Gly Ser Gly
705                 710                 715                 720

Thr Asp Tyr Ser Leu Thr Ile Ser Asn Leu Glu Gln Glu Asp Ile Ala
                725                 730                 735

Thr Tyr Phe Cys Gln Gln Gly Asn Thr Leu Pro Trp Thr Phe Ala Gly
            740                 745                 750

Gly Thr Lys Leu Glu Ile Lys Gly Gly Gly Gly Ser Gly Gly Gly Gly
        755                 760                 765

Ser Gly Gly Gly Gly Ser Glu Val Gln Leu Gln Gln Ser Gly Pro Glu
    770                 775                 780

Leu Val Lys Pro Gly Ala Ser Met Lys Ile Ser Cys Lys Ala Ser Gly
785                 790                 795                 800
```

```
Tyr Ser Phe Thr Gly Tyr Thr Met Asn Trp Val Lys Gln Ser His Gly
                805                 810                 815

Lys Asn Leu Glu Trp Met Gly Leu Ile Asn Pro Tyr Lys Gly Val Ser
            820                 825                 830

Thr Tyr Asn Gln Lys Phe Lys Asp Lys Ala Thr Leu Thr Val Asp Lys
        835                 840                 845

Ser Ser Ser Thr Ala Tyr Met Glu Leu Leu Ser Leu Thr Ser Glu Asp
850                 855                 860

Ser Ala Val Tyr Tyr Cys Ala Arg Ser Gly Tyr Tyr Gly Asp Ser Asp
865                 870                 875                 880

Trp Tyr Phe Asp Val Trp Gly Ala Gly Thr Thr Val Thr Val Ser Ser
                885                 890                 895

<210> SEQ ID NO 19
<211> LENGTH: 895
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 19

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270
```

```
Phe Ala Gly Ala Asn Tyr Ala Ala Trp Ala Val Asn Val Ala Gln Val
            275                 280                 285
Ile Asp Ser Glu Thr Ala Asp Asn Leu Glu Lys Thr Thr Ala Ala Leu
        290                 295                 300
Ser Ile Leu Pro Gly Ile Gly Ser Val Met Gly Ile Ala Asp Gly Ala
305                 310                 315                 320
Val His His Asn Thr Glu Glu Ile Val Ala Gln Ser Ile Ala Leu Ser
                325                 330                 335
Ser Leu Met Val Ala Gln Ala Ile Pro Leu Val Gly Glu Leu Val Asp
            340                 345                 350
Ile Gly Phe Ala Ala Tyr Asn Phe Val Glu Ser Ile Ile Asn Leu Phe
        355                 360                 365
Gln Val Val His Asn Ser Tyr Asn Arg Pro Ala Tyr Ser Pro Gly His
    370                 375                 380
Lys Thr Gln Pro Phe Leu Pro Trp Asp Ile Gln Met Thr Gln Thr Thr
385                 390                 395                 400
Ser Ser Leu Ser Ala Ser Leu Gly Asp Arg Val Thr Ile Ser Cys Arg
                405                 410                 415
Ala Ser Gln Asp Ile Arg Asn Tyr Leu Asn Trp Tyr Gln Gln Lys Pro
            420                 425                 430
Asp Gly Thr Val Lys Leu Leu Ile Tyr Tyr Thr Ser Arg Leu His Ser
        435                 440                 445
Gly Val Pro Ser Lys Phe Ser Gly Ser Gly Ser Gly Thr Asp Tyr Ser
    450                 455                 460
Leu Thr Ile Ser Asn Leu Glu Gln Glu Asp Ile Ala Thr Tyr Phe Cys
465                 470                 475                 480
Gln Gln Gly Asn Thr Leu Pro Trp Thr Phe Ala Gly Gly Thr Lys Leu
                485                 490                 495
Glu Ile Lys Gly Gly Gly Gly Ser Gly Gly Gly Gly Ser Gly Gly Gly
            500                 505                 510
Gly Ser Glu Val Gln Leu Gln Gln Ser Gly Pro Glu Leu Val Lys Pro
        515                 520                 525
Gly Ala Ser Met Lys Ile Ser Cys Lys Ala Ser Gly Tyr Ser Phe Thr
    530                 535                 540
Gly Tyr Thr Met Asn Trp Val Lys Gln Ser His Gly Lys Asn Leu Glu
545                 550                 555                 560
Trp Met Gly Leu Ile Asn Pro Tyr Lys Gly Val Ser Thr Tyr Asn Gln
                565                 570                 575
Lys Phe Lys Asp Lys Ala Thr Leu Thr Val Asp Lys Ser Ser Ser Thr
            580                 585                 590
Ala Tyr Met Glu Leu Leu Ser Leu Thr Ser Glu Asp Ser Ala Val Tyr
        595                 600                 605
Tyr Cys Ala Arg Ser Gly Tyr Tyr Gly Asp Ser Asp Trp Tyr Phe Asp
    610                 615                 620
Val Trp Gly Ala Gly Thr Thr Val Thr Val Ser Ser Gly Gly Gly Gly
625                 630                 635                 640
Ser Gly Gly Gly Gly Ser Gly Gly Gly Gly Ser Asp Ile Gln Met Thr
                645                 650                 655
Gln Thr Thr Ser Ser Leu Ser Ala Ser Leu Gly Asp Arg Val Thr Ile
            660                 665                 670
Ser Cys Arg Ala Ser Gln Asp Ile Arg Asn Tyr Leu Asn Trp Tyr Gln
        675                 680                 685
```

```
Gln Lys Pro Asp Gly Thr Val Lys Leu Leu Ile Tyr Tyr Thr Ser Arg
    690                 695                 700

Leu His Ser Gly Val Pro Ser Lys Phe Ser Gly Ser Gly Ser Gly Thr
705                 710                 715                 720

Asp Tyr Ser Leu Thr Ile Ser Asn Leu Glu Gln Glu Asp Ile Ala Thr
                725                 730                 735

Tyr Phe Cys Gln Gln Gly Asn Thr Leu Pro Trp Thr Phe Ala Gly Gly
            740                 745                 750

Thr Lys Leu Glu Ile Lys Gly Gly Gly Gly Ser Gly Gly Gly Gly Ser
        755                 760                 765

Gly Gly Gly Gly Ser Glu Val Gln Leu Gln Gln Ser Gly Pro Glu Leu
770                 775                 780

Val Lys Pro Gly Ala Ser Met Lys Ile Ser Cys Lys Ala Ser Gly Tyr
785                 790                 795                 800

Ser Phe Thr Gly Tyr Thr Met Asn Trp Val Lys Gln Ser His Gly Lys
                805                 810                 815

Asn Leu Glu Trp Met Gly Leu Ile Asn Pro Tyr Lys Gly Val Ser Thr
            820                 825                 830

Tyr Asn Gln Lys Phe Lys Asp Lys Ala Thr Leu Thr Val Asp Lys Ser
        835                 840                 845

Ser Ser Thr Ala Tyr Met Glu Leu Leu Ser Leu Thr Ser Glu Asp Ser
850                 855                 860

Ala Val Tyr Tyr Cys Ala Arg Ser Gly Tyr Tyr Gly Asp Ser Asp Trp
865                 870                 875                 880

Tyr Phe Asp Val Trp Gly Gln Gly Thr Thr Leu Thr Val Phe Ser
                885                 890                 895

<210> SEQ ID NO 20
<211> LENGTH: 895
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 20

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160
```

```
Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu Pro Trp Asp Ile Gln Met Thr Gln Thr Thr
385                 390                 395                 400

Ser Ser Leu Ser Ala Ser Leu Gly Asp Arg Val Thr Ile Ser Cys Arg
                405                 410                 415

Ala Ser Gln Asp Ile Arg Asn Tyr Leu Asn Trp Tyr Gln Gln Lys Pro
            420                 425                 430

Asp Gly Thr Val Lys Leu Leu Ile Tyr Tyr Thr Ser Arg Leu His Ser
        435                 440                 445

Gly Val Pro Ser Lys Phe Ser Gly Ser Gly Ser Gly Thr Asp Tyr Ser
    450                 455                 460

Leu Thr Ile Ser Asn Leu Glu Gln Glu Asp Ile Ala Thr Tyr Phe Cys
465                 470                 475                 480

Gln Gln Gly Asn Thr Leu Pro Trp Thr Phe Ala Gly Thr Lys Leu
                485                 490                 495

Glu Ile Lys Gly Gly Gly Ser Gly Gly Gly Ser Gly Gly Gly
            500                 505                 510

Gly Ser Glu Val Gln Leu Gln Gln Ser Gly Pro Glu Leu Val Lys Pro
        515                 520                 525

Gly Ala Ser Met Lys Ile Ser Cys Lys Ala Ser Gly Tyr Ser Phe Thr
    530                 535                 540

Gly Tyr Thr Met Asn Trp Val Lys Gln Ser His Gly Lys Asn Leu Glu
545                 550                 555                 560

Trp Met Gly Leu Ile Asn Pro Tyr Lys Gly Val Ser Thr Tyr Asn Gln
                565                 570                 575
```

```
Lys Phe Lys Asp Lys Ala Thr Leu Thr Val Asp Lys Ser Ser Ser Thr
            580                 585                 590

Ala Tyr Met Glu Leu Leu Ser Leu Thr Ser Glu Asp Ser Ala Val Tyr
        595                 600                 605

Tyr Cys Ala Arg Ser Gly Tyr Tyr Gly Asp Ser Asp Trp Tyr Phe Asp
    610                 615                 620

Val Trp Gly Ala Gly Thr Thr Val Thr Val Ser Ser Gly Gly Gly Gly
625                 630                 635                 640

Ser Gly Gly Gly Gly Ser Gly Gly Gly Gly Ser Asp Ile Gln Met Thr
                645                 650                 655

Gln Thr Thr Ser Ser Leu Ser Ala Ser Leu Gly Asp Arg Val Thr Ile
            660                 665                 670

Ser Cys Arg Ala Ser Gln Asp Ile Arg Asn Tyr Leu Asn Trp Tyr Gln
        675                 680                 685

Gln Lys Pro Asp Gly Thr Val Lys Leu Leu Ile Tyr Tyr Thr Ser Arg
    690                 695                 700

Leu His Ser Gly Val Pro Ser Lys Phe Ser Gly Ser Gly Ser Gly Thr
705                 710                 715                 720

Asp Tyr Ser Leu Thr Ile Ser Asn Leu Glu Gln Glu Asp Ile Ala Thr
                725                 730                 735

Tyr Phe Cys Gln Gln Gly Asn Thr Leu Pro Trp Thr Phe Ala Gly Gly
            740                 745                 750

Thr Lys Leu Glu Ile Lys Gly Gly Gly Gly Ser Gly Gly Gly Gly Ser
        755                 760                 765

Gly Gly Gly Gly Ser Glu Val Gln Leu Gln Gln Ser Gly Pro Glu Leu
    770                 775                 780

Val Lys Pro Gly Ala Ser Met Lys Ile Ser Cys Lys Ala Ser Gly Tyr
785                 790                 795                 800

Ser Phe Thr Gly Tyr Thr Met Asn Trp Val Lys Gln Ser His Gly Lys
                805                 810                 815

Asn Leu Glu Trp Met Gly Leu Ile Asn Pro Tyr Lys Gly Val Ser Thr
            820                 825                 830

Tyr Asn Gln Lys Phe Lys Asp Lys Ala Thr Leu Thr Val Asp Lys Ser
        835                 840                 845

Ser Ser Thr Ala Tyr Met Glu Leu Leu Ser Leu Thr Ser Glu Asp Ser
    850                 855                 860

Ala Val Tyr Tyr Cys Ala Arg Ser Gly Tyr Tyr Gly Asp Ser Asp Trp
865                 870                 875                 880

Tyr Phe Asp Val Trp Gly Ala Gly Thr Thr Val Thr Val Ser Ser
                885                 890                 895

<210> SEQ ID NO 21
<211> LENGTH: 638
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 21

Met Gly Ala Asp Asp Val Val Asp Ser Ser Lys Ser Phe Val Met Glu
 1               5                  10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45
```

```
Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr Gln Pro Phe Leu Pro Trp Asp Ile Gln Met Thr Gln Thr
385                 390                 395                 400

Thr Ser Ser Leu Ser Ala Ser Leu Gly Asp Arg Val Thr Ile Ser Cys
                405                 410                 415

Arg Ala Ser Gln Asp Ile Arg Asn Tyr Leu Asn Trp Tyr Gln Gln Lys
            420                 425                 430

Pro Asp Gly Thr Val Lys Leu Leu Ile Tyr Tyr Thr Ser Arg Leu His
        435                 440                 445

Ser Gly Val Pro Ser Lys Phe Ser Gly Ser Gly Ser Gly Thr Asp Tyr
450                 455                 460
```

```
Ser Leu Thr Ile Ser Asn Leu Glu Gln Glu Asp Ile Ala Thr Tyr Phe
465                 470                 475                 480

Cys Gln Gln Gly Asn Thr Leu Pro Trp Thr Phe Ala Gly Gly Thr Lys
            485                 490                 495

Leu Glu Ile Lys Arg Gly Gly Gly Ser Gly Gly Gly Gly Ser Gly
        500                 505                 510

Gly Gly Gly Ser Glu Val Gln Leu Gln Gln Ser Gly Pro Glu Leu Val
            515                 520                 525

Lys Pro Gly Ala Ser Met Lys Ile Ser Cys Lys Ala Ser Gly Tyr Ser
        530                 535                 540

Phe Thr Gly Tyr Thr Met Asn Trp Val Lys Gln Ser His Gly Lys Asn
545                 550                 555                 560

Leu Glu Trp Met Gly Leu Ile Asn Pro Tyr Lys Gly Val Ser Thr Tyr
                565                 570                 575

Asn Gln Lys Phe Lys Asp Lys Ala Thr Phe Thr Val Asp Lys Ser Ser
            580                 585                 590

Ser Thr Ala Tyr Met Glu Leu Leu Ser Leu Thr Ser Glu Asp Ser Ala
        595                 600                 605

Val Tyr Tyr Cys Ala Arg Ser Gly Tyr Tyr Gly Asp Ser Asp Trp Tyr
    610                 615                 620

Phe Asp Val Trp Gly Gln Gly Thr Thr Leu Thr Val Phe Ser
625                 630                 635

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 22
gctatccaca gaagaggtgg t                                               21

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 23

Ala Ile His Arg Arg Gly Gly
1               5

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 24
gccatccacc gaagaggtgg t                                               21

<210> SEQ ID NO 25
<211> LENGTH: 21
<212> TYPE: PRT
<213> ORGANISM: Artificial Sequence
<220> FEATURE:
```

```
<223> OTHER INFORMATION: Description of Artificial Sequence:/Note =
      synthetic construct

<400> SEQUENCE: 25

Met Glu Thr Asp Thr Leu Leu Leu Trp Val Leu Leu Leu Trp Val Pro
 1               5                  10                  15

Gly Ala Asp Ala Ala
            20

<210> SEQ ID NO 26
<211> LENGTH: 896
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 26

Ala Gly Ala Asp Asp Val Val Asp Ser Ser Lys Ser Phe Val Met Glu
 1               5                  10                  15

Asn Phe Ala Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Ala Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300
```

```
Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr Gln Pro Phe Leu Pro Trp Asp Ile Gln Met Thr Gln Thr
385                 390                 395                 400

Thr Ser Ser Leu Ser Ala Ser Leu Gly Asp Arg Val Thr Ile Ser Cys
                405                 410                 415

Arg Ala Ser Gln Asp Ile Arg Asn Tyr Leu Asn Trp Tyr Gln Gln Lys
                420                 425                 430

Pro Asp Gly Thr Val Lys Leu Leu Ile Tyr Tyr Thr Ser Arg Leu His
            435                 440                 445

Ser Gly Val Pro Ser Lys Phe Ser Gly Ser Gly Ser Gly Thr Asp Tyr
        450                 455                 460

Ser Leu Thr Ile Ser Asn Leu Glu Gln Glu Asp Ile Ala Thr Tyr Phe
465                 470                 475                 480

Cys Gln Gln Gly Asn Thr Leu Pro Trp Thr Phe Ala Gly Gly Thr Lys
                485                 490                 495

Leu Glu Ile Lys Gly Gly Gly Gly Ser Gly Gly Gly Gly Ser Gly Gly
                500                 505                 510

Gly Gly Ser Glu Val Gln Leu Gln Gln Ser Gly Pro Glu Leu Val Lys
            515                 520                 525

Pro Gly Ala Ser Met Lys Ile Ser Cys Lys Ala Ser Gly Tyr Ser Phe
        530                 535                 540

Thr Gly Tyr Thr Met Asn Trp Val Lys Gln Ser His Gly Lys Asn Leu
545                 550                 555                 560

Glu Trp Met Gly Leu Ile Asn Pro Tyr Lys Gly Val Ser Thr Tyr Asn
                565                 570                 575

Gln Lys Phe Lys Asp Lys Ala Thr Leu Thr Val Asp Lys Ser Ser Ser
                580                 585                 590

Thr Ala Tyr Met Glu Leu Leu Ser Leu Thr Ser Glu Asp Ser Ala Val
            595                 600                 605

Tyr Tyr Cys Ala Arg Ser Gly Tyr Tyr Gly Asp Ser Asp Trp Tyr Phe
        610                 615                 620

Asp Val Trp Gly Ala Gly Thr Thr Val Thr Val Ser Ser Gly Gly Gly
625                 630                 635                 640

Gly Ser Gly Gly Gly Gly Ser Gly Gly Gly Gly Ser Asp Ile Gln Met
                645                 650                 655

Thr Gln Thr Thr Ser Ser Leu Ser Ala Ser Leu Gly Asp Arg Val Thr
            660                 665                 670

Ile Ser Cys Arg Ala Ser Gln Asp Ile Arg Asn Tyr Leu Asn Trp Tyr
        675                 680                 685

Gln Gln Lys Pro Asp Gly Thr Val Lys Leu Leu Ile Tyr Tyr Thr Ser
    690                 695                 700

Arg Leu His Ser Gly Val Pro Ser Lys Phe Ser Gly Ser Gly Ser Gly
705                 710                 715                 720

Thr Asp Tyr Ser Leu Thr Ile Ser Asn Leu Glu Gln Glu Asp Ile Ala
```

-continued

```
                725                 730                 735
Thr Tyr Phe Cys Gln Gln Gly Asn Thr Leu Pro Trp Thr Phe Ala Gly
            740                 745                 750

Gly Thr Lys Leu Glu Ile Lys Gly Gly Gly Ser Gly Gly Gly Gly
            755                 760                 765

Ser Gly Gly Gly Ser Glu Val Gln Leu Gln Gln Ser Gly Pro Glu
            770                 775                 780

Leu Val Lys Pro Gly Ala Ser Met Lys Ile Ser Cys Lys Ala Ser Gly
785                 790                 795                 800

Tyr Ser Phe Thr Gly Tyr Thr Met Asn Trp Val Lys Gln Ser His Gly
                805                 810                 815

Lys Asn Leu Glu Trp Met Gly Leu Ile Asn Pro Tyr Lys Gly Val Ser
            820                 825                 830

Thr Tyr Asn Gln Lys Phe Lys Asp Lys Ala Thr Leu Thr Val Asp Lys
            835                 840                 845

Ser Ser Ser Thr Ala Tyr Met Glu Leu Leu Ser Leu Thr Ser Glu Asp
            850                 855                 860

Ser Ala Val Tyr Tyr Cys Ala Arg Ser Gly Tyr Tyr Gly Asp Ser Asp
865                 870                 875                 880

Trp Tyr Phe Asp Val Trp Gly Gln Gly Thr Thr Leu Thr Val Phe Ser
                885                 890                 895
```

<210> SEQ ID NO 27
<211> LENGTH: 895
<212> TYPE: PRT
<213> ORGANISM: Artificial Sequence
<220> FEATURE:
<223> OTHER INFORMATION: Description of Artificial Sequence:/Note = synthetic construct

<400> SEQUENCE: 27

```
Gly Ala Asp Asp Val Val Asp Ser Ser Lys Ser Phe Val Met Glu Asn
1               5                   10                  15

Phe Ala Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190
```

-continued

```
Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Ala Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu Pro Trp Asp Ile Gln Met Thr Gln Thr Thr
385                 390                 395                 400

Ser Ser Leu Ser Ala Ser Leu Gly Asp Arg Val Thr Ile Ser Cys Arg
                405                 410                 415

Ala Ser Gln Asp Ile Arg Asn Tyr Leu Asn Trp Tyr Gln Gln Lys Pro
            420                 425                 430

Asp Gly Thr Val Lys Leu Leu Ile Tyr Tyr Thr Ser Arg Leu His Ser
        435                 440                 445

Gly Val Pro Ser Lys Phe Ser Gly Ser Gly Ser Gly Thr Asp Tyr Ser
    450                 455                 460

Leu Thr Ile Ser Asn Leu Glu Gln Glu Asp Ile Ala Thr Tyr Phe Cys
465                 470                 475                 480

Gln Gln Gly Asn Thr Leu Pro Trp Thr Phe Ala Gly Gly Thr Lys Leu
                485                 490                 495

Glu Ile Lys Gly Gly Gly Gly Ser Gly Gly Gly Gly Ser Gly Gly Gly
            500                 505                 510

Gly Ser Glu Val Gln Leu Gln Gln Ser Gly Pro Glu Leu Val Lys Pro
        515                 520                 525

Gly Ala Ser Met Lys Ile Ser Cys Lys Ala Ser Gly Tyr Ser Phe Thr
    530                 535                 540

Gly Tyr Thr Met Asn Trp Val Lys Gln Ser His Gly Lys Asn Leu Glu
545                 550                 555                 560

Trp Met Gly Leu Ile Asn Pro Tyr Lys Gly Val Ser Thr Tyr Asn Gln
                565                 570                 575

Lys Phe Lys Asp Lys Ala Thr Leu Thr Val Asp Lys Ser Ser Ser Thr
            580                 585                 590

Ala Tyr Met Glu Leu Leu Ser Leu Thr Ser Glu Asp Ser Ala Val Tyr
        595                 600                 605

Tyr Cys Ala Arg Ser Gly Tyr Tyr Gly Asp Ser Asp Trp Tyr Phe Asp
```

```
            610                 615                 620
Val Trp Gly Ala Gly Thr Thr Val Thr Val Ser Ser Gly Gly Gly Gly
625                 630                 635                 640

Ser Gly Gly Gly Ser Gly Gly Gly Ser Asp Ile Gln Met Thr
                645                 650                 655

Gln Thr Thr Ser Ser Leu Ser Ala Ser Leu Gly Asp Arg Val Thr Ile
                660                 665                 670

Ser Cys Arg Ala Ser Gln Asp Ile Arg Asn Tyr Leu Asn Trp Tyr Gln
            675                 680                 685

Gln Lys Pro Asp Gly Thr Val Lys Leu Leu Ile Tyr Tyr Thr Ser Arg
690                 695                 700

Leu His Ser Gly Val Pro Ser Lys Phe Ser Gly Ser Gly Ser Gly Thr
705                 710                 715                 720

Asp Tyr Ser Leu Thr Ile Ser Asn Leu Glu Gln Glu Asp Ile Ala Thr
                725                 730                 735

Tyr Phe Cys Gln Gln Gly Asn Thr Leu Pro Trp Thr Phe Ala Gly Gly
                740                 745                 750

Thr Lys Leu Glu Ile Lys Gly Gly Gly Gly Ser Gly Gly Gly Gly Ser
            755                 760                 765

Gly Gly Gly Gly Ser Glu Val Gln Leu Gln Gln Ser Gly Pro Glu Leu
            770                 775                 780

Val Lys Pro Gly Ala Ser Met Lys Ile Ser Cys Lys Ala Ser Gly Tyr
785                 790                 795                 800

Ser Phe Thr Gly Tyr Thr Met Asn Trp Val Lys Gln Ser His Gly Lys
                805                 810                 815

Asn Leu Glu Trp Met Gly Leu Ile Asn Pro Tyr Lys Gly Val Ser Thr
                820                 825                 830

Tyr Asn Gln Lys Phe Lys Asp Lys Ala Thr Leu Thr Val Asp Lys Ser
            835                 840                 845

Ser Ser Thr Ala Tyr Met Glu Leu Leu Ser Leu Thr Ser Glu Asp Ser
            850                 855                 860

Ala Val Tyr Tyr Cys Ala Arg Ser Gly Tyr Tyr Gly Asp Ser Asp Trp
865                 870                 875                 880

Tyr Phe Asp Val Trp Gly Gln Gly Thr Thr Leu Thr Val Phe Ser
                885                 890                 895

<210> SEQ ID NO 28
<211> LENGTH: 899
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 28

Tyr Val Glu Phe Gly Ala Asp Asp Val Asp Ser Ser Lys Ser Phe
1               5                   10                  15

Val Met Glu Asn Phe Ala Ser Tyr His Gly Thr Lys Pro Gly Tyr Val
                20                  25                  30

Asp Ser Ile Gln Lys Gly Ile Gln Lys Pro Lys Ser Gly Thr Gln Gly
            35                  40                  45

Asn Tyr Asp Asp Asp Trp Lys Gly Phe Tyr Ser Thr Asp Asn Lys Tyr
        50                  55                  60

Asp Ala Ala Gly Tyr Ser Val Asp Asn Glu Asn Pro Leu Ser Gly Lys
65                  70                  75                  80
```

-continued

```
Ala Gly Gly Val Val Lys Val Thr Tyr Pro Gly Leu Thr Lys Val Leu
                85                  90                  95
Ala Leu Lys Val Asp Asn Ala Glu Thr Ile Lys Lys Glu Leu Gly Leu
            100                 105                 110
Ser Leu Thr Glu Pro Leu Met Glu Gln Val Gly Thr Glu Glu Phe Ile
        115                 120                 125
Lys Arg Phe Gly Asp Gly Ala Ser Arg Val Val Leu Ser Leu Pro Phe
    130                 135                 140
Ala Glu Gly Ser Ser Ser Val Glu Tyr Ile Asn Asn Trp Glu Gln Ala
145                 150                 155                 160
Lys Ala Leu Ser Val Glu Leu Glu Ile Asn Phe Glu Thr Arg Gly Lys
                165                 170                 175
Arg Gly Gln Asp Ala Met Tyr Glu Tyr Met Ala Gln Ala Cys Ala Gly
            180                 185                 190
Asn Arg Val Arg Arg Ser Val Gly Ser Ser Leu Ser Cys Ile Asn Leu
        195                 200                 205
Asp Trp Asp Val Ile Arg Asp Lys Thr Lys Thr Lys Ile Glu Ser Leu
    210                 215                 220
Lys Glu His Gly Pro Ile Lys Asn Lys Met Ser Glu Ser Pro Ala Lys
225                 230                 235                 240
Thr Val Ser Glu Glu Lys Ala Lys Gln Tyr Leu Glu Glu Phe His Gln
                245                 250                 255
Thr Ala Leu Glu His Pro Glu Leu Ser Glu Leu Lys Thr Val Thr Gly
            260                 265                 270
Thr Asn Pro Val Phe Ala Gly Ala Asn Tyr Ala Ala Trp Ala Val Asn
        275                 280                 285
Val Ala Gln Val Ile Asp Ser Glu Thr Ala Asp Asn Leu Glu Lys Thr
    290                 295                 300
Thr Ala Ala Leu Ser Ile Leu Pro Gly Ile Gly Ser Val Met Gly Ile
305                 310                 315                 320
Ala Asp Gly Ala Val His His Asn Thr Glu Glu Ile Val Ala Gln Ser
                325                 330                 335
Ile Ala Leu Ser Ser Leu Met Val Ala Gln Ala Ile Pro Leu Val Gly
            340                 345                 350
Glu Leu Val Asp Ile Gly Phe Ala Ala Tyr Asn Phe Val Glu Ser Ile
        355                 360                 365
Ile Asn Leu Phe Gln Val Val His Asn Ser Tyr Asn Arg Pro Ala Tyr
    370                 375                 380
Ser Pro Gly His Lys Thr Gln Pro Phe Leu Pro Trp Asp Ile Gln Met
385                 390                 395                 400
Thr Gln Thr Thr Ser Ser Leu Ser Ala Ser Leu Gly Asp Arg Val Thr
                405                 410                 415
Ile Ser Cys Arg Ala Ser Gln Asp Ile Arg Asn Tyr Leu Asn Trp Tyr
            420                 425                 430
Gln Gln Lys Pro Asp Gly Thr Val Lys Leu Leu Ile Tyr Tyr Thr Ser
        435                 440                 445
Arg Leu His Ser Gly Val Pro Ser Lys Phe Ser Gly Ser Gly Ser Gly
    450                 455                 460
Thr Asp Tyr Ser Leu Thr Ile Ser Asn Leu Glu Gln Glu Asp Ile Ala
465                 470                 475                 480
Thr Tyr Phe Cys Gln Gln Gly Asn Thr Leu Pro Trp Thr Phe Ala Gly
                485                 490                 495
Gly Thr Lys Leu Glu Ile Lys Gly Gly Gly Gly Ser Gly Gly Gly Gly
```

```
                    500                 505                 510
Ser Gly Gly Gly Ser Glu Val Gln Leu Gln Ser Gly Pro Glu
        515                 520                 525
Leu Val Lys Pro Gly Ala Ser Met Lys Ile Ser Cys Lys Ala Ser Gly
    530                 535                 540
Tyr Ser Phe Thr Gly Tyr Thr Met Asn Trp Val Lys Gln Ser His Gly
545                 550                 555                 560
Lys Asn Leu Glu Trp Met Gly Leu Ile Asn Pro Tyr Lys Gly Val Ser
                565                 570                 575
Thr Tyr Asn Gln Lys Phe Lys Asp Lys Ala Thr Leu Thr Val Asp Lys
            580                 585                 590
Ser Ser Ser Thr Ala Tyr Met Glu Leu Leu Ser Leu Thr Ser Glu Asp
        595                 600                 605
Ser Ala Val Tyr Tyr Cys Ala Arg Ser Gly Tyr Tyr Gly Asp Ser Asp
    610                 615                 620
Trp Tyr Phe Asp Val Trp Gly Ala Gly Thr Thr Val Thr Val Ser Ser
625                 630                 635                 640
Gly Gly Gly Gly Ser Gly Gly Gly Ser Gly Gly Gly Gly Ser Asp
                645                 650                 655
Ile Gln Met Thr Gln Thr Thr Ser Ser Leu Ser Ala Ser Leu Gly Asp
            660                 665                 670
Arg Val Thr Ile Ser Cys Arg Ala Ser Gln Asp Ile Arg Asn Tyr Leu
        675                 680                 685
Asn Trp Tyr Gln Gln Lys Pro Asp Gly Thr Val Lys Leu Leu Ile Tyr
    690                 695                 700
Tyr Thr Ser Arg Leu His Ser Gly Val Pro Ser Lys Phe Ser Gly Ser
705                 710                 715                 720
Gly Ser Gly Thr Asp Tyr Ser Leu Thr Ile Ser Asn Leu Glu Gln Glu
                725                 730                 735
Asp Ile Ala Thr Tyr Phe Cys Gln Gln Gly Asn Thr Leu Pro Trp Thr
            740                 745                 750
Phe Ala Gly Gly Thr Lys Leu Glu Ile Lys Gly Gly Gly Gly Ser Gly
        755                 760                 765
Gly Gly Gly Ser Gly Gly Gly Gly Ser Glu Val Gln Leu Gln Gln Ser
    770                 775                 780
Gly Pro Glu Leu Val Lys Pro Gly Ala Ser Met Lys Ile Ser Cys Lys
785                 790                 795                 800
Ala Ser Gly Tyr Ser Phe Thr Gly Tyr Thr Met Asn Trp Val Lys Gln
                805                 810                 815
Ser His Gly Lys Asn Leu Glu Trp Met Gly Leu Ile Asn Pro Tyr Lys
            820                 825                 830
Gly Val Ser Thr Tyr Asn Gln Lys Phe Lys Asp Lys Ala Thr Leu Thr
        835                 840                 845
Val Asp Lys Ser Ser Ser Thr Ala Tyr Met Glu Leu Leu Ser Leu Thr
    850                 855                 860
Ser Glu Asp Ser Ala Val Tyr Tyr Cys Ala Arg Ser Gly Tyr Tyr Gly
865                 870                 875                 880
Asp Ser Asp Trp Tyr Phe Asp Val Trp Gly Gln Gly Thr Thr Leu Thr
                885                 890                 895
Val Phe Ser

<210> SEQ ID NO 29
<211> LENGTH: 89
```

<212> TYPE: PRT
<213> ORGANISM: Artificial Sequence
<220> FEATURE:
<223> OTHER INFORMATION: Description of Artificial Sequence:/Note = synthetic construct

<400> SEQUENCE: 29

```
Met Arg Phe Pro Ser Ile Phe Thr Ala Val Leu Phe Ala Ala Ser Ser
1               5                   10                  15
Ala Leu Ala Ala Pro Cys Asn Thr Thr Thr Glu Asp Glu Thr Ala Gln
            20                  25                  30
Ile Pro Ala Glu Ala Val Ile Gly Tyr Ser Asp Leu Glu Gly Asp Phe
        35                  40                  45
Asp Val Ala Val Leu Pro Phe Ser Asn Ser Thr Asn Asn Gly Leu Leu
    50                  55                  60
Phe Ile Asn Thr Thr Ile Ala Ser Ile Ala Lys Glu Glu Gly Val
65                  70                  75                  80
Ser Leu Glu Lys Arg Glu Ala Glu Ala
                85
```

<210> SEQ ID NO 30
<211> LENGTH: 2952
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 30

| | | | | | |
|---|---|---|---|---|---|
| atgagatttc | cttcaatttt | tactgctgtt | ttattcgcag | catcctccgc | attagctgct | 60 |
| ccagtcaaca | ctacaacaga | agatgaaacg | gcacaaattc | cggctgaagc | tgtcatcggt | 120 |
| tactcagatt | tagaagggga | tttcgatgtt | gctgttttgc | cattttccaa | cagcacaaat | 180 |
| aacgggttat | tgtttataaa | tactactatt | gccagcattg | ctgctaaaga | agaaggggta | 240 |
| tctctcgaga | aaagagctgg | cgctgatgat | gtcgtcgact | cctccaagtc | cttcgtcatg | 300 |
| gagaacttcg | cttcctacca | cgggaccaag | ccaggttacg | tcgactccat | ccagaagggt | 360 |
| atccagaagc | caaagtccgg | cacccaaggt | aactacgacg | acgactggaa | ggggttctac | 420 |
| tccaccgaca | caagtacga | cgctgcggga | tactctgtag | ataatgaaaa | cccgctctct | 480 |
| ggaaaagctg | gaggcgtggt | caaagtgacg | tatccaggac | tgacgaaggt | tctcgcacta | 540 |
| aaagtggata | tgccgaaac | tattaagaaa | gagttaggtt | taagtctcac | tgaaccgttg | 600 |
| atggagcaag | tcggaacgga | agagtttatc | aaaaggttcg | gtgatggtgc | ttcgcgtgta | 660 |
| gtgctcagcc | ttccccttcgc | tgaggggagt | tctagcgttg | aatatattaa | taactgggaa | 720 |
| caggcgaaag | cgttaagcgt | agaacttgag | attaattttg | aaacccgtgg | aaaacgtggc | 780 |
| caagatgcga | tgtatgagta | tatggctcaa | gcctgtgcag | aaatcgtgt | caggcgatca | 840 |
| gtaggtagct | cattgtcatg | cataaatctt | gattgggatg | tcataaggga | taaaactaag | 900 |
| acaaagatag | agtctttgaa | agagcatggc | ccaatcaaga | acaagatgtc | cgaatccccc | 960 |
| gctaagaccg | tctccgagga | aaaggccaag | caataccctag | aagagttcca | ccaaaccgcc | 1020 |
| ttggagcatc | ctgaattgtc | agaacttaaa | accgttactg | ggaccaatcc | tgtattcgct | 1080 |
| ggggctaact | atgcggcgtg | ggcagtaaac | gttgcgcaag | ttatcgatag | cgaaacagct | 1140 |
| gataatttgg | aaaagacaac | tgctgctctt | tcgatacttc | ctggtatcgg | tagcgtaatg | 1200 |
| ggcattgcag | acggtgccgt | tcaccacaat | acagaagaga | tagtggcaca | atccatcgct | 1260 |

```
ttgtcctctt tgatggttgc tcaagctatc ccattggtcg gtgagttggt tgacatcggt   1320
ttcgctgcct acaacttcgt cgagtccatc atcaacttgt tccaagtcgt ccacaactcc   1380
tacaaccgtc cggcttactc cccaggtcac aagacccaac cattcttgcc atgggacatc   1440
cagatgaccc agaccacctc ctccctgtct gcctccctgg gcgacagagt caccatcagt   1500
tgcagggcaa gtcaggacat tagaaattat ttaaactggt atcaacagaa accagatgga   1560
actgttaaac tcctgatcta ctacacatca agattacact caggagtccc atcaaagttc   1620
agtggcagtg ggtctggaac agattattct ctcaccatta gcaacctgga gcaagaggat   1680
attgccactt acttttgcca acagggtaat acgcttccgt ggacgttcgc tggaggcacc   1740
aagctggaga taaaaggagg cggaggcagc ggaggcggtg gctcgggagg gggaggctcg   1800
gaggtgcagc tccagcagtc tggacctgag ctggtgaagc ctggagcttc aatgaagata   1860
tcctgcaagg cttctggtta ctcattcact ggctacacca tgaactgggt gaagcagagt   1920 catgaaaga accttgagtg gatgggactt attaatcctt acaaaggtgt tagtacctac   1980
aaccagaagt tcaaggacaa ggccacatta actgtagaca agtcatccag cacagcctac   2040
atggaactcc tcagtctgac atctgaggac tctgcagtct attactgtgc aagatcgggg   2100
tactacggtg atagtgactg gtacttcgat gtctggggcg caggcaccac tgtcacagtc   2160
tcctcaggag gtggcggatc cggaggaggc ggtagtggcg gaggcggttc ggacatccag   2220
atgacccaga ccacctcctc cctgtctgcc tccctgggcg acagagtcac catcagttgc   2280
agggcaagtc aggacattag aaattattta aactggtatc aacagaaacc agatggaact   2340
gttaaactcc tgatctacta cacatcaaga ttacactcag gagtcccatc aaagttcagt   2400
ggcagtgggt ctggaacaga ttattctctc accattagca acctggagca agaggatatt   2460
gccacttact tttgccaaca gggtaatacg cttccgtgga cgttcgctgg aggcaccaag   2520
ctggagataa aaggaggcgg aggcagcgga ggcggtggct cgggaggggg aggctcggag   2580
gtgcagctcc agcagtctgg acctgagctg gtgaagcctg agcttcaat gaagatatcc   2640 tgcaaggctt ctggttactc attcactggc tacaccatga actgggtgaa gcagagtcat   2700
ggaaagaacc ttgagtggat gggacttatt aatccttaca aggtgttag tacctacaac   2760 cagaagttca aggacaaggc cacattaact gtagacaagt catccagcac agcctacatg   2820
gaactcctca gtctgacatc tgaggactct gcagtctatt actgtgcaag atcggggtac   2880
tacggtgata gtgactggta cttcgatgtc tggggccaag gcaccactct cacagtcttc   2940
tcatgagaat tc                                                        2952
```

<210> SEQ ID NO 31
<211> LENGTH: 85
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 31

Met Arg Phe Pro Ser Ile Phe Thr Ala Val Leu Phe Ala Ala Ser Ser
 1               5                  10                  15

Ala Leu Ala Ala Pro Cys Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu

```
                50                  55                  60
Phe Ile Asn Thr Thr Ile Ala Ser Ile Ala Ala Lys Glu Glu Gly Val
 65                  70                  75                  80

Ser Leu Glu Lys Arg
                 85
```

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 32

```
Ala Ile His Arg Gly Gly Gly
 1               5
```

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 33
gccatccacc gaggaggtgg t                                           21

<210> SEQ ID NO 34
<211> LENGTH: 21
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 34

```
Met Gly Thr Asp Thr Leu Leu Leu Trp Val Leu Leu Leu Trp Val Pro
 1               5                  10                  15

Gly Ala Asp Ala Ala
             20
```

<210> SEQ ID NO 35
<211> LENGTH: 210
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 35
gttcaccaca atacagaaga gatagtggca caatccatcg ctttgtcctc tttgatggtt    60
gctcaagcta tcccattggt cggtgagttg gttgacatcg gtttcgctgc ctacaacttc   120
gtcgagtcca tcatcaactt gttccaagtc gtccacaact cctacaaccg tccggcttac   180
tccccaggtc acaagaccca accattcttg                                    210

<210> SEQ ID NO 36
<211> LENGTH: 21
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 36

```
Met Gly Ser Ser His His His His His His Ser Ser Gly Leu Val Pro
1               5                   10                  15

Arg Gly Ser His Met
            20
```

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence:/Note = synthetic construct

<400> SEQUENCE: 37

```
Ala Ser Ala Gly Gly Ser
1               5
```

<210> SEQ ID NO 38
<211> LENGTH: 642
<212> TYPE: PRT
<213> ORGANISM: Artificial Sequence
<220> FEATURE:
<223> OTHER INFORMATION: Description of Artificial Sequence:/Note = synthetic construct

<400> SEQUENCE: 38

```
Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240
```

-continued

```
Glu Lys Ala Lys Gln Tyr Leu Glu Glu Phe His Gln Thr Ala Leu Glu
                245                 250                 255
His Pro Glu Leu Ser Glu Leu Lys Thr Val Thr Gly Thr Asn Pro Val
            260                 265                 270
Phe Ala Gly Ala Asn Tyr Ala Ala Trp Ala Val Asn Val Ala Gln Val
        275                 280                 285
Ile Asp Ser Glu Thr Ala Asp Asn Leu Glu Lys Thr Thr Ala Ala Leu
290                 295                 300
Ser Ile Leu Pro Gly Ile Gly Ser Val Met Gly Ile Ala Asp Gly Ala
305                 310                 315                 320
Val His His Asn Thr Glu Glu Ile Val Ala Gln Ser Ile Ala Leu Ser
                325                 330                 335
Ser Leu Met Val Ala Gln Ala Ile Pro Leu Val Gly Glu Leu Val Asp
            340                 345                 350
Ile Gly Phe Ala Ala Tyr Asn Phe Val Glu Ser Ile Ile Asn Leu Phe
        355                 360                 365
Gln Val Val His Asn Ser Tyr Asn Arg Pro Ala Tyr Ser Pro Gly His
370                 375                 380
Lys Thr Gln Pro Phe Ala Ser Ala Gly Gly Ser Asp Ile Gln Met Thr
385                 390                 395                 400
Gln Thr Thr Ser Ser Leu Ser Ala Ser Leu Gly Asp Arg Val Thr Ile
                405                 410                 415
Ser Cys Arg Ala Ser Gln Asp Ile Arg Asn Tyr Leu Asn Trp Tyr Gln
            420                 425                 430
Gln Lys Pro Asp Gly Thr Val Lys Leu Leu Ile Tyr Tyr Thr Ser Arg
        435                 440                 445
Leu His Ser Gly Val Pro Ser Lys Phe Ser Gly Ser Gly Ser Gly Thr
450                 455                 460
Asp Tyr Ser Leu Thr Ile Ser Asn Leu Glu Gln Glu Asp Ile Ala Thr
465                 470                 475                 480
Tyr Phe Cys Gln Gln Gly Asn Thr Leu Pro Trp Thr Phe Ala Gly Gly
                485                 490                 495
Thr Lys Leu Glu Ile Lys Arg Ala Gly Gly Ser Gly Gly Gly Gly Ser
            500                 505                 510
Gly Gly Gly Ser Gly Gly Ser Glu Val Gln Leu Gln Gln Ser Gly
        515                 520                 525
Pro Glu Leu Val Lys Pro Gly Ala Ser Met Lys Ile Ser Cys Lys Ala
530                 535                 540
Ser Gly Tyr Ser Phe Thr Gly Tyr Thr Met Asn Trp Val Lys Gln Ser
545                 550                 555                 560
His Gly Lys Asn Leu Glu Trp Met Gly Leu Ile Asn Pro Tyr Lys Gly
                565                 570                 575
Val Ser Thr Tyr Asn Gln Lys Phe Lys Asp Lys Ala Thr Leu Thr Val
            580                 585                 590
Asp Lys Ser Ser Ser Thr Ala Tyr Met Glu Leu Leu Ser Leu Thr Ser
        595                 600                 605
Glu Asp Ser Ala Val Tyr Tyr Cys Ala Arg Ser Gly Tyr Tyr Gly Asp
610                 615                 620
Ser Asp Trp Tyr Phe Asp Val Trp Gly Ala Gly Thr Thr Val Thr Val
625                 630                 635                 640
Ser Ser

<210> SEQ ID NO 39
```

```
<211> LENGTH: 656
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 39
```

| Gly | Ser | Ser | His | His | His | His | His | Ser | Ser | Gly | Leu | Val | Pro | Arg |
|---|---|---|---|---|---|---|---|---|---|---|---|---|---|---|
| 1 | | | | 5 | | | | | 10 | | | | | 15 |

Gly Ser His Gly Ala Asp Asp Val Val Asp Ser Ser Lys Ser Phe Val
              20                  25                  30

Met Glu Asn Phe Ser Ser Tyr His Gly Thr Lys Pro Gly Tyr Val Asp
         35                  40                  45

Ser Ile Gln Lys Gly Ile Gln Lys Pro Lys Ser Gly Thr Gln Gly Asn
 50                  55                  60

Tyr Asp Asp Asp Trp Lys Gly Phe Tyr Ser Thr Asp Asn Lys Tyr Asp
 65                  70                  75                  80

Ala Ala Gly Tyr Ser Val Asp Asn Glu Asn Pro Leu Ser Gly Lys Ala
                 85                  90                  95

Gly Gly Val Val Lys Val Thr Tyr Pro Gly Leu Thr Lys Val Leu Ala
            100                 105                 110

Leu Lys Val Asp Asn Ala Glu Thr Ile Lys Lys Glu Leu Gly Leu Ser
        115                 120                 125

Leu Thr Glu Pro Leu Met Glu Gln Val Gly Thr Glu Glu Phe Ile Lys
130                 135                 140

Arg Phe Gly Asp Gly Ala Ser Arg Val Val Leu Ser Leu Pro Phe Ala
145                 150                 155                 160

Glu Gly Ser Ser Ser Val Glu Tyr Ile Asn Asn Trp Glu Gln Ala Lys
                165                 170                 175

Ala Leu Ser Val Glu Leu Glu Ile Asn Phe Glu Thr Arg Gly Lys Arg
            180                 185                 190

Gly Gln Asp Ala Met Tyr Glu Tyr Met Ala Gln Ala Cys Ala Gly Asn
        195                 200                 205

Arg Val Arg Arg Ser Val Gly Ser Ser Leu Ser Cys Ile Asn Leu Asp
210                 215                 220

Trp Asp Val Ile Arg Asp Lys Thr Lys Thr Lys Ile Glu Ser Leu Lys
225                 230                 235                 240

Glu His Gly Pro Ile Lys Asn Lys Met Ser Glu Ser Pro Asn Lys Thr
                245                 250                 255

Val Ser Glu Glu Lys Ala Lys Gln Tyr Leu Glu Glu Phe His Gln Thr
            260                 265                 270

Ala Leu Glu His Pro Glu Leu Ser Glu Leu Lys Thr Val Thr Gly Thr
        275                 280                 285

Asn Pro Val Phe Ala Gly Ala Asn Tyr Ala Ala Trp Ala Val Asn Val
290                 295                 300

Ala Gln Val Ile Asp Ser Glu Thr Ala Asp Asn Leu Glu Lys Thr Thr
305                 310                 315                 320

Ala Ala Leu Ser Ile Leu Pro Gly Ile Gly Ser Val Met Gly Ile Ala
                325                 330                 335

Asp Gly Ala Val His His Asn Thr Glu Glu Ile Val Ala Gln Ser Ile
            340                 345                 350

Ala Leu Ser Ser Leu Met Val Ala Gln Ala Ile Pro Leu Val Gly Glu
        355                 360                 365

Leu Val Asp Ile Gly Phe Ala Ala Tyr Asn Phe Val Glu Ser Ile Ile

```
                        370                 375                 380
Asn Leu Phe Gln Val Val His Asn Ser Tyr Asn Arg Pro Ala Tyr Ser
385                 390                 395                 400

Pro Gly His Lys Thr Gln Pro Phe Leu Pro Trp Asp Ile Gln Met Thr
                405                 410                 415

Gln Thr Thr Ser Ser Leu Ser Ala Ser Leu Gly Asp Arg Val Thr Ile
            420                 425                 430

Ser Cys Arg Ala Ser Gln Asp Ile Arg Asn Tyr Leu Asn Trp Tyr Gln
        435                 440                 445

Gln Lys Pro Asp Gly Thr Val Lys Leu Leu Ile Tyr Tyr Thr Ser Arg
450                 455                 460

Leu His Ser Gly Val Pro Ser Lys Phe Ser Gly Ser Gly Ser Gly Thr
465                 470                 475                 480

Asp Tyr Ser Leu Thr Ile Ser Asn Leu Glu Gln Glu Asp Ile Ala Thr
                485                 490                 495

Tyr Phe Cys Gln Gln Gly Asn Thr Leu Pro Trp Thr Phe Ala Gly Gly
            500                 505                 510

Thr Lys Leu Glu Ile Lys Arg Gly Gly Gly Gly Ser Gly Gly Gly Gly
        515                 520                 525

Ser Gly Gly Gly Gly Ser Glu Val Gln Leu Gln Gln Ser Gly Pro Glu
530                 535                 540

Leu Val Lys Pro Gly Ala Ser Met Lys Ile Ser Cys Lys Ala Ser Gly
545                 550                 555                 560

Tyr Ser Phe Thr Gly Tyr Thr Met Asn Trp Val Lys Gln Ser His Gly
                565                 570                 575

Lys Asn Leu Glu Trp Met Gly Leu Ile Asn Pro Tyr Lys Gly Val Ser
            580                 585                 590

Thr Tyr Asn Gln Lys Phe Lys Asp Lys Ala Thr Phe Thr Val Asp Lys
        595                 600                 605

Ser Ser Ser Thr Ala Tyr Met Glu Leu Leu Ser Leu Thr Ser Glu Asp
610                 615                 620

Ser Ala Val Tyr Tyr Cys Ala Arg Ser Gly Tyr Tyr Gly Asp Ser Asp
625                 630                 635                 640

Trp Tyr Phe Asp Val Trp Gly Gln Gly Thr Thr Leu Thr Val Phe Ser
                645                 650                 655

<210> SEQ ID NO 40
<211> LENGTH: 1943
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 40
ccatgggcgc tgatgatgtt gttgattctt ctaaatcttt tgtgatggaa aacttttctt      60
cgtaccacgg gactaaacct ggttatgtag attccattca aaaggtata caaaagccaa     120 aatctggtac acaaggaaat tatgacgatg attggaaagg tttttatagt accgacaata    180
aatacgacgc tgcgggatac tctgtagata tgaaaacccc gctctctgga aaagctggag    240
gcgtggtcaa agtgacgtat ccaggactga cgaaggttct cgcactaaaa gtggataatg    300
ccgaaactat taagaaagag ttaggtttaa gtctcactga accgttgatg gagcaagtcg    360
gaacggaaga gttatcaaa aggttcggtg atggtgcttc gcgtgtagtg ctcagccttc     420
ccttcgctga ggggagttct agcgttgaat atattaataa ctgggaacag gcgaaagcgt    480
```

```
taagcgtaga acttgagatt aattttgaaa cccgtggaaa acgtggccaa gatgcgatgt      540
atgagtatat ggctcaagcc tgtgcaggaa atcgtgtcag gcgatcagta ggtagctcat      600
tgtcatgcat aaatcttgat tgggatgtca taagggataa aactaagaca agatagagt       660 ctttgaaaga gcatggccct atcaaaaata aaatgagcga aagtcccaat aaaacagtat      720
ctgaggaaaa agctaaacaa tacctagaag aatttcatca aacggcatta gagcatcctg      780
aattgtcaga acttaaaacc gttactggga ccaatcctgt attcgctggg gctaactatg      840
cggcgtgggc agtaaacgtt gcgcaagtta tcgatagcga aacagctgat aatttggaaa      900
agacaactgc tgctctttcg atacttcctg gtatcggtag cgtaatgggc attgcagacg      960
gtgccgttca ccacaataca gaagagatag tggcacaatc aatagcttta tcgtctttaa     1020
tggttgctca agctattcca ttggtaggag agctagttga tattggtttc gctgcatata     1080
attttgtaga gagtattatc aatttatttc aagtagttca taattcgtat aatcgtcccg     1140
cgtattctcc ggggcataaa acgcaaccat ttgcttccgc cggtggatcc gacatccaga     1200
tgacccagac cacctcctcc ctgtctgcct ctctgggaga cagagtcacc atcagttgca     1260
gggcaagtca ggacattaga aattatttaa actggtatca acagaaacca gatggaactg     1320
ttaaactcct gatctactac acatcaagat tacactcagg agtcccatca agttcagtg      1380 gcagtgggtc tggaacagat tattctctca ccattagcaa cctggagcaa gaggatattg     1440
ccacttactt ttgccaacag ggtaatacgc ttccgtggac gttcgctgga ggcaccaagc     1500
tggaaatcaa acgggctgga ggcggtagtg gcggtggatc aggtggaggc agcggtggcg     1560
gatctgaggt gcagctccag cagtctggac ctgagctggt gaagcctgga gcttcaatga     1620
agatatcctg caaggcttct ggttactcat tcactggcta caccatgaac tgggtgaagc     1680
agagtcatgg aaagaacctt gagtggatgg gacttattaa tccttacaaa ggtgttagta     1740
cctacaacca gaagttcaag gacaaggcca cattaactgt agacaagtca tccagcacag     1800
cctacatgga actcctcagt ctgacatctg aggactctgc agtctattac tgtgcaagat     1860
cggggtacta cggtgatagt gactggtact cgatgtctg gggcgcaggg accacggtca      1920
ccgtctcctc atgatagaga tct                                             1943
```

<210> SEQ ID NO 41
<211> LENGTH: 1940
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 41

```
tgggcgctga tgatgttgtt gattcttcta aatcttttgt gatggaaaac ttttcttcgt       60
accacgggac taaacctggt tatgtagatt ccattcaaaa aggtatacaa aagccaaaat      120
ctggtacaca aggaaattat gacgatgatt ggaaagggtt ttatagtacc gacaataaat      180
acgacgctgc gggatactct gtagataatg aaaacccgct ctctggaaaa gctggaggcg      240
tggtcaaagt gacgtatcca ggactgacga aggttctcgc actaaaagtg ataatgccg       300 aaactattaa gaaagagtta ggtttaagtc tcactgaacc gttgatggag caagtcggaa      360
cggaagagtt tatcaaaagg ttcggtgatg gtgcttcgcg tgtagtgctc agccttccct      420
tcgctgaggg gagttctagc gttgaatata ttaataactg gaacaggcg aaagcgttaa       480 gcgtagaact tgagattaat tttgaaaccc gtggaaaacg tggccaagat gcgatgtatg     540
```

```
agtatatggc tcaagcctgt gcaggaaatc gtgtcaggcg atcagtaggt agctcattgt    600
catgcataaa tcttgattgg gatgtcataa gggataaaac taagacaaag atagagtctt    660
tgaaagagca tggccctatc aaaaataaaa tgagcgaaag tcccaataaa acagtatctg    720
aggaaaaagc taaacaatac ctagaagaat ttcatcaaac ggcattagag catcctgaat    780
tgtcagaact aaaaccgtt actgggacca atcctgtatt cgctggggct aactatgcgg    840
cgtgggcagt aaacgttgcg caagttatcg atagcgaaac agctgataat ttggaaaaga    900
caactgctgc tctttcgata cttcctggta tcggtagcgt aatgggcatt gcagacggtg    960
ccgttcacca aatacagaa gagatagtgg cacaatcaat agctttatcg tctttaatgg   1020
ttgctcaagc tattccattg gtaggagagc tagttgatat tggtttcgct gcatataatt   1080
ttgtagagag tattatcaat ttatttcaag tagttcataa ttcgtataat cgtcccgcgt   1140
attctccggg gcataaaacg caaccatttg cttccgccgg tggatccgac atccagatga   1200
cccagaccac ctcctccctg tctgcctctc tgggagacag agtcaccatc agttgcaggg   1260
caagtcagga cattagaaat tatttaaact ggtatcaaca gaaaccagat ggaactgtta   1320
aactcctgat ctactacaca tcaagattac actcaggagt cccatcaaag ttcagtggca   1380
gtgggtctgg aacagattat tctctcacca ttagcaacct ggagcaagag atattgccac   1440
cttacttttg ccaacagggt aatacgcttc cgtggacgtt cgctggaggc accaagctgg   1500
aaatcaaacg ggctggaggc ggtagtggcg gtggatcagg tggaggcagc ggtggcggat   1560
ctgaggtgca gctccagcag tctggacctg agctggtgaa gcctgagct tcaatgaaga   1620 tatcctgcaa ggcttctggt tactcattca ctggctacac catgaactgg gtgaagcaga   1680
gtcatggaaa gaaccttgag tggatgggac ttattaatcc ttacaaaggt gttagtacct   1740
acaaccagaa gttcaaggac aaggccacat taactgtaga caagtcatcc agcacagcct   1800
acatggaact cctcagtctg acatctgagg actctgcagt ctattactgt gcaagatcgg   1860
ggtactacgg tgatagtgac tggtacttcg atgtctgggg cgcagggacc acggtcaccg   1920
tctcctcatg atagagatct                                                1940
```

<210> SEQ ID NO 42
<211> LENGTH: 24
<212> TYPE: PRT
<213> ORGANISM: Artificial Sequence
<220> FEATURE:
<223> OTHER INFORMATION: Description of Artificial Sequence:/Note = synthetic construct

<400> SEQUENCE: 42

Pro Gly Gly Asn Arg Gly Thr Thr Arg Pro Ala Thr Ser Gly Ser Ser
 1               5                  10                  15

Pro Gly Pro Thr Asn Ser His Tyr
            20

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence:/Note = synthetic construct

<400> SEQUENCE: 43

Gly Gly Gly Gly Ser Gly Gly Gly Gly Ser Gly Gly Gly Gly Ser
 1               5                  10                  15

<210> SEQ ID NO 44
<211> LENGTH: 63
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 44
cgggatccag tcgacatgga gacagacaca ctcctgttat gggtactgct gctctgggtt    60
cca                                                                  63

<210> SEQ ID NO 45
<211> LENGTH: 57
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 45
gtactgctgc tctgggttcc aggtgccgac gctgctggcg ctgatgatgt tgttgat       57

<210> SEQ ID NO 46
<211> LENGTH: 56
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 46
atagaattct tagtggtggt ggtggtggtg tgagaagact gtgagagtgg tgcctt        56

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence:/Note = synthetic construct

<400> SEQUENCE: 47

Glu Ala Glu Ala Tyr Val Glu Phe
 1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence:/Note = synthetic construct

<400> SEQUENCE: 48

Glu Ala Tyr Val Glu Phe
 1               5

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence:/Note = synthetic construct

```
<400> SEQUENCE: 49

Tyr Val Glu Phe
 1

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 50
tataccatgg gcgctgatga tgttgttgat                                          30

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 51
actgcccacg ccgcatagtt agc                                                 23

<210> SEQ ID NO 52
<211> LENGTH: 38
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 52
ttgcgcaacg tttactgccc acgccgcata gttagccc                                 38

<210> SEQ ID NO 53
<211> LENGTH: 33
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 53
cgctatcgat aacttgcgca acgtttactg ccc                                      33

<210> SEQ ID NO 54
<211> LENGTH: 44
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 54
gcagttgtct tttccaaatt atcagctgtt tcgctatcga taac                          44

<210> SEQ ID NO 55
<211> LENGTH: 46
<212> TYPE: DNA
<213> ORGANISM: Artificial Sequence
<220> FEATURE:
<223> OTHER INFORMATION: Description of Artificial Sequence:/Note =
      synthetic construct
```

<400> SEQUENCE: 55
gctaccgata ccaggaagta tcgaaagagc agcagttgtc tttcc         46

<210> SEQ ID NO 56
<211> LENGTH: 57
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 56
gaacggcacc gtctgcaatg cccattacgc taccgatacc aggaagtatc gaaagag    57

<210> SEQ ID NO 57
<211> LENGTH: 42
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 57
actatctctt ctgtattgtg gtgaacggca ccgtctgcaa tg         42

<210> SEQ ID NO 58
<211> LENGTH: 48
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 58
caaccattaa agacgataaa gctattgatt gtgccactat ctcttctg          48

<210> SEQ ID NO 59
<211> LENGTH: 80
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 59
ctacaaaatt atatgcagcg aaaccaatat caactagctc tcctaccaat ggaatagctt    60
gagcaaccat taaagacgat                                              80

<210> SEQ ID NO 60
<211> LENGTH: 66
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 60
cgattatacg aattatgaac tacttgaaat aaattgataa tactctctac aaaattatat    60
gcagcg                                                              66

<210> SEQ ID NO 61
<211> LENGTH: 83
<212> TYPE: DNA
<213> ORGANISM: Artificial Sequence
<220> FEATURE:

<223> OTHER INFORMATION: Description of Artificial Sequence:/Note = synthetic construct

<400> SEQUENCE: 61
gcgaattcgg atccaccggc ggaagcaaat ggttgcgttt tatgccccgg agaatacgcg    60
ggacgattat acgaattatg aac    83

<210> SEQ ID NO 62
<211> LENGTH: 83
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 62
gcgaattcgg atccaccggc ggaagcaaat ggttgcgttt tatgccccgg agaatacgcg    60
ggacgattat acgaattatg aac    83

<210> SEQ ID NO 63
<211> LENGTH: 41
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 63
aagtagttca taattcgtat aatcgtcccg cgtattctcc g    41

<210> SEQ ID NO 64
<211> LENGTH: 32
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 64
gcggatccga catccagatg acccagacca cc    32

<210> SEQ ID NO 65
<211> LENGTH: 32
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 65
cctctagaag cccgtttgat ttccagcttg gt    32

<210> SEQ ID NO 66
<211> LENGTH: 29
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 66
ccgtcgacga ggtgcagctc cagcagtct    29

<210> SEQ ID NO 67
<211> LENGTH: 35

```
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 67
ccaagctttc atgaggagac ggtgaccgtg gtccc                                35

<210> SEQ ID NO 68
<211> LENGTH: 657
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 68
```

Met Gly Ser Ser His His His His His His Ser Ser Gly Leu Val Pro
 1               5                  10                  15

Arg Gly Ser His Gly Ala Asp Asp Val Val Asp Ser Ser Lys Ser Phe
             20                  25                  30

Val Met Glu Asn Phe Ser Ser Tyr His Gly Thr Lys Pro Gly Tyr Val
         35                  40                  45

Asp Ser Ile Gln Lys Gly Ile Gln Lys Pro Lys Ser Gly Thr Gln Gly
     50                  55                  60

Asn Tyr Asp Asp Asp Trp Lys Gly Phe Tyr Ser Thr Asp Asn Lys Tyr
 65                  70                  75                  80

Asp Ala Ala Gly Tyr Ser Val Asp Asn Glu Asn Pro Leu Ser Gly Lys
                 85                  90                  95

Ala Gly Gly Val Val Lys Val Thr Tyr Pro Gly Leu Thr Lys Val Leu
            100                 105                 110

Ala Leu Lys Val Asp Asn Ala Glu Thr Ile Lys Lys Glu Leu Gly Leu
        115                 120                 125

Ser Leu Thr Glu Pro Leu Met Glu Gln Val Gly Thr Glu Glu Phe Ile
    130                 135                 140

Lys Arg Phe Gly Asp Gly Ala Ser Arg Val Val Leu Ser Leu Pro Phe
145                 150                 155                 160

Ala Glu Gly Ser Ser Ser Val Glu Tyr Ile Asn Asn Trp Glu Gln Ala
                165                 170                 175

Lys Ala Leu Ser Val Glu Leu Glu Ile Asn Phe Glu Thr Arg Gly Lys
            180                 185                 190

Arg Gly Gln Asp Ala Met Tyr Glu Tyr Met Ala Gln Ala Cys Ala Gly
        195                 200                 205

Asn Arg Val Arg Arg Ser Val Gly Ser Ser Leu Ser Cys Ile Asn Leu
    210                 215                 220

Asp Trp Asp Val Ile Arg Asp Lys Thr Lys Thr Lys Ile Glu Ser Leu
225                 230                 235                 240

Lys Glu His Gly Pro Ile Lys Asn Lys Met Ser Glu Ser Pro Asn Lys
                245                 250                 255

Thr Val Ser Glu Glu Lys Ala Lys Gln Tyr Leu Glu Glu Phe His Gln
            260                 265                 270

Thr Ala Leu Glu His Pro Glu Leu Ser Glu Leu Lys Thr Val Thr Gly
        275                 280                 285

Thr Asn Pro Val Phe Ala Gly Ala Asn Tyr Ala Ala Trp Ala Val Asn
    290                 295                 300

Val Ala Gln Val Ile Asp Ser Glu Thr Ala Asp Asn Leu Glu Lys Thr

```
            305                 310                 315                 320
Thr Ala Ala Leu Ser Ile Leu Pro Gly Ile Gly Ser Val Met Gly Ile
                325                 330                 335

Ala Asp Gly Ala Val His His Asn Thr Glu Glu Ile Val Ala Gln Ser
            340                 345                 350

Ile Ala Leu Ser Ser Leu Met Val Ala Gln Ala Ile Pro Leu Val Gly
                355                 360                 365

Glu Leu Val Asp Ile Gly Phe Ala Ala Tyr Asn Phe Val Glu Ser Ile
            370                 375                 380

Ile Asn Leu Phe Gln Val Val His Asn Ser Tyr Asn Arg Pro Ala Tyr
385                 390                 395                 400

Ser Pro Gly His Lys Thr Gln Pro Phe Leu Pro Trp Asp Ile Gln Met
                405                 410                 415

Thr Gln Thr Thr Ser Ser Leu Ser Ala Ser Leu Gly Asp Arg Val Thr
            420                 425                 430

Ile Ser Cys Arg Ala Ser Gln Asp Ile Arg Asn Tyr Leu Asn Trp Tyr
                435                 440                 445

Gln Gln Lys Pro Asp Gly Thr Val Lys Leu Leu Ile Tyr Tyr Thr Ser
450                 455                 460

Arg Leu His Ser Gly Val Pro Ser Lys Phe Ser Gly Ser Gly Ser Gly
465                 470                 475                 480

Thr Asp Tyr Ser Leu Thr Ile Ser Asn Leu Glu Gln Glu Asp Ile Ala
                485                 490                 495

Thr Tyr Phe Cys Gln Gln Gly Asn Thr Leu Pro Trp Thr Phe Ala Gly
                500                 505                 510

Gly Thr Lys Leu Glu Ile Lys Arg Gly Gly Gly Ser Gly Gly Gly
                515                 520                 525

Gly Ser Gly Gly Gly Ser Glu Val Gln Leu Gln Gln Ser Gly Pro
            530                 535                 540

Glu Leu Val Lys Pro Gly Ala Ser Met Lys Ile Ser Cys Lys Ala Ser
545                 550                 555                 560

Gly Tyr Ser Phe Thr Gly Tyr Thr Met Asn Trp Val Lys Gln Ser His
                565                 570                 575

Gly Lys Asn Leu Glu Trp Met Gly Leu Ile Asn Pro Tyr Lys Gly Val
            580                 585                 590

Ser Thr Tyr Asn Gln Lys Phe Lys Asp Lys Ala Thr Phe Thr Val Asp
                595                 600                 605

Lys Ser Ser Thr Ala Tyr Met Glu Leu Leu Ser Leu Thr Ser Glu
            610                 615                 620

Asp Ser Ala Val Tyr Tyr Cys Ala Arg Ser Gly Tyr Tyr Gly Asp Ser
625                 630                 635                 640

Asp Trp Tyr Phe Asp Val Trp Gly Gln Gly Thr Leu Thr Val Phe
                645                 650                 655

Ser
```

<210> SEQ ID NO 69
<211> LENGTH: 643
<212> TYPE: PRT
<213> ORGANISM: Artificial Sequence
<220> FEATURE:
<223> OTHER INFORMATION: Description of Artificial Sequence:/Note = synthetic construct

<400> SEQUENCE: 69

Met Gly Ala Asp Asp Val Val Asp Ser Ser Lys Ser Phe Val Met Glu

-continued

```
  1               5                   10                  15
Asn Phe Ser Ser Tyr His Gly Thr Lys Pro Gly Tyr Val Asp Ser Ile
                 20                  25                  30
Gln Lys Gly Ile Gln Lys Pro Lys Ser Gly Thr Gln Gly Asn Tyr Asp
                 35                  40                  45
Asp Asp Trp Lys Gly Phe Tyr Ser Thr Asp Asn Lys Tyr Asp Ala Ala
 50                  55                  60
Gly Tyr Ser Val Asp Asn Glu Asn Pro Leu Ser Gly Lys Ala Gly Gly
 65                  70                  75                  80
Val Val Lys Val Thr Tyr Pro Gly Leu Thr Lys Val Leu Ala Leu Lys
                 85                  90                  95
Val Asp Asn Ala Glu Thr Ile Lys Lys Glu Leu Gly Leu Ser Leu Thr
                100                 105                 110
Glu Pro Leu Met Glu Gln Val Gly Thr Glu Glu Phe Ile Lys Arg Phe
                115                 120                 125
Gly Asp Gly Ala Ser Arg Val Val Leu Ser Leu Pro Phe Ala Glu Gly
                130                 135                 140
Ser Ser Ser Val Glu Tyr Ile Asn Asn Trp Glu Gln Ala Lys Ala Leu
145                 150                 155                 160
Ser Val Glu Leu Glu Ile Asn Phe Glu Thr Arg Gly Lys Arg Gly Gln
                165                 170                 175
Asp Ala Met Tyr Glu Tyr Met Ala Gln Ala Cys Ala Gly Asn Arg Val
                180                 185                 190
Arg Arg Ser Val Gly Ser Ser Leu Ser Cys Ile Asn Leu Asp Trp Asp
                195                 200                 205
Val Ile Arg Asp Lys Thr Lys Thr Lys Ile Glu Ser Leu Lys Glu His
                210                 215                 220
Gly Pro Ile Lys Asn Lys Met Ser Glu Ser Pro Asn Lys Thr Val Ser
225                 230                 235                 240
Glu Glu Lys Ala Lys Gln Tyr Leu Glu Glu Phe His Gln Thr Ala Leu
                245                 250                 255
Glu His Pro Glu Leu Ser Glu Leu Lys Thr Val Thr Gly Thr Asn Pro
                260                 265                 270
Val Phe Ala Gly Ala Asn Tyr Ala Ala Trp Ala Val Asn Val Ala Gln
                275                 280                 285
Val Ile Asp Ser Glu Thr Ala Asp Asn Leu Glu Lys Thr Thr Ala Ala
                290                 295                 300
Leu Ser Ile Leu Pro Gly Ile Gly Ser Val Met Gly Ile Ala Asp Gly
305                 310                 315                 320
Ala Val His His Asn Thr Glu Glu Ile Val Ala Gln Ser Ile Ala Leu
                325                 330                 335
Ser Ser Leu Met Val Ala Gln Ala Ile Pro Leu Val Gly Glu Leu Val
                340                 345                 350
Asp Ile Gly Phe Ala Ala Tyr Asn Phe Val Glu Ser Ile Ile Asn Leu
                355                 360                 365
Phe Gln Val Val His Asn Ser Tyr Asn Arg Pro Ala Tyr Ser Pro Gly
                370                 375                 380
His Lys Thr Gln Pro Phe Ala Ser Ala Gly Gly Ser Asp Ile Gln Met
385                 390                 395                 400
Thr Gln Thr Thr Ser Ser Leu Ser Ala Ser Leu Gly Asp Arg Val Thr
                405                 410                 415
Ile Ser Cys Arg Ala Ser Gln Asp Ile Arg Asn Tyr Leu Asn Trp Tyr
                420                 425                 430
```

```
Gln Gln Lys Pro Asp Gly Thr Val Lys Leu Leu Ile Tyr Tyr Thr Ser
        435                 440                 445

Arg Leu His Ser Gly Val Pro Ser Lys Phe Ser Gly Ser Gly Ser Gly
        450                 455                 460

Thr Asp Tyr Ser Leu Thr Ile Ser Asn Leu Glu Gln Glu Asp Ile Ala
465                 470                 475                 480

Thr Tyr Phe Cys Gln Gln Gly Asn Thr Leu Pro Trp Thr Phe Ala Gly
                485                 490                 495

Gly Thr Lys Leu Glu Ile Lys Arg Ala Gly Gly Ser Gly Gly Gly
        500                 505                 510

Ser Gly Gly Gly Ser Gly Gly Ser Glu Val Gln Leu Gln Gln Ser
        515                 520                 525

Gly Pro Glu Leu Val Lys Pro Gly Ala Ser Met Lys Ile Ser Cys Lys
        530                 535                 540

Ala Ser Gly Tyr Ser Phe Thr Gly Tyr Thr Met Asn Trp Val Lys Gln
545                 550                 555                 560

Ser His Gly Lys Asn Leu Glu Trp Met Gly Leu Ile Asn Pro Tyr Lys
                565                 570                 575

Gly Val Ser Thr Tyr Asn Gln Lys Phe Lys Asp Lys Ala Thr Leu Thr
                580                 585                 590

Val Asp Lys Ser Ser Ser Thr Ala Tyr Met Glu Leu Leu Ser Leu Thr
        595                 600                 605

Ser Glu Asp Ser Ala Val Tyr Tyr Cys Ala Arg Ser Gly Tyr Tyr Gly
        610                 615                 620

Asp Ser Asp Trp Tyr Phe Asp Val Trp Gly Ala Gly Thr Thr Val Thr
625                 630                 635                 640

Val Ser Ser

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 70

Met Ser Glu Ser Pro Asn Lys Thr Val Ser Glu Glu
  1               5                  10

<210> SEQ ID NO 71
<211> LENGTH: 36
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 71
atgagcgaaa gtcccaataa aacagtatct gaggaa                                 36

<210> SEQ ID NO 72
<211> LENGTH: 32
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 72
```

```
gagcgaaagt ccccagaaga cagtatctga gg                                32
```

<210> SEQ ID NO 73
<211> LENGTH: 12
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 73

```
gaagacgaag ac                                                      12
```

<210> SEQ ID NO 74
<211> LENGTH: 36
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 74

```
gtcttcgtct tcgtcttcgt cttcgtcttc gtcttc                            36
```

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 75

```
Met Ser Glu Ser Pro Asn Lys Thr Val Ser Glu Glu
 1               5                  10
```

<210> SEQ ID NO 76
<211> LENGTH: 36
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 76

```
atgagcgaaa gtcccaataa aacagtatct gaggaa                            36
```

<210> SEQ ID NO 77
<211> LENGTH: 32
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 77

```
gagcgaaagt ccggccaaaa cagtatctga gg                                32
```

<210> SEQ ID NO 78
<211> LENGTH: 6
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 78

-continued cggcca                                                          6

<210> SEQ ID NO 79
<211> LENGTH: 6
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 79 tggccg                                                          6

<210> SEQ ID NO 80
<211> LENGTH: 14
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 80

Met Ser Glu Ser Pro Asn Lys Thr Val Ser Glu Glu Lys Ala
 1               5                  10

<210> SEQ ID NO 81
<211> LENGTH: 42
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 81
atgagcgaaa gtcccaataa aacagtatct gaggaaaaac ct                  42

<210> SEQ ID NO 82
<211> LENGTH: 39
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 82
gagcgaaagt cccaataaag cggtctctga ggaaaaacc                      39

<210> SEQ ID NO 83
<211> LENGTH: 6
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 83 ggtctc                                                          6

<210> SEQ ID NO 84
<211> LENGTH: 30
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 84
gagaccgaga ccgagaccga gaccgagacc                                      30

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 85

Ser Phe Val Met Glu Asn Phe Ser Ser Tyr His Gly
 1               5                  10

<210> SEQ ID NO 86
<211> LENGTH: 36
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 86 tctttttgtga tggaaaactt ttcttcgtac cacggg                              36

<210> SEQ ID NO 87
<211> LENGTH: 33
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 87
cttttgtgat ggaagctttt tcttcgtacc acg                                  33

<210> SEQ ID NO 88
<211> LENGTH: 6
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 88 aagctt                                                                 6

<210> SEQ ID NO 89
<211> LENGTH: 6
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 89 aagctt                                                                 6

<210> SEQ ID NO 90
<211> LENGTH: 14
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 90

Phe Val Met Glu Asn Phe Ser Ser Tyr His Gly Thr Lys Pro
 1               5                   10

<210> SEQ ID NO 91
<211> LENGTH: 42
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 91
tttgtgatgg aaaactttc ttcgtaccac gggactaaac ct                            42

<210> SEQ ID NO 92
<211> LENGTH: 38
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 92
gtgatggaaa actttgctag ctaccacggg actaaacc                                38

<210> SEQ ID NO 93
<211> LENGTH: 6
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 93 gctagc                                                                    6

<210> SEQ ID NO 94
<211> LENGTH: 6
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 94 gctagc                                                                    6

<210> SEQ ID NO 95
<211> LENGTH: 180
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 95
ggcgctgatg atgttgttga ttcttctaaa tcttttgtga tggaaaactt ttcttcgtac         60
cacgggacta aacctggtta tgtagattcc attcaaaaag gtatacaaaa gccaaaatct       120
ggtacacaag gaaattatga cgatgattgg aaagggtttt atagtaccga caataaatac       180

<210> SEQ ID NO 96
<211> LENGTH: 180
<212> TYPE: DNA
<213> ORGANISM: Artificial Sequence
<220> FEATURE:

<223> OTHER INFORMATION: Description of Artificial Sequence:/Note =
      synthetic construct

<400> SEQUENCE: 96
ggcgctgatg atgtcgtcga ctcctccaag tccttcgtca tggagaactt cgcttcctac      60
cacgggacca agccaggtta cgtcgactcc atccagaagg gtatccagaa gccaaagtcc     120
ggcacccaag gtaactacga cgacgactgg aagggttct actccaccga caacaagtac     180

<210> SEQ ID NO 97
<211> LENGTH: 120
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 97
aaagagcatg gccctatcaa aaataaaatg agcgaaagtc ccaataaaac agtatctgag      60
gaaaaagcta acaataccct agaagaattt catcaaacgg cattagagca tcctgaattg     120

<210> SEQ ID NO 98
<211> LENGTH: 120
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 98
aaagagcatg gcccaatcaa gaacaagatg tccgaatccc ccgctaagac cgtctccgag      60
gaaaaggcca agcaatacct agaagagttc caccaaaccg ccttggagca tcctgaattg     120

<210> SEQ ID NO 99
<211> LENGTH: 210
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 99
gttcaccaca atacagaaga gatagtggca caatcaatag ctttatcgtc tttaatggtt      60
gctcaagcta ttccattggt aggagagcta gttgatattg gtttcgctgc atataatttt     120
gtagagagta ttatcaattt atttcaagta gttcataatt cgtataatcg tcccgcgtat     180
tctccggggc ataaaacgca accatttctt                                     210

<210> SEQ ID NO 100
<211> LENGTH: 56
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 100
ccctgcacgc cgatgctatc cacagaagag gaggacaagt cattccaacc atgaag          56

<210> SEQ ID NO 101
<211> LENGTH: 21
<212> TYPE: DNA
<213> ORGANISM: Artificial Sequence
<220> FEATURE:

```
<223> OTHER INFORMATION: Description of Artificial Sequence:/note =
      synthetic construct

<400> SEQUENCE: 101
gccgatgcta tccacagaag a                                             21

<210> SEQ ID NO 102
<211> LENGTH: 2691
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 102
gctggtgctg acgacgtcgt cgactcctcc aagtccttcg tcatggagaa cttcgcttcc     60
taccacggga ccaagccagg ttacgtcgac tccatccaga agggtatcca gaagccaaag    120
tccggcaccc aaggtaacta cgacgacgac tggaaggggt tctactccac cgacaacaag    180
tacgacgctg cgggatactc tgtagataat gaaaacccgc tctctggaaa agctggaggc    240
gtggtcaagt tcacctaccc aggtctgact aaggtcttgg ctttgaaggt cgacaacgct    300
gagaccatca agaaggagtt gggtttgtcc ttgactgagc cattgatgga gcaagtcggt    360
accgaagagt tcatcaagag attcggtgac ggtgcttcca gagtcgtctt gtccttgcca    420
ttcgctgagg gttcttctag cgttgaatat attaataact gggaacaggc taaggctttg    480
tctgttgaat ggagattaa cttcgaaacc agaggtaaga gaggtcaaga tgcgatgtat    540
gagtatatgg ctcaagcctg tgctggtaac agagtcagac gttctgttgg ttcctctttg    600
tcctgtatca acctgactg ggacgtcatc agagacaaga ctaagaccaa gatcgagtct    660
ttgaaagagc atggcccaat caagaacaag atgtccgaat ccccgctaa gaccgtctcc    720 gaggaaaagg ccaagcaata cctagaagag ttccaccaaa ccgccttgga gcatcctgaa    780
ttgtcagaac ttaaaaccgt tactgggacc aatcctgtat tcgctggggc taactatgcg    840
gcgtgggcag taaacgttgc gcaagttatc gatagcgaaa cagctgataa tttggaaaag    900
acaactgctg ctcttttcgat acttcctggt atcggtagcg taatgggcat tgcagacggt    960
gccgttcacc acaatacaga agagatagtg cacaatcca tcgctttgtc ctctttgatg   1020
gttgctcaag ctatcccatt ggtcggtgag ttggttgaca tcggtttcgc tgcctacaac   1080
ttcgtcgagt ccatcatcaa cttgttccaa gtcgtccaca actcctacaa ccgtccggct   1140
tactccccag gtcacaagac ccaaccattc ttgccatggg acatccagat gacccagacc   1200
acctcctccc tgtctgcctc cctgggcgac agagtcacca tcagttgcag ggcaagtcag   1260
gacatcagaa actacttgaa ctggtatcag cagaagccag acggtactgt caagttgttg   1320
atctactaca cttccagatt gcactctggt gtcccatcta gttctctgg atctggttct   1380 ggtactgact actccttgac catctccaac ttggagcaag aggatattgc cacttacttt   1440
tgccaacagg gtaatacgct tccgtggacg ttcgctggag gcaccaagtt ggagatcaag   1500
ggtggaggag gttctggagg tggtggatct ggaggtggag gttctgaggt tcaattgcaa   1560
caatctggac ctgagctggt gaagcctgga gcttcaatga agatatcctg caaggcttct   1620
ggttactcat tcactggcta caccatgaac tgggtgaagc agagtcatgg aaagaacctt   1680
gagtggatgg gtttgattaa cccttacaag ggtgtctcga cctacaacca gaagttcaag   1740
gacaaggcta ctttcactgt agacaagtca tccagcacag cctacatgga actcctcagt   1800
ctgacatctg aggactctgc agtctattac tgtgcaagat cggggtacta cggtgatagt   1860
```

```
gactggtact tcgatgtctg gggtgctggt actactgtca ctgtctcctc tggaggtgga   1920
ggatctggag gaggtggttc tggtggtgga ggttctgaca tccagatgac ccagaccacc   1980
tcctccctgt ctgcctccct gggcgacaga gtcaccatca gttgcagggc aagtcaggac   2040
atcagaaact acttgaactg gtatcagcag aagccagacg gtactgtcaa gttgttgatc   2100
tactacactt ccagattgca ctctggtgtc ccatctaagt tctctggatc tggttctggt   2160
actgactact ccttgaccat ctccaacttg gagcaagagg atattgccac ttacttttgc   2220
caacagggta atacgcttcc gtggacgttc gctggaggca ccaagttgga gatcaagggt   2280
ggaggaggtt ctggaggtgg tggatctgga ggtggaggtt ctgaggttca attgcaacaa   2340
tctggacctg agctggtgaa gcctggagct tcaatgaaga tatcctgcaa ggcttctggt   2400
tactcattca ctggctacac catgaactgg gtgaagcaga gtcatggaaa gaaccttgag   2460
tggatgggtt tgattaaccc ttacaagggt gtctcgacct acaaccagaa gttcaaggac   2520
aaggctactt tcactgtaga caagtcatcc agcacagcct acatggaact cctcagtctg   2580
acatctgagg actctgcagt ctattactgt gcaagatcgg ggtactacgg tgatagtgac   2640
tggtacttcg atgtctgggg tgctggtact actgtcactg tctcctctta a           2691
```

```
<210> SEQ ID NO 103
<211> LENGTH: 20
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 103

Met Ser Val Pro Thr Gln Val Leu Gly Leu Leu Leu Leu Trp Leu Thr
1               5                   10                  15

Asp Ala Arg Cys
            20

<210> SEQ ID NO 104
<211> LENGTH: 16
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 104

Gly Gly Gly Ser Gly Gly Gly Ser Gly Gly Ser Gly Gly Gly Ser
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 105

Gly Gly Gly Gly Ser Gly Gly Gly Gly Ser Gly Gly Gly Gly Ser
1               5                   10                  15

<210> SEQ ID NO 106
<211> LENGTH: 5
<212> TYPE: PRT
<213> ORGANISM: Artificial Sequence
```

-continued

```
<220> FEATURE:
<223> OTHER INFORMATION: Description of Artificial Sequence:/note =
      synthetic construct

<400> SEQUENCE: 106

Met Leu Ala Asp Asp
1               5

<210> SEQ ID NO 107
<211> LENGTH: 4
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 107

Met Leu Asp Asp
1

<210> SEQ ID NO 108
<211> LENGTH: 4
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 108

Ser Ala Asp Asp
1

<210> SEQ ID NO 109
<211> LENGTH: 6
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 109

Ser Pro Gly Ala Asp Asp
1               5

<210> SEQ ID NO 110
<211> LENGTH: 4
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 110

Gly Ala Asp Asp
1

<210> SEQ ID NO 111
<211> LENGTH: 5
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 111

Met Gly Ala Asp Asp
1               5
```

```
<210> SEQ ID NO 112
<211> LENGTH: 5
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 112

Met Ala Ala Asp Asp
1               5

<210> SEQ ID NO 113
<211> LENGTH: 4
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 113

Ala Ala Asp Asp
1

<210> SEQ ID NO 114
<211> LENGTH: 5
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 114

Met Ser Ala Asp Asp
1               5

<210> SEQ ID NO 115
<211> LENGTH: 5
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 115

Met Gly Ser Asp Asp
1               5

<210> SEQ ID NO 116
<211> LENGTH: 5
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 116

Met Gly Gly Asp Asp
1               5

<210> SEQ ID NO 117
<211> LENGTH: 5
<212> TYPE: PRT
<213> ORGANISM: Artificial Sequence
<220> FEATURE:
<223> OTHER INFORMATION: Description of Artificial Sequence:/note =
      synthetic construct
```

-continued

```
<400> SEQUENCE: 117

Met Gly Val Asp Asp
 1               5

<210> SEQ ID NO 118
<211> LENGTH: 4
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 118

Gly Gly Asp Asp
 1

<210> SEQ ID NO 119
<211> LENGTH: 4
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 119

Gly Val Asp Asp
 1

<210> SEQ ID NO 120
<211> LENGTH: 652
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 120

Ala Gly Ala Asp Asp Val Val Asp Ser Ser Lys Ser Phe Val Met Glu
 1               5                  10                  15

Asn Phe Ala Ser Tyr His Gly Thr Lys Pro Gly Tyr Val Asp Ser Ile
                20                  25                  30

Gln Lys Gly Ile Gln Lys Pro Lys Ser Gly Thr Gln Gly Asn Tyr Asp
            35                  40                  45

Asp Asp Trp Lys Gly Phe Tyr Ser Thr Asp Asn Lys Tyr Asp Ala Ala
        50                  55                  60

Gly Tyr Ser Val Asp Asn Glu Asn Pro Leu Ser Gly Lys Ala Gly Gly
 65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190
```

```
Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Ala Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr Gln Pro Phe Leu Pro Trp Asp Ile Gln Met Thr Gln Thr
385                 390                 395                 400

Thr Ser Ser Leu Ser Ala Ser Leu Gly Asp Arg Val Thr Ile Ser Cys
                405                 410                 415

Arg Ala Ser Gln Asp Ile Arg Asn Tyr Leu Asn Trp Tyr Gln Gln Lys
            420                 425                 430

Pro Asp Gly Thr Val Lys Leu Leu Ile Tyr Tyr Thr Ser Arg Leu His
        435                 440                 445

Ser Gly Val Pro Ser Lys Phe Ser Gly Ser Gly Ser Gly Thr Asp Tyr
    450                 455                 460

Ser Leu Thr Ile Ser Asn Leu Glu Gln Glu Asp Ile Ala Thr Tyr Phe
465                 470                 475                 480

Cys Gln Gln Gly Asn Thr Leu Pro Trp Thr Phe Ala Gly Gly Thr Lys
                485                 490                 495

Leu Glu Ile Lys Gly Gly Gly Ser Gly Gly Gly Ser Gly Gly
            500                 505                 510

Gly Gly Ser Glu Val Gln Leu Gln Gln Ser Gly Pro Glu Leu Val Lys
    515                 520                 525

Pro Gly Ala Ser Met Lys Ile Ser Cys Lys Ala Ser Gly Tyr Ser Phe
        530                 535                 540

Thr Gly Tyr Thr Met Asn Trp Val Lys Gln Ser His Gly Lys Asn Leu
545                 550                 555                 560

Glu Trp Met Gly Leu Ile Asn Pro Tyr Lys Gly Val Ser Thr Tyr Asn
                565                 570                 575

Gln Lys Phe Lys Asp Lys Ala Thr Phe Thr Val Asp Lys Ser Ser Ser
            580                 585                 590

Thr Ala Tyr Met Glu Leu Leu Ser Leu Thr Ser Glu Asp Ser Ala Val
        595                 600                 605
```

```
-continued

Tyr Tyr Cys Ala Arg Ser Gly Tyr Tyr Gly Asp Ser Asp Trp Tyr Phe
    610             615             620

Asp Val Trp Gly Ala Gly Thr Thr Val Thr Val Ser Ser Gly Gly Gly
625             630             635             640

Gly Ser Gly Gly Gly Gly Ser Gly Gly Gly Gly Ser
            645                 650

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 121

Gly Gly Gly Ser Ser Gly Gly Gly Ser Ser
1               5                   10

<210> SEQ ID NO 122
<211> LENGTH: 4
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 122

Gly Ser Asp Asp
1
```